US010118970B2

(12) United States Patent
Fuh et al.

(10) Patent No.: US 10,118,970 B2
(45) Date of Patent: Nov. 6, 2018

(54) MULTISPECIFIC ANTIBODIES

(75) Inventors: Germaine Fuh, Pacifica, CA (US);
Jenny M. Bostrom, Moss Beach, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 11/893,693

(22) Filed: Aug. 17, 2007

(65) Prior Publication Data

US 2008/0069820 A1    Mar. 20, 2008

Related U.S. Application Data

(60) Provisional application No. 60/841,350, filed on Aug. 30, 2006, provisional application No. 60/937,814, filed on Jun. 28, 2007.

(51) Int. Cl.
| | | |
|---|---|---|
| C07K 16/32 | (2006.01) | |
| C07K 16/22 | (2006.01) | |
| C07K 16/28 | (2006.01) | |
| C07K 16/42 | (2006.01) | |
| C07K 16/46 | (2006.01) | |

(52) U.S. Cl.
CPC .............. *C07K 16/32* (2013.01); *C07K 16/22* (2013.01); *C07K 16/2878* (2013.01); *C07K 16/4283* (2013.01); *C07K 16/468* (2013.01); C07K 2317/55 (2013.01); C07K 2317/56 (2013.01); C07K 2317/622 (2013.01); C07K 2317/73 (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,491,074 A | 2/1996 | Aldwin et al. |
| 5,500,362 A | 3/1996 | Robinson et al. |
| 5,545,806 A | 8/1996 | Lonberg et al. |
| 5,545,807 A | 8/1996 | Surani et al. |
| 5,569,825 A | 10/1996 | Lonberg et al. |
| 5,582,996 A | 12/1996 | Curtis |
| 5,591,669 A | 1/1997 | Krimpenfort et al. |
| 5,591,828 A | 1/1997 | Bosslet et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,661,016 A | 8/1997 | Lonberg et al. |
| 5,821,337 A | 10/1998 | Carter et al. |
| 5,932,448 A | 8/1999 | Tso et al. |
| 6,331,415 B1 | 12/2001 | Cabilly et al. |
| 6,833,441 B2 | 12/2004 | Wang et al. |
| 7,179,595 B2 | 2/2007 | Li |
| 8,597,652 B2 | 12/2013 | Fuh et al. |
| 9,327,035 B2 | 5/2016 | Fuh et al. |
| 2005/0186208 A1 | 8/2005 | Fyfe et al. |
| 2005/0282233 A1 | 12/2005 | Eriksson et al. |
| 2006/0088529 A1 | 4/2006 | Leung et al. |
| 2006/0280747 A1* | 12/2006 | Fuh et al. ................. 424/155.1 |
| 2008/0050370 A1 | 2/2008 | Glaser et al. |
| 2008/0069820 A1 | 3/2008 | Fuh et al. |
| 2008/0181892 A1 | 7/2008 | Ledbetter et al. |
| 2009/0048122 A1 | 2/2009 | Glaser et al. |
| 2009/0148905 A1 | 6/2009 | Ashman et al. |
| 2009/0214541 A1 | 8/2009 | Gillies et al. |
| 2014/0056899 A1 | 2/2014 | Fuh et al. |

FOREIGN PATENT DOCUMENTS

| | | |
|---|---|---|
| EP | 0 368 684 | 3/1994 |
| EP | 0 404 097 | 9/1996 |
| JP | 2002 355074 | 12/2002 |
| WO | WO 90/05144 | 5/1990 |
| WO | WO 91/10741 | 7/1991 |
| WO | WO 92/10209 | 6/1992 |
| WO | WO 93/11161 | 6/1993 |
| WO | WO 93/11162 | 6/1993 |
| WO | WO 93/15210 | 8/1993 |
| WO | WO 96/33735 | 10/1996 |
| WO | WO 96/34096 | 10/1996 |
| WO | WO 98/24893 | 6/1998 |
| WO | WO 02/02773 | 1/2002 |
| WO | WO 03/102157 | * 6/2003 |
| WO | WO 2003/102157 | 12/2003 |
| WO | WO 04/003019 | 1/2004 |
| WO | WO 05/62967 | 7/2005 |
| WO | WO 05/62972 | 7/2005 |
| WO | WO 07/011363 | 1/2007 |

(Continued)

OTHER PUBLICATIONS

Lederman et al (Molecular Immunology 28:1171-1181, 1991).*
Li et al (Proc. Natl. Acad. Sci. USA 77:3211-3214, 1980).*
MacCallum et al. (J. Mol. Biol. (1996) 262:732-745).*
De Pascalis et al. The Journal of Immunology (2002) 169, 3076-3084.*
Casset et al. (2003) BBRC 307, 198-205.*
Vajdos et al. (2002) J. Mol. Biol. 320, 415-428.*
Holm et al (2007) Mol. Immunol. 44: 1075-1084.*
Chen et al. J. Mol. Bio. (1999) 293, 865-881.*
Wu et al. J. Mol. Biol. (1999) 294, 151-162.*
Dufner (Trends Biotechnol. 24(11):523-29 (2006)).*

(Continued)

*Primary Examiner* — Nelson B Moseley, II

(74) *Attorney, Agent, or Firm* — Clark & Elbing LLP; Karen L. Elbing

(57) ABSTRACT

The invention provides multispecific antibodies and methods of making and using such antibodies. In general, the multispecific antibodies are made by methods involving the steps of altering the nucleic acid sequence encoding the light chain variable domain ($V_L$) of an antibody that binds a first epitope, and selecting a multispecific antibody capable of binding the first and a second epitope.

26 Claims, 55 Drawing Sheets

Specification includes a Sequence Listing.

(56) References Cited

FOREIGN PATENT DOCUMENTS

| WO | WO 2007/076923 | 7/2007 |
|---|---|---|
| WO | WO 2007/109254 | 9/2007 |
| WO | WO 08/027236 | 3/2008 |
| WO | WO 2009/068649 | 6/2009 |
| WO | WO 10/027981 | 3/2010 |

OTHER PUBLICATIONS

Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Rudikoff et al. (PNAS, 79:1979-1983, 1982).*
Clackson et al. (Nature, 352:624-628, 1991).*
Zhang et al. (J. Mol. Biol. 335:209-219, 2004).*
Pegram et al. (Breast Cancer Res. Treat. 88, No. suppl 1, abstract 3039, (2004): S124-S125).*
Bostrom et al., "Variants of the antibody herceptin that interact with HER2 and VEGF at the antigen binding site," *Science* 323: 1610-1614 (2009) (including supplemental online material).
Brüggemann et al., "Designer mice: the production of human antibody repertoires in transgenic animals," *Year Immunol.* 7: 33-40 (1993).
Capel et al., "Heterogeneity of human IgG Fc receptors," *Immunomethods* 4: 25-34 (1994).
Chan et al., "Enhanced killing of primary ovarian cancer by retargeting autologous cytokine-induced killer cells with bispecific antibodies: a preclinical study," *Clin Cancer Res.* 12: 1859-1867 (2006).
Chen et al., "Selection and analysis of an optimized anti-VEGF antibody: crystal structure of an affinity-matured Fab in complex with antigen," *J Mol Biol.* 293: 865-881 (1999).
Cho et al., "Structure of the extracellular region of HER2 alone and in complex with the herceptin Fab," *Nature* 421: 756-760 (2003).
Chothia and Lesk, "Canonical structures for the hypervariable regions of immunoglobulins," *J Mol Biol.* 196: 901-917 (1987).
Christinger et al., "Crystallization of the receptor binding domain of vascular endothelial growth factor," *Proteins* 26: 353-357 (1996).
Clackson et al., "Making antibody fragments using phage display libraries," *Nature* 352: 624-628 (1991).
Clynes et al., "Fc receptors are required in passive and active immunity to melanoma," *Proc Natl Acad Sci USA* 95: 652-656 (1998).
Collaborative Computational Project, No. 4, "The CCP4 suite: programs for protein crystallography," *Acta Crystallogr D* 50: 760-763 (1994).
Daëron, "Fc receptor biology," *Annu Rev Immunol.* 15: 203-234 (1997).
De Haas et al., "Fcγ receptors of phagocytes," *J Lab Clin Med.* 126: 330-341 (1995).
De Kruif and Logtenberg, "Leucine zipper dimerized bivalent and bispecific scFv antibodies from a semi-synthetic antibody phage display library," *J Biol Chem.* 271: 7630-7634 (1996).
Emsley and Cowtan, "Coot: model-building tools for molecular graphics," *Acta Crystallogr D* 60: 2126-2132 (2004).
Fellouse et al., "Molecular recognition by a binary code," *J Mol Biol.* 348: 1153-1162 (2005).
Fellouse et al., "Synthetic antibodies from a four-amino-acid code: a dominant role for tyrosine in antigen recognition," *Proc Natl Acad Sci USA* 101: 12467-12472 (2004).
Fishwild et al., "High-avidity human IgGκ monoclonal antibodies from a novel strain of minilocus transgenic mice," *Nat Biotechnol.* 14: 845-851 (1996).

Franklin et al., "Insights into ErbB signaling from the structure of the ErbB2-pertuzumab complex," *Cancer Cell* 5: 317-328 (2004).
Fuh et al., "Requirements for binding and signaling of the kinase domain receptor for vascular endothelial growth factor," *J Biol Chem.* 273: 11197-11204 (1998).
Fuh et al., "Structure-function studies of two synthetic anti-vascular endothelial growth factor Fabs and comparison with the Avastin™ Fab," *J Biol Chem.* 281: 6625-6631 (2006).
Garrard and Henner, "Selection of an anti-IGF-1 Fab from a Fab phage library created by mutagenesis of multiple CDR loops," *Gene* 128: 103-109 (1993).
Gazzano-Santoro et al., "A non-radioactive complement-dependent cytotoxicity assay for anti-CD20 monoclonal antibody," *J Immunol Methods* 202: 163-171 (1997).
Guyer et al., "Immunoglobulin binding by mouse intestinal epithelial cell receptors," *J Immunol.* 117: 587-593 (1976).
Holliger et al., "'Diabodies': small bivalent and bispecific antibody fragments," *Proc Natl Acad Sci USA* 90: 6444-6448 (1993).
Hoogenboom, "Mix and match: building manifold binding sites," *Nat Biotechnol.* 15: 125-126 (1997).
Hudziak and Ullrich, "Cell transformation potential of a HER2 transmembrane domain deletion mutant retained in the endoplasmic reticulum," *J Biol Chem.* 266: 24109-24115 (1991).
Huston et al., "Protein engineering of antibody binding sites: recovery of specific activity in an anti-digoxin single-chain Fv analogue produced in *Escherichia coli*," *Proc Natl Acad Sci USA* 85: 5879-5883 (1988).
International Preliminary Report on Patentability for PCT/US2007/018385, dated Mar. 3, 2009.
International Search Report for PCT/US2007/018385, dated Nov. 5, 2008.
Jakobovits et al., "Germ-line transmission and expression of a human-derived yeast artificial chromosome," *Nature* 362: 255-258 (1993).
Jakobovits et al., "Analysis of homozygous mutant chimeric mice: deletion of the immunoglobulin heavy-chain joining region blocks B-cell development and antibody production," *Proc Natl Acad Sci USA* 90: 2551-2555 (1993).
James et al., "Antibody multispecificity mediated by conformational diversity," *Science* 299: 1362-1367 (2003).
Jimenez et al., "Flexibility and molecular recognition in the immune system," *Proc Natl Acad Sci USA* 100: 92-97 (2003).
Johnson and Wu, "Kabat database and its applications: 30 years after the first variability plot," *Nucleic Acids Res.* 28: 214-218 (2000).
Kelley and O'Connell, "Thermodynamic analysis of an antibody functional epitope," *Biochemistry* 32: 6828-6835 (1993).
Kiewe et al., "Phase I trial of the trifunctional anti-HER2 × anti-CD3 antibody ertumaxomab in metastatic breast cancer," *Clin Cancer Res.* 12: 3085-3091 (2006).
Kim et al., "Localization of the site of the murine IgG1 molecule that is involved in binding to the murine intestinal Fc receptor," *Eur J Immunol.* 24: 2429-2434 (1994).
Knappik et al., "Fully synthetic human combinatorial antibody libraries (HuCAL) based on modular consensus frameworks and CDRs randomized with trinucleotides," *J Mol Biol.* 296: 57-86 (2000).
Köhler and Milstein, "Continuous cultures of fused cells secreting antibody of predefined specificity," *Nature* 256: 495-497 (1975).
Kostelny et al., "Formation of a bispecific antibody by the use of leucine zippers," *J Immunol.* 148: 1547-1553 (1992).
Kufer et al., "A revival of bispecific antibodies," *Trends Biotechnol.* 22: 238-244 (2004).
Kunkel et al., "Rapid and efficient site-specific mutagenesis without phenotypic selection," *Methods Enzymol.* 154: 367-382 (1987).
Lasky and Dowbenko, "DNA sequence analysis of the type-common glycoprotein-D genes of herpes simplex virus types 1 and 2," *DNA* 3: 23-29 (1984).
Lee et al., "Bivalent antibody phage display mimics natural immunoglobulin," *J Immunol Methods* 284: 119-132 (2004).
Lee et al., "High-affinity human antibodies from phage-displayed synthetic Fab libraries with a single framework scaffold," *J Mol Biol.* 340: 1073-1093 (2004).

(56) References Cited

OTHER PUBLICATIONS

Liang et al., "Cross-species vascular endothelial growth factor (VEGF)-blocking antibodies completely inhibit the growth of human tumor xenografts and measure the contribution of stromal VEGF," *J Biol Chem.* 281: 951-961 (2006).

Lonberg and Huszar, "Human antibodies from transgenic mice," *Intern Rev Immunol.* 13: 65-93 (1995).

Lonberg et al., "Antigen-specific human antibodies from mice comprising four distinct genetic modifications," *Nature* 368: 856-859 (1994).

Lovell et al., "Structure validation by Cα geometry: φ, ψ and Cβ deviation," *Proteins* 50: 437-450 (2003).

Lowman et al., "Selecting high-affinity binding proteins by monovalent phage display," *Biochemistry* 30: 10832-10838 (1991).

Lum et al., "The new face of bispecific antibodies: targeting cancer and much more," *Exp Hematol.* 34: 1-6 (2006).

Marks et al., "By-passing immunization: building high affinity human antibodies by chain shuffling," *Biotechnology* 10: 779-783 (1992).

Marks et al., "By-passing immunization. Human antibodies from V-gene libraries displayed on phage," *J Mol Biol.* 222: 581-597 (1991).

Marvin and Zhu, "Recombinant approaches to IgG-like bispecific antibodies," *ACTA Pharmacol Sin.* 26: 649-658 (2005).

Maynard and Georgiou, "Antibody engineering," *Annu Rev Biomed Eng.* 2: 339-376 (2000).

Merk et al., "Cell-free expression of two single-chain monoclonal antibodies against lysozyme: effect of domain arrangement on the expression," *J Biochem.* 125: 328-333 (1999).

Mølhøj et al., "CD19-/CD3-bispecific antibody of the BiTE class is far superior to tandem diabody with respect to redirected tumor cell lysis," *Mol Immunol.* 44: 1935-1943 (2007).

Morrison, "Success in specification," *Nature* 368: 812-813 (1994).

Muller et al., "Vascular endothelial growth factor: crystal structure and functional mapping of the kinase domain receptor binding site," *Proc Natl Acad Sci USA* 94: 7192-7197 (1997).

Muller et al., "VEGF and the Fab fragment of a humanized neutralizing antibody: crystal structure of the complex at 2.4 Å resolution and mutational analysis of the interface." *Structure* 6: 1153-1167 (1998).

Mylvaganam et al., "Structural basis for the binding of an anti-cytochrome c antibody to its antigen: crystal structures of FabE8-cytochrome c complex to 1.8 Å resolution and FabE8 to 2.26 Å resolution," *J Mol Biol.* 281: 301-322 (1998).

Otwinowski and Minor, "Processing of X-ray diffraction data collected in oscillation mode," *Methods Enzymol.* 276: 307-326 (1997).

Parren and Burton, "Two-in-one designer antibodies," *Science* 323: 1567-1568 (2009).

Presta, "Antibody engineering," *Curr Op Struct Biol.* 2: 593-596 (1992).

Presta et al., "Humanization of an anti-vascular endothelial growth factor monoclonal antibody for the therapy of solid tumors and other disorders," *Cancer Res.* 57: 4593-4599 (1997).

Ravetch and Kinet, "Fc receptors," *Annu Rev Immunol.* 9: 457-492 (1991).

Read, "Pushing the boundaries of molecular replacement with maximum likelihood," *Acta Ctystallogr D* 57: 1373-1382 (2001).

Riechmann et al., "Reshaping human antibodies for therapy," *Nature* 332: 323-327 (1988).

Senn et al., "Combinatorial immunoglobulin light chain variability creates sufficient B cell diversity to mount protective antibody responses against pathogen infections," *Eur J Immunol.* 33: 950-961 (2003).

Sethi et al., "Differential epitope positioning within the germline antibody paratope enhances promiscuity in the primary immune response," *Immunity* 24: 429-438 (2006).

Shen et al., "Single variable domain-IgG fusion. A novel recombinant approach to Fc domain-containing bispecific antibodies," *J Biol Chem.* 281: 10706-10714 (2006).

Shen et al., "Single variable domain antibody as a versatile building block for the construction of IgG-like bispecific antibodies," *J Immunol Methods* 318: 65-74 (2007).

Sidhu et al., "Phage-displayed antibody libraries of synthetic heavy chain complementarity determining regions," *J Mol Biol.* 338: 299-310 (2004).

Sidhu et al., "Phage display for selection of novel binding peptides," *Methods Enzymol.* 328: 333-63 (2000).

Stone et al., "The assembly of single domain antibodies into bispecific decavalent molecules," *J Immunol Methods* 318: 88-94 (2007).

Storoni et al., "Likelihood-enhanced fast rotation functions," *Acta Crystallogr D* 60: 432-438 (2004).

Takagi et al., "C-terminal opening mimics 'inside-out' activation of integrin α5β1," *Nat Struct Biol.* 8: 412-416 (2001).

Tsumoto et al., "Effect of the order of antibody variable regions on the expression of the single-chain HyHel10 Fv fragment in *E. coli* and the thermodynamic analysis of its antigen-binding properties," *Biochem Biophys Res Comm.* 201: 546-551 (1994).

Vajdos et al., "Comprehensive functional maps of the antigen-binding site of an anti-ErbB2 antibody obtained with shotgun scanning mutagenesis," *J Mol Biol.* 320: 415-428 (2002).

Weiss et al., "Rapid mapping of protein functional epitopes by combinatorial alanine scanning," *Proc Natl Acad Sci USA* 97: 8950-8954 (2000).

Wiesmann et al., "Crystal structure at 1.7 Å resolution of VEGF in complex with domain 2 of the Flt-1 receptor," *Cell* 91: 695-704 (1997).

Written Opinion of the International Searching Authority for PCT/US2007/018385, dated Nov. 5, 2008.

Zapata et al., "Engineering linear F(ab')$_2$ fragments for efficient production in *Escherichia coli* and enhanced antiproliferative activity," *Protein Eng.* 8: 1057-1062 (1995).

Agus et al., "Targeting Ligand-Activated ErbB2 Signaling Inhibits Breast and Prostate Tumor Growth," *Cancer Cell* 2:127-137 (2002).

Arevalo et al., "Molecular Basis of Crossreactivity and the Limits of Antibody-Antigen Complementarity," *Nature* 365:859-863 (1993).

Austin et al., "Endocytosis and Sorting of ErbB2 and the Site of Action of Cancer Therapeutics Trastuzumab and Geldanamycin," *Mol. Biol. Cell* 15:5268-5282 (2004).

Birk et al., "Current Insights on the Biology and Clinical Aspects of VEGF Regulation," *Vasc. Endovascular Surg.* 42:517-530 (2008).

Boder et al., "Directed Evolution of Antibody Fragments with Monovalent Femtomolar Antigen-Binding Affinity," *Proc. Natl. Acad. Sci. USA* 97:10701-10705 (2000).

Boder et al., "Yeast Surface Display for Screening Combinatorial Polypeptide Libraries," *Nat. Biotechnol.* 15:553-557 (1997).

Boniface et al., "Thermodynamics of T Cell Receptor Binding to Peptide-MHC: Evidence for a General Mechanism of Molecular Scanning," *Proc. Natl. Acad. Sci. USA* 96:11446-11451 (1999).

Bostrom et al., "Design and Construction of Synthetic Phage-Displayed Fab Libraries," *Methods Mol. Biol.* 562:17-35 (2009).

Bostrom et al., "Improving Antibody Binding Affinity and Specificity for Therapeutic Development," *Methods Mol. Biol.* 525:353-376 (2009).

Boulanger et al., "Convergent Mechanisms for Recognition of Divergent Cytokines by the Shared Signaling Receptor Gp130," *Mol. Cell* 12:577-589 (2003).

Carter et al., "Potent Antibody Therapeutics by Design," *Nat. Rev. Immunol.* 6:343-357 (2006).

Clackson et al., "A Hot Spot of Binding Energy in a Hormone-Receptor Interface," *Science* 267:383-386 (1995).

Clynes et al., "Inhibitory Fc Receptors Modulate In Vivo Cytoxicity Against Tumor Targets," *Nat. Med.* 6:443-446 (2000).

Dall'Acqua et al., "A Mutational Analysis of the Binding of Two Different Proteins to the Same Antibody," *Biochemistry* 35:9667-9676 (1996).

Daugherty et al., "Development of an Optimized Expression System for the Screening of Antibody Libraries Displayed on the *Escherichia coli* Surface," *Protein Eng.* 12:613-621 (1999).

Davis et al., "Ligand Recognition by Alpha Beta T Cell Receptors," *Annu. Rev. Immunol.* 16:523-544 (1998).

(56) References Cited

OTHER PUBLICATIONS

Epstein et al., "HER-2/Neu-Overexpressing Human Breast Cancer Xenografts Exhibit Increased Angiogenic Potential Mediated by Vascular Endothelial Growth Factor (VEGF)," *Breast Cancer Res. Treat.* 76: 569-572. (2002).
Ferrara et al., "The Biology of VEGF and Its Receptors," *Nat. Med.* 9:669-676 (2003).
Fields et al., "Molecular Basis of Antigen Mimicry by an Anti-Idiotype," *Nature* 374:739-742 (1995).
Foote et al., "Antibody Framework Residues Affecting the Conformation of the Hypervariable Loops," *J. Mol. Biol.* 224:487-499 (1992).
Foote et al., "Conformational Isomerism and the Diversity of Antibodies," *Proc. Natl. Acad. Sci. USA* 91:10370-10374 (1994).
Garcia et al., "The Molecular Basis of TCR Germline Bias for MHC Is Surprisingly Simple," *Nat. Immunol.* 10:143-147 (2009).
Gerber et al., "Complete Inhibition of Rhabdomyosarcoma Xenograft Growth and Neovascularization Requires Blockade of Both Tumor and Host Vascular Endothelial Growth Factor," *Cancer Res.* 60:6253-6258 (2000).
Grothey et al., "Targeting Angiogenesis: Progress with Anti-VEGF Treatment with Large Molecules," *Nat. Rev. Clin. Oncol.* 6:507-518 (2009).
Guo et al., "Breaking the One Antibody-One Target Axiom," *Proc. Natl. Acad. Sci. USA* 103: 11009-11014 (2006).
Hanes et al., "In Vitro Selection and Evolution of Functional Proteins by Using Ribosome Display," *Proc. Natl. Acad. Sci. USA* 94:4937-4942 (1997).
Harvey et al., "Anchored Periplasmic Expression, a Versatile Technology for the Isolation of High-Affinity Antibodies from *Escherichia coli*-Expressed Libraries," *Proc. Natl. Acad. Sci. USA* 101:9193-9198 (2004).
Hommelgaard et al., "Association with Membrane Protrusions Makes ErbB2 an Internalization-Resistant Receptor," *Mol. Biol Cell* 15:1557-1567 (2004).
Hoogenboom, "Selecting and Screening Recombinant Antibody Libraries," *Nat. Biotechnol.* 23:1105-1116 (2005).
Hudziak et al., "P185HER2 Monoclonal Antibody has Antiproliferative Effects In Vitro and Sensitizes Human Breast Tumor Cells to Tumor Necrosis Factor," *Mol. Cell Biol.* 9:1165-1172 (1989).
Hurwitz, "Integrating the Anti-VEGF—A Humanized Monoclonal Antibody Bevacizumab with Chemotherapy in Advanced Colorectal Cancer," *Clin. Colorectal Cancer* 4(Suppl. 2):S62-S68 (2004).
Jones et al., "Replacing the Complementarity-Determining Regions in a Human Antibody with Those From a Mouse," *Nature* 321:522-525 (1986).
Junttila et al., "Ligand-Independent HER2/HER3/PI3K Complex Is Disrupted by Trastuzumab and Is Effectively Inhibited by the PI3K Inhibitor GDC-0941," *Cancer Cell* 15:429-440 (2009).
Kabat et al., "Identical V Region Amino Acid Sequences and Segments of Sequences in Antibodies of Different Specificities: Relative Contributions of VH and VL Genes, Minigenes, and Complementarity-Determining Regions to Binding of Antibody-Combining Sites," *J. Immunol.* 147:1709-1719 (1991).
Keitel et al., "Crystallographic Analysis of Anti-P24 (HIV-1) Monoclonal Antibody Crossreactivity and Polyspecificity," *Cell* 91:811-820 (1997).
Kelley et al., "Antigen Binding Thermodynamics and Antiproliferative Effects of Chimeric and Humanized Anti-P185HER2 Antibody Fab Fragments," *Biochemistry* 31:5434-5441 (1992).
Kim et al., "Inhibition of Vascular Endothelial Growth Factor-Induced Angiogenesis Suppresses Tumour Growth In Vivo," *Nature* 362:841-844 (1993).
Konecny et al., "Association Between HER-2/Neu and Vascular Endothelial Growth Factor Expression Predicts Clinical Outcome in Primary Breast Cancer Patients," *Clin. Cancer. Res.* 10:1706-1716 (2004).
Konner et al., "Use of Soluble Recombinant Decoy Receptor Vascular Endothelial Growth Factor Trap (VEGF Trap) to Inhibit Vascular Endothelial Growth Factor Activity," *Clin. Colorectal Cancer* 4(Suppl. 2):S81-S85 (2004).
Lane et al., "ErbB2 Potentiates Breast Tumor Proliferation Through Modulation of P27(Kip1)-Cdk2 Complex Formation: Receptor Overexpression Does Not Determine Growth Dependency," *Mol. Cell. Biol.* 20:3210-3223 (2000).
Lee et al., "Synthetic Anti-BR3 Antibodies That Mimic BAFF Binding and Target Both Human and Murine B Cells," *Blood* 108:3103-3111 (2006).
Lewis et al., "Growth Regulation of Human Breast and Ovarian Tumor Cells by Heregulin: Evidence for the Requirement of ErbB2 as a Critical Component in Mediating Heregulin Responsiveness," *Cancer Res.* 56:1457-1465 (1996).
Lipovsek et al., "In-Vitro Protein Evolution by Ribosome Display and mRNA Display," *J. Immunol. Methods* 290:51-67 (2004).
Ma et al., "Multiple Diverse Ligands Binding at a Single Protein Site: A Matter of Pre-Existing Populations," *Protein Sci.* 11:184-197 (2002).
Manivel et al., "The Primary Antibody Repertoire Represents a Linked Network of Degenerate Antigen Specificities," *J. Immunol.* 169:888-897 (2002).
Mohan et al., "Association Energetics of Cross-Reactive and Specific Antibodies," *Biochemistry* 48:1390-1398 (2009).
Nagata et al., "PTEN Activation Contributes to Tumor Inhibition by Trastuzumab, and Loss of PTEN Predicts Trastuzumab Resistance in Patients," *Cancer Cell* 6:117-127 (2004).
Neuberger et al., "Generating High-Avidity Human Mabs in Mice," *Nat. Biotechnol.* 14:826 (1996).
Parren et al., "Two-in-one designer antibodies," *Immunology* 323:1567-1568 (2009).
Prabhakar et al., "Lymphocytes Capable of Making Monoclonal Autoantibodies That React with Multiple Organs Are a Common Feature of the Normal B Cell Repertoire," *J. Immunol.* 133:2815-2817 (1984).
Prewett et al., "Antivascular Endothelial Growth Factor Receptor (Fetal Liver Kinase 1) Monoclonal Antibody Inhibits Tumor Angiogenesis and Growth of Several Mouse and Human Tumors," *Cancer Res.* 59:5209-5218 (1999).
Reichert et al., "Monoclonal Antibody Successes in the Clinic," *Nat. Biotechnol.* 23:1073-1078 (2005).
Sarup et al., "Characterization of an Anti-P185HER2 Monoclonal Antibody that Stimulates Receptor Function and Inhibits Tumor Cell Growth," *Growth Regul.* 1:72-82 (1991).
Stites et al., "Protein-Protein Interactions: Interface Structure, Binding Thermodynamics, and Mutational Analysis," *Chem. Rev.* 97:1233-1250 (1997).
Tomlinson et al., "The Imprint of Somatic Hypermutation on the Repertoire of Human Germline V Genes," *J. Mol. Biol.* 256:813-817 (1996).
Tonegawa et al., "Somatic Generation of Antibody Diversity," *Nature* 302:575-581 (1983).
Trinh et al., "Antibody Fragment Fv4155 Bound to Two Closely Related Steroid Hormones: The Structural Basis of Fine Specificity," *Structure* 5:937-948 (1997).
Wardemann et al., "Predominant Autoantibody Production by Early Human B Cell Precursors," *Science* 301:1374-1377 (2003).
Wedemayer et al., "Structural Insights into the Evolution of an Antibody Combining Site," *Science* 276:1665-1669 (1997).
Willcox et al., "TCR Binding to Peptide-MHC Stabilizes a Flexible Recognition Interface," *Immunity* 10:357-365 (1999).
Winter et al., "Making Antibodies by Phage Display Technology," *Annu. Rev. Immunol.* 12:433-455 (1994).
Xu et al., "Diversity in the CDR3 Region of V(H) Is Sufficient for Most Antibody Specificities," *Immunity* 13:37-45 (2000).
Yang et al., "Mutational Analysis of the Affinity Maturation of Antibody 48G7," *J. Mol. Biol.* 294:1191-1201 (1999).
Baselga et al., "Recombinant Humanized Anti-HER2 Antibody (Herceptin) Enhances the Antitumor Activity of Paclitaxel and Doxorubicin Against HER2/Neu Overexpressing Human Breast Cancer Xenografts," *Cancer Res.* 58:2825-2831 (1998).
Beck, "4th European Antibody Congress 2008: Dec. 1-3, 2008, Geneva, Switzerland," *MAbs* 1: 93-103 (2009).

(56) References Cited

OTHER PUBLICATIONS

Davies et al., "Affinity Improvement of Single Antibody VH Domains: Residues in all Three Hypervariable Regions Affect Antigen Binding," *Immunotechnol* 2:169-179 (1996).
Delano et al., "Convergent solutions to binding at a protein-protein interface," *Science* 287: 1279-1283 (2000).
Eigenbrot et al., "X-ray structures of the antigen-binding domains from three variants of humanized anti-p185HER2 antibody 4D5 and comparison with molecular modeling," *J. Mol. Biol.* 4: 969-995 (1993).
Enever et al., "Next generation immunotherapeutics—honing the magic bullet," *Curr. Opin. Biotechnol.* 4: 405-411 (2009).
Fellouse et al., "Tyrosine plays a dominant functional role in the paratope of a synthetic antibody derived from a four amino acid code," *J. Mol. Biol.* 1: 100-114 (2005).
Franklin et al., "Insights into ErbB signaling from the structure of the ErbB2-pertuzumab complex," *Cancer. Cell.* 4: 317-328 (2004).
Fukada et al., "Enthalpy and heat capacity changes for the proton dissociation of various buffer components in 0.1 M potassium chloride," *Proteins* 2: 159-166 (1998).
Gallop et al., "Applications of Combinatorial Technologies to Drug Discovery. 1. Background and Peptide Combinatorial Libraries," *J. Med. Chem.* 37:1233-1251 (1994).
Garber et al., "A broad range of Fab stabilities within a host of therapeutic IgGs,"*Biochem. Biophys. Res. Commun.* 3: 751-757 (2007).
Griffiths et al., "An Antibody Which Behaves Like a Man with a Wife and Mistress," *Rev. Med. Viral.* 19:181-183 (2009).
Holt et al., "Domain Antibodies: Proteins for Therapy," *TIB* 21(11):484-490 (2003).
Kossiakoff et al., "Understanding mechanisms governing protein-protein interactions from synthetic binding interfaces," *Curr. Opin. Struct. Biol.* 4: 499-506 (2008).
Kramer et al., "Molecular Basis for the Binding Promiscuity of an Anti-P24 (HIV-1) Monoclonal Antibody," *Cell* 91:799-809 (1997).
Krogsgaard et al., "Evidence that structural rearrangements and/or flexibility during TCR binding can contribute to T cell activation," *Mol. Cell.* 6: 1367-1378 (2003).
McFarland et al., "Thermodynamic analysis of degenerate recognition by the NKG2D immunoreceptor: not induced fit but rigid adaptation," *Immunity* 6:803-812 (2003).
Mietzner et al., "Autoreactive IgG memory antibodies in patients with systemic lupus erythematosus arise from nonreactive and polyreactive precursors," *Proc. Natl. Acad. Sci. U.S.A.* 28: 9727-9732 (2008).
Murphy et al., "Configurational effects in antibody-antigen interactions studied by microcalorimetry," *Proteins* 2: 83-90 (1995).
Murphy et al, "Entropy in biological binding processes: estimation of translational entropy loss," 18: 63-37 (1994).
Nemazee et al., "Receptor Editing in Lymphocyte Development and Central Tolerance," *Nat. Rev. Immunol.* 6:728-740 (2006).
Notkins et al., "Polyreactivity of Antibody Molecules," *Trends Immunol.* 25:174-179 (2004).
Pini et al., "Design and Use of a Phage Display Library: Human Antibodies with Subnanomolar Affinity Against a Marker of Angiogenesis Eluted From a Two-Dimensional Gel," *J. Biol. Chem.* 273:21769-21776 (1998).
Petri et al., "Thermodynamic and kinetic characterization of the binding of the TATA binding protein to the adenovirus E4 promoter," *Biochemistry* 34: 9977-9984 (1995).
Prabhu et al., "Heat capacity in proteins," *Annu. Rev. Phys. Chem.* 56: 521-548 (2005).
Reese and Karnovsky, "Fine structural localization of a blood-brain barrier to exogenous peroxidase," *J. Cell. Biol.* 34: 207-217 (1967).

Reichmann et al., "The modular architecture of protein-protein binding interfaces," *Proc. Natl. Acad. Sci. U.S.A.* 102: 57-62 (2004).
Rudolph et al., "How TCRs bind MHCs, peptides, and coreceptors,"*Annu. Rev. Immunol.* 24: 419-466 (2006).
Sundberg et al., "Molecular recognition in antibody-antigen complexes," *Adv. Protein Chem.* 61: 119-160 (2002).
Thiegles et al., "Exploring the energy landscape of antibody-antigen complexes: protein dynamics, flexibility, and molecular recognition," *Biochemistry* 47: 7237-7247 (2008).
Valladares et al., "Designing two-in-one antibodies," *Immunotherapy* 1: 749-751 (2009).
Van der Merwe et al., "Analysis of cell-adhesion molecule interactions using surface plasmon resonance" *Curr. Opin. Immunol.* 8: 257-261 (1996).
Walker et al., "Anti-serum albumin domain antibodies in the development of highly potent, efficacious and long-acting interferon," *Protein Eng. Des. Sel.* 23: 271-278 (2010).
Walker et al., "Single domain antibodies against the collagen signalling receptor glycoprotein VI are inhibitors of collagen induced thrombus formation," *Platelets* 20: 268-276 (2009).
Wells et al., "The molecular basis for growth hormone-receptor interactions," *Recent Prog. Horm. Res.* 48: 253-275 (1993).
Winn et al., "Use of TLS Parameters to Model Anisotropic Displacements in Macromolecular Refinement," *Acta Crystallograph.* 57:122-133 (2001).
Winzor et al., "Interpretation of the temperature dependence of rate constants in biosensor studies," *Anal. Biochem.* 337: 289-293 (2005).
Ferrara et al., "Clinical applications of angiogenic growth factors and their inhibitors," *Nat Med.* 5: 1359-1364 (1999).
Klagsbrun and D'Amore, "Regulators of angiogenesis," *Annu Rev Physiol.* 53: 217-239 (1991 ).
Sato et al., "Molecular diagnosis of tumor angiogenesis and anti-angiogenic cancer therapy," *Int J Clin Oncol.* 8: 200-206 (2003).
Streit and Detmar, "Angiogenesis, lymphangiogenesis, and melanoma metastasis," *Oncogene* 22: 3172-3179 (2003).
Tonini et al., "Molecular basis of angiogenesis and cancer," *Oncogene* 22: 6549-6556 (2003).
Office Action for U.S. Appl. No. 11/893,693, dated Jul. 17, 2009.
Office Action for U.S. Appl. No. 11/893,693 dated Apr. 12, 2010.
International Search Report for PCT/US2009/055625, dated Jan. 5, 2010.
International Preliminary Report on Patentability (PCT/US2009/055625) dated Mar. 8, 2011.
Holt et al., "Anti-Serum Albumin Domain Antibodies for Extending the Half-Lives of Short Lived Drugs," *Protein Eng. Des. Sel.* 21: 283-288 (2008).
Koenig and Fuh, "Two-in-One Antibodies," in *Bispecific Antibodies.* Ed. R. Kontermann. Springer-Verlag Berlin Heidelberg, pp. 187-198 (2011).
James et el., "Antibody multispecificity mediated by conformational diversity," *Science,* 299:1362-1367 (2003).
Marvin et al., "Recombinant approaches to IgG-like bispecific antibodies," *Acta Pharmacologica Sinica,* 26:649-658 (2005).
Starovasnik et al., "Antibody Variable Region Binding by Staphylococcal Protein A: Thermodynamic Analysis and Location of the Fv Binding Site on E-Domain," *Protein Sci.* 8: 1423-1431 (1999).
Wurch et al., "Keystone Symposium on Antibodies as Drugs: Mar. 27-Apr. 1, 2009, Whistler, BC CA," *MAbs*1: 318-325 (2009).
European Patent Office Communication for European Patent Application No. 07837065.7 dated May 18, 2012.
European Patent Office Communication for European Patent Application No. 07837065.7 dated Nov. 24, 2009.
European Patent Office Communication for European Patent Application No. 11191823.1 dated Jun. 5, 2012.

\* cited by examiner

| Library | 28 | 29 | 30 | 30a | 30b | 30c | 30d | 30e | 30f | 31 | 32 |
|---|---|---|---|---|---|---|---|---|---|---|---|
| | | | | | | CDR-L1 | | | | | |
| L1/L3 | Ss | | NNK | (NNK) | (NNK) | (NNK) | (NNK) | (NNK) | - | NNK | Ys |
| L1/L4 | Ss | | NNK | (NNK) | (NNK) | (NNK) | (NNK) | (NNK) | (NNK) | NNK | Ys |
| L1/L2/L3-A_1 | Ss | V/L | NNK | (NNK) | (NNK) | (NNK) | (NNK) | (NNK) | (NNK) | NNK | Ys |
| L1/L2/L3-A_2 | Ss | | NNK | (NNK) | (NNK) | (NNK) | (NNK) | (NNK) | (NNK) | NNK | Ys |
| L1/L2/L3-B_1 | NNK | NNK | NNK | - | - | - | - | - | - | NNK | NNK |
| L1/L2/L3-B_2 | NNK | NNK | NNK | (NNK) | (NNK) | - | - | - | - | NNK | NNK |
| L1/L2/L3-C | Ds | I/V | NNK | (NNK) | (NNK) | (NNK) | (NNK) | (NNK) | (NNK) | NNK | Y WRG YSPHNTDA |
| L1/L2/L3-D | Ds | I/V | NNK | (NNK) | (NNK) | (NNK) | (NNK) | (NNK) | (NNK) | NNK | Y WRG YSPHNTDA |

| | | CDR-L2 | | | | Framework 3 | | | | | CDR-L3 | | | | | | |
|---|---|---|---|---|---|---|---|---|---|---|---|---|---|---|---|---|---|
| 50 | 51 | 52 | 53 | | 66 | 67 | 68 | 69 | 70 | 91 | 92 | 93 | a | b | c | d | e f 94 |
| | | | | | NNK | Ss | - | T/Ts | D/Ds | | | | | | | | |
| | | | | | NNK | NNK | Ss | NNK | NNK | | | | | | | | |
| NNK | | S | NNK | | | | | | | XYZ | XYZ | XYZ | (XYZ) | (XYZ) | | | |
| W | GAS | | | | | | | | | XYZ | XYZ | - | | | | | |
| NNK | | S | NNK | | | | | | | XYZ | XYZ | XYZ | (XYZ) | (XYZ) | | | |
| W | GAS | | | | | | | | | | | | | | | | |
| NNK | | S | NNK | | | | | | | XYZ | XYZ | XYZ | (XYZ) | (XYZ) | | | |
| W | GAS | | | | | | | | | | | | | | | | |
| NNK | | | YS | | | | | | | NNK | NNK | - | - | | | | |
| W | GA | S | NNK | | | | | | | | | | | | | | |
| WG | | | | | | | | | | NNK | NNK | - | - | | | | |
| NNK | | | YS | | NNK | Ss | | T | D | YADS | XYZ | XYZ | XYZ | (XYZ) | (XYZ) | - | - ATSG |
| W | GA | S | NNK | | | | | Ts | Ds | H | | | | | | | |
| WG | | | | | | | | | | WRG | | | | | | | |
| | | | | | | | | | | | XYZ | XYZ | | | | | - ATSG |

FIG.1

| Library | | L1/L3 | L1/L4 | L1/L2/L3-A | L1/L2/L3-B | L1/L2/L3-C, +L4-D |
|---|---|---|---|---|---|---|
| | template<br>Format<br>Stop | 2C4<br>Fab-C<br>L1 | 2C4<br>Fab-C<br>L1 | 2C4<br>Fab-C<br>L1 | 4D5¹ G6-Av²<br>ScFv Fab-C<br>L1 | 4D5<br>ScFv<br>L1 |
| L1 | 28<br>29<br>30<br>30a-e<br>31<br>32<br>33 | Ss<br>NNK<br>(NNK)0-4<br>NNK<br>Ys | NNK<br>(NNK)0-5<br>NNK<br>Ys | Ss<br>VL XYZ<br>NNK (XYZ)5<br>(NNK)5 P<br>P Y<br>Y | NNK<br>NNK<br>NNK<br>NNK<br>NNK | Ds<br>I/V<br>NNK<br>(NNK)0-5<br>NNK<br>Y/WRG/YSPHSTDA |
| L2 | 50<br>51<br>52<br>53 | | | NNK/W<br>GAS<br>S<br>NNK | NNK/W<br>GAS<br>S<br>NNK | NNK/W/WG<br>GA<br>S<br>YS/NNK |
| L4 | 66<br>67<br>68<br>69<br>70 | NNK<br>Ss<br>T/Ts<br>D/Ds<br>NNK | NNK<br>NNK<br>Ss<br>NNK<br>NNK | | | NNK<br>Ss<br>T/Ts<br>D/Ds |
| L3 | 91<br>92<br>93<br>93a<br>94 | XYZ<br>(XYZ)<br>(XYZ)0-2 | XYZ<br>(XYZ) | XYZ<br>XYZ<br>(XYZ)0-2 | NNK<br>NNK | YADS/H/WRG<br>XYZ<br>XYZ<br>(XYZ)0-2<br>ATSG |
| | Display | 5-7% | 5-7% | 5-7% | ~15-25% | ~17% |
| | Target | VEGF<br>DR5<br>Albumin | VEGF<br>DR5 | VEGF<br>DR5 | VEGF | VEGF<br>DR5<br>IgG-Fc fusion protein |

| Sorting Round | Binding condition | Protein | Titer | Enrichment | OD/mL |
|---|---|---|---|---|---|
| 1 | bind 4 hrs. wash 4X BSA | Human Fc fusion hVEGF hDR5 - long L - 3 (short L1's) L - 4 (long L1's) | $1.8 \times 10^6$ $1.5 \times 10^6$ $8 \times 10^5$ $4.8 \times 10^6$ $1 \times 10^6$ | | 21 18.3 20.9 |
| 2 | bind 3 hrs. wash 5X BSA/ovalbumin | Human Fc fusion hVEGF hDR5 - long | $5.2 \times 10^5$ $3.6 \times 10^6$ $4.2 \times 10^5$ | 1.86 1.33 1.05 | 26.6 18.2 15.4 |
| 3 | bind 3 hrs. wash 10X BSA/milk | Human Fc fusion hVEGF hDR5 - long | $9 \times 10^3$ $8 \times 10^3$ $1.4 \times 10^4$ | 1.5 0.75 2.8 | 16.2 8.17 17.3 |
| 4 | bind 2 hrs. wash 12X casein | Human Fc fusion hVEGF hDR5 - long | $5.5 \times 10^5$ $7.4 \times 10^6$ $4.5 \times 10^7$ | 22.9 96.1 818.2 | 25.3 14.8 9.7 |
| 5 | bind 1.75 hrs. wash 12X BSA | Human Fc fusion hVEGF hDR5 - long | $1.4 \times 10^6$ $2.2 \times 10^7$ $6.5 \times 10^7$ | 14 110 325 | |

FIG. 4

FIG. 6 hVEGF Binders-Combined plate and solution selection

| | L1 | | | | | | | | | | L2 | | | | L3 | | | | | Phage IC50(nM) | |
|---|---|---|---|---|---|---|---|---|---|---|---|---|---|---|---|---|---|---|---|---|---|
| | 28 | 29 | 30 | 30a | 30b | 30c | 30d | 31 | 32 | 33 | 50 | 51 | 52 | 53 | 91 | 92 | 93 | 93a | 94 | hVEGF | HER2 |
| 4D5 | D | V | S | | | | | T | A | V | S | A | S | F | H | Y | T | | T | | |
| H6 | Y | I | W | | | | | N | Y | V | G | G | S | S | S | W | W | A | G | 87 | ND |
| H7 | N | V | W | | | | | D | W | V | P | A | S | S | G | W | Y | I | A | 60 | ND |
| H8 | E | I | F | P | | | | Y | Y | V | L | G | S | S | G | W | D | | G | 226 | ND |
| H9 | Y | V | W | | | | | Q | Y | V | H | A | S | S | G | Y | W | V | A | 41 | ND |
| H10 | D | V | F | | | | | T | S | V | D | A | S | Y | R | Y | I | W | A | 170 | ND |

DR5 Binders Plate-Sorted Directly on HER2

| | L1 | | | | | | | | | | L2 | | | | L3 | | | | | Phage IC50(nM) | |
|---|---|---|---|---|---|---|---|---|---|---|---|---|---|---|---|---|---|---|---|---|---|
| | 28 | 29 | 30 | 30a | 30b | 30c | 30d | 31 | 32 | 33 | 50 | 51 | 52 | 53 | 91 | 92 | 93 | 93a | 94 | DR5 | HER2 |
| 4D5 | D | V | S | | | | | T | A | V | S | A | S | F | H | Y | T | | T | | |
| D1 | N | V | S | N | | | G | K | H | V | W | G | S | Y | S | Y | S | | G | >1000 | 30 |
| D2 | N | I | R | | | | | G | G | L | S | A | S | F | H | Y | T | | T | >1000 | 17 |
| D3 | A | I | S | H | | | | L | G | L | S | A | S | F | H | Y | T | | T | ND | +++ |
| D4 | D | I | H | A | | | | N | T | V | S | A | S | F | H | Y | T | | T | ND | +++ |
| D5 | D | I | G | | | | | A | S | V | S | A | S | F | H | Y | T | | T | ND | +++ |
| D6 | D | V | P | A | | | | G | A | V | S | A | S | F | H | Y | T | | T | ND | +++ |
| D7 | E | V | A | S | | | | V | S | V | S | A | S | F | H | Y | T | | T | ND | +++ |

FIG.10

DR5 Binders

| | L1 | | | | | | | | | | L2 | | | L3 | | | | | | Phage IC50(nM) | |
|---|---|---|---|---|---|---|---|---|---|---|---|---|---|---|---|---|---|---|---|---|---|
| | 28 | 29 | 30 | 30a | 30b | 30c | 30d | 31 | 32 | 33 | 50 | 51 | 52 | 53 | 91 | 92 | 93 | 93a | 93b | 94 | DR5 | HER2 |
| 4D5 | D | V | S | | | | | T | A | V | S | A | S | F | H | Y | T | | | T | | |
| 4-1 | D | I | W | N | R | | | R | A | L | E | G | S | S | G | G | S | Y | S | S | 20 | ND |
| 4-2 | R | I | N | S | | | | H | T | V | W | G | S | H | Y | S | N | R | | T | >1000 | ND |
| 4-4 | V | V | G | | | | | M | T | V | G | A | S | S | Y | G | S | Y | S | A | >1000 | ND |
| 4-5 | N | V | G | | | | | R | P | V | G | G | S | S | Y | G | S | F | G | T | 640 | ND |
| 4-6 | S | V | S | | | | | S | A | V | S | A | S | S | Y | S | S | | | S | 16 | ND |

FIG.14 hVEGF Binders Plate-Sorted Directly on HER2

| | 28 | 29 | 30 | 30a | 30b | 30c | 30d | 31 | 32 | 33 | 50 | 51 | 52 | 53 | 91 | 92 | 93 | 93a | 94 | Phage IC50(nM) | |
|---|---|---|---|---|---|---|---|---|---|---|---|---|---|---|---|---|---|---|---|---|---|
| | | | | L1 | | | | | | | | L2 | | | | | L3 | | | hVEGF | HER2 |
| 4D5 | D | V | S | | | | | T | A | V | S | A | S | F | H | Y | T | T | T | | |
| H1 | D | I | P | R | S | | | T | G | V | W | G | S | Y | H | Y | T | T | T | 77 | 10 |
| H3 | D | I | G | L | | | | G | S | V | W | A | S | Y | H | Y | T | T | T | 232 | 2.6 |
| H4 | N | I | R | T | | | | G | S | V | W | G | S | Y | H | Y | T | T | T | 115 | 0.54 |
| H5 | D | I | R | M | | | | G | S | V | W | S | S | F | H | Y | T | T | T | 242 | 721 |

DR5 Binders Plate-Sorted Directly on HER2

| | 28 | 29 | 30 | 30a | 30b | 30c | 30d | 31 | 32 | 33 | 50 | 51 | 52 | 53 | 91 | 92 | 93 | 93a | 94 | Phage IC50(nM) | |
|---|---|---|---|---|---|---|---|---|---|---|---|---|---|---|---|---|---|---|---|---|---|
| | | | | L1 | | | | | | | | L2 | | | | | L3 | | | DR5 | HER2 |
| 4D5 | D | V | S | | | | | T | A | V | S | A | S | F | H | Y | T | T | T | | |
| D1 | N | V | S | R | N | G | | K | H | V | W | G | S | Y | S | Y | S | G | G | >1000 | 30 |
| D2 | N | I | R | N | G | | | L | G | L | S | A | S | F | H | Y | T | T | T | >1000 | 17 |
| D3 | A | I | S | H | | | | N | T | V | S | A | S | F | H | Y | T | T | T | ND | +++ |
| D4 | D | I | H | A | | | | A | S | V | S | A | S | F | H | Y | T | T | T | ND | +++ |
| D5 | D | I | G | | | | | G | A | V | S | A | S | F | H | Y | T | T | T | ND | +++ |
| D6 | D | V | P | A | | | | V | S | V | S | A | S | F | H | Y | T | T | T | ND | +++ |
| D7 | E | V | A | S | | | | V | S | V | S | A | S | F | H | Y | T | T | T | ND | +++ |

FIG.15

| | L1 | | | | | | | | | | L2 | | | | L3 | | | | | | Single/Dual Specificity |
|---|---|---|---|---|---|---|---|---|---|---|---|---|---|---|---|---|---|---|---|---|---|
| | 28 | 29 | 30 | 30a | 30b | 30c | 30d | 31 | 32 | 33 | 50 | 51 | 52 | 53 | 91 | 92 | 93 | 93a | 93b | 94 | |
| 4D5 | D | V | S | | | | | T | A | V | S | A | S | F | H | Y | T | | | T | |
| 3-1 | N | V | W | | | | | D | W | V | P | A | S | S | G | W | Y | | | A | hVEGF |
| 3-6 | Y | V | W | | | | | Q | Y | V | H | A | S | S | G | Y | V | | | A | |
| 3-7 | Y | I | W | | | | | R | Y | V | W | G | S | S | G | L | W | Y | | S | |
| H1 | D | I | P | R | | | | G | Y | V | W | G | S | Y | H | Y | T | | | T | hVEGF/Her2 |
| H3 | D | I | G | L | | S | | G | S | V | W | A | S | Y | H | Y | T | | | T | |
| H4_N | N | I | R | S | | | | G | S | V | W | A | S | Y | H | Y | T | | | T | |
| H4_D | D | I | R | S | | | | G | S | V | W | G | S | Y | H | Y | T | | | T | |
| 4-1 | D | I | W | N | | | | R | A | L | E | G | S | S | G | Y | S | Y | S | S | DR5 |
| 4-5 | N | V | G | | | | | R | P | V | G | G | S | S | Y | G | S | F | G | T | |
| 4-6 | S | V | S | R | | | | S | A | V | S | A | S | S | Y | S | S | | | S | |
| D1 | N | V | S | | | | | K | H | V | W | G | S | Y | S | Y | S | | | G | DR5/Her2 |
| D2 | N | I | R | N | | | | G | G | L | S | A | S | F | H | Y | T | | | T | |

FIG. 16

| Clone | Specificity | Yield | | | Aggregation (%) | |
|---|---|---|---|---|---|---|
| | | Fab/L E. Coli Small Scale | Fab/L E. Coli Fermentor Run | hIgG/L 293 | Fab | hIgG |
| 3_1 | hVEGF | 8.5 mg** | / | 60 mg | 3 | 2 |
| H1 | hVEGF/Her2 | 0.8 mg* | 66.8 mg | 40 mg | 4 | 5 |
| H3 | hVEGF/Her2 | 9.2 mg** | / | 40 mg | / | 4 |
| H4_N | hVEGF/Her2 | 0.8 mg* | / | 37 mg | / | / |
| H4_D | hVEGF/Her2 | / | / | 43 mg | / | / |
| 4_1 | DR5 | 15.2 mg** | / | 10 mg | / | / |
| 4_5 | DR5 | ND | / | 6.7 mg | / | / |
| D1 | DR5/Her2 | ND | / | 10 mg | / | / |
| D2 | DR5/Her2 | ND | / | 6.7 mg | / | / |

\* Based on 1 L Culture
\*\* Based on 4 L Culture
/ Not Determined
ND=No Fab detected in soluble fraction

FIG. 17

| Clone | Format | Specificity | Her2-ECD | | | hVEGF$_{109}$ | | | mVEGF |
|---|---|---|---|---|---|---|---|---|---|
| | | | $k_{on}$ (1/Ms) | $k_{off}$ (1/s) | $K_D$ (nM) | $k_{on}$ (1/Ms) | $k_{off}$ (1/s) | $K_D$ (nM) | $k_{on}$ (1/Ms) |
| 3_1 | Fab | hVEGF | | NB | | 1.4E+05 | 2.2E-03 | 15 | 3.5E+04 |
| | IgG | hVEGF | | NB | | 8.0E+04 | 9.6E-04 | 12 | 3.6E+05 |
| 3_6 | Fab | hVEGF | | NB | | 4.5E+05 | 1.1E-03 | 3 | 8.3E+04 |
| 3_7 | IgG | hVEGF | | NB | | 2.0E+05 | 9.7E-04 | 5 | 1.8E+05 |
| | Fab | hVEGF | | NB | | 8.0E+05 | 2.5E-03 | 3 | 7.2E+04 |
| | IgG | hVEGF | | NB | | 5.8E+05 | 4.2E-03 | 7 | 5.0E+05 |
| H1 | Fab | hVEGF/Her2 | | | 59 | 2.7E+04 | 9.3E-03 | 350 | |
| H3 | IgG | hVEGF/Her2 | 1.7E+05 | 1.7E-03 | 9.8 | 3.4E+04 | 4.6E-03 | 140 | |
| | Fab | hVEGF/Her2 | 1.0E+05 | 2.1E-03 | 8 | 1.5E+03 | 5.9E-03 | 3930 | |
| H4_N | IgG | hVEGF/Her2 | 1.4E+05 | 1.3E-03 | 20 | * | * | ** | |
| | Fab | hVEGF/Her2 | 2.3E+05 | 1.3E-03 | 10 | * | * | 550 | |
| H4_D | IgG | hVEGF/Her2 | | / | 6 | * | * | ** | |
| | Fab | hVEGF/Her2 | 1.0E+05 | 1.2E-03 | 11 | * | * | / | |
| | IgG | hVEGF/Her2 | | | | | | 2300 | |

*Accurate kinetic analysis not possible, use steady state binding analysis
**repeat experiment with higher analyte concentration to enable SS binding analysis
NB=No Binding detected

FIG. 21

| CDR | Wild Type Codon | Alanine-scan m1 | m2 | m3 |
|---|---|---|---|---|
| CDR-L1 | D28 | GMT | A | |
| | I29 | RYT | A | T | V |
| | P30 | SCA | A | |
| | R30a | SST | A | G | P |
| | S30b | KCC | A | |
| | I30c | RYT | A | T | V |
| | S30d | KCC | A | |
| | G31 | GST | A | |
| | Y32 | KMT | A | D | S |
| CDR-L2 | W50 | KSG | A | G | S |
| | G51 | GST | A | |
| | S52 | KCC | A | D | S |
| | Y53 | KMT | A | | P |
| CDR-L3 | H91 | SMT | A | D | S |
| | Y92 | KMT | A | | |
| | T93 | RCT | A | |
| | T94 | RCT | A | |
| CDR-H1 | K30 | RMA | A | E | T |
| | D31 | GMT | A | |
| | T32 | RCT | A | D | S |
| | Y33 | KMT | A | | P |
| CDR-H2 | R50 | SST | A | G | S |
| | Y52 | KMT | A | D | |
| | T53 | RCT | A | |
| | N54 | RMC | A | D | T |
| | Y56 | KMT | A | G | S |
| | R58 | SST | A | G | P |
| CDR-H3 | W95 | KSG | A | G | S |
| | G96 | GST | A | |
| | G97 | GST | A | |
| | D98 | GMT | A | |
| | G99 | GST | A | |
| | F100 | KYT | A | S | V |
| | Y100a | KMT | A | D | S |

| CDR | Wild Type Codon | Homolog-scan m1 (Hom Res) | m2 | m3 | m4 | m5 |
|---|---|---|---|---|---|---|
| CDR-L1 | Q27 | SAA | E | | | | |
| | D28 | RAM | E | N | K | | |
| | I29 | VTY | V | L | | | |
| | P30 | SCA | A | | | | |
| | R30a | ARG | K | | | | |
| | S30b | RST | A | G | T | | |
| | I30c | VTY | V | L | | | |
| | S30d | RST | A | G | | | |
| | G31 | RST | A | S | T | | |
| | Y32 | THY | F | S | T | | |
| CDR-L2 | W50 | TKG | L | | | | |
| | G51 | GST | A | | | | |
| | S52 | KCC | A | | | | |
| | Y53 | TWC | F | | | | |
| CDR-L3 | H91 | HWT | N | | | | |
| | Y92 | TWC | F | F | Y | L | |
| | T93 | ASC | S | | | | |
| | T94 | RST | S | A | G | | |
| CDR-H1 | K30 | ARG | R | | | | |
| | D31 | GAM | E | | | | |
| | T32 | ASC | S | | | | |
| | Y33 | TWC | F | | | | |
| CDR-H2 | R50 | ARG | K | | | | |
| | Y52 | TWC | F | | | | |
| | T53 | ASC | S | | | | |
| | N54 | RAC | D | | | | |
| | Y56 | TWC | F | | | | |
| | R58 | ARG | K | | | | |
| CDR-H3 | W95 | TKG | L | | | | |
| | G96 | GST | A | | | | |
| | G97 | GST | A | | | | |
| | D98 | GAM | E | | | | |
| | G99 | GST | A | | | | |
| | F100 | TWC | Y | | | | |
| | Y100a | TWC | F | | | I | |

FIG. 28

Library Construction

| Library | CDRs | Residues | Shotgun Codons | Oligonucleotides | Theoretical Diversity |
|---|---|---|---|---|---|
| LC-Ala | L1 | D28, I29, P30, R30a, S30b, I30c, S30d, G31, Y32 | Alanine | L1-ALA | 3.3 e7 |
| | L2 | W50, G51, S52, Y53 | | L2-ALA | |
| | L3 | H91, Y92, T93, T94 | | L3-ALA | |
| LC-Hom | L1 | Q27, D28, I29, P30, R30a, S30b, I30c, S30d, G31, Y32 | Homolog | L1-HOM | 1.4 e7 |
| | L2 | W50, G51, S52, Y53 | | L2-HOM | |
| | L3 | H91, Y92, T93, T94 | | L3-HOM | |
| HC-Ala | H1 | K30 D31 T32 Y33 | Alanine | H1-ALA | 1.3 e8 |
| | H2 | R50 Y52 T53 N54 Y56 R58 | | H2-ALA | |
| | H3 | W95 G96 G97 D98 G99 F100 Y100a | | H3-ALA | |
| HC-Hom | H1 | K30 D31 T32 Y33 | Homolog | H1-HOM | 1.3 e5 |
| | H2 | R50 Y52 T53 N54 Y56 R58 | | H2-HOM | |
| | H3 | W95 G96 G97 D98 G99 F100 Y100a | | H3-HOM | |

FIG.29

|  |  | Antigen selection (VEGF) | | | | Display Selection (anti-gD) | | | | | Fwt/mut values | | | |
|---|---|---|---|---|---|---|---|---|---|---|---|---|---|---|
|  |  | wt/m1 | wt/m2 | wt/m3 | wt/m4 | wt/m1 | wt/m2 | wt/m3 | wt/m4 |  | Fwt/m1 | Fwt/m2 | Fwt/m3 | Fwt/m4 |
| CDR-L1 | Q27 |  |  |  |  | 1.73 |  |  | 0.97 | Q27 |  |  |  | 1.44 |
|  | D28 | 2.38 | 8.33 |  | 1.39 | 1.95 | 3.00 | 0.98 | (1.29)$^E$ | D28 | 1.38 | 2.78 |  | (4.65)$^E$ |
|  | I29 | 8.33 | 3.50 | 1.32 | (6.0)$^E$ | 1.18 |  |  | (1.15)$^L$ | I29 | 4.27 |  | 1.35 | (0.81)$^L$ |
|  | P30 | 1.83 |  | 2.63 | (0.94)$^L$ | 2.38 | 0.91 | 0.94 | 1.33 | P30 | 1.56 | 3.84 | 2.79 | 3.22 |
|  | R30a | 1.91 |  |  | 4.27 | 1.06 |  |  | 1.93 | R30a | 0.80 |  |  | 0.47 |
|  | S30b | 4.75 | 7.67 | 1.05 | 0.90 | 3.23 | 2.80 | 1.00 | 1.03 | S30b | 4.49 | 2.74 | 1.05 | (0.80)$^I$ |
|  | I30c | 7.67 |  |  | (0.85)$^T$ | 1.44 |  |  | (1.3)$^T$ | I30c | 2.37 |  |  | (46.8)$^I$ |
|  | S30d | 8.80 |  |  | 48.00 | 2.00 |  |  |  | S30d | 6.09 |  |  | (9.36)$^T$ |
|  | G31 | 9.20 |  |  | (12.2)$^T$ | 1.44 | 1.89 | 1.13 | (2.90)$^A$ | G31 | 4.60 |  |  | (13.3)$^A$ |
|  | Y32 | 14.00 | 42.00 | 14.00 | (38.5)$^A$ |  |  |  | (0.82)$^F$ | Y32 | 9.72 | 22.17 | 12.44 | (47.0)$^F$ |
|  |  |  |  |  | (38.5)$^F$ |  |  |  |  |  |  |  |  |  |
| CDR-L2 | W50 | 22.0 | 14.7 | 46.0 | 78.0 | 4.20 | 1.20 | 1.68 | 1.77 | W50 | 5.24 | 12.22 | 27.38 | 44.13 |
|  | G51 | 9.2 |  |  | 78.0 | 3.00 |  |  | 2.00 | G51 | 3.07 |  |  | 39.00 |
|  | S52 | 1.8 | 32.0 | 5.3 | 7.8 | 1.60 | 2.00 | 1.08 | 1.61 | S52 | 1.14 | 16.00 | 4.93 | 4.83 |
|  | Y53 | 5.3 |  |  | 0.1 | 2.67 |  |  | 0.83 | Y53 | 2.00 |  |  | 0.06 |
| CDR-L3 | H91 | 46.0 | 46.0 | 23.0 | (>79)$^N$ | 2.67 | 2.09 | 2.09 | (1.86)$^N$ | H91 | 17.25 | 22.04 | 11.02 | (>42.5)$^N$ |
|  | Y92 | 41.0 | 8.2 | 41.0 | 1.2 | 2.36 | 1.74 | 0.72 | 0.50 | Y92 | 17.39 | 4.72 | 57.15 | 2.33 |
|  | T93 | 0.9 |  |  | 1.1 | 1.02 |  |  | 1.50 | T93 | 0.86 |  |  | 0.74 |
|  | T94 | 0.8 |  |  | (0.58)$^S$ | 0.65 |  |  | (1.28)$^S$ | T94 | 1.16 |  |  | (0.45)$^S$ |
| CDR-H1 | K30 | 4.36 | 1.92 | 3.00 | 1.50 | 3.31 | 1.65 | 1.87 | 1.14 | K30 | 1.32 | 1.16 | 1.60 | 1.31 |
|  | D31 | 2.19 |  |  | 0.63 | 1.63 |  |  | 0.93 | D31 | 1.35 |  |  | 0.68 |
|  | T32 | 0.82 |  |  | 2.10 | 1.50 |  |  | 0.64 | T32 | 0.55 |  |  | 3.27 |
|  | Y33 | 2.50 | 0.26 | 0.21 | 5.86 | 1.48 | 1.31 | 1.55 | 2.47 | Y33 | 1.69 | 0.20 | 0.14 | 2.37 |
| CDR-H2 | R50 | 0.63 | 0.55 | 11.00 | 1.57 | 1.13 | 0.53 | 9.00 | 0.98 | R50 | 0.56 | 1.04 | 1.22 | 1.60 |
|  | Y52 | 4.35 | 74.00 | 9.25 | 1.18 | 2.17 | 1.63 | 1.63 | 0.91 | Y52 | 2.01 | 45.54 | 5.69 | 1.30 |
|  | T53 | 0.39 |  |  | 0.68 | 0.93 |  |  | 0.58 | T53 | 0.42 |  |  | 1.19 |
|  | N54 | 0.65 | 0.20 | 0.61 | 0.68 | 0.97 | 1.07 | 1.88 | 1.02 | N54 | 0.67 | 0.19 | 0.33 | 0.67 |
|  | Y56 | 5.33 | 6.40 | 4.92 | 0.83 | 3.85 | 3.13 | 1.92 | 0.76 | Y56 | 1.39 | 2.05 | 2.56 | 1.08 |
|  | R58 | 0.83 | 0.55 | 24.00 | 1.19 | 1.12 | 0.76 | 2.42 | 2.09 | R58 | 0.74 | 0.71 | 9.93 | 0.57 |
| CDR-H3 | W95 | >102 | >102 | 1.56 | >96 | 3.63 | 1.12 | 0.69 | 0.46 | W95 | >28.1 | >91.4 | 2.27 | >209 |
|  | G96 | 1.86 |  |  | 5.27 | 1.33 |  |  | 1.39 | G96 | 1.39 |  |  | 3.80 |
|  | G97 | 1.38 |  |  | 4.88 | 1.69 |  |  | 1.23 | G97 | 0.82 |  |  | 3.95 |
|  | D98 | 0.96 |  |  | 1.64 | 1.00 |  |  | 0.94 | D98 | 0.96 |  |  | 1.74 |
|  | G99 | 0.30 |  |  | 0.52 | 1.17 |  |  | 1.89 | G99 | 0.26 |  |  | 0.28 |
|  | F100 | 11.50 | 23.00 | 0.96 | 8.60 | 3.38 | 2.20 | 1.63 | 2.50 | F100 | 3.40 | 10.45 | 0.59 | 3.44 |
|  | Y100a | 4.75 | 57.00 | 1.90 | 0.27 | 2.11 | 2.35 | 1.43 | 0.46 | Y100a | 2.26 | 24.23 | 1.33 | 0.59 |

FIG.30

|  |  | Antigen Selection (Her2) | | | Display Selection (anti-gD) | | | | Fwd/mut values | | | |
| --- | --- | --- | --- | --- | --- | --- | --- | --- | --- | --- | --- | --- |
|  |  | wt/m1 | wt/m2 | wt/m3 | wt/m4 | wt/m1 | wt/m2 | wt/m3 | wt/m4 |  | Fwd/m1 | Fwd/m2 | Fwd/m3 | Fwd/m4 |
| CDR-L1 | Q27 |  |  |  |  | 1.73 |  |  | 0.97 | Q27 |  |  |  | 2.94 |
|  | D28 | 1.82 | 2.00 | 0.78 | 2.85 | 1.95 | 3.00 | 0.98 | (1.29)ᴱ | D28 | 1.05 | 0.67 | 0.80 | (1.55)ᴱ |
|  | I29 | 1.47 |  |  | (2.0)ᴱ | 1.18 |  |  | (1.15)ᴸ | I29 | 0.76 |  |  | (0.98)ᴸ |
|  | P30 | 1.31 |  |  | (1.13)ᴸ | 2.38 | 0.91 | 0.94 | 1.33 | P30 | 1.11 | 1.92 | 1.77 | 0.92 |
|  | R30a | 1.67 | 1.75 | 1.67 | 1.22 | 1.06 |  |  | 1.93 | R30a | 0.70 |  |  | 1.20 |
|  | S30b | 1.74 |  |  | 2.31 | 3.23 | 2.80 | 1.00 | (1.1)ᵀ | S30b | 1.64 |  |  | (3.86)ᵀ |
|  | I30c | 14.75 | 11.80 | 2.03 | (4.25)ᵀ | 1.44 |  |  | (1.02)ᴸ | I30c | 4.57 | 4.21 | 2.03 | (1.38)ᴸ |
|  | S30d | 1.00 |  |  | (1.41)ᴸ | 2.00 |  |  | (1.3)ᵀ | S30d | 0.69 |  |  | (0.769)ᵀ |
|  | G31 | 3.36 |  |  | (1.0)ᵀ | 1.44 | 1.89 | 1.13 | (2.9)ᴬ | G31 | 1.68 |  |  | (1.43)ᴬ |
|  | Y32 | 0.36 | 12.00 | 0.24 | (4.17)ᴬ |  |  |  | (0.82)ᶠ | Y32 | 0.25 | 6.33 | 0.21 | (2.20)ᶠ |
|  |  |  |  |  | (1.8)ᶠ |  |  |  |  |  |  |  |  |  |
| CDR-L2 | W50 | 45.50 | 22.75 | >98 | 16.00 | 4.20 | 1.20 | 1.68 | 1.77 | W50 | 10.83 | 18.96 | >58.3 | 9.05 |
|  | G51 | 1.94 |  |  | 2.57 | 3.00 |  |  | 2.00 | G51 | 0.65 |  |  | 1.29 |
|  | S52 | 2.88 |  |  | 4.67 | 1.60 |  |  | 1.61 | S52 | 1.79 |  |  | 2.90 |
|  | Y53 | 11.29 | 39.50 | 8.78 | 0.65 | 2.67 | 2.00 | 1.08 | 0.83 | Y53 | 4.23 | 19.75 | 8.12 | 0.78 |
| CDR-L3 | H91 | 12.43 | 0.98 | >98 | (3.0)ᴺ | 2.67 | 2.09 | 2.09 | (1.86)ᴺ | H91 | 4.66 | 0.47 | >47.0 | (1.61)ᴺ |
|  | Y92 | 5.50 | 38.50 | 81.00 | 1.83 | 2.36 | 1.74 | 0.72 | 0.50 | Y92 | 2.33 | 22.17 | 112.91 | 3.67 |
|  | T93 | 0.54 |  |  | 31.00 | 1.02 |  |  | 1.50 | T93 | 0.53 |  |  | 20.67 |
|  | T94 | 6.46 |  |  | (4.3)ˢ | 0.65 |  |  | (1.28)ˢ | T94 | 9.99 |  |  | (3.36)ˢ |
| CDR-H1 | K30 | 2.13 | 1.68 | 2.13 | 1.13 | 3.31 | 1.65 | 1.87 | 1.14 | K30 | 0.64 | 1.02 | 1.14 | 0.99 |
|  | D31 | 3.05 |  |  | 0.66 | 1.63 |  |  | 0.93 | D31 | 1.88 |  |  | 0.71 |
|  | T32 | 0.76 |  |  | 0.75 | 1.50 |  |  | 0.64 | T32 | 0.51 |  |  | 1.16 |
|  | Y33 | >81 | >81 | >81 | 47.00 | 1.48 | 1.31 | 1.55 | 2.47 | Y33 | >54.8 | >61.9 | >52.4 | 19.05 |
| CDR-H2 | R50 | >81 | >81 | >81 | 95.00 | 1.13 | 0.53 | 9.00 | 0.98 | R50 | >72 | >153 | >9.0 | 96.83 |
|  | Y52 | 0.55 | 2.67 | 0.53 | 0.60 | 2.17 | 1.63 | 1.63 | 0.91 | Y52 | 0.25 | 1.64 | 0.33 | 0.66 |
|  | T53 | 1.03 |  |  | 0.70 | 0.93 |  |  | 0.58 | T53 | 1.11 |  |  | 1.22 |
|  | N54 | 0.26 | 0.50 | 0.45 | 1.04 | 0.97 | 1.07 | 1.88 | 1.02 | N54 | 0.27 | 0.47 | 0.24 | 1.02 |
|  | Y56 | >81 | >81 | >81 | 1.21 | 3.85 | 3.13 | 1.92 | 0.76 | Y56 | >21.1 | >25.9 | >42.1 | 1.59 |
|  | R58 | >81 | 80.00 | >81 | >96 | 1.12 | 0.76 | 2.42 | 2.09 | R58 | >72.6 | 104.83 | >33.5 | >46.0 |
| CDR-H3 | W95 | >81 | >81 | >81 | >96 | 3.63 | 1.12 | 0.69 | 0.46 | W95 | >22.3 | >72.6 | >117 | >209 |
|  | G96 | 1.53 |  |  | 0.61 | 1.33 |  |  | 1.39 | G96 | 1.15 |  |  | 0.44 |
|  | G97 | 3.05 |  |  | 3.75 | 1.69 |  |  | 1.23 | G97 | 1.80 |  |  | 3.04 |
|  | D98 | 0.80 |  |  | 0.40 | 1.00 |  |  | 0.94 | D98 | 0.80 |  |  | 0.42 |
|  | G99 | 26.00 |  |  | 18.00 | 1.17 |  |  | 1.89 | G99 | 22.29 |  |  | 9.53 |
|  | F100 | >81 | >81 | 39.50 | 95.00 | 3.38 | 2.20 | 1.63 | 2.50 | F100 | >23.9 | >36.8 | 24.24 | 38.00 |
|  | Y100a | 80.00 | >81 | >81 | 6.31 | 2.11 | 2.35 | 1.43 | 0.46 | Y100a | 38.00 | >34.4 | >56.7 | 13.76 |

FIG. 31

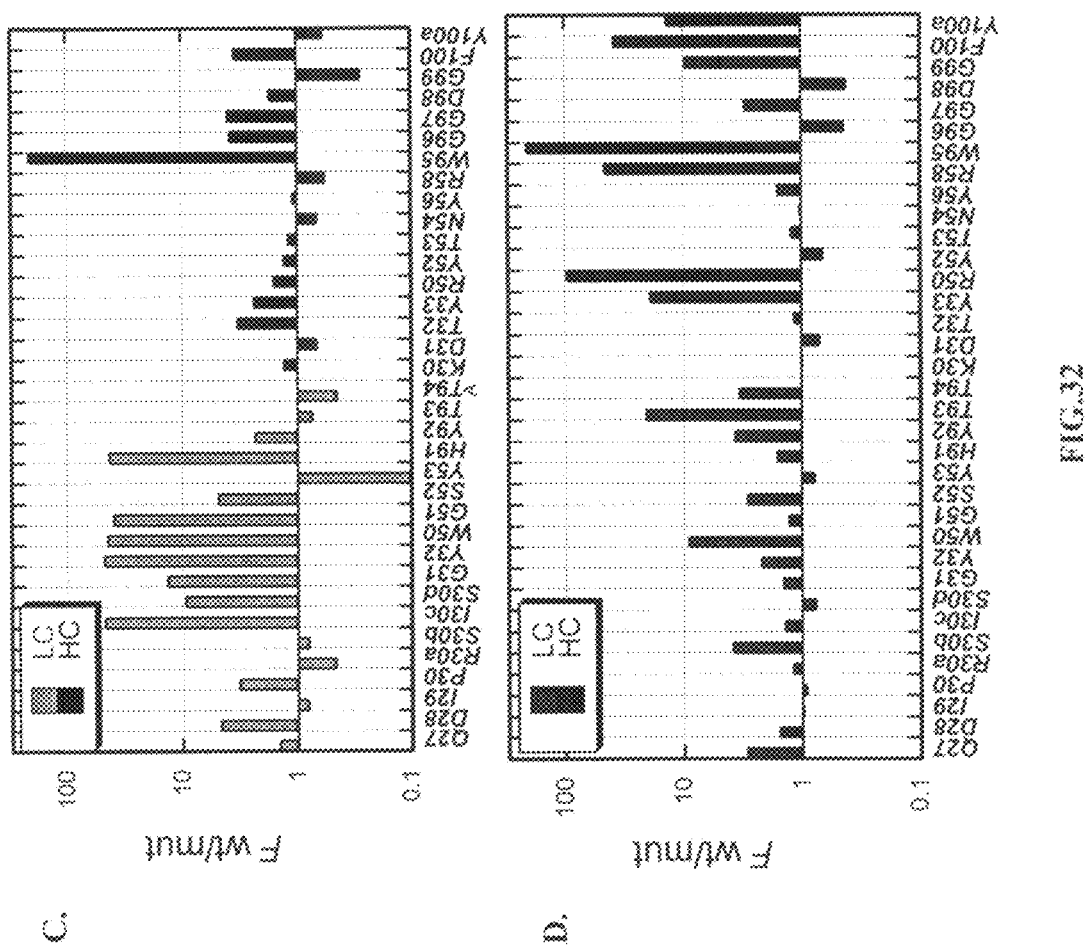

FIG. 34

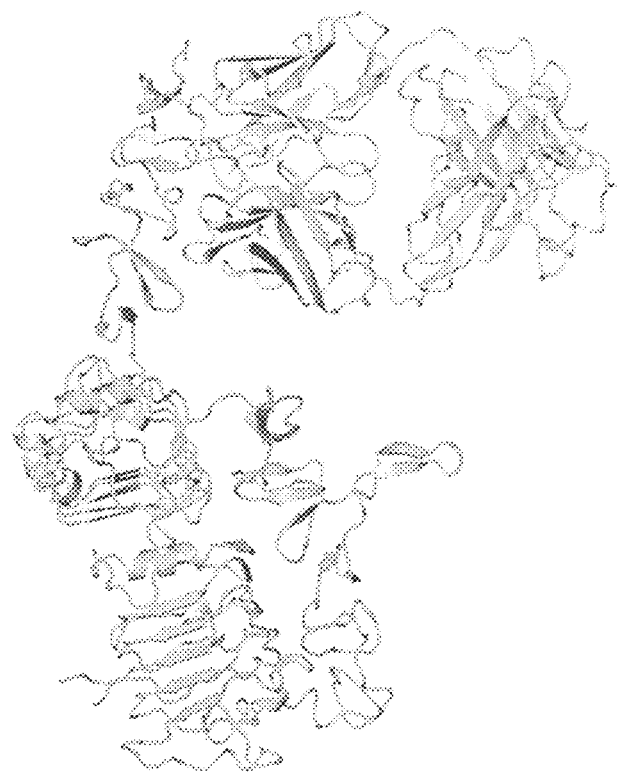
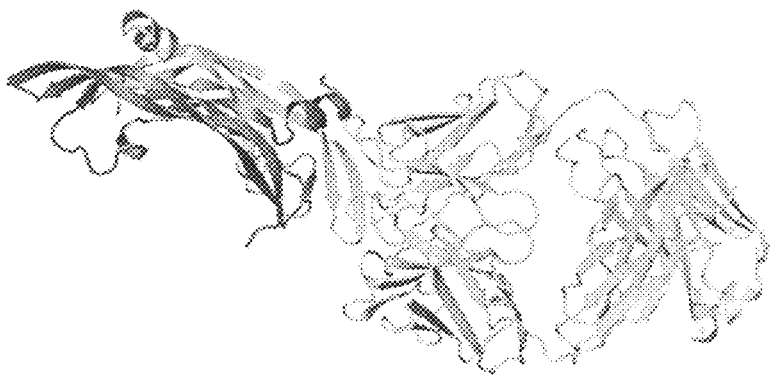
FIG. 35A

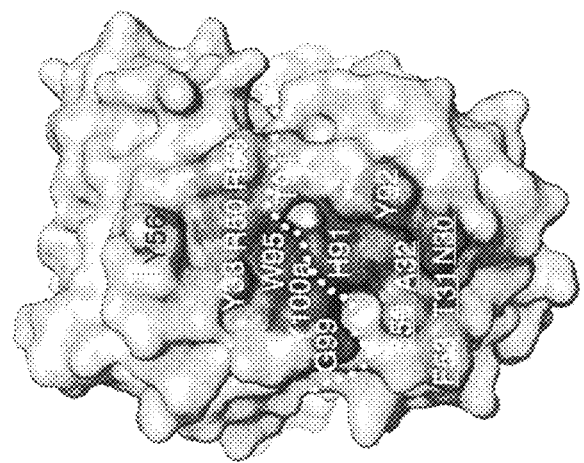
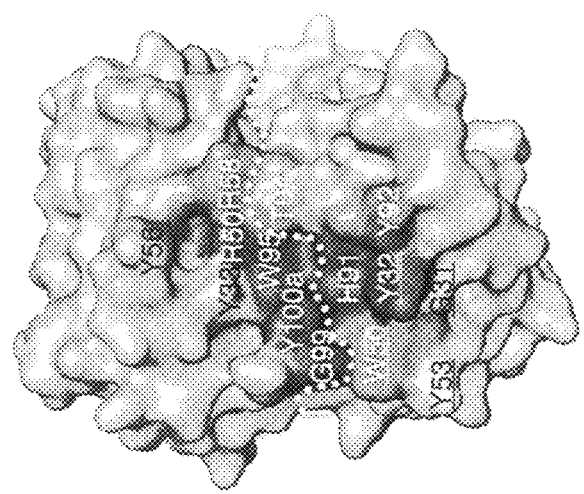
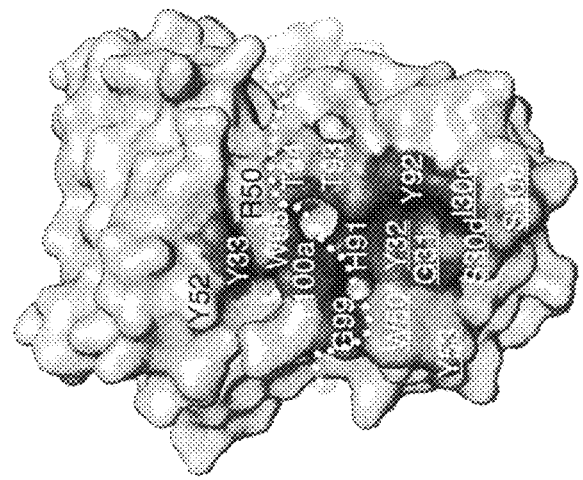
FIG. 35B

| | | Antigen Selection (VEGF) | | | | Display Selection (anti-gD) | | | | $F_{wt/mut}$ values | | | | $\Delta\Delta G_{wt/mut}$ (kcal/mol) | | | |
|---|---|---|---|---|---|---|---|---|---|---|---|---|---|---|---|---|---|
| | | wt/m1 | wt/m2 | wt/m3 | wt/m4 | wt/m1 | wt/m2 | wt/m3 | wt/m4 | $F_{wt/m1}$ | $F_{wt/m2}$ | $F_{wt/m3}$ | $F_{wt/m4}$ | $\Delta\Delta G_{wt/m1}$ | $\Delta\Delta G_{wt/m2}$ | $\Delta\Delta G_{wt/m3}$ | $\Delta\Delta G_{wt/m4}$ |
| CDR-L1 | Q27 | | | | 1.4 | | | | 1.0 | | | | 1.4$^E$ | | | | 0.6$^E$ |
| | D28 | 1.8 | 17.0 | | 3.5 | 1.7 | | | 1.3 | 1.1$^A$ | | | 2.7$^E$ | 0$^A$ | | | 0.2$^E$ |
| | I29 | 12.8 | 17.0 | 1.9 | 1.4 | 2.0 | 3.0 | 1.0 | 1.2 | 6.5$^A$ | 5.7$^T$ | 1.9$^V$ | 1.2$^L$ | 1.1$^A$ | 1.0$^T$ | 0.4$^V$ | 0.1$^L$ |
| | P30 | 1.7 | | | 3.8 | 1.2 | | | 1.3 | 1.5$^A$ | | | 2.9$^A$ | 0.2$^A$ | | | 0.6$^A$ |
| | R30a | 1.9 | 4.1 | 1.9 | 0.8 | 2.4 | 0.9 | 0.9 | 1.9 | 0.8$^A$ | 4.5$^G$ | 2.1$^P$ | 0.4$^K$ | -0.2$^A$ | 0.9$^G$ | 0.4$^P$ | -0.5$^K$ |
| | S30b** | 5.5 | | | 0.7 | 1.1 | | | 1.1 | 5.2$^A$ | | | 0.6$^T$ | 1.0$^A$ | | | -0.3$^T$ |
| | I30c*** | 12.7 | 7.6 | 1.0 | 23.8 | 3.2 | 2.8 | 1.0 | 1.0 | 3.9$^A$ | 2.7$^T$ | 1.0$^V$ | 23.2$^L$ | 0.8$^A$ | 0.6$^T$ | 0$^V$ | 1.9$^L$ |
| | S30d*** | 13.2 | | | 16.9 | 1.4 | | | 1.3 | 9.1$^A$ | | | 13.0$^T$ | 1.3$^A$ | | | 1.5$^T$ |
| | G31*** | 16.0 | | | 35.5 | 2.0 | | | 2.9 | 8.0$^A$ | | | 12.2$^A$ | 1.2$^A$ | | | 1.5$^A$ |
| | Y32*** | 26.0 | 78.0 | 16.0 | 23.0 | 1.4 | 1.9 | 1.1 | 0.8 | 18.1$^A$ | 41.2$^D$ | 23.1$^S$ | >28$^F$ | 1.7$^A$ | 2.2$^D$ | 1.9$^S$ | >2.0$^F$ |
| CDR-L2 | W50** | 39.0 | 26.0 | 39.0 | 20.4 | 4.2 | 1.2 | 1.7 | 1.8 | 9.3$^A$ | 21.7$^G$ | 23.2$^S$ | 11.6$^L$ | 1.3$^A$ | 1.8$^G$ | 1.9$^S$ | 1.5$^L$ |
| | G51 | 16.0 | | | 20.4 | 3.0 | | | 2.0 | 5.3$^A$ | | | 10.2$^A$ | 1.0$^A$ | | | 1.4$^A$ |
| | S52 | 2.0 | | | 6.5 | 1.6 | | | 1.6 | 1.3$^A$ | | | 4.0$^A$ | 0.1$^A$ | | | 0.8$^A$ |
| | Y53** | 9.0 | 63.0 | 4.5 | 0.1 | 2.7 | 2.0 | 1.1 | 0.8 | 3.4$^A$ | 31.5$^D$ | 4.2$^S$ | 0.1$^F$ | 0.7$^A$ | 2.0$^D$ | 0.8$^S$ | -1.4$^F$ |

Fig. 37A-1

| | | Antigen Selection (VEGF) | | | | Display Selection (anti-gD) | | | | $F_{wt/mut}$ values | | | | $\Delta\Delta G_{wt/mut}$ (kcal/mol) | | | |
|---|---|---|---|---|---|---|---|---|---|---|---|---|---|---|---|---|---|
| | | wt/m1 | wt/m2 | wt/m3 | wt/m4 | wt/m1 | wt/m2 | wt/m3 | wt/m4 | $F_{wt/m1}$ | $F_{wt/m2}$ | $F_{wt/m3}$ | $F_{wt/m4}$ | $\Delta\Delta G_{wt/m1}$ | $\Delta\Delta G_{wt/m2}$ | $\Delta\Delta G_{wt/m3}$ | $\Delta\Delta G_{wt/m4}$ |
| CDR-L3 | H91*** | 80.0 | 40.0 | 40.0 | >150 | 2.7 | 2.1 | 2.1 | 1.9 | $30^A$ | $19.2^D$ | $19.2^P$ | $>80^N$ | $2.0^A$ | $1.7^D$ | $1.7^P$ | $>2.6^N$ |
| | Y92*** | 25.0 | 12.5 | 75.0 | 1.0 | 2.4 | 1.7 | 0.7 | 0.5 | $10.6^A$ | $7.2^D$ | $104.5^S$ | $2.0^F$ | $1.4^A$ | $1.2^D$ | $2.8^S$ | $0.4^F$ |
| | T93** | 0.7 | | | 0.9 | 1.0 | | | 1.5 | $0.7^A$ | | | $0.6^S$ | $-0.3^A$ | | | $-0.3^S$ |
| | T94** | 0.7 | | | 0.6 | 0.6 | | | 1.3 | $1.1^A$ | | | $0.4^S$ | $0^A$ | | | $-0.5^S$ |
| CDR-H1 | K30 | 4.4 | 1.9 | 3.0 | 1.5 | 3.3 | 1.7 | 1.9 | 1.1 | $1.3^A$ | $1.2^E$ | $1.6^T$ | $1.3^R$ | $0.2^A$ | $0.1^E$ | $0.3^T$ | $0.2^R$ |
| | D31 | 2.2 | | | 0.6 | 1.6 | | | 0.9 | $1.3^A$ | | | $0.7^E$ | $0.2^A$ | | | $-0.2^E$ |
| | T32 | 0.8 | | | 2.1 | 1.5 | | | 0.6 | $0.5^A$ | | | $3.3^S$ | $-0.4^A$ | | | $0.7^S$ |
| | Y33*** | 2.5 | 0.3 | 0.2 | 5.9 | 1.5 | 1.3 | 1.5 | 2.5 | $1.7^A$ | $0.2^D$ | $0.1^S$ | $2.4^F$ | $0.3^A$ | $-1.0^D$ | $-1.2^S$ | $0.5^F$ |

Fig. 37A-2

|  |  | Antigen Selection (VEGF) | | | | Display Selection (anti-gD) | | | | $F_{wt/mut}$ values | | | | $\Delta\Delta G_{wt/mut}$ (kcal/mol) | | | |
|---|---|---|---|---|---|---|---|---|---|---|---|---|---|---|---|---|---|
|  |  | wt/m1 | wt/m2 | wt/m3 | wt/m4 | wt/m1 | wt/m2 | wt/m3 | wt/m4 | $F_{wt/m1}$ | $F_{wt/m2}$ | $F_{wt/m3}$ | $F_{wt/m4}$ | $\Delta\Delta G_{wt/m1}$ | $\Delta\Delta G_{wt/m2}$ | $\Delta\Delta G_{wt/m3}$ | $\Delta\Delta G_{wt/m4}$ |
| CDR-H2 | R50* | 0.6 | 0.6 | 11.0 | 1.6 | 1.1 | 0.5 | 9.0 | 1.0 | 0.6$^A$ | 1.0$^G$ | 1.2$^P$ | 1.6$^K$ | -0.3$^A$ | 0$^G$ | 0.1$^P$ | 0.3$^K$ |
|  | Y52* | 4.4 | 74.0 | 9.3 | 1.2 | 2.2 | 1.6 | 1.6 | 0.9 | 2.0$^A$ | 45.5$^D$ | 5.7$^S$ | 1.3$^F$ | 0.4$^A$ | 2.3$^D$ | 1.0$^S$ | 0.2$^F$ |
|  | T53 | 0.4 |  |  | 0.7 | 0.9 |  |  | 0.6 | 0.4$^A$ |  |  | 1.2$^S$ | -0.5$^A$ |  |  | 0.1$^S$ |
|  | N54 | 0.6 | 0.2 | 0.6 | 0.7 | 1.0 | 1.1 | 1.9 | 1.0 | 0.7$^A$ | 0.2$^D$ | 0.3$^T$ | 0.7$^D$ | -0.2$^A$ | -1.0$^D$ | -0.7$^T$ | -0.2$^D$ |
|  | Y56 | 5.3 | 6.4 | 4.9 | 0.8 | 3.8 | 3.1 | 1.9 | 0.8 | 1.4$^A$ | 2.0$^D$ | 2.6$^S$ | 1.1$^F$ | 0.2$^A$ | 0.4$^D$ | 0.6$^S$ | 0$^F$ |
|  | R58 | 0.8 | 0.5 | 24.0 | 1.2 | 1.1 | 0.8 | 2.4 | 2.1 | 0.7$^A$ | 0.7$^G$ | 9.9$^P$ | 0.6$^K$ | -0.2$^A$ | -0.2$^G$ | 1.4$^P$ | -0.3$^K$ |
| CDR-H3 | W95** | >102 | >102 | 1.6 | >96 | 3.6 | 1.1 | 0.7 | 0.5 | >28$^A$ | >91$^G$ | 2.3$^S$ | >209$^L$ | >2.0$^A$ | >2.7$^G$ | 0.5$^S$ | >3.2$^L$ |
|  | G96 | 1.9 |  |  | 5.3 | 1.3 |  |  | 1.4 | 1.4$^A$ |  |  | 3.8$^A$ | 0.2$^A$ |  |  | 0.8$^A$ |
|  | G97 | 1.4 |  |  | 4.9 | 1.7 |  |  | 1.2 | 0.8$^A$ |  |  | 4.0$^A$ | -0.1$^A$ |  |  | 0.8$^A$ |
|  | D98 | 1.0 |  |  | 1.6 | 1.0 |  |  | 0.9 | 1.0$^A$ |  |  | 1.7$^E$ | 0$^A$ |  |  | 0.3$^E$ |
|  | G99*** | 0.3 |  |  | 0.5 | 1.2 |  |  | 1.9 | 0.3$^A$ |  |  | 0.3$^A$ | -0.8$^A$ |  |  | -0.8$^A$ |
|  | F100 | 11.5 | 23.0 | 1.0 | 8.6 | 3.4 | 2.2 | 1.6 | 2.5 | 3.4$^Y$ | 10.5$^S$ | 0.6$^V$ | 3.4$^Y$ | 0.7$^A$ | 1.4$^S$ | -0.3$^V$ | 0.7$^Y$ |
|  | Y100a*** 4.8 | 4.8 | 57.0 | 1.9 | 0.3 | 2.1 | 2.4 | 1.4 | 0.5 | 2.3$^A$ | 24.2$^D$ | 1.3$^S$ | 0.6$^F$ | 0.5$^A$ | 1.9$^D$ | 0.2$^S$ | -0.3$^F$ |

Fig. 37A-3

| | | Antigen Selection (Her2) | | | Display Selection (anti-gD) | | | | $F_{wt/mut}$ values | | | | $\Delta\Delta G_{wt/mut}$ (kcal/mol) | | | |
|---|---|---|---|---|---|---|---|---|---|---|---|---|---|---|---|---|
| | | wt/m1 | wt/m2 | wt/m3 | wt/m4 | wt/m1 | wt/m2 | wt/m3 | wt/m4 | $F_{wt/m1}$ | $F_{wt/m2}$ | $F_{wt/m3}$ | $F_{wt/m4}$ | $\Delta\Delta G_{wt/m1}$ | $\Delta\Delta G_{wt/m2}$ | $\Delta\Delta G_{wt/m3}$ | $\Delta\Delta G_{wt/m4}$ |
| CDR-L1 | Q27 | | | | 1.6 | | | | 1.0 | | | | 1.6$^E$ | | | | 0.3$^E$ |
| | D28 | 1.8 | | | 1.7 | 1.7 | | | 1.3 | 1.1$^A$ | | | 1.3$^E$ | 0$^A$ | | | 0.2$^E$ |
| | I29 | 1.5 | 2.0 | 0.8 | 1.3 | 2.0 | 3.0 | 1.0 | 1.2 | 0.8$^A$ | 0.7$^T$ | 0.8$^V$ | 1.1$^L$ | -0.2$^A$ | -0.2$^T$ | -0.1$^V$ | 0.1$^L$ |
| | P30 | 1.3 | | | 0.8 | 1.2 | | | 1.3 | 1.1$^A$ | | | 0.6$^A$ | 0.1$^A$ | | | -0.3$^A$ |
| | R30a | 1.7 | 1.8 | 1.7 | 1.4 | 2.4 | 0.9 | 0.9 | 1.9 | 0.7$^A$ | 1.9$^G$ | 1.8$^P$ | 0.7$^K$ | -0.2$^A$ | 0.4$^G$ | 0.3$^P$ | -0.2$^K$ |
| | S30b | 1.7 | | | 1.7 | 1.1 | | | 1.1 | 1.6$^A$ | | | 1.6$^T$ | 0.3$^A$ | | | 0.3$^T$ |
| | I30c | 14.8 | 11.8 | 2.0 | 1.3 | 3.2 | 2.8 | 1.0 | 1.0 | 4.6$^A$ | 4.2$^T$ | 2.0$^V$ | 1.2$^L$ | 0.9$^A$ | 0.9$^T$ | 0.4$^V$ | 0.1$^L$ |
| | S30d | 1.0 | | | 2.2 | 1.4 | | | 1.3 | 0.7$^A$ | | | 1.7$^T$ | -0.2$^A$ | | | 0.3$^T$ |
| | G31* | 3.4 | | | 5.1 | 2.0 | | | 2.9 | 1.7$^A$ | | | 1.8$^A$ | 0.3$^A$ | | | 0.3$^A$ |
| | Y32*** | 0.4 | 12.0 | 0.2 | 1.8 | 1.4 | 1.9 | 1.1 | 0.8 | 0.3$^A$ | 6.3$^D$ | 0.2$^S$ | 2.1$^F$ | -0.8$^A$ | 1.1$^D$ | -1.0$^S$ | 0.4$^F$ |
| CDR-L2 | W50** | 45.5 | 22.8 | >98 | 17.0 | 4.2 | 1.2 | 1.7 | 1.8 | 10.8$^A$ | 19$^G$ | >58$^S$ | 9.6$^L$ | 1.4$^A$ | 1.7$^G$ | >2.4$^S$ | 1.3$^L$ |
| | G51 | 1.9 | | | 1.7 | 3.0 | | | 2.0 | 0.6$^A$ | | | 0.9$^A$ | -0.3$^A$ | | | -0.1$^A$ |
| | S52 | 2.9 | | | 3.0 | 1.6 | | | 1.6 | 1.8$^A$ | | | 1.9$^A$ | 0.3$^A$ | | | 0.4$^A$ |
| | Y53* | 11.3 | 39.5 | 8.8 | 0.6 | 2.7 | 2.0 | 1.1 | 0.8 | 4.2$^A$ | 19.8$^D$ | 8.1$^S$ | 0.8$^F$ | 0.9$^A$ | 1.8$^D$ | 1.2$^S$ | -0.1$^F$ |

Fig. 37B-1

| | | Antigen Selection (Her2) | | | | Display Selection (anti-gD) | | | | Fwt/mut values | | | | ΔΔG$_{wt/mut}$ (kcal/mol) | | | |
|---|---|---|---|---|---|---|---|---|---|---|---|---|---|---|---|---|---|
| | | wt/m1 | wt/m2 | wt/m3 | wt/m4 | wt/m1 | wt/m2 | wt/m3 | wt/m4 | F$_{wt/m1}$ | F$_{wt/m2}$ | F$_{wt/m3}$ | F$_{wt/m4}$ | ΔΔG$_{wt/m1}$ | ΔΔG$_{wt/m2}$ | ΔΔG$_{wt/m3}$ | ΔΔG$_{wt/m4}$ |
| CDR-L3 | H91*** | 12.4 | 1.0 | >98 | 2.8 | 2.7 | 2.1 | 2.1 | 1.9 | 4.7$^A$ | 0.5$^D$ | >47$^P$ | 1.5$^N$ | 0.9$^A$ | -0.4$^D$ | >2.3$^P$ | 0.2$^N$ |
| | Y92** | 5.5 | 38.5 | 81.0 | 1.8 | 2.4 | 1.7 | 0.7 | 0.5 | 2.3$^A$ | 22.2$^D$ | 112.9$^S$ | 3.5$^F$ | 0.5$^A$ | 1.8$^D$ | 2.8$^S$ | 0.7$^F$ |
| | T93 | 0.5 | | | 0.7 | 1.0 | | | 1.5 | 0.5$^A$ | | | 0.5$^S$ | -0.4$^A$ | | | -0.4$^S$ |
| | T94** | 6.5 | | | 1.4 | 0.6 | | | 1.3 | 10$^A$ | | | 1.1$^S$ | 1.4$^A$ | | | 0.1$^S$ |
| CDR-H1 | K30 | 2.1 | 1.7 | 2.1 | 1.1 | 3.3 | 1.7 | 1.9 | 1.1 | 0.6$^A$ | 1.0$^E$ | 1.1$^T$ | 1.0$^R$ | -0.3$^A$ | 0$^E$ | 0.1$^T$ | 0$^R$ |
| | D31 | 3.1 | | | 0.7 | 1.6 | | | 0.9 | 1.9$^A$ | | | 0.7$^E$ | 0.4$^A$ | | | -0.2$^E$ |
| | T32 | 0.8 | | | 0.7 | 1.5 | | | 0.6 | 0.5$^A$ | | | 1.2$^S$ | -0.4$^A$ | | | 0.1$^S$ |
| | Y33* | >81 | >81 | >81 | 47.0 | 1.5 | 1.3 | 1.5 | 2.5 | >55$^A$ | >62$^D$ | >52$^S$ | 19.1$^F$ | >2.4$^A$ | >2.4$^D$ | >2.3$^S$ | 1.7$^F$ |

Fig. 37B-2

| | Antigen Selection (Her2) | | | | Display Selection (anti-gD) | | | | $F_{wt/mut}$ values | | | | $\Delta\Delta G_{wt/mut}$ (kcal/mol) | | | |
|---|---|---|---|---|---|---|---|---|---|---|---|---|---|---|---|---|
| | wt/m1 | wt/m2 | wt/m3 | wt/m4 | wt/m1 | wt/m2 | wt/m3 | wt/m4 | $F_{wt/m1}$ | $F_{wt/m2}$ | $F_{wt/m3}$ | $F_{wt/m4}$ | $\Delta\Delta G_{wt/m1}$ | $\Delta\Delta G_{wt/m2}$ | $\Delta\Delta G_{wt/m3}$ | $\Delta\Delta G_{wt/m4}$ |
| CDR-H2 | | | | | | | | | | | | | | | | |
| R50*** | >81 | >81 | >81 | 95.0 | 1.1 | 0.5 | 9.0 | 1.0 | >72$^A$ | >153$^G$ | >9$^P$ | 96.8$^K$ | >2.5$^A$ | >3.0$^G$ | >1.3$^P$ | 2.7$^K$ |
| Y52 | 0.6 | 2.7 | 0.5 | 0.6 | 2.2 | 1.6 | 1.6 | 0.9 | 0.3$^A$ | 1.6$^D$ | 0.3$^S$ | 0.7$^F$ | -0.8$^A$ | 0.3$^D$ | -0.7$^S$ | -0.2$^F$ |
| T53 | 1.0 | | | 0.7 | 0.9 | | | 0.6 | 1.1$^A$ | | | 1.2$^S$ | 0.1$^A$ | | | 0.1$^S$ |
| N54 | 0.3 | 0.5 | 0.5 | 1.0 | 1.0 | 1.1 | 1.9 | 1.0 | 0.3$^A$ | 0.5$^D$ | 0.2$^T$ | 1.0$^D$ | -0.8$^A$ | -0.5$^D$ | -0.9$^T$ | 0$^D$ |
| Y56* | >81 | >81 | >81 | 1.2 | 3.8 | 3.1 | 1.9 | 0.8 | >21$^A$ | >26$^D$ | >42$^S$ | 1.6$^F$ | >1.8$^A$ | >1.9$^D$ | >2.2$^S$ | 0.3$^F$ |
| R58** | >81 | 80.0 | >81 | >96 | 1.1 | 0.8 | 2.4 | 2.1 | >73$^A$ | 104.8$^G$ | >33$^P$ | >46$^K$ | >2.5$^A$ | 2.8$^G$ | >2.1$^P$ | >2.3$^K$ |
| CDR-H3 | | | | | | | | | | | | | | | | |
| W95*** | >81 | >81 | >81 | >96 | 3.6 | 1.1 | 0.7 | 0.5 | >22$^A$ | >73$^G$ | >117$^S$ | >209$^L$ | >1.8$^A$ | >2.5$^G$ | >2.8$^S$ | >3.2$^L$ |
| G96 | 1.5 | | | 0.6 | 1.3 | | | 1.4 | 1.1$^A$ | | | 0.4$^A$ | 0.1$^A$ | | | -0.5$^A$ |
| G97 | 3.1 | | | 3.8 | 1.7 | | | 1.2 | 1.8$^A$ | | | 3.0$^A$ | 0.3$^A$ | | | 0.7$^A$ |
| D98 | 0.8 | | | 0.4 | 1.0 | | | 0.9 | 0.8$^A$ | | | 0.4$^E$ | -0.1$^A$ | | | -0.5$^E$ |
| G99*** | 26.0 | | | 18.0 | 1.2 | | | 1.9 | 22.3$^A$ | | | 9.5$^A$ | 1.8$^A$ | | | 1.3$^A$ |
| F100 | >81 | >81 | 39.5 | 95.0 | 3.4 | 2.2 | 1.6 | 2.5 | >24$^A$ | >37$^S$ | 24.2$^V$ | 38.0$^Y$ | >1.9$^A$ | >2.1$^S$ | 1.9$^V$ | 2.2$^Y$ |
| Y100a*** | 80.0 | >81 | >81 | 6.3 | 2.1 | 2.4 | 1.4 | 0.5 | 38$^A$ | >34$^D$ | >56.7$^S$ | 13.8$^F$ | 2.2$^A$ | >2.1$^D$ | >2.4$^S$ | -1.6$^F$ |

|  | CDR-L1 | | | | | | | CDR-L2 | | | | | | | CDR-L3 | | | | | Mutations/ |
|---|---|---|---|---|---|---|---|---|---|---|---|---|---|---|---|---|---|---|---|---|
|  | 28 | 29 | 30 | 30a | 30b | 30c | 30d | 30e | 31 | 32 | 33 | 50 | 51 | 52 | 53 | 91 | 92 | 93 | 93a | 93b | 94 | Insertions |
| hu4D5 | D | V | N | | | | | | T | A | V | S | A | S | F | H | Y | T | | | T | - |
| anti-VEGF | D | I | G | G | | | | | G | S | V | W | G | S | F | H | Y | T | | | T | 7 |
|  | D | I | H | S | | | | | G | S | V | W | G | S | Y | H | Y | T | | | T | 8 |
|  | D | V | F | | | | | | T | S | V | D | A | S | Y | R | Y | I | W | | A | 8 |
|  | D | I | W | | | | | | R | A | V | P | A | S | N | G | Y | Y | I | | A | 9 |
|  | D | I | W | | | | | | R | W | V | A | A | S | S | H | A | G | | | A | 9 |
|  | Y | V | W | | | | | | Q | Y | V | H | A | S | S | G | Y | W | V | | A | 10 |
|  | D | I | P | S | | | | | I | Y | V | G | A | S | Y | R | Y | W | V | | A | 11 |
|  | D | I | W | | | | | | R | W | L | A | G | S | S | H | D | Q | | | A | 11 |
|  | E | V | Y | | | | | | S | Y | V | P | A | S | S | G | F | W | I | | G | 11 |
|  | N | V | W | | | | | | D | W | V | P | A | S | S | G | W | Y | I | | A | 11 |
|  | N | V | W | | | | | | S | H | V | G | G | S | S | R | L | W | F | | T | 11 |
|  | W | V | P | S | | | | | H | T | V | L | G | S | Y | S | D | Y | | | T | 11 |
|  | Y | V | Y | S | | | | | T | T | V | N | G | S | S | A | S | S | | | A | 11 |
|  | E | I | F | P | | | | | Y | Y | V | L | G | S | S | G | W | D | | | G | 13 |
|  | N | I | F | | | | | | S | H | V | P | G | S | Y | A | F | W | V | | S | 13 |
|  | Q | I | W | | | | | | R | H | L | T | G | S | S | S | Y | W | V | | A | 13 |
|  | Y | I | W | | | | | | N | Y | V | G | G | S | S | S | W | W | A | | G | 13 |
| anti-DR5 | S | V | S | | | | | | S | A | V | S | A | S | S | Y | S | S | | | S | 8 |
|  | V | V | S | | | | | | M | T | V | G | A | S | Y | G | S | Y | | | S | 11 |
|  | N | V | G | | | | | | R | P | V | G | G | S | S | Y | G | S | F | | G | 12 |
|  | R | I | N | S | | | | | H | T | V | W | G | S | H | Y | S | N | R | | T | 12 |
|  | D | I | W | N | R | | | | R | A | L | E | G | S | S | G | G | S | Y | | S | 14 |
|  | D | I | W | N | R | | | | R | A | L | K | G | S | S | G | G | S | Y | | S | 14 |
| anti-Fc | E | V | L | | | | | | T | S | V | S | A | S | F | H | Y | T | | | T | 3 |
|  | K | I | Q | | | | | | A | Y | V | S | A | S | F | H | Y | T | | | T | 5 |
|  | N | I | V | V | R | | | | P | Y | V | S | A | S | F | H | Y | T | | | T | 7 |
|  | D | V | G | G | G | | | | S | G | V | G | G | S | S | H | Y | T | | | T | 8 |
|  | D | I | G | | | | | | A | G | L | S | A | S | F | S | E | S | R | | S | 10 |
|  | D | I | S | | | | | | R | Y | L | S | A | S | F | Y | G | W | R | R | T | 10 |
|  | D | V | G | G | | | | | L | G | L | S | A | S | S | G | G | A | D | | T | 10 |
|  | D | V | N | | | | | | R | Y | V | A | G | S | Y | G | I | D | L | | A | 10 |
|  | V | V | R | | | | | | Y | D | L | F | A | S | S | S | G | Y | H | | T | 11 |
|  | D | V | H | R | | | | | Q | H | V | R | A | S | S | S | D | A | S | | A | 11 |
|  | D | V | H | P | S | | | | D | S | V | W | G | S | Q | W | T | W | A | D | T | 12 |
|  | E | I | S | R | | | | | P | R | V | L | G | S | S | A | N | V | D | | T | 12 |
|  | N | V | P | R | | | | | Y | A | V | W | A | S | S | G | V | Y | N | | A | 12 |
|  | P | V | F | R | | | | | W | S | L | W | A | S | S | W | V | T | H | E | T | 12 |
|  | A | V | P | R | | | | | R | G | L | S | A | S | S | G | L | R | H | | G | 12 |
|  | A | V | S | R | | | | | Y | G | V | W | G | S | D | S | G | W | S | | A | 13 |
|  | D | I | G | L | | | | | H | A | L | W | G | S | S | W | D | G | K | | A | 13 |
|  | D | I | R | G | Q | | | | L | N | L | W | A | S | S | W | A | D | I | S | T | 13 |
|  | D | V | S | G | R | | | | R | G | V | S | G | S | S | G | S | G | S | S | T | 13 |
|  | E | I | V | | | | | | R | G | L | D | A | S | S | G | A | A | Y | | A | 13 |
|  | N | V | P | L | | | | | F | S | V | G | G | S | S | G | D | S | K | | S | 13 |
|  | V | I | A | R | | | | | N | D | V | H | G | S | S | W | A | H | Y | | G | 13 |
|  | D | I | P | E | H | | | | Y | D | L | W | A | S | S | A | G | A | R | | A | 14 |
|  | Y | I | P | R | | | | | F | R | L | G | G | S | S | G | G | W | S | E | T | 15 |
|  | R | V | S | D | S | L | Q | | D | A | L | W | G | S | Y | W | A | S | W | D | A | 15 |
|  | N | V | S | R | V | S | W | F | N | S | V | L | G | S | S | G | L | D | L | | A | 16 |
|  | | | | | | | | | E | T | L | G | G | S | Y | W | F | T | W | | G | 17 |

Fig. 39A

|  | \multicolumn{11}{c|}{CDR-L1} | \multicolumn{4}{c|}{CDR-L2} | \multicolumn{6}{c|}{CDR-L3} | Mutations/ |
|---|---|---|---|---|---|---|---|---|---|---|---|---|---|---|---|---|---|---|---|---|---|---|
|  | 28 | 29 | 30 | 30a | 30b | 30c | 30d | 30e | 31 | 32 | 33 | 50 | 51 | 52 | 53 | 91 | 92 | 93 | 93a | 93b | 94 | Insertions |
| hu4D5 | D | V | N |  |  |  |  |  | T | A | V | S | A | S | F | H | Y | T |  |  | T | - |
| anti-HER2/VEGF | D | V | W |  |  |  |  |  | K | W | V | A | A | S | S | H | Y | T |  |  | T | 5 |
|  | D | I | K | N |  |  |  |  | G | S | V | W | A | S | F | H | Y | T |  |  | T | 6 |
|  | D | I | L | G |  |  |  |  | G | S | V | W | A | S | F | H | Y | T |  |  | T | 6 |
|  | D | I | M | S |  |  |  |  | G | S | V | W | A | S | F | H | Y | T |  |  | T | 6 |
|  | D | I | R | A |  |  |  |  | G | S | V | W | A | S | F | H | Y | T |  |  | T | 6 |
|  | D | I | R | G |  |  |  |  | G | S | V | W | A | S | F | H | Y | T |  |  | T | 6 |
|  | D | V | R | Q |  |  |  |  | G | S | V | W | G | S | F | H | Y | T |  |  | T | 6 |
|  | D | I | A | A |  |  |  |  | G | S | V | W | A | S | Y | H | Y | T |  |  | T | 7 |
|  | D | I | A | G |  |  |  |  | G | S | V | W | A | S | Y | H | Y | T |  |  | T | 7 |
|  | D | I | A | H |  |  |  |  | G | S | V | W | A | S | Y | H | Y | T |  |  | T | 7 |
|  | D | I | A | K |  |  |  |  | G | S | V | W | G | S | F | H | Y | T |  |  | T | 7 |
|  | D | I | G | A |  |  |  |  | G | S | V | W | G | S | F | H | Y | T |  |  | T | 7 |
|  | D | I | G | A |  |  |  |  | G | S | V | W | G | S | F | H | Y | T |  |  | T | 7 |
|  | D | I | G | G |  |  |  |  | G | S | V | W | G | S | F | H | Y | T |  |  | T | 7 |
|  | D | I | G | L |  |  |  |  | G | S | V | W | A | S | Y | H | Y | T |  |  | T | 7 |
|  | D | I | G | M |  |  |  |  | G | S | V | W | A | S | Y | H | Y | T |  |  | T | 7 |
|  | D | I | K | H |  |  |  |  | G | S | V | W | G | S | F | H | Y | T |  |  | T | 7 |
|  | D | I | L | A |  |  |  |  | G | S | V | W | G | S | F | H | Y | T |  |  | T | 7 |
|  | D | I | L | G |  |  |  |  | G | S | V | W | G | S | F | H | Y | T |  |  | T | 7 |
|  | D | I | L | I |  |  |  |  | G | S | V | W | G | S | F | H | Y | T |  |  | T | 7 |
|  | D | I | L | T |  |  |  |  | G | S | V | W | G | S | F | H | Y | T |  |  | T | 7 |
|  | D | I | M | L |  |  |  |  | G | S | V | W | G | S | F | H | Y | T |  |  | T | 7 |
|  | D | I | Q | S |  |  |  |  | G | S | V | W | G | S | F | H | Y | T |  |  | T | 7 |
|  | D | I | R | I |  |  |  |  | G | S | V | W | G | S | F | H | Y | T |  |  | T | 7 |
|  | D | I | R | M |  |  |  |  | G | S | V | W | G | S | F | H | Y | T |  |  | T | 7 |
|  | D | I | R | Q |  |  |  |  | G | S | V | W | A | S | Y | H | Y | T |  |  | T | 7 |
|  | D | I | R | T |  |  |  |  | G | S | V | W | G | S | F | H | Y | T |  |  | T | 7 |
|  | D | I | R | V |  |  |  |  | G | S | V | W | G | S | F | H | Y | T |  |  | T | 7 |
|  | D | I | S | M |  |  |  |  | G | S | V | W | G | S | F | H | Y | T |  |  | T | 7 |
|  | D | I | S | R |  |  |  |  | G | S | V | W | G | S | F | H | Y | T |  |  | T | 7 |
|  | D | I | S | V |  |  |  |  | G | S | V | W | G | S | F | H | Y | T |  |  | T | 7 |
|  | D | I | V | S |  |  |  |  | G | S | V | W | G | S | F | H | Y | T |  |  | T | 7 |
|  | D | I | W |  |  |  |  |  | H | W | V | A | G | S | S | H | Y | T |  |  | T | 7 |
|  | N | I | A | Q |  |  |  |  | G | S | V | W | A | S | F | H | Y | T |  |  | T | 7 |
|  | D | I | A | F |  |  |  |  | G | S | L | W | G | S | F | H | Y | T |  |  | T | 8 |
|  | D | I | A | M |  |  |  |  | G | S | V | W | G | S | Y | H | Y | T |  |  | T | 8 |
|  | D | I | A | R |  |  |  |  | G | S | V | W | G | S | M | H | Y | T |  |  | T | 8 |
|  | D | I | A | S |  |  |  |  | G | S | V | W | G | S | L | H | Y | T |  |  | T | 8 |
|  | D | I | A | S |  |  |  |  | G | S | V | W | G | S | S | H | Y | T |  |  | T | 8 |
|  | D | I | G | S |  |  |  |  | G | S | V | W | G | S | Y | H | Y | T |  |  | T | 8 |
|  | D | I | I | G |  |  |  |  | G | S | V | W | G | S | Y | H | Y | T |  |  | T | 8 |
|  | D | I | K | A |  |  |  |  | G | S | V | W | G | S | Y | H | Y | T |  |  | T | 8 |
|  | D | I | K | F |  |  |  |  | G | S | V | W | G | S | S | H | Y | T |  |  | T | 8 |
|  | D | I | K | L |  |  |  |  | G | S | V | W | G | S | L | H | Y | T |  |  | T | 8 |
|  | D | I | K | L |  |  |  |  | G | S | V | W | G | S | M | H | Y | T |  |  | T | 8 |
|  | D | I | K | S |  |  |  |  | G | S | V | W | G | S | T | H | Y | T |  |  | T | 8 |

Fig. 39B-1

|  | CDR-L1 | | | | | | | | | | CDR-L2 | | | | CDR-L3 | | | | | Mutations/ |
| --- | --- | --- | --- | --- | --- | --- | --- | --- | --- | --- | --- | --- | --- | --- | --- | --- | --- | --- | --- | --- |
|  | 28 | 29 | 30 | 30a | 30b | 30c | 30d | 30e | 31 | 32 | 33 | 50 | 51 | 52 | 53 | 91 | 92 | 93 | 93a | 93b | 94 | Insertions |
| hu4D5 | D | V | N |  |  |  |  |  | T | A | V | S | A | S | F | H | Y | T |  |  | T | - |
|  | D | I | K | V |  |  |  |  | G | S | V | W | G | S | Y | H | Y | T |  |  | T | 8 |
|  | D | I | K | W |  |  |  |  | G | S | V | W | G | S | T | H | Y | T |  |  | T | 8 |
|  | D | I | L | K |  |  |  |  | G | S | V | W | G | S | Y | H | Y | T |  |  | T | 8 |
|  | D | I | L | S |  |  |  |  | G | S | V | W | G | S | W | H | Y | T |  |  | T | 8 |
|  | D | I | Q | R |  |  |  |  | G | S | V | W | G | S | C | H | Y | T |  |  | T | 8 |
|  | D | I | Q | S |  |  |  |  | G | S | V | W | G | S | Y | H | Y | T |  |  | T | 8 |
|  | D | I | Q | T |  |  |  |  | G | S | V | W | G | S | Y | H | Y | T |  |  | T | 8 |
|  | D | I | R | E |  |  |  |  | G | S | V | W | G | S | S | H | Y | T |  |  | T | 8 |
|  | D | I | R | F |  |  |  |  | G | S | V | W | G | S | Y | H | Y | T |  |  | T | 8 |
|  | D | I | R | G |  |  |  |  | G | S | V | W | G | S | Y | H | Y | T |  |  | T | 8 |
|  | D | I | R | L |  |  |  |  | G | S | V | W | G | S | Y | H | Y | T |  |  | T | 8 |
|  | D | I | R | M |  |  |  |  | G | S | V | W | G | S | S | H | Y | T |  |  | T | 8 |
|  | D | I | R | R |  |  |  |  | G | S | V | W | G | S | Y | H | Y | T |  |  | T | 8 |
|  | D | I | R | R |  |  |  |  | G | S | V | W | G | S | A | H | Y | T |  |  | T | 8 |
|  | D | I | R | S |  |  |  |  | G | S | V | W | G | S | Y | H | Y | T |  |  | T | 8 |
|  | D | I | R | S |  |  |  |  | G | S | V | W | G | S | T | H | Y | T |  |  | T | 8 |
|  | D | I | R | S |  |  |  |  | G | S | V | W | G | S | N | H | Y | T |  |  | T | 8 |
|  | D | I | R | S |  |  |  |  | G | S | V | W | G | S | E | H | Y | T |  |  | T | 8 |
|  | D | I | R | S |  |  |  |  | G | S | V | W | G | S | S | H | Y | T |  |  | T | 8 |
|  | D | I | R | V |  |  |  |  | G | S | V | W | G | S | Y | H | Y | T |  |  | T | 8 |
|  | D | I | S | S |  |  |  |  | G | S | V | W | G | S | Y | H | Y | T |  |  | T | 8 |
|  | D | I | T | M |  |  |  |  | G | S | V | W | G | S | L | H | Y | T |  |  | T | 8 |
|  | D | I | Y | M |  |  |  |  | G | S | V | W | G | S | Y | H | Y | T |  |  | T | 8 |
|  | D | I | A | T |  |  |  |  | G | S | L | W | G | S | Y | H | Y | T |  |  | T | 9 |
|  | D | I | K | S |  |  |  |  | G | S | L | W | G | S | Y | H | Y | T |  |  | T | 9 |
|  | D | I | R | G |  |  |  |  | G | S | V | G | G | S | Y | Y | Y | T |  |  | T | 9 |
|  | G | I | R | T |  |  |  |  | G | S | V | W | G | S | Y | H | Y | T |  |  | T | 9 |
|  | N | I | A | M |  |  |  |  | G | S | V | W | G | S | Y | H | Y | T |  |  | T | 9 |
|  | N | I | R | S |  |  |  |  | G | S | V | W | G | S | V | H | Y | T |  |  | T | 9 |
|  | N | I | R | T |  |  |  |  | G | S | V | W | G | S | Y | H | Y | T |  |  | T | 9 |
|  | D | I | R | A |  |  |  |  | G | S | V | W | G | S | Y | H | F | N |  |  | A | 11 |
|  | N | I | Y | A |  |  |  |  | G | S | L | W | G | S | Y | H | Y | T |  |  | T | 10 |
|  | N | I | Y | S |  |  |  |  | G | S | L | W | G | S | Y | H | Y | T |  |  | T | 10 |
|  | D | I | P | R | S | I | S |  | G | Y | V | W | G | S | Y | H | Y | T |  |  | T | 11 |
| anti-HER2/DR5 | N | I | R | N | G |  |  |  | G | G | L | S | A | S | F | H | Y | T |  |  | T | 8 |
|  | N | V | S |  |  |  |  |  | K | H | V | W | G | S | Y | S | Y | S |  |  | G | 10 |
| anti-HER2/Fc | Q | V | S | K |  |  |  |  | Y | D | V | W | G | S | S | S | G | F | R |  | S | 13 |

Fig. 39B-2

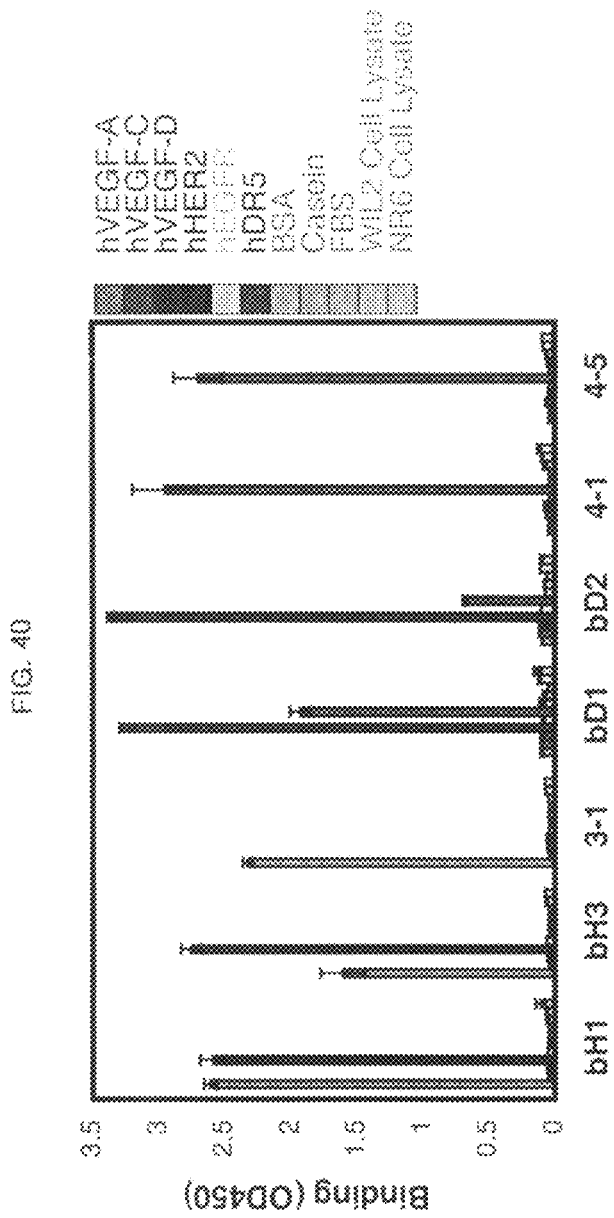

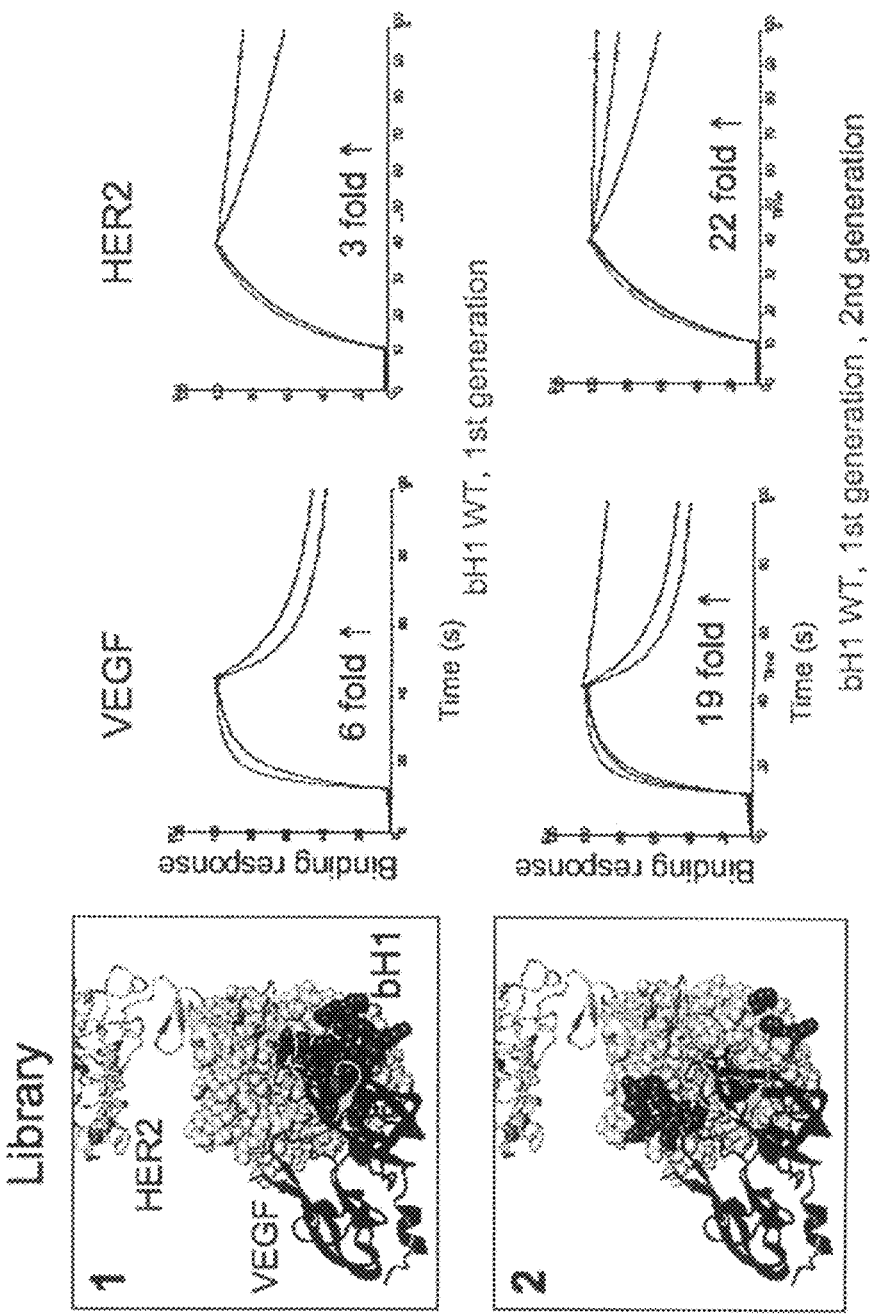

MULTISPECIFIC ANTIBODIES

CROSS-REFERENCE TO RELATED APPLICATIONS

This application claims benefit of U.S. Application Ser. No. 60/841,350 filed Aug. 30, 2006 and U.S. Application Ser. No. 60/937,814, filed Jun. 28, 2007, the disclosures of which are hereby incorporated by reference.

FIELD OF THE INVENTION

The present invention relates to multispecific antibodies, and methods of making and using such antibodies.

BACKGROUND OF THE INVENTION

Antibodies are specific immunoglobulin polypeptides produced by the vertebrate immune system in response to challenge by foreign proteins, glycoproteins, cells, or other antigenic foreign substances. An important part of this process is the generation of antibodies that bind specifically to a particular foreign substance. The binding specificity of such polypeptides to a particular antigen is highly refined, and the multitude of specificities capable of being generated by the individual vertebrate is remarkable in its complexity and variability. Thousands of antigens are capable of eliciting responses, each almost exclusively directed to the particular antigen which elicited it.

Specific antigen recognition is essential for antibodies to function in the adaptive immune response. The combinatorial association of heavy chain (HC) and light chain (LC) is conserved in all vertebrates in the generation of the antibody repertoire. There is, however, asymmetry of diversity in the two chains. The variable domain of HC ($V_H$) contains significantly higher sequence diversity and contributes the determinants of antigen recognition more often than the variable domain of the LC ($V_L$). The role of the LC in determining antigen-specificity is indicated by a process called receptor editing. Ongoing recombination of the $V_L$ genes to edit the B cell receptor is the main mechanism to correct self reactive antibody precursors, which appear to constitute a significant portion of the initial repertoire (~75%). Altering of the light chain is demonstrated to extinguish unwanted binding specificity or multi-specificity.

The specificity of antibodies and antibody fragments for a particular antigen or antigens makes antibodies desirable therapeutic agents. Antibodies and antibody fragments can be used to target particular tissues, for example, a tumor, and thereby minimize the potential side effects of non-specific targeting. As such, there is a current and continuing need to identify and characterize therapeutic antibodies, especially antibodies, fragments, and derivatives thereof, useful in the treatment of cancer and other proliferative disorders.

SUMMARY OF THE INVENTION

The present invention provides a method of making a multispecific antibody comprising the steps of (1) diversifying the amino acid sequence of a light chain variable domain ($V_L$) of an antibody, wherein prior to the diversification, the antibody comprised a $V_L$ and a heavy chain variable domain ($V_H$) capable of binding to a first epitope and (2) selecting a diversified antibody capable of binding to the first epitope and a second epitope. According to one embodiment, prior to diversification, the antibody in step 1 is monospecific. According to another embodiment, the $V_L/V_H$ of the antibody after using the methods of this invention, is bispecific. In one embodiment, the $V_L$ amino acid sequence is diversified by altering the nucleic acid sequence encoding the $V_L$ and expressing the diversified $V_L$. In a further embodiment, the diversification is by altering a plurality of predetermined amino acid residue positions. According to one embodiment, the residues are diversified based on the diversity of a plurality of naturally occurring light chain amino acid sequences. Additionally or alternatively, the residues are diversified based on the accessibility to solvent. According to one embodiment, the diversified $V_L$ are displayed on phage with the $V_H$ during the selection step. According to a further embodiment, the binding affinity of the multispecific antibody can be improved by subjecting the antibody to affinity maturation (e.g., homolog scanning or other mutations of the $V_L$ and/or $V_H$).

According to one embodiment the residue positions diversified are selected from the group consisting of: (1) positions 28, 30-32, 66-70, 92-93, optionally at positions 30a-e and 93(a)-(b); (2) positions 28, 30-32, 66-70, 92-93, optionally at positions 30a-f; (3) positions 28-32, 50-53, 92-93, optionally at positions 30a-f and 93a-b; (4) positions 28, 30-32, 50-53, 92-93, optionally at positions 30a-f and 93a-b; (5) positions 28-32, 50-53, 92-93; (6) positions 28-32, 50-53, 92-93, optionally at 30a-b (7) positions 28-32, 50-53, 91-93, 94, optionally at 30a-f and 93a-b; and (8) positions 29-32, 50-53, 66-67, 69-70, 92-93, 94, optionally at 30a-f. According to one preferred embodiment, the $V_L$ residues are diversified according to any one of the library designs described in FIG. 1.

According to one embodiment, the selection step for binding to the first epitope or the selection for binding to the second epitope occurs in the presence of both diversified $V_L$ and $V_H$. According to another embodiment, the diversified $V_L$ and $V_H$ can bind the first epitope and second epitope simultaneously. In an alternative embodiment, the diversified $V_L$ and $V_H$ bind the first epitope and second epitope mutually exclusively. In one embodiment, the first epitope is from one biological molecule and the second epitope is from the same biological molecule. In another embodiment, the first epitope is from one biological molecule and the second epitope is from a second biological molecule. According to one embodiment the first biological molecule and the second biological molecule are structurally unsimilar.

According to one embodiment, the first biological molecule and second biological molecule pairs are selected from the following group of pairs: VEGF/HER2, VEGF-A/HER2, HER2/DR5, VEGF-A/PDGF, HER1/HER2, CD20/BR3, VEGF-A/VEGF-C, VEGF-C/VEGF-D, TNFalpha/TGF-beta, TNFalpha/IL-2, TNF alpha/IL-3, TNFalpha/IL-4, TNFalpha/IL-5, TNFalpha/IL6, TNFalpha/IL8, TNFalpha/mL-9, TNFalpha/IL-10, TNFalpha/IL-11, TNFalpha/IL-12, TNFalpha/IL-13, TNFalpha/IL-14, TNFalpha/IL-15, TNFalpha/IL-16, TNFalpha/IL-17, TNFalpha/IL-18, TNFalpha/IL-19, TNFalpha/IL-20, TNFalpha/IFNalpha, TNFalpha/CD4, VEGF/IL-8, VEGF/MET, VEGFR/MET receptor, HER2/Fc, HER2/HER3; EGFR/HER2, EGFR/HER3, EGFR/HER4, TNFalpha/IL-3, TNFalpha/IL-4, IL-13/CD40L, IL4/CD40L, TNFalpha/ICAM-1, TNFR/IL-1R, TNFR1/IL-6R and TNFR1/IL-18R. In particular embodiments, the first biological molecule and second biological molecule are VEGF/HER2, HER2/DR5, or HER2/Fc.

According to one embodiment, one of the biological molecules is a molecule that can increase the half-life of the multispecific antibody when bound to the antibody in vivo.

In another embodiment, the biological molecule is serum albumin or the neonatal Fc receptor (FcRn).

According to another embodiment, one of the biological molecules is a molecule that can increase the effector function of a multispecific antibody when bound to the antibody in vivo. In one embodiment, the biological molecule binds to a cell surface protein on natural killer cells or macrophages. The cell surface protein may be C1q or an Fc receptor.

The present invention also provides multispecific antibodies made by the methods of this invention. It is contemplated that a multispecific antibody of this invention can comprise one or a plurality of the $V_L/V_H$ domains created by the methods of this invention alone or in combination with the hypervariable domains of antibodies not created by the methods of this invention. A multispecific antibody of this invention can exist in a variety of forms (e.g., antibody fragments, multimeric, etc). According to one embodiment, the multispecific antibody is any one of the antibodies of FIGS. 5-10, 13-16, FIG. 34, FIG. 39, and Table 2. In a particular embodiment, the multispecific antibody is a bH1 antibody of FIG. 34 or a fragment thereof.

The multispecific antibodies of this invention can be used in a variety of ways, e.g., in therapies to treat illnesses or diseases, in research or in purification. In one embodiment, the invention provides a method of treating a tumor (e.g., a cancerous tumor) in a subject. This method involves administering to the subject the multispecific antibody of any one of the antibodies of FIGS. 5-10, 13-16, FIG. 34, FIG. 39, and Table 2, a fragment thereof, or an antibody made by the methods of the invention, where the administering is for a time and in an amount sufficient to treat or prevent the tumor in the subject. In a particular embodiment, the multispecific antibody is a bH1 antibody of FIG. 34 or a fragment thereof.

In another aspect, the invention features a method of treating a subject at risk of developing a tumor. The method of the invention are also advantageous in reducing or preventing the recurrence of a tumor, for example, a dormant tumor that persists after removal of the primary tumor, or in reducing or preventing the occurrence or proliferation of metastatic tumors. This method involves administering to the subject the multispecific antibody of any one of the antibodies of FIGS. 5-10, 13-16, FIG. 34, FIG. 39, and Table 2, a fragment thereof, or an antibody made by the methods of the invention.

In a further aspect, the invention features a method of treating a subject having or being at risk of developing an autoimmune disease. This method involves administering to the subject the multispecific antibody of any one of the antibodies of FIGS. 5-10, 13-16, FIG. 34, FIG. 39, and Table 2, a fragment thereof, or an antibody made by the methods of the invention, where the administering is for a time and in an amount sufficient to treat or prevent the autoimmune disease in the subject.

Also, contemplated are kits, compositions, and articles of manufacture comprising the multispecific antibodies.

BRIEF DESCRIPTION OF THE DRAWINGS

FIG. 1 shows the designed diversity in various LC libraries.

FIG. 2 shows a summary of four light chain libraries used to alter anti-VEGF antibodies or anti-Her2 antibodies to bind to an additional target. The italicized NNK and XYZ refer to codon sets. Ys, Ds, Ts and Ss refer to soft randomizations by having tyrosine, aspartic acid, threonine and serine, respectively, occurring 50% of the time and any one of the 20 amino acids occurring the other 50% of the time. D/Ds and T/Ts refer to a soft randomization having D or T, respectively, occurring 75% of the time and any one of the 20 amino acids occurring the other 25% of the time.

FIG. 3 shows sequences of HC, LC CDR residues of light chain templates (SEQ ID NOS:1-16 and 18).

FIG. 4 shows sorting conditions and enrichment of Library C and D.

FIG. 6 shows DR5 binders (SEQ ID NOS:5, 25-26, 30-31, 33-34, 94, 99, and 106-185).

FIG. 7 shows human VEGF binders, combined plate and solution selection (SEQ ID NOS:4-5, 22-23, 26, 34, 77, 152, 217-218, and 220-227).

FIGS. 8A and 8B show clones that bind both VEGF and HER2 (SEQ ID NOS:24-26, 28-29, 64-69, 74-75, 78, 81, 88-91, 93-95, 150, 232-243, and 245-292).

FIG. 9 shows clones that only bind VEGF and lost the binding activity with HER2 (SEQ ID NOS:22-23, 25-26, 34, 70, 77, 79, 82, 85, 87, 91-92, 94, 96-99, 152, 217-218, 220-227, 272, 290, and 421-440).

FIG. 10 shows DR5 binders plate sorted directly on HER2 (SEQ ID NOS:4-5, 25-26, 36-38, and 500-504).

FIG. 14 shows a summary of specific binders from LC library (SEQ ID NOS:4-5, 30-31, 33-34, 106-108, 140, 142-143, 156, and 533-535).

FIG. 15 shows clones that can bind both (FIG. 15A) hVEGF and HER2 or (FIG. 15B) DR5 and HER2 (SEQ ID NOS:4-5, 24-26, 28, 36-38, 78, 91, 233, 250, and 500-504).

FIG. 16 shows the LC library binders used in scFv'2 formation and displayed on phage (SEQ ID NOS:5, 21-26, 28-31, 33-34, 36-38, 94, 108, 143, 159, 222-224, 233, 280, 440, 509, 533, and 535).

FIG. 17 shows the expression of various clones in Fab or hIgG form.

FIG. 21 shows a Biacore Analysis of binding to VEGF or HER2.

FIG. 28 shows codons of H1 that were shotgun scanned.

FIG. 29 shows a library consortium (SEQ ID NOS:25-26 and 591-595).

FIG. 30 shows an antibody clone with shotgun scan mutations screened by binding to VEGF.

FIG. 31 shows an antibody clone with shotgun scan mutations screened by binding to HER2.

FIG. 34 shows bH1 VEGF-affinity matured clone sequences and binding affinity for VEGF or HER2 (SEQ ID NOS:25, 91, and 603-631).

FIGS. 35A through 35D show crystal structures of the bispecific bH1 Fab bound to HER2 or VEGF.

FIGS. 37A 37A-1 through 37A-3 and 37B-1 through 37B-3 show shotgun alanine- and homolog scanning of bH1 Fab for binding to VEGF and HER2.

FIG. 38 shows the natural and designed diversity of light chain CDRs. At each position, the Herceptin® antibody sequence is shown in parenthesis. An "*" denotes an insertion not present in the Herceptin® antibody.

FIGS. 39A, 39B-1, and 39B 2 show the sequences of specific antigen-binding clones isolated from the light chain (LC) library. FIG. 39A shows the LC CDR sequences of monospecific phage clones biding to VEGF, DR5, and Fc (SEQ ID NOS:5, 22-23, 25-26, 30-31, 33-34, 70, 77, 79, 82, 85, 87, 91-92, 94, 96-99, 106-117, 119-121, 123, 125-131, 133-146, 148-167, 169-171, 173, 175-185, 217-218, 220-227, 272, 421-426, and 428-439), and FIG. 39B shows bispecific Fabs binding to VEGF/HER2, DR5/HER2, and Fc/HER2 (SEQ ID NOS:5, 24-26, 28-29, 36-38, 64-69, 74-76, 78, 81, 88-91, 93-95, 99, 122, 172, 232-243, 245-271, 273-275, and 277-291). The light chain framework and heavy chain sequences correspond to that of the Herceptin® antibody with the exception of LC framework substitution R66G.

FIG. 40 is a graph showing binding specificity of the antibodies derived from the LC library. The results for antibodies bH1, bH3, 3-1, bD1, bD2, 4-1, and 4-5 are shown. Bound IgG antibodies were detected spectrophotometrically (optical density at 450 nm, y-axis). The proteins included in the assay were (left to right for each antibody) human vascular endothelial growth factor A (hVEGF-A), hVEGF-C, hVEGF-D, hHER2 extracellular domain (ECD), epidermal growth factor receptor extracellular domain (hEGFR), human death receptor 5 (hDR5), bovine serum albumin (BSA), casein, fetal bovine serum (FBS), WIL2 cell lysate, and NR6 cell lysate.

FIG. 41 shows results from affinity maturation experiments indicating that the libraries described herein can be used to improve the affinity for both VEGF and HER2.

DETAILED DESCRIPTION OF THE INVENTION

Figure 5:
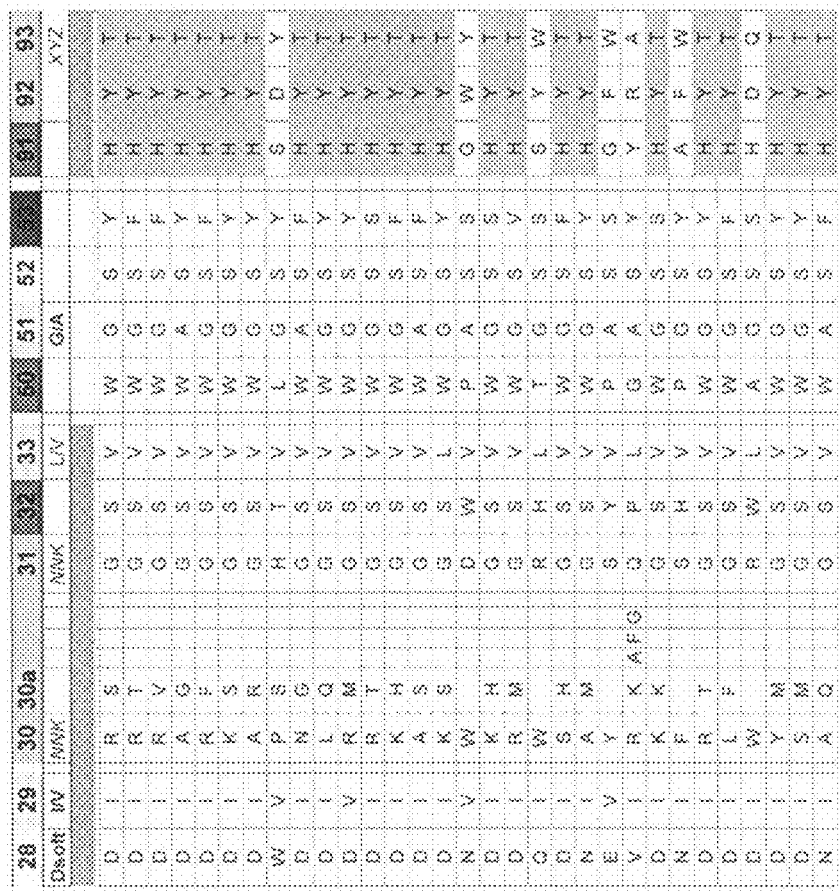
FIG. 5 shows VEGF binders (SEQ ID NOS:22, 25, 28-29, and 64-99). Residues 28, 30, 30a, 31, 92, 93, and 93a were fully diverse. Residues 32, 50, 53, 91 and 94 were restricted. Residues 29, 33, and 51 were limited (<3).

The present invention provides methods of making multispecific antibodies and antibody fragments, as well as antibodies identified using these methods and their use. In general, the methods of the invention involve diversifying the light chain variable domain or the heavy chain variable domain of an antibody to generate variants that can be stably expressed in a library. Diversified antibodies that are capable of specifically binding two epitopes are then selected from this library and further characterized.

Exemplary antibodies identified using the methods of the invention include antibodies that bind both HER2 (human epithelial growth factor receptor 2) and VEGF (vascular endothelial growth factor), as well as antibodies that bind both HER2 and DR5 (death receptor 5). In particular, the data described herein, for instance, in the below Examples, show that mutations in the light chain complementarity determining regions (CDRs) of a HER2 antibody confer dual binding capabilities for unrelated protein antigens as well as HER2. One bi-specific high affinity HER2/VEGF antibody is extensively characterized. In addition, the crystal structures of this bi-specific Fab in complex with HER2 and VEGF are shown and the energetic contribution of the Fab residues by mutagenesis is evaluated. The binding sites for the two antigens overlap extensively; most of the CDR residues that contact HER2 also engage VEGF. Energetically, however, the residues of the heavy chain dominate the HER2 specificity while the light chain dominates VEGF specificity.

The HER2/VEGF bi-specific antibody inhibits both HER2 and VEGF-mediated cell proliferation. These results demonstrate that altering the sequence of the light chain variable domain of an antibody can generate antibodies with dual specificity and function. For example, bH1 has the potential to target two mechanisms of tumor progression: tumor cell proliferation mediated by HER2 and tumor angiogenesis mediated by VEGF.

I. Definitions

The term "multispecific antibody" is used in the broadest sense and specifically covers an antibody comprising a heavy chain variable domain ($V_H$) and a light chain variable domain ($V_L$), where the $V_H V_L$ unit has polyepitopic specificity (i.e., is capable of binding to two different epitopes on one biological molecule or each epitope on a different biological molecule). Such multispecific antibodies include, but are not limited to, full length antibodies, antibodies having two or more $V_L$ and $V_H$ domains, antibody fragments such as Fab, Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Monospecific" refers to the ability to bind only one epitope. According to one embodiment the multispecific antibody in an IgG1 form binds to each epitope with an affinity of 5 µM to 0.001 pM, 3 µM to 0.001 pM, 1 µM to 0.001 pM, 0.5 µM to 0.001 pM or 0.1 µM to 0.001 pM.

The basic 4-chain antibody unit is a heterotetrameric glycoprotein composed of two identical light (L) chains and two identical heavy (H) chains (an IgM antibody consists of 5 of the basic heterotetramer units along with an additional polypeptide called J chain, and therefore contains 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has, at the N-terminus, a variable domain ($V_H$) followed by three constant domains ($C_H$) for each of the α and γ chains and four $C_H$ domains for μ and ε isotypes. Each L chain has, at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology*, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, γ, ε, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g., around about residues 24-34 (L1), 50-56 (L2) and 89-97 (L3) in the $V_L$, and around about residues 26-35 (H1), 50-65 (H2) and 95-102 (H3) in the $V_H$ (in one embodiment, H1 is around about residues 31-35); Kabat et al., *Sequences of Proteins of Immunological Interest*, 5th Ed. Public Health Service, National Institutes of Health, Bethesda, Md. (1991)) and/or those residues from a "hypervariable loop" (e.g., residues 26-32 (L1), 50-52 (L2), and 91-96 (L3) in the $V_L$, and 26-32 (H1), 53-55 (H2), and 96-101 (H3) in the $V_H$; Chothia and Lesk, J. Mol. Biol. 196:901-917 (1987)).

The term "monoclonal antibody" as used herein refers to an antibody from a population of substantially homogeneous antibodies, i.e., the individual antibodies comprising the population are substantially similar and bind the same epitope(s), except for possible variants that may arise during production of the monoclonal antibody, such variants generally being present in minor amounts. Such monoclonal antibody typically includes an antibody comprising a variable region that binds a target, wherein the antibody was obtained by a process that includes the selection of the antibody from a plurality of antibodies. For example, the selection process can be the selection of a unique clone from a plurality of clones, such as a pool of hybridoma clones, phage clones or recombinant DNA clones. It should be understood that the selected antibody can be further altered, for example, to improve affinity for the target, to humanize the antibody, to improve its production in cell culture, to reduce its immunogenicity in vivo, to create a multispecific antibody, etc., and that an antibody comprising the altered variable region sequence is also a monoclonal antibody of this invention. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including the hybridoma method (e.g., Kohler et al., Nature, 256:495 (1975); Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681, (Elsevier, N.Y., 1981), recombinant DNA methods (see, e.g., U.S. Pat. No. 4,816,567), phage display technologies (see, e.g., Clackson et al., Nature, 352:624-628 (1991); Marks et al., J. Mol. Biol., 222:581-597 (1991); Sidhu et al., J. Mol. Biol. 338(2):299-310 (2004); Lee et al., J. Mol. Biol. 340 (5):1073-1093 (2004); Fellouse, Proc. Nat. Acad. Sci. USA 101(34):12467-12472 (2004); and Lee et al. J. Immunol. Methods 284(1-2):119-132 (2004) and technologies for producing human or human-like antibodies from animals that have parts or all of the human immunoglobulin loci or genes encoding human immunoglobulin sequences (see, e.g., WO98/24893, WO/9634096, WO/9633735, and WO/9110741, Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); U.S. Pat. No. 5,545,807; WO 97/17852, U.S. Pat. Nos. 5,545,807; 5,545,806; 5,569,825; 5,625,126; 5,633,425; and 5,661,016, and Marks et al., Bio/Technology, 10: 779-783 (1992); Lonberg et al., Nature, 368: 856-859 (1994); Morrison, Nature, 368: 812-813 (1994); Fishwild et al., Nature Biotechnology, 14: 845-851 (1996); Neuberger, Nature Biotechnology, 14: 826 (1996); and Lonberg and Huszar, Intern. Rev. Immunol., 13: 65-93 (1995).

An "intact" antibody is one which comprises an antigen-binding site as well as a $C_L$ and at least heavy chain constant domains, $C_H1$, $C_H2$, and $C_H3$. The constant domains can be native sequence constant domains (e.g., human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., Protein Eng. 8(10): 1057-1062 (1995)); single-chain antibody molecules; and multispecific antibodies formed from antibody fragments.

The expression "linear antibodies" generally refers to the antibodies described in Zapata et al., Protein Eng., 8(10): 1057-1062 (1995). Briefly, these antibodies comprise a pair of tandem Fd segments ($V_H$-$C_H1$-$V_H$-$C_H1$) which, together with complementary light chain polypeptides, form a pair of antigen binding regions. Linear antibodies can be bispecific or monospecific.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region; this region is also the part recognized by Fc receptors (FcR) found on certain types of cells.

"Fv" consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although often at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

As used herein, "codon set" refers to a set of different nucleotide triplet sequences used to encode desired variant amino acids. A set of oligonucleotides can be synthesized, for example, by solid phase synthesis, including sequences that represent all possible combinations of nucleotide triplets provided by the codon set and that will encode the desired group of amino acids. A standard form of codon designation is that of the IUB code, which is known in the art and described herein. A codon set typically is represented by 3 capital letters in italics, e.g., NNK, NNS, XYZ, DVK, and the like (e.g., NNK codon refers to N=A/T/G/C at positions 1 and 2 in the codon and K=G/T at equimolar ratio in position 3 to encode all 20 natural amino acids). A "non-random codon set", as used herein, thus refers to a codon set that encodes select amino acids that fulfill partially, preferably completely, the criteria for amino acid selection as described herein. Synthesis of oligonucleotides with selected nucleotide "degeneracy" at certain positions is well known in that art, for example the TRIM approach (Knappek et al., J. Mol. Biol. 296:57-86, 1999); Garrard and Henner, Gene 128:103, 1993). Such sets of oligonucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can, but do not necessarily, include restriction enzyme sites useful for, for example, cloning purposes.

An antibody of this invention "which binds" an antigen of interest is one that binds the antigen with sufficient affinity such that the antibody is useful as a diagnostic and/or therapeutic agent in targeting a protein or a cell or tissue expressing the antigen, and does not significantly cross-react with other proteins. In such embodiments, the extent of binding of the antibody to a "non-target" protein will be less than about 10% of the binding of the antibody to its particular target protein as determined by fluorescence activated cell sorting (FACS) analysis or radioimmunoprecipitation (RIA) or ELISA. With regard to the binding of a antibody to a target molecule, the term "specific binding" or "specifically binds to" or is "specific for" a particular polypeptide or an epitope on a particular polypeptide target means binding that is measurably different from a nonspecific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

"Biologically active" and "biological activity" and "biological characteristics" with respect to a polypeptide of this invention means having the ability to bind to a biological molecule, except where specified otherwise.

"Biological molecule" refers to a nucleic acid, a protein, a carbohydrate, a lipid, and combinations thereof. In one embodiment, the biologic molecule exists in nature.

"Isolated," when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated antibody includes antibodies in situ within recombinant cells, because at least one component of the polypeptide natural environment will not be present. Ordinarily, however, isolated polypeptide will be prepared by at least one purification step.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Percent (%) amino acid sequence identity" with respect to the polypeptide sequences identified herein is defined as the percentage of amino acid residues in a candidate sequence that are identical with the amino acid residues in the polypeptide being compared, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

The amino acid sequences described herein are contiguous amino acid sequences unless otherwise specified.

"Structurally unsimilar" biological molecules according to this invention refers to biological molecules that are not in the same class (protein, nucleic acid, lipid, carbohydrates, etc.) or, for example, when referring to proteins, having less than 60% amino acid identity, less than 50% amino acid identity, less than 40% amino acid identity, less than 30% amino acid identity, less than 20% amino acid identity or less than 10% amino acid identity compared to each other.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, can be identified by those that: (1) employ low ionic strength and high temperature for washing, for example 0.015 M sodium chloride/0.0015 M sodium citrate/ 0.1% sodium dodecyl sulfate at 50 C; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with a 10 minute wash at 42° C. in 0.2×SSC (sodium chloride/ sodium citrate) followed by a 10 minute high-stringency wash consisting of 0.1×SSC containing EDTA at 55° C.

"Moderately stringent conditions" can be identified as described by Sambrook et al., *Molecular Cloning: A Laboratory Manual*, New York: Cold Spring Harbor Press, 1989, and include the use of washing solution and hybridization conditions (e.g., temperature, ionic strength, and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, Annu. Rev. Immunol. 9:457-92 (1991). To assess ADCC activity of a molecule of interest, an in vitro ADCC assay, such as that described in U.S. Pat. Nos. 5,500,362 or 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in a animal model such as that disclosed in Clynes et al. (Proc. Natl. Acad. Sci. USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, Annu. Rev. Immunol. 15:203-234 (1997)). FcRs are reviewed in Ravetch and Kinet, Annu. Rev. Immunol. 9:457-492 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells, and neutrophils; with PBMCs and NK cells being preferred. The effector cells can be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., J. Immunol. Methods 202:163 (1996), can be performed.

The term "therapeutically effective amount" refers to an amount of an antibody or antibody fragment to treat a disease or disorder in a subject. In the case of tumor (e.g., a cancerous tumor), the therapeutically effective amount of the antibody or antibody fragment (e.g., a multispecific antibody or antibody fragment for HER2 and VEGF or HER2 and DR5) may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the antibody or antibody fragment may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

By "reduce or inhibit" is meant the ability to cause an overall decrease preferably of 20% or greater, more preferably of 50% or greater, and most preferably of 75%, 85%, 90%, 95%, or greater. Reduce or inhibit can refer to the symptoms of the disorder being treated, the presence or size of metastases, the size of the primary tumor, or the size or number of the blood vessels in angiogenic disorders.

The terms "cancer" and "cancerous" refer to or describe the physiological condition in mammals that is typically characterized by unregulated cell growth. Included in this definition are benign and malignant cancers. By "early stage cancer" is meant a cancer that is not invasive or metastatic or is classified as a Stage 0, 1, or II cancer.

The term "precancerous" refers to a condition or a growth that typically precedes or develops into a cancer.

By "non-metastatic" is meant a cancer that is benign or that remains at the primary site and has not penetrated into the lymphatic or blood vessel system or to tissues other than the primary site. Generally, a non-metastatic cancer is any cancer that is a Stage 0, I, or II cancer, and occasionally a Stage III cancer.

An "autoimmune disease" herein is a disease or disorder arising from and directed against an individual's own tissues or a co-segregate or manifestation thereof or resulting condition therefrom. Examples of autoimmune diseases or disorders include, but are not limited to arthritis (rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, and ataxic sclerosis, inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), pyoderma gangrenosum, erythema nodosum, primary sclerosing cholangitis, episcleritis), respiratory distress syndrome, including adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, allergic conditions, allergic reaction, eczema including allergic or atopic eczema, asthma such as asthma bronchiale, bronchial asthma, and autoimmune asthma, conditions involving infiltration of T cells and chronic inflammatory responses, chronic pulmonary inflammatory disease, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, extra-renal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis (including large vessel vasculitis (including polymyalgia rheumatica and giant cell (Takayasu's) arteritis), medium vessel vasculitis (including Kawasaki's disease and polyarteritis nodosa), microscopic polyarteritis, CNS vasculitis, necrotizing, cutaneous, or hypersensitivity vasculitis, systemic necrotizing vasculitis, and ANCA-associated vasculitis, such as Churg-Strauss vasculitis or syndrome (CSS)), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, immune complex nephritis, antibody-mediated nephritis, neuromyelitis optica, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multi focal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transplant) vs NSIP, Guillain-Barré syndrome, Berger's disease (IgA nephropathy), idiopathic IgA nephropathy, linear IgA dermatosis, primary biliary cirrhosis, pneumonocirrhosis, auto immune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia greata, CREST syndrome (calcinosis, Raynaud's phenomenon, esophageal dysmotility, sclerodactyl), and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, infertility due to antispermatozoan antobodies, non-malignant thymoma, vitiligo, SCID and Epstein-Barr virus-associated diseases, acquired immune deficiency syndrome (AIDS), parasitic diseases such as Lesihmania, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine-induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis.

A "subject" is a vertebrate, preferably a mammal, more preferably a human. Mammals include, but are not limited to, farm animals (such as cows), sport animals, pets (such as cats, dogs and horses), primates, mice, and rats.

Commercially available reagents referred to in the Examples were used according to manufacturer's instructions unless otherwise indicated. The source of those cells identified in the following Examples, and throughout the specification, by ATCC accession numbers is the American Type Culture Collection, Manassas, Va. Unless otherwise noted, the present invention uses standard procedures of recombinant DNA technology, such as those described hereinabove and in the following textbooks: Sambrook et al., supra; Ausubel et al., *Current Protocols in Molecular Biology* (Green Publishing Associates and Wiley Interscience, N.Y., 1989); Innis et al., *PCR Protocols: A Guide to Methods and Applications* (Academic Press, Inc.: N.Y., 1990); Harlow et al., *Antibodies: A Laboratory Manual* (Cold Spring Harbor Press: Cold Spring Harbor, 1988); Gait, *Oligonucleotide Synthesis* (IRL Press: Oxford, 1984); Freshney, *Animal Cell Culture,* 1987; Coligan et al., *Current Protocols in Immunology,* 1991.

Throughout this specification and claims, the word "comprise," or variations such as "comprises" or "comprising," will be understood to imply the inclusion of a stated integer or group of integers but not the exclusion of any other integer or group of integers.

II. Therapeutic Uses

The antibodies and antibody fragments described herein which bind both HER2 and VEGF (e.g., bH1 or fragments thereof) or HER2 and DR5 can be used for the treatment of tumors, including pre-cancerous, non-metastatic, and cancerous tumors (e.g., early stage cancer), for the treatment of autoimmune disease, or for the treatment of a subject at risk for developing cancer, for example, breast cancer or an autoimmune disease.

The term cancer embraces a collection of proliferative disorders, including but not limited to pre-cancerous growths, benign tumors, and malignant tumors. Benign tumors remain localized at the site of origin and do not have the capacity to infiltrate, invade, or metastasize to distant sites. Malignant tumors will invade and damage other tissues around them. They can also gain the ability to break off from where they started and spread to other parts of the body (metastasize), usually through the bloodstream or through the lymphatic system where the lymph nodes are located. Primary tumors are classified by the type of tissue from which they arise; metastatic tumors are classified by the tissue type from which the cancer cells are derived. Over time, the cells of a malignant tumor become more abnormal and appear less like normal cells. This change in the appearance of cancer cells is called the tumor grade and cancer cells are described as being well-differentiated, moderately-differentiated, poorly-differentiated, or undifferentiated. Well-differentiated cells are quite normal appearing and resemble the normal cells from which they originated. Undifferentiated cells are cells that have become so abnormal that it is no longer possible to determine the origin of the cells.

The tumor can be a solid tumor or a non-solid or soft tissue tumor. Examples of soft tissue tumors include leukemia (e.g., chronic myelogenous leukemia, acute myelogenous leukemia, adult acute lymphoblastic leukemia, acute myelogenous leukemia, mature B-cell acute lymphoblastic leukemia, chronic lymphocytic leukemia, polymphocytic leukemia, or hairy cell leukemia), or lymphoma (e.g., non-Hodgkin's lymphoma, cutaneous T-cell lymphoma, or Hodgkin's disease). A solid tumor includes any cancer of body tissues other than blood, bone marrow, or the lymphatic system. Solid tumors can be further separated into those of epithelial cell origin and those of non-epithelial cell origin. Examples of epithelial cell solid tumors include tumors of the gastrointestinal tract, colon, breast, prostate, lung, kidney, liver, pancreas, ovary, head and neck, oral cavity, stomach, duodenum, small intestine, large intestine, anus, gall bladder, labium, nasopharynx, skin, uterus, male genital organ, urinary organs, bladder, and skin. Solid tumors of non-epithelial origin include sarcomas, brain tumors, and bone tumors.

Epithelial cancers generally evolve from a benign tumor to a preinvasive stage (e.g., carcinoma in situ), to a malignant cancer, which has penetrated the basement membrane and invaded the subepithelial stroma.

Multispecific antibodies that bind both VEGF and HER2 or DR5 and HER2 desirably are used to treat breast cancer.

Examples of autoimmune diseases or disorders include, but are not limited to arthritis (rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, and ataxic sclerosis, inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), pyoderma gangrenosum, erythema nodosum, primary sclerosing cholangitis, episcleritis), respiratory distress syndrome, including adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, allergic conditions, allergic reaction, eczema including allergic or atopic eczema, asthma such as asthma bronchiale, bronchial asthma, and autoimmune asthma, conditions involving infiltration of T cells and chronic inflammatory responses, chronic pulmonary inflammatory disease, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, extra-renal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis (including large vessel vasculitis (including polymyalgia rheumatica and giant cell (Takayasu's) arteritis), medium vessel vasculitis (including Kawasaki's disease and polyarteritis nodosa), microscopic polyarteritis, CNS vasculitis, necrotizing, cutaneous, or hypersensitivity vasculitis, systemic necrotizing vasculitis, and ANCA-associated vasculitis, such as Churg-Strauss vasculitis or syndrome (CSS)), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), auto immune polyendocrinopathies, Reiter's disease or syndrome, immune complex nephritis, antibody-mediated nephritis, neuromyelitis optica, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, autoimmune disease of the testis and ovary including autoimune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transplant) vs NSIP, Guillain-Barré syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deaffiess, blindness, periodic paralysis, and channelopathies of the CNS, autism, inflammatory myopathy, focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia greata, CREST syndrome (calcinosis, Raynaud's phenomenon, esophageal dysmotility, sclerodactyl), and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, infertility due to antispermatozoan antobodies, non-malignant thymoma, vitiligo, SCID and Epstein-Barr virus-associated diseases, acquired immune deficiency syndrome (AIDS), parasitic diseases such as Lesihmania, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine-induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis.

III. Dosages and Formulations

The antibody (e.g., bH1) or antibody fragment compositions will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody or antibody fragment to be administered will be governed by such considerations, and is the minimum amount necessary to prevent, ameliorate, or treat a cancer. The antibody or antibody fragment need not be, but is optionally formulated with one or more agents currently used to prevent or treat cancer or a risk of developing a cancer. The effective amount of such other agents depends on the amount of antibody or antibody fragment present in the formulation, the type of disorder or treatment, and other factors discussed above. These are generally used in the same dosages and with administration routes as used hereinbefore or about from 1 to 99% of the heretofore employed dosages. Generally, alleviation or treatment of a cancer involves the lessening of one or more symptoms or medical problems associated with the cancer. The therapeutically effective amount of the drug can accomplish one or a combination of the following: reduce (by at least 10%, 20%, 30%, 40%, 50%, 60%, 70%, 80%, 90%, 100% or more) the number of cancer cells; reduce or inhibit the tumor size or tumor burden; inhibit (i.e., to decrease to some extent and/or stop) cancer cell infiltration into peripheral organs; reduce hormonal secretion in the case of adenomas; reduce vessel density; inhibit tumor metastasis; reduce or inhibit tumor growth; and/or relieve to some extent one or more of the symptoms associated with the cancer. In some embodiments, the antibody or antibody fragment is used to prevent the occurrence or reoccurrence of cancer in the subject.

In one embodiment, the present invention can be used for increasing the duration of survival of a human patient susceptible to or diagnosed with a cancer. Duration of survival is defined as the time from first administration of the drug to death. Duration of survival can also be measured by stratified hazard ratio (HR) of the treatment group versus control group, which represents the risk of death for a patient during the treatment.

In yet another embodiment, the treatment of the present invention significantly increases response rate in a group of human patients susceptible to or diagnosed with a cancer who are treated with various anti-cancer therapies. Response rate is defined as the percentage of treated patients who responded to the treatment. In one aspect, the combination treatment of the invention using an antibody or antibody fragment and surgery, radiation therapy, or one or more chemotherapeutic agents significantly increases response rate in the treated patient group compared to the group treated with surgery, radiation therapy, or chemotherapy alone, the increase having a Chi-square p-value of less than 0.005.

Additional measurements of therapeutic efficacy in the treatment of cancers are described in U.S. Patent Application Publication No. 20050186208.

Therapeutic formulations are prepared using standard methods known in the art by mixing the active ingredient having the desired degree of purity with optional physiologically acceptable carriers, excipients or stabilizers (Remington's Pharmaceutical Sciences ($20^{th}$ edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, supra.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The antibodies and antibody fragments described herein (e.g., bH1 or fragments thereof) are administered to a human subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration may be particularly desired if extensive side effects or toxicity is associated with VEGF, HER2, or DR5 antagonism. An ex vivo strategy can also be used for therapeutic applications. Ex vivo strategies involve transfecting or transducing cells obtained from the subject with a polynucleotide encoding an antibody or antibody fragment. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells.

In one example, the antibody or antibody fragment is administered locally, e.g., by direct injections, when the disorder or location of the tumor permits, and the injections can be repeated periodically. The antibody or antibody fragment can also be delivered systemically to the subject or directly to the tumor cells, e.g., to a tumor or a tumor bed following surgical excision of the tumor, in order to prevent or reduce local recurrence or metastasis.

Articles of Manufacture and Kits

Another embodiment of the invention is an article of manufacture containing materials useful for the treatment of autoimmune diseases and cancers. Yet another embodiment of the invention is an article of manufacture containing materials useful for the treatment of immunodeficiency diseases. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is a multispecific antibody or antibody fragment antibody of the invention. The label or package insert indicates that the composition is used for treating the particular condition. The label or package insert will further comprise instructions for administering the antibody composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In one embodiment, the package insert indicates that the composition is used for treating breast cancer.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for purification or immunoprecipitation of VEGF, HER2 or DR5 from cells. For isolation and purification of VEGF, HER2, or DR5, the kit can contain a VEGF/HER2 or HER2/DR5 antibody coupled to beads (e.g., sepharose beads). Kits can be provided which contain the antibodies for detection and quantitation of VEGF, HER2, or DR5 in vitro, e.g., in an ELISA or a Western blot. As with the article of manufacture, the kit comprises a container and a label or package insert on or associated with the container. The container holds a composition comprising at least one multispecific antibody or antibody fragment of the invention. Additional containers may be included that contain, e.g., diluents and buffers or control antibodies. The label or package insert may provide a description of the composition as well as instructions for the intended in vitro or diagnostic use.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1. Library Design and Construction

The antigen-binding site of antibody is formed by the association of the variable domain ($V_H$, $V_L$) of heavy chain (HC) and light chain (LC), each containing three CDR loops for antigen recognition. In many cases one of the two variable domains, often $V_H$, determines the antigen specificity. Mice with transgenic HC but intact LC repertoire generate neutralizing antibody titers (Senn et al., Eur. J. Immunol. 33:950-961, 2003). We set out to investigate how bi-specificity of an antibody can occur and whether different utilization of the $V_H$ and the $V_L$ domains can enable dual antigen binding specificity.

A semi-empirical approach was taken to find a design for diversifying the amino acid composition and CDR length of antibody light chain and a library template that enabled generation of a functional phage-displayed antibody library from which antibodies binding specifically to a protein antigen could be selected. The sequence and length diversity of the CDR regions of approximately 1500 human kappa light chain sequences, as represented in the Kabat database, served to guide the library design process. Solvent exposed residues were targeted for randomization. A subset of the randomized positions were tailored to represent amino acids which are part of the natural repertoire at these sites, whereas the remaining sites were randomized to include all 20 naturally occurring amino acids.

In particular, the light chain template (variable domain) set forth below was modified as described herein (underlined residues are randomized) (SEQ ID NO:19).

DIQMTQSPSSLSASVGDRVTITCRASQD[28]VNTAVAWYQQKPGKAPKLLI

YS[50]ASFLYSGVPSRFSGSGSGTDFTLTISSLQPEDFATYYCQQH[91]YTT

PPTFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVYAC

EVTHQGLSSPVTKSFNRGEC

Four sets of libraries were generated based on 3 human Fab and scFv templates where distinct sets of positions were targeted for randomization (FIG. 1).

In all of the libraries the heavy chain was held constant with its sequence defined by the library template. The heavy chain template (variable domain) sequence is set forth below (SEQ ID NO:20).

EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTH

Figure 3:
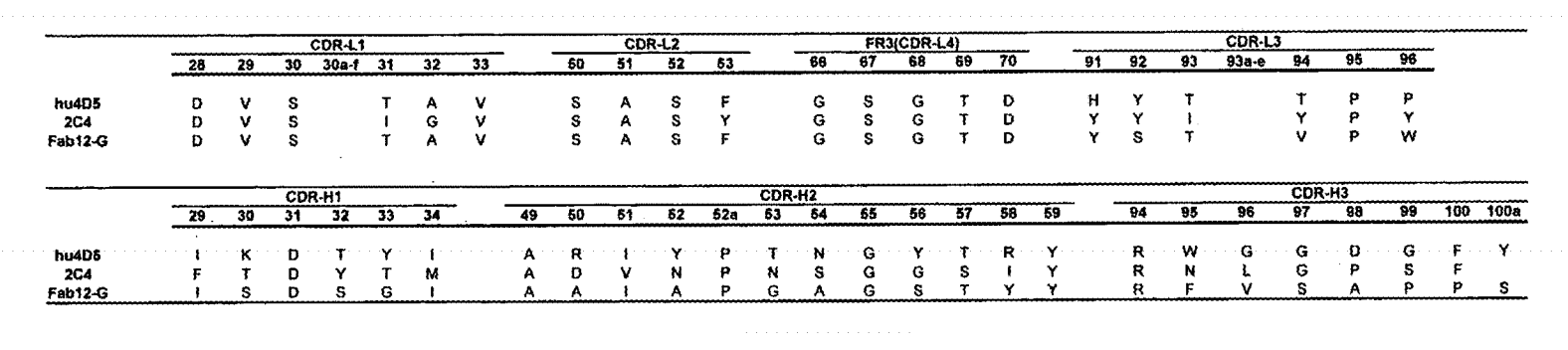

All library templates contained a stop codon (Sidhu et al., 2004) embedded in CDR L1 preventing the presence of template light chain among the phage-displayed antibody library members. The template CDR sequences are summarized in FIG. 3. The library designs are summarized in FIG. 1 and FIG. 2.

Figure 38:
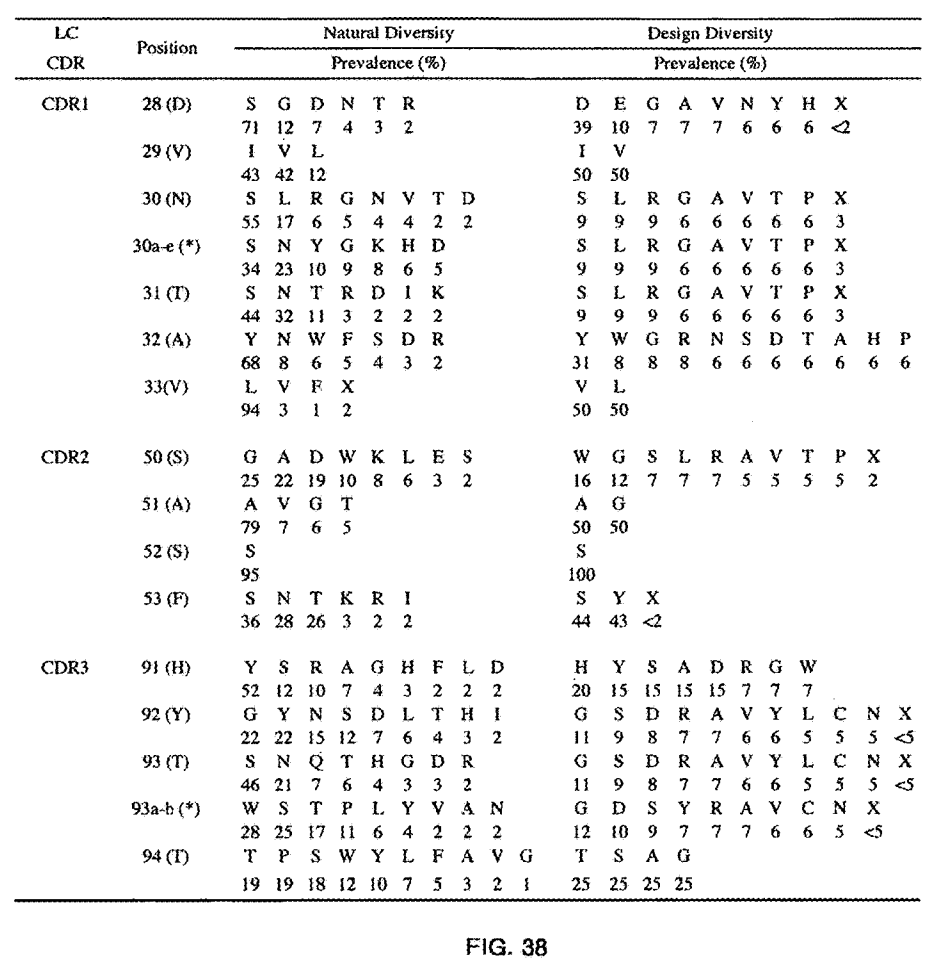

In one example, we introduced mutations in the LC variable domain of a HER2-specific antibody to identify variants that can bind a different protein antigen while retaining the original binding specificity. We took a conservative approach to randomize the LC CDRs in order to generate variants that can be stably expressed. Twelve solvent exposed LC CDR positions were selected for randomization: five in CDR1 (28, 29, 30, 31, 32), three in CDR2 (50, 51, 53) and four in CDR3 (91, 92, 93, 94). Further, to guide the design of amino acid diversity at elected sites, the natural diversity of these positions was examined by analysis of approximately 1500 human kappa LC CDR sequences (Johnson and Wu, Nucleic Acids Res. 28:214, 2000; Chothia and Lesk, J. Mol. Biol. 196:901, 1987) (FIG. 38). Some positions with relatively high natural diversity (30, 31, 50, 92, 93) were fully randomized while other positions were limited to as few as two amino acid types to mimic natural antibodies. The length variation of natural LC CDR1 and CDR3 was also reflected in the library (FIG. 38). In FIG. 38, X denotes the amino acid types designed at low frequencies as shown. Length diversity is constructed by inserting 1 to 5 residues between residues 30 and 31 and between residues 93 and 94.

The LC library is a productive naive repertoire (Table 1). Listed are results from the screening of 95 random clones at the end of four rounds of selection. In particular, selection for new binding specificity was performed as described on immobilized targets (VEGF, DR5, and human Fc) (Sidhu et al., J. Mol. Biol. 338:299, 2004). After four rounds of selection 95 phage clones were assayed using ELISA for binding to the target, HER2, and a non-target protein, BSA, to ensure specific binding. To enrich for target binding clones that maintained HER2 binding, a final round of selection on HER2 was performed. The positive clones were sequenced. To identify the highest affinity binders, the $IC_{50}$ for antigen binding was determined by competitive ELISA (Sidhu et al., J. Mol. Biol. 338:299, 2004). The number of unique clones as determined by sequence analysis and the number of unique clones that maintain HER2 binding (bispecific clones) are shown. These clones show minimum background binding signals to irrelevant antigens, such as BSA.

TABLE 1

Light chain library selection summary

| | Positive % | Unique Seq. | HER2 positive |
|---|---|---|---|
| Human Fc fusion | 63 | 31 out of 61 | 1 |
| hVEGF | 77 | 41 out of 74 | 30 out of 41 |
| DR5 long | 85 | 5 out of 82 | 2* out of 5 |

*= weak binding signal

| Target | Bi-Specific, Screen | Bi-Specific, Selection |
|---|---|---|
| Human Fc fusion | 1 out of 31 | Not determined |
| hVEGF | 30 out of 41 | 94 out of 94 |
| DR5 long | 2* out of 5 | 2 out of 7** |

*= weak binding signal Her2
**= weak binding signal DR5

Selection against three protein antigens: human vascular endothelial growth factor (hVEGF), death receptor 5 (DR5), and complement binding fragment of IgG (Fc) generated many binding clones (FIG. 39A). Some clones lost binding affinity for HER2, while others maintained HER2-binding and were thus bi-specific. Sequence analysis of the 131 unique Herceptin® antibody variants with new binding specificity identified the amino acid substitutions and insertions compared to the Herceptin® antibody (FIGS. 39B-1 and 39B-2).

The number of mutations ranged from 3-17. The clones that retained HER2 binding (the bi-specific clones) contained fewer mutations on average than those that lost HER2 binding. Retaining the Herceptin® antibody CDR-L3 sequence was preferred but not sufficient to conserve HER2 binding. This is consistent with the report that the Herceptin® antibody CDR-L3 is the most important LC CDR for HER2 binding (Kelley and O'Connell, Biochemistry 32:6828. 1993). Representative VEGF and DR5-binding clones were expressed as Fab and IgG proteins (Table 2).

Materials

Enzymes and M13-KO7 helper phage were from New England Biolabs. *E. coli* XL1-Blue was from Stratagene. Bovine serum albumin (BSA), ovalbumin, and Tween 20 were from Sigma. Neutravidin, casein, and Superblock were from Pierce. Immobilized protein G and anti-M13 conjugated horse-radish peroxidase (HRP) were from GE Healthcare (Piscataway, N.J.). Maxisorp immunoplates were from NUNC (Roskilde, Denmark). Tetramethylbenzidine (TMB) substrate was from Kirkegaard and Perry Laboratories (Gaithersburg, Md.). All protein antigens were generated by research groups at Genentech, Inc. DNA degeneracies were represented using the IUB code and represent equimolar mixtures unless indicated otherwise: N=A/C/G/T, D=A/G/T, V=A/C/G, B=C/G/T, H=A/C/T, K=G/T, M=A/C, R=A/G, S=G/C, W=A/T, Y=C/T.

For example, at certain randomized positions, the wild-type codon was replaced by a degenerate NNK codon (N=A/T/G/C, K=G/T in an equimolar ratio) that encodes all 20 natural amino acids. The XYZ codon refers to a codon with unequal nucleotide ratios at each position of the codon triplet. X contained 38% G, 19% A, 26% T and 17% C; Y contained 31% G, 34% A, 17% T and 18% C; and Z contained 24% G and 76% C.

Phagemid Vectors for Library Construction

Standard molecular biology techniques were used for vector construction. Three templates were constructed for library generation. All templates are derivatives of plasmid pV0354 used in heavy chain libraries based on modified humanized 4D5 (version 8) (Lee et al., 2004a).

The 2C4 Fab-C template phagemid pJB0290 was constructed by cloning the 2C4 heavy chain variable domain into a pV0354-Fab-C vector containing the alkaline phosphatase promoter (Lowman et al., 1991) and stII secretion signal for both light and heavy chain of Fab. It is engineered to contain a single cysteine at the C-terminus of the heavy

TABLE 2

The representative antibodies isolated from the light chain library of the Herceptin® antibody (SEQ ID NOS: 5 and 21-38).

| | CDR-L1 | | | | | | | CDR-L2 | | | | | | CDR-L3 | | | | | | |
|---|---|---|---|---|---|---|---|---|---|---|---|---|---|---|---|---|---|---|---|---|
| | 28 | 29 | 30 | 30a | 30b | 30c | 30d | 31 | 32 | 33 | 50 | 51 | 52 | 53 | 91 | 92 | 93 | 93a | 93b | 94 | Specificity | $K_D$ (nM) |
| Herceptin | D | V | N | — | — | — | — | T | A | V | S | A | S | F | H | Y | T | | | T | HER2 | 0.1 |
| 3-1 | N[a] | V | W | | | | | D | W | V | P | A | S | S | G | W | Y | I | | A | VEGF | 15 |
| bH1 | D | I | P | R | S | I | S | G | Y | V | W | G | S | Y | H | Y | T | | | T | VEGF/HER2 | 300/26 |
| bH3 | D | I | G | L | | | | G | S | V | W | A | S | Y | H | Y | T | | | T | | 19,000/8 |
| bH4 | D | I | R | S | | | | G | S | V | W | G | S | Y | H | Y | T | | | T | | 3,500/11 |
| 4-1 | D | I | W | N | R | | | R | A | L | E | G | S | S | G | G | S | Y | S | S | DR5 | 120 |
| 4-5 | N | V | G | | | | | R | P | V | G | G | S | S | Y | G | S | F | G | T | | 150 |
| bD1 | N | V | S | | | | | K | H | V | W | G | S | Y | S | Y | S | | | G | DR5/HER2 | 14,000/200 |
| bD2 | N | I | R | N | G | | | G | G | L | S | A | S | F | H | Y | T | | | T | | 67,000/100 |

[a] Differences from Herceptin are shown in bold

To demonstrate that these antibodies bound specifically to their cognate antigens and did not interact non-specifically with other proteins, we showed that there was no detectable binding to a panel of mammalian cell lysates and non-antigen proteins. The assay confirmed the mono- and bi-specificity of the purified IgGs or Fabs (FIG. 40).

Equilibrium binding affinities ($K_D$) of the LC library-derived mono-specific antibodies ranged from 15-150 nM. The bi-specific antibodies bound the new antigens (i.e., VEGF and DR5) with high nM to low µM affinity and HER2 with low nM affinity (Table 2). The antibody bH1 displayed the highest bi-specific affinity for the two different protein antigens VEGF ($K_D$=300 nM) and HER2 ($K_D$=26 nM).

chain variable domain 1 to allow bivalent M13 phage display of the 2C4 Fab as previously described (Lee et al., 2004b). The 2C4 light chain CDRs were incorporated into the Fab-C vector by site-directed mutagenesis using the method of Kunkel et al (Kunkel et al., 1987). An epitope tag (gD tag) (Lasky and Dowbenko, 1984) was added at the C-terminus of the light chain to enable determination of the level of display as described (Sidhu et al., 2004). The Fab12-G library template pV1283 was created by cloning a highly displayed heavy chain variable domain into pV0354-Fab-C, and the light chain variable domain was modified to contain CDR-L3 of Fab-12 (humanized A4.6.1, an anti-VEGF antibody). The highly-displayed $V_H$ was selected from a Fab library that randomized heavy chain CDR residues of G6 Fab using shotgun alanine scanning mutagenesis (Liang et al., 2006; Vajdos et al., 2002) with CDR-L3 converted to Fab-12 ($Y_{91}$STVP$W_{96}$) by panning on immobilized anti-gD antibody. The design and construction of the phagemid pV1384, displaying 4d5 (LC-R66G) scFv bivalently on the surface of M13 phage particles was modified from the template pS2018 described previously (Sidhu et al., 2004). The scFv fragment contained a gD epitope tag in the linker region between light chain and heavy chain. LC framework residue Arg66 was mutated to Gly66, which is the prevalent residue in this position in over 95% of natural kappa light chains. The mutation R66G reduces Herceptin® antibody binding affinity to HER2 only slightly (<2 fold) as described in Kelley and Connell (Biochemistry 32:6828, 1993). The CDR sequences of the library templates are summarized in FIG. 3.

Library Construction

Phage-displayed libraries were created using oligonucleotide-directed mutagenesis as described (Sidhu et al., 2004). The library template vectors contained a stop codon (TAA) embedded in CDR-L1, which was repaired during the mutagenesis reaction using degenerate oligonucleotides that annealed over the sequences encoding CDR-L1, CDR-L3 (all libraries), CDR-L2 (L1/L2/L3–A, –B, –C, +L4-D) and the light chain framework 3 (L1/LA and L1/L2/L3+L4-D). The library mutagenesis reactions were performed according to the method of Kunkel et al (Kunkel et al., 1987). The light chain CDR designs for the libraries are described in FIG. 1, which summarizes the degenerate codons used at each position for the different libraries. Three or four oligonucleotides were mixed at certain ratios for each CDR to encode the desired frequency of amino acid types at each position targeted for randomization (FIG. 38). The oligonucleotides were combined in different ratios to fine-tune the diversity to reflect the amino acid frequency in natural light chain kappa sequences at selected positions. For CDR1, three oligonucleotides containing codons for positions 91-94: CAT NNK NNK RST (SEQ ID NO:43), KMT XYZ XYZ RST (SEQ ID NO:44), or DGG XYZ XYZ RST (SEQ ID NO:45) were mixed at 1:3:1 ratios. XYZ is a variation of NNK that has equal proportions of the A/G/T/C for each site to reduce the coverage of aliphatic hydrophobic amino acids (Lee et al., J. Mol. Biol. 340:1073, 2004). For CDR2, four oligonucleotides containing codons for positions 50-53: NNK GST TCC NNK (SEQ ID NO:46), TGG GST TCC NNK (SEQ ID NO:47), KGG GST TCC TMT (SEQ ID NO:48), or NNK GST TCC TMT (SEQ ID NO:49) were mixed at 1:1:2:10 ratios. For CDR3, each length was a mixture of three oligonucleotides containing codons for position 28-33: $G_{70}A_{70}C_{70}$ RTT NNK NNK TAC STA (SEQ ID NO:50), $G_{70}A_{70}C_{70}$ RTT NNK NNK DGG STA (SEQ ID NO:51), or $G_{70}A_{70}C_{70}$ RTT NNK NNK NMT STA (SEQ ID NO:52) at 1:1:2 ratios. $G_{70}A_{70}C_{70}$ is a "soft" codon that allows 70% of the designated nucleotide and 10% each of the other three, encoding ~50% of Glu and ~50% of the other amino acids.

Structural analysis of a number of representative antibodies with kappa LCs shows that CDR1 has the widest range of conformations, which is likely a result of the variation in loop lengths (11-17 residues between position 24 and 34). Different CDR-L1 lengths (lengths 11-16) were thus included in the library. Natural CDR-L3 also varies in length (lengths 7-10 residues between position 89-96), which is reflected by the library design (lengths 8-10; FIG. 38).

FIG. 1 shows the comparison of the light chain natural diversity and the actual library designs. The mutagenesis products were pooled into one reaction per library and electroporated into E. coli SS320 cells supplemented with KO7 helper phage and were grown overnight at 30° C. (Lee et al., J. Mol. Biol. 340:1073, 2004). ~$10^{11}$ cells and ~5-10 µg DNA were used in each electroporation reaction. The library phage were purified (Sidhu et al., J. Mol. Biol. 338:299, 2004). The number of transformants ranged from $10^9$-$10^{10}$. The display level of intact Fabs or scFv on the surface of phage was determined in an ELISA binding assay where 96 randomly selected clones from each library were tested for their ability to bind an anti-gD antibody. The display level ranged from 5-25% (FIG. 2). 25% of the clones displaying antibody retained HER2 binding. Approximately 150 displaying clones were sequenced to examine the actual library diversity as compared to the design diversity. A portion (~30%) of the functionally displayed library members retained the Herceptin® antibody CDR-L2 and/or CDR-L3 sequence due to incomplete mutagenesis (a template stop codon in CDR-1 ensured 100% mutation of this CDR in expressed scFvs). These were excluded from the sequence analysis of the actual library diversity. At the majority of the randomized positions, the diversity of the phage displayed library of the displaying clones did not deviate significantly (p>0.05, odds ratio test) from the designed diversity. Exceptions were position 29 of the CDR-L1 where Val was found to be slightly over-represented compared to Ile (p=0.005) and positions 51 and 53 of CDR-L2, where Gly and Ser were more prevalent than Ala and Tyr, respectively (p<0.01).

Example 2. Evaluation of Library Performance

Library Sorting and Screening

A library was considered functional when antibodies binding specifically to various protein antigens could be isolated after 4-5 rounds of sorting. Many protein targets were known to allow functional immobilization for library panning and specific antibodies have been generated from validated phage-displayed libraries (Fellouse et al., 2005) (Lee et al., 2004a). To evaluate each set of libraries, we chose a subset of these targets for selection (FIG. 2). The libraries were subjected to an initial round of binding selection with anti-gD antibody or protein L as the capture target to eliminate clones in which the Fab/scFv gene had been deleted, followed by 4-5 rounds of antigen selection. Alternatively, they were directly subjected to target binding selection without pre-selection with anti-gD or protein L. NUNC 96-well Maxisorp plates were coated overnight with antigen (5 µg/ml) and blocked for 1 hour with alternating blocking agents (FIG. 4). Phage solutions of $10^{13}$ phage/ml were added to the coated immunoplates in the first selection cycle. The phage concentration was decreased in each round of selection. Following incubation of the phage solutions on the immunoplates to allow binding to the immobilized antigen, the plates were washed with PBS, 0.5% Tween 20, repeatedly. To increase the stringency, the incubation time was decreased (4 hours for $1^{st}$ round, 3 hours $2^{nd}$, 3 hours $3^d$, 2 hours $4^{th}$, 1.75 hours $5^{th}$) and the number of washes was increased in each round of selection (FIG. 4). Bound phage was eluted with 0.1 M HCl for 30 minutes and the eluant was neutralized with 1.0 M Tris base. The recovery of phage per antigen-coated immunoplate well was calculated and compared to that of a blocked well without coated antigen to study the enrichment of phage clones displaying Fabs or scFvs that specifically bound the target antigen (FIG. 4). Eluted phage were amplified in E. coli and used for further rounds of selection. Random clones from rounds 4 and 5 were selected for screening and assayed using phage ELISA in which binding to target and anti-gD was compared to binding of a non-relevant protein (BSA) for checking non-specific binding. Clones that bound the anti-gD antibody and target but not the non-specific protein were considered specific positives. Libraries L1/L3, L1/L4, L1/L2/L3-A, L1/L2/L3-B_1 and L1/L2/L3-B_2 did not yield any specific positive clones whereas libraries L1/L2/L3-C and L1/L2/L3+L4-D enabled isolation of specific antibodies to the target antigens.

For example, random clones from round four were assayed using phage ELISA where binding of individually amplified clones to the target and HER2 was compared to binding of a non-target protein (BSA) to test binding specificity. To enrich the phage clones that maintained HER2 binding, the eluted phage from the third and fourth round of VEGF or DR5 selection were amplified and subjected to another round of selection on HER2 coated wells. The $V_L$ and $V_H$ regions of the positive clones were amplified by PCR and sequenced.

The hit rate for hFC, hVEGF and hDR5-lf, was 63, 77, and 85% respectively. The $V_L$ regions of the positive clones were amplified by PCR and sequenced as described (Sidhu et al., 2004). The DNA sequence analysis of the positive specific binders revealed a percentage of unique clones of 51% (hFC), 55% (hVEGF), and 6.1% (hDR5-lf). The sequences of unique hVEGF, hDR5 and hFc binding clones are summarized in FIG. 5 and FIG. 6, respectively.

Combined Plate and Solution Selection of hVEGF Binding Clones

High diversity of hVEGF binding clones after four rounds of sorting was observed. In order to identify high affinity hVEGF binding clones a solution based selection approach was taken following the $4^{th}$ plate based sort. 50 nM biotinylated hVEGF was incubated with the phage propagated from the $4^{th}$ round of selection on immobilized antigen. After 2 hours of incubation at room temperature with shaking, hVEGF-bound phage was captured on neutravidin-coated and blocked immunoplates followed by repeated washes. Phage clones were eluted, screened, and sequenced as previously described. Sequences of hVEGF binding clones from the last solution selection step are found in FIG. 7.

Isolation of Bi-Specific Clones from Libraries L1/L2/L3-C and L1/L2/L3+L4-D

Figure 8A:
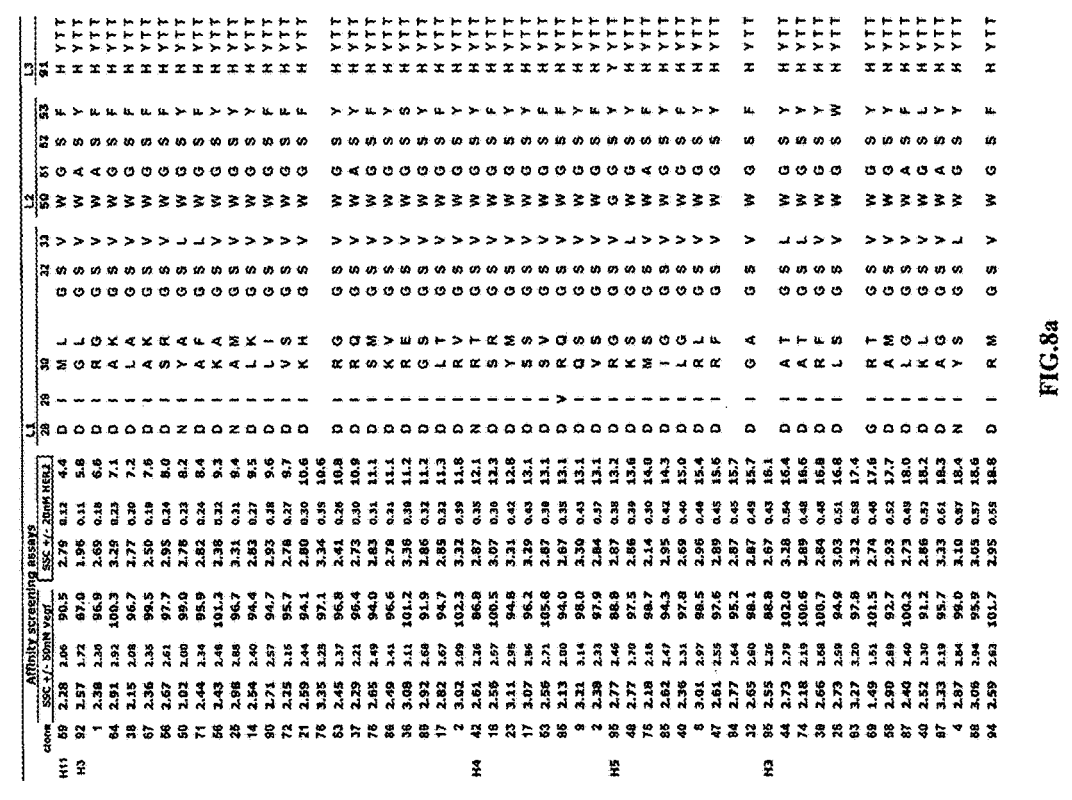
Figure 8B:
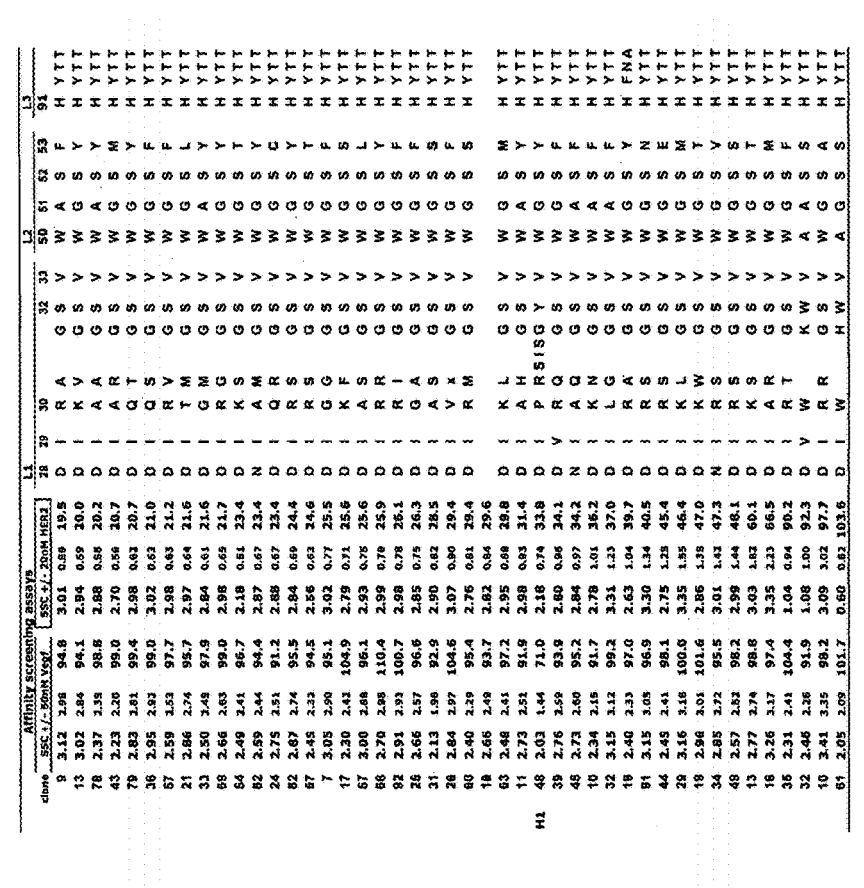
Figure 9:
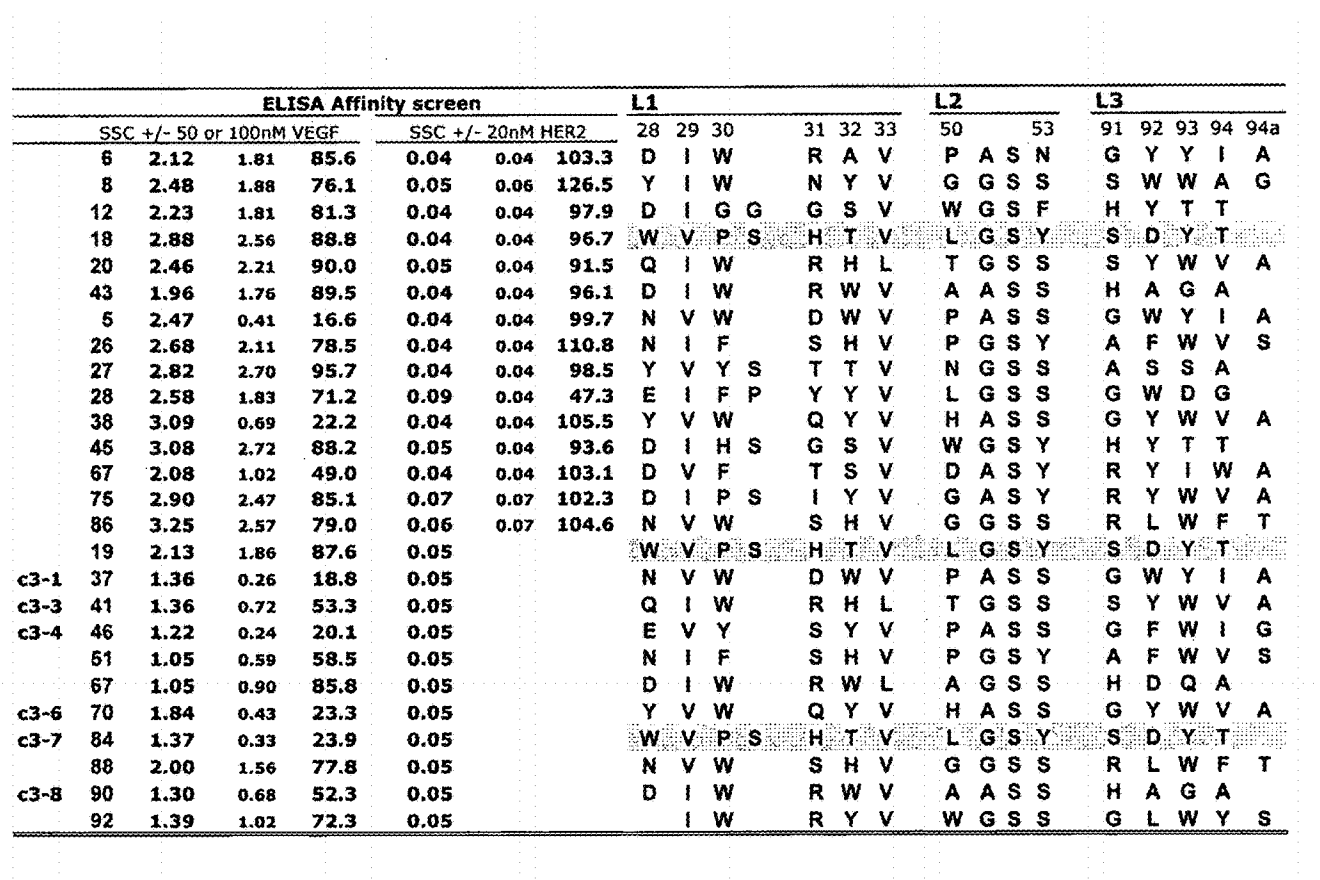

The library template for libraries L1/L2/L3-C and L1/L2/L3+L4-D was an scFv fragment modified from the hu4D5 antibody, which binds Her2 with high affinity. Mapping of the functional paratope of hu4D5-5 for Her2 binding by alanine-scan mutagenesis of the CDR regions showed that heavy chain residues contribute the majority of the free energy of binding, whereas individual light chain residues contribute to a lesser extent (Kelley and O'Connell, 1993). Analysis of the atomic structure of the Herceptin® antibody Fab in complex with human Her2-ECD demonstrates that while the light chain is involved in making antigen contact, the heavy chain provides most of the structural interface with the antigen (Cho et al., Nature 421:756, 2003). We observed that some members of the functional light chain libraries built upon Herceptin® antibody template retained Her2 binding ability. In an attempt to isolate bi-specific scFv fragments from the functional libraries L1/L2/L3-C and L1/L2/L3+L4-D, capable of binding Her2 as well as a second antigen, two strategies were applied. In one approach the positive clones from the previously described target antigen selection was screened by ELISA for ones that retained Her2 binding. The percentage of specific positive clones capable of binding Her2 varied depending on the second antigen specificity. Only 1 out of 61 unique hFc specific positive clones clone still bound Her2 (1.6%), 30 out of 41 unique hVEGF binding clones still bound Her2 (73%), and 2 out of 5 unique hDR5 binders still bound Her2 (40%). In addition, a selection-based approach was taken to isolate bi-specific antibodies by selecting Her2 binders from the pool of hVEGF and hDR5 binding antibodies. The elution from round 4 of target antigen sorting was subjected to an additional round of selection by incubating $2 \times 10^{13}$ phage/ml on Her2 coated (51 g/ml) and BSA-blocked Maxisorp immunoplates for 1 hour. The plates were washed 15 times with PBS, 0.5% Tween 20 and bound phage eluted as described previously. Random clones were selected and assayed for Her2, anti-gD and target binding and compared to non-specific binding to an un-relevant protein (BSA). All 192 clones tested were identified as specific positives and sequenced as described previously. Sequencing revealed 94 unique sequences. In summary, this method generated 94 Her2/hVEGF bi-specific clones out of the 94 unique clones tested (100%) (FIG. 5). The sequences of all isolated unique hVEGF/Her2 bi-specific antibodies from both isolation strategies are summarized in FIG. 8. The sequences of isolated clones that lost all detectable binding to Her2 are shown in FIG. 9. Of the clones that have dual specificity, nearly all retained the Herceptin® antibody CDR-L3, making it likely that maintaining CDR-L3 is important for maintaining HER2 binding. In the case of hDR5, 2 out of the 7 unique Her2-binding clones were bi-specific (29%, 12 clones sequenced). The sequences of these clones are summarized in FIG. 10. One of the dual specific clones had some homologous changes in CDR-L3.

High-Throughput Characterization of hVEGF Binding Clones

Figure 11:
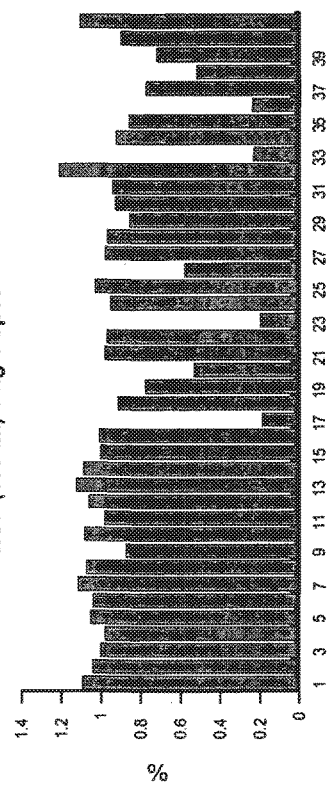
FIG. 11 shows clones binding to VEGF.
Figure 12A:
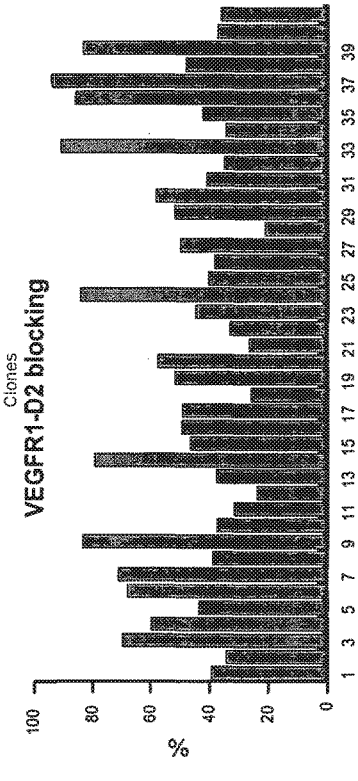
FIGS. 12A and 12B show clones that block VEGF binding to VEGFR1-D2 or D1.
Figure 12B:
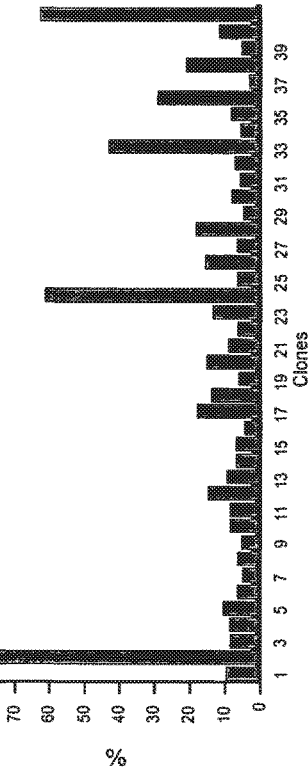

A high-throughput single spot competitive ELISA in a 96-well format (Sidhu et al., 2004) was used to screen for high affinity clones for hVEGF and to study the VEGFR1-blocking profiles. Briefly, Maxisorp Immunoplates were coated with 2 μg/ml $hVEGF_{109}$, overnight at 4° C. and blocked with 1% (w/v) BSA for 1 hour. Phagemid clones in E. coli XL1-Blue were grown in 150 μl of 2YT broth supplemented with carbenicillin and M13-KO7 helper phage; the cultures were grown with shaking overnight at 37° C. in a 96-well format. Culture supernatants containing phage were diluted fivefold in PBST (PBS with 0.05% Tween 20 and 0.5% (w/v) BSA) with or without the addition of 100 nM $hVEGF_{109}$ for affinity screen. For receptor blocking screens, hVEGF coated wells were incubated with or without VEGFR1 Domain 1-3 (D1-3) and VEGFR1 Domain 2 (D2) before adding five-fold diluted phage supernatant (Liang et al., 2006; Wiesmann et al., 1997). After incubation for 1 hour at room temperature (RT), the mixtures were transferred to the coated plates with $hVEGF_{109}$ and incubated for 10 minutes. The plate was washed with PBT (PBS with 0.05% Tween 20) and incubated for 30 minutes with anti-M13 antibody horse-radish peroxidase conjugate diluted 5000-fold to 1 nM in PBST. The plates were washed, developed with TMB substrate for approximately five minutes, quenched with 1.0 M $H_3PO_4$, and read spectrophotometrically at 450 mm. In the single-spot affinity assay, the ratio of the absorbance in the presence of solution-phase $hVEGF_{109}$ to that in the absence of solution-phase $hVEGF_{109}$ was used as an indication of the affinity. A low ratio would indicate that most of the Fab-phage were bound to solution-phase $hVEGF_{109}$ in the initial incubation stage and, therefore, were unavailable for capture by immobilized $hVEGF_{109}$. The high-throughput affinity assay results of the first 41 unique clones are summarized in FIG. 11. Similarly, for the blocking assay, a low ratio indicated that the binding of a clone to $hVEGF_{109}$ is blocked by the $hVEGF_{109}$-VEGFR1 interaction, indicating that some clones have an overlapping binding site (epitope) on VEGF with the respective VEGF receptor fragments (FIG. 12) and these clones are likely to be displaying the blocking antibodies.

High-Throughput Characterization of Bi-Specific hVEGF/Her2 Clones

Figure 13:
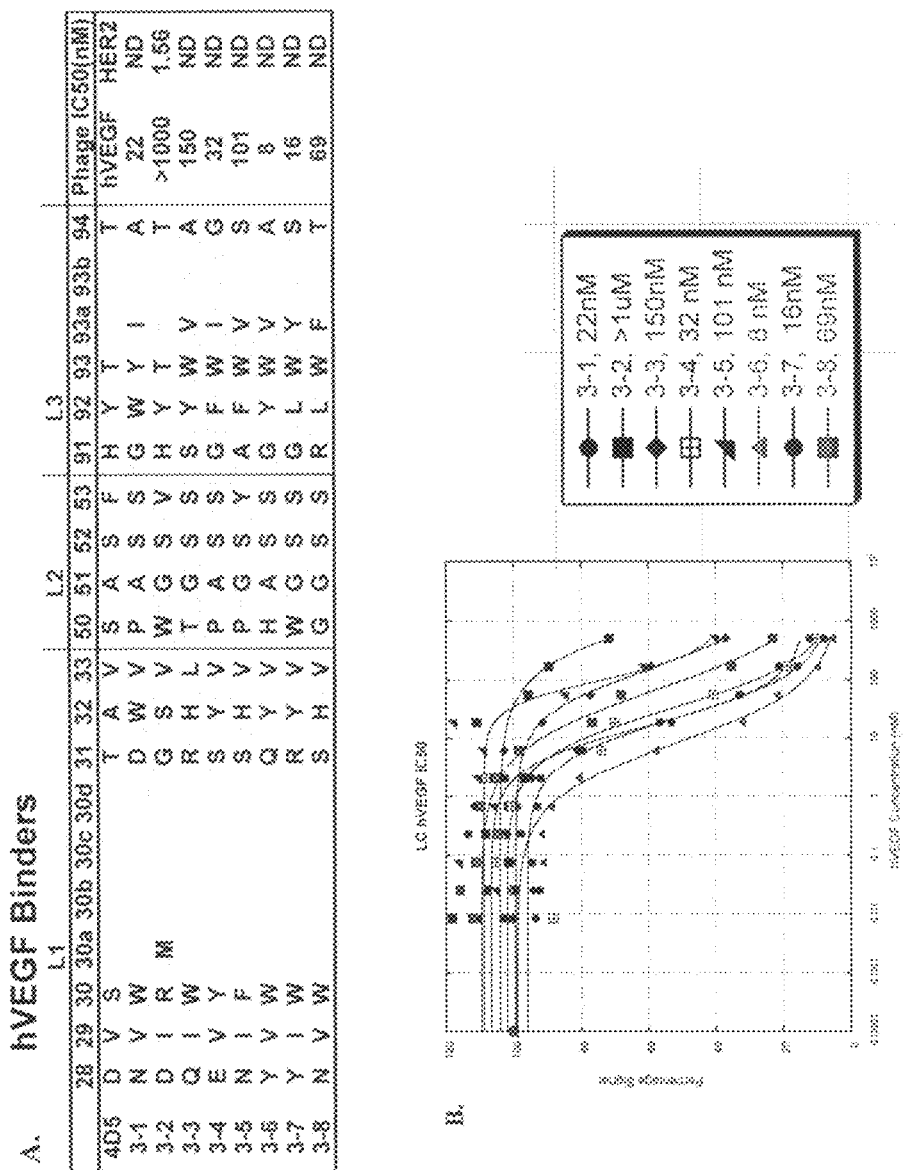
FIGS. 13A and 13B show the affinities of VEGF binders (SEQ ID NOS:4-5, 22-23, 26, 34, 77-79, 82, 85, 94-96, 98, 222-224, 426, 432, 434, 437-438, 440, and 509) from library L1/L2/L3-C,D.

The same principle as described in the previous section was applied to enable isolation of clones with high affinity for hVEGF and Her2 for further characterization. The high-throughput single point competitive ELISA was used to screen for high affinity clones for hVEGF and Her2 by coating Maxisorp Immunoplates with 2 μg/ml $hVEGF_{109}$, and Her2-ECD overnight at 4° C., followed by blocking with 1% (w/v) BSA for 1 hour. Phage clones that were identified as bi-specific in the previous single spot ELISA screen were grown as described previously and incubated with and without the addition of 20 nM Her2-ECD and 50 nM hVEGF. After incubation for 1 hour at room temperature, the solutions were applied to the coated immunoplates and the binding signals recorded and analyzed as described in the previous section. Clones with low ratio for both hVEGF and Her2 were selected for further characterization. hVEGF-specific and hVEGF/Her2 bi-specific phage clones that gave rise to the lowest signal ratios in the single spot competitive ELISA were selected for affinity measurement by competitive ELISA as well as the DR5-binding and DR5/Her2 bi-specific phage clones from the initial single spot ELISA screen and VEGF binding clones from the combined plate and solution selection. Phage clones were propagated from a single colony by growing in 25 ml of 2YT culture supplemented with carbenicillin and KO7 helper phage overnight at 30° C. Phage purified by precipitation in PEG/NaCl were first diluted serially in PBST and tested for binding to an antigen-coated plate. The dilution that gave 50-70% saturating signal was used in the solution binding assay in which phage were first incubated with increasing concentration of antigen for one to two hours and then transferred to antigen-coated plates for 10-15 minutes to capture the unbound phage. $IC_{50}$ was calculated as the concentration of antigen in solution-binding stage that inhibited 50% of the phage from binding to immobilized antigen (Lee et al., 2004a). FIG. 13B depicts the curves from which the $IC_{50}$ was calculated for the analyzed hVEGF binding clones from the plate sorting strategy. The $IC_{50}$ values ranged from 22 nM to >1 μM (FIG. 13B). The $IC_{50}$ values for the hVEGF binders isolated by combined plate and solution based selection ranged from 41 nM-226 nM (FIG. 7). $IC_{50}$ values of DR5-binding clones ranged from 20 nM to >1 μM (FIG. 14). The $IC_{50}$ values for hVEGF/Her2 and DR5/Her2 bi-specific clones are summarized in FIG. 15A and FIG. 15B. $IC_{50}$ values for Fc binding clones have not been determined.

Example 3. Characterization of Antibodies from the Light Chain Library

Conversion of scFvs to Fabs

To test whether conversion of the scFvs'2 as displayed on phage to Fabs affected the affinity of the binding clones from the library, 2 clones (3-7 anti-hVEGF and 4-1 anti-hDR5) were chosen for conversion to Fab and displayed on phage. The $V_L$ region of Phagemid DNA for selected hVEGF and DR5 scFv fragments was digested with restriction enzymes, which cleaved the DNA upstream of the region encoding for CDR-L1 (EcoRV) and downstream of the region encoding for CDR-L3 (KpnI). The digested DNA fragment was ligated into a similarly digested vector (pAP2009) designed for the phage display of Fab hu4D5 by fusion to the C-terminal domain of the M13 gene-3 minor coat protein (Lee et al., 2004b). The resulting bi-cistronic phagemid contains the light chain fused to an epitope (gD) tag at the C-terminus and heavy chain ($V_H$ and $C_H1$) fused to the gene for M13 minor coat protein (p3) C-terminally under the control of the alkaline phosphatase promoter. The first open reading frame encoded a polypeptide consisting of the stII secretion signal followed by the Fab4D5 light chain, with the CDRs replaced by those of 3-7 anti-hVEGF and 4-1 anti-hDR5 scFv'2, followed by a gD-tag epitope. The second open reading frame encoded a fusion polypeptide consisting of the following: the stII secretion signal, the Fab4D5 heavy chain, an amber (TAG) stop codon, a Gly/Ser linker sequence and c-terminal domain of g3 protein (cP3). Expression in E. coli XL-1 Blue co-infected with M13-KO7 resulted in the production of M13 bacteriophage displaying Fab versions of 3-7 and 4-1 scFv'2. Competitive phage ELISAs were used to estimate the affinities of the phage-displayed scFvs and Fabs for hVEGF and hDR5 as $IC_{50}$ values. The data from the two different formats were in good agreement (data not shown).

To enable display of bH1 Fab on the surface of M13 bacteriophage, plasmid pAP2009 was modified to encode bH1Fab. Versions of the bH1 Fab were used as library templates containing stop codons (TAA) in either the three LC CDRs or the three HC CDRs for the LC and HC library, respectively. Separate heavy chain and light chain alanine and homolog scanning libraries were constructed as previously described (Vajdos et al., J. Mol. Biol. 320:415, 2002). The degeneracy ranged from $1 \times 10^5$ to $1 \times 10^8$ and the actual library size from $6 \times 10^9$ to $4 \times 10^{10}$. The libraries were constructed as described above. Two to three rounds of selection were performed on immobilized targets (VEGF, HER2-ECD, protein L, or anti-gD mIgG) (Vajdos et al., J. Mol. Biol. 320:415, 2002). Target binding clones were screened by phage ELISA for target binding followed by DNA sequencing and sequence alignment to calculate the wild-type/mutation ratios at each position. The ratios from sequence analysis of approximately 100 unique sequences of VEGF and HER2 binding clones were corrected for display and protein folding effect by dividing with ratios calculated from the sequences of more than 100 anti-gD binding clones to yield the $F_{wt/mut}$ values. As only the Fab heavy chain is fused to the phage coat, the phage display of the gD tag, which is fused to the light chain, is indicative of proper folding and association of light chain and heavy chain. Consistently, protein L binding to a non-linear epitope on the light chain of the Fab also resulted in similar wild-type/mutation ratios as gD tag selections. $F_{wt/mut}$ values were converted to $\Delta\Delta G$ using the formula $\Delta\Delta G = RT \ln(K_{a,wt}/K_{a,mut}) = RT\ln(F_{wt/mut})$ as described in Vajdos et al. (J. Mol. Biol. 320:415, 2002).

Expression of Library Binders as Free Human Fab and IgG

To accurately determine the affinity, specificity and other properties of the antibodies, representative clones from each specificity group exhibiting the highest affinity in the competition ELISA experiments were selected for expression as free Fab and hIgG (FIG. 16). The variable domain of light chain and heavy chain was cloned into a vector previously designed for Fab expression in E. coli or transient human IgG expression in mammalian cells (Lee et al., 2004a). Fab protein was generated by growing the transformed 34B8 E. coli cells in complete C.R.A.P. medium at 30° C. for 26 hours as described (Presta et al., 1997). The hIgGs were expressed by transient transfection of 293 cells and hIgG was purified with protein A affinity chromatography (Fuh et al., J. Biol. Chem. 273:11197, 1998). The 1 L E. coli cultures were purified with protein G affinity chromatography. The columns were washed with PBS and Fab protein was eluted with 100 mM acetic acid and dialyzed against PBS. The 4 L E. coli cultures were purified on a protein A affinity column followed by cation exchange chromatography as previously described (Muller et al., 1998). Protein concentrations were determined spectrophotometrically. The final yield for Fab was typically 0.8-15 mg/l purified from a small-scale shake flask growth. IgG production yield was medium to high at 6.7-60 mg/l in small-scale culture (FIG. 17). The purified proteins were first characterized using size exclusion chromatography and light scattering to ensure that the proteins did not exhibit significant levels of protein aggregation (<5%).

Figure 18:
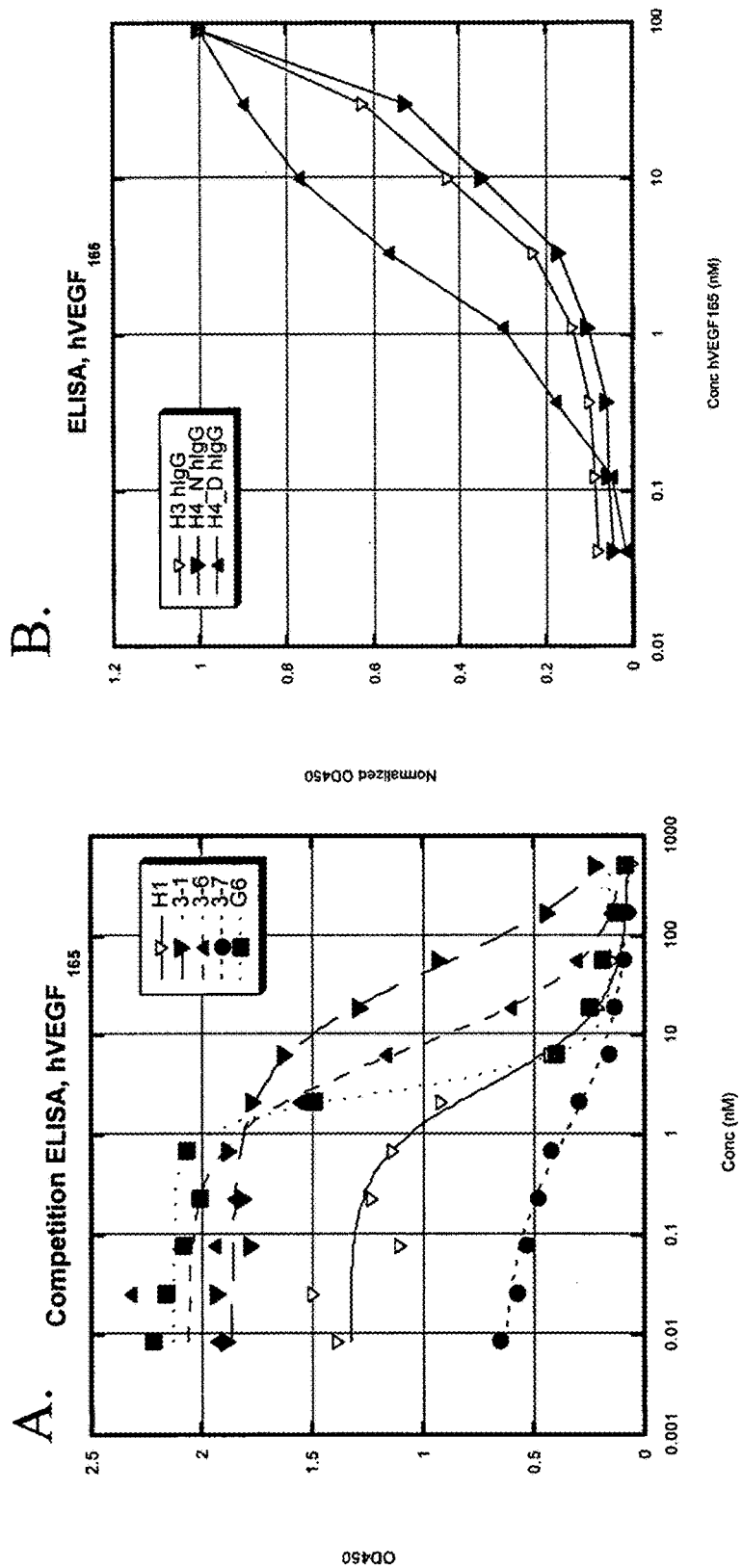
FIGS. 18A and 18B show ELISAs of clones in hIgG form binding to hVEGF165.

Briefly, the Fabs and hIgGs expressed were screened by ELISA for binding their respective antigen(s). All but one variant were found to bind their cognate antigen(s). Clone 4-6 lost hDR5 binding ability when converted to Fab and hIgG. Selected anti-VEGF clones, raised against the shorter form hVEGF$_{109}$, were tested for binding to hVEGF$_{165}$ using standard ELISA (H3, H4_N, H4_D hIgG), and competitive ELISA (bH1, 3-1, 3-6, 3-7 hIgG). G6 hIgG (Fuh et al., 2006) was used as a positive control (FIG. 18). As expected, all clones bound hVEGF$_{165}$.

To study the extent of protein aggregation selected clones were analyzed by Size-Exclusion chromatography (SEC) followed by Light Scattering (LS) Analysis as purified Fab and IgG. The samples were assayed in PBS at a concentration of 0.5 mg/ml (hIgG) and 1 mg/ml (Fab). A maximum of 5% aggregation was observed for all samples at the given concentration (FIG. 17), which is within range of what we have previously observed for other phage-display derived antibodies. Clones 3-6 and 3-7 did not come out at the expected time point, which suggested these reformatted IgG and Fab exhibit aggregation and or non-specific interaction with the resin (data not shown). These clones were taken out of the set of clones that underwent further analysis.

Figure 19:
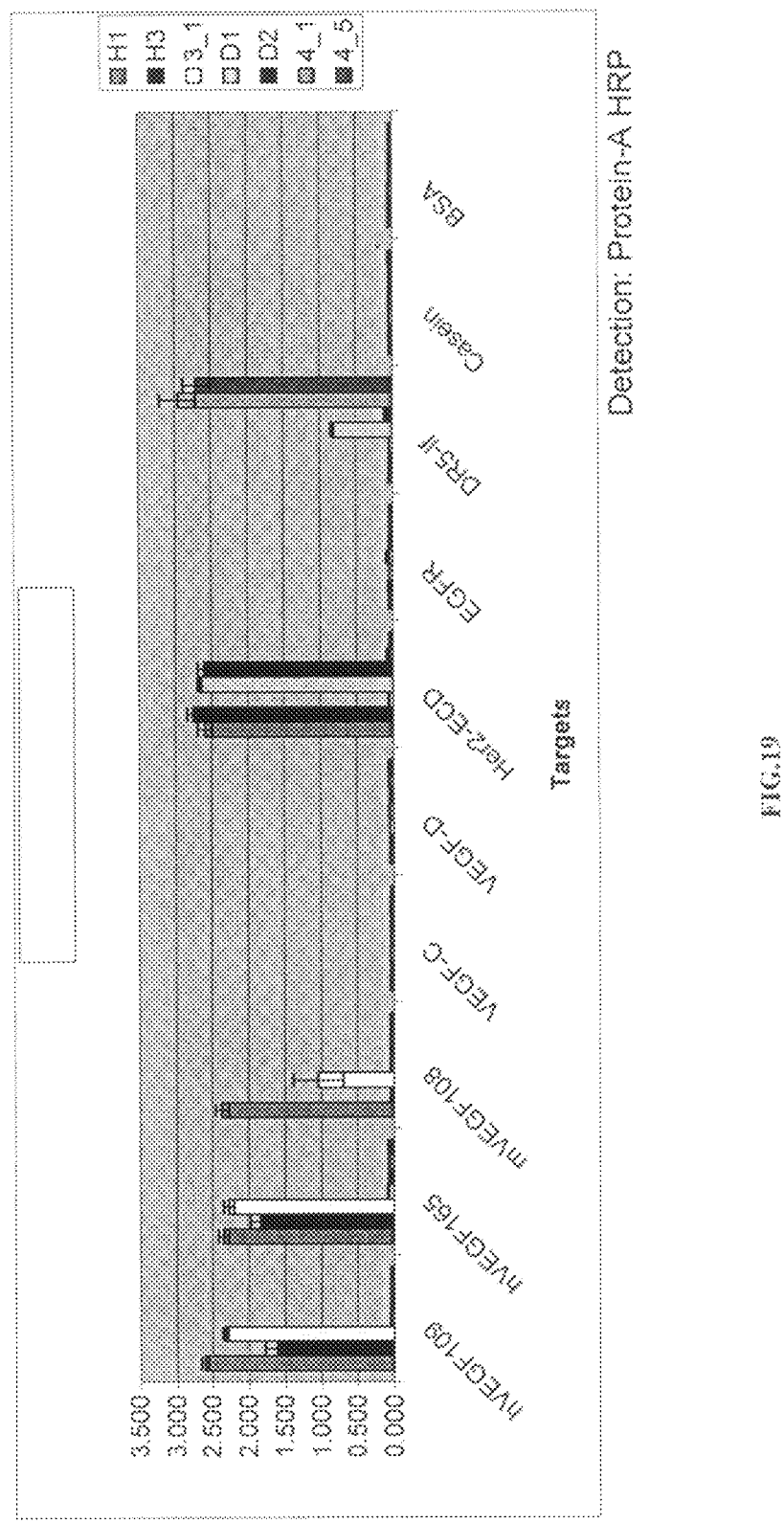
FIG. 19 shows ELISAs of clones in hIgG form binding to immobilized protein targets.

To rule out cross-reactivity and non-specific binding, we studied binding of selected hIgG at high concentration (100 nM) to a panel of immobilized a panel of protein targets including whole cell lysates, the cognate antigens, and homologues in a standard ELISA assay. In addition to antigen, we immobilized a murine version of hVEGF to test cross-species reactivity of the anti-hVEGF clones. In particular, the panel of proteins was immobilized on Maxisorp plates and blocked with 1% BSA in PBS for 1 hour. The hIgGs (or Fabs) were diluted in PBST to a concentration of 100 or 500 nM and transferred to the coated plates. After a 1 hour incubation, the plates were washed and incubated with HRP-conjugated protein A. The binding signals were developed by addition of TMB substrate for approximately 5 minutes, quenched with 1M $H_3PO_4$, and read spectrophotometrically at $A_{450}$. The hIgGs tested bound specifically to their antigen(s). Clones bH1 and 3-1 exhibited cross-reactivity to murine VEGF (mVEGF) (FIG. 19).

Figure 20:
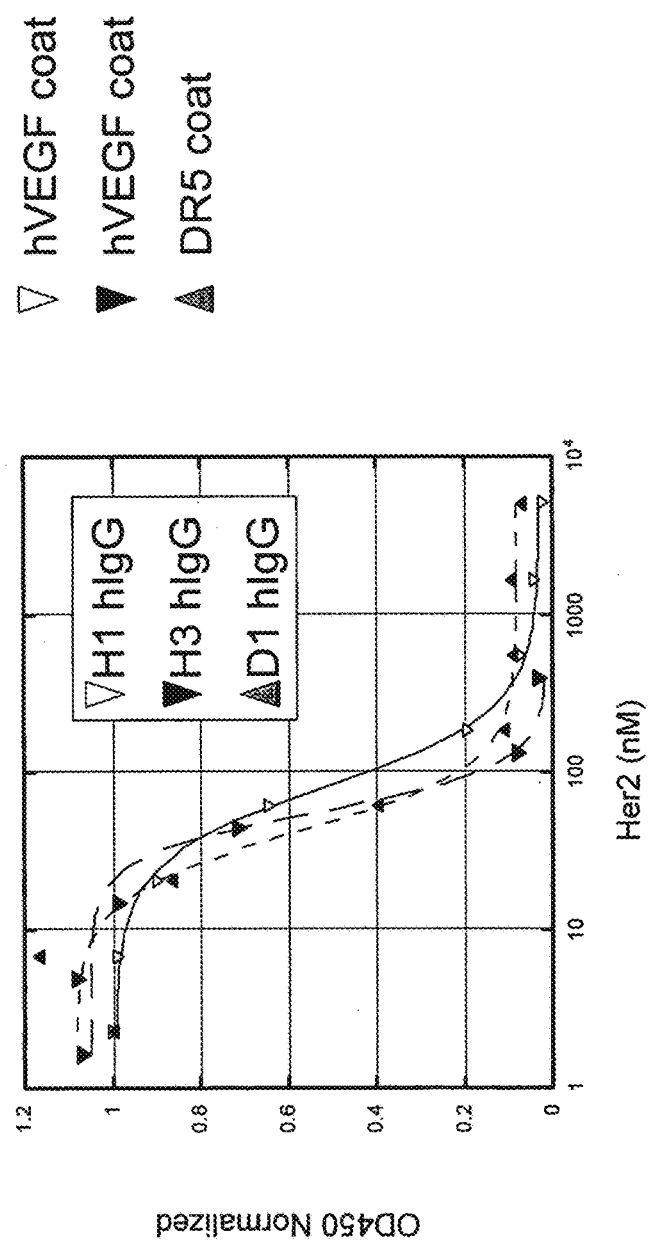
FIG. 20 shows competitive ELISAs of clones in hIgG form in the presence of Her2 and VEGF or DR5.

To test whether the bi-specific antibodies bH1, H3 (anti-hVEGF/Her2), and D1 (anti-hDR5/Her2) could simultaneously bind their cognate antigens or if the antigens compete for antibody binding, hVEGF and hDR5 were immobilized at a concentration of 2 μg/ml. A fixed concentration of hIgG was incubated with serial dilutions of Her2-ECD followed by capture of the hIgG on the immobilized antigen. In each case, Her2-ECD binding was found competitive with binding to the other antigens (FIG. 20).

To accurately determine the affinity of IgGs and Fabs (i.e., anti-hVEGF and anti-hVEGF/Her2 Fab and IgG isolated from the libraries) and to study the binding profiles in real time, we used surface plasmon resonance (SPR) assays on a BIAcore™-3000 (BIAcore, Uppsala, Sweden) machine with immobilized hVEGF, mVEGF, DR5, and Her2-ECD CM5 sensor chips at response units (RU) of 40-300 depending on the analyte studied. Immobilization was performed as described (Chen et al., 1999). To minimize avidity effects of the bivalent IgG analytes, a lower density of ligand was targeted on the sensor chip in these cases. Samples of increasing concentrations ranging from a concentration approximately 10-fold below to 10-fold above the estimated $K_D$ (based on competition ELISA experiments) were injected at 22-30 μl/minute, and binding responses were corrected by subtraction of RU from a reference flow-cell. In addition, the responses were double referenced to normalize for instrument drift by subtracting RU from ligand-conjugated flow-cell injected with sample buffer (PBS with 0.05% Tween 20). For kinetic analysis of the Fabs, a 1:1 Langmuir binding model of was used to calculate the $k_{on}$ and $k_{off}$. When necessary (at high analyte concentrations) a 1:1 Langmuir binding model with mass-transfer limitation was applied. For the IgG analytes, a bivalent analyte binding model with or without mass-transfer limitation was used (BIAcore Evaluation Software 3.2). In the case of H3 hIgG, H4_N Fab, and H4_D hIgG, the fit of responses to the kinetic binding models was not satisfactory. Therefore, steady state binding analysis was applied where the equilibrium response was plotted against analyte concentration. The $K_D$ was estimated as the $EC_{50}$. A summary of the BIAcore binding analysis can be found in FIG. 21. The affinity of the hVEGF binding antibodies 3-1, 3-6 and 3-7 was found to be in the nano molar range. The bi-specific antibodies analyzed (bH1, H3, H4_N, H4_D) showed low micromolar to micromolar affinities for hVEGF. In contrast, the affinities for Her2 ranged from 8-59 nM (Fab).

Figure 22:
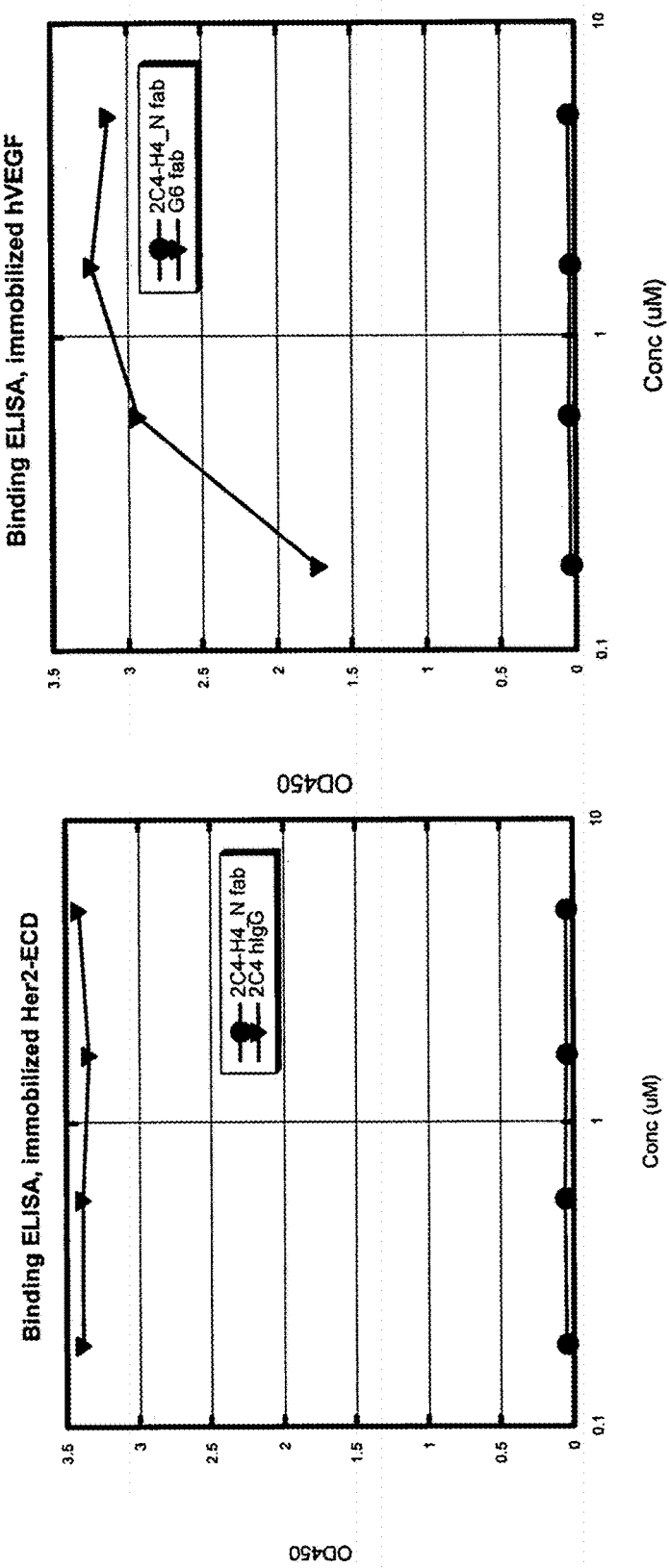
FIG. 22 shows binding to HER2-ECD or hVEGF with an IgG or Fab having a light chain obtained from a different binding clone.

To determine whether the light chain of anti-hVEGF binders bH1, H3, and H4_N could bind hVEGF independent of the sequence of the associated heavy chain, the light chain variable domains were grafted onto the anti-Her2 2C4 Fab by cloning the light chain variable domains into a 2C4 Fab expression vector pJB0524, thus replacing 2C4 light chain variable domain. The Fabs were expressed as previously described. The bH1/2C4 and H3/2C4 chimeric Fabs did not express at detectable levels. The H4_N/2C4 chimeric Fab protein was isolated and tested for binding to hVEGF (bH1 original specificity) and Her2 (bH1, 2C4 original specificity). No binding was detected to hVEGF and Her2 by a standard ELISA binding assay (FIG. 22). The results indicate that the heavy chain of bH1 is required for antigen binding.

Comparison of Anti-hVEGF Epitopes

Figure 23:
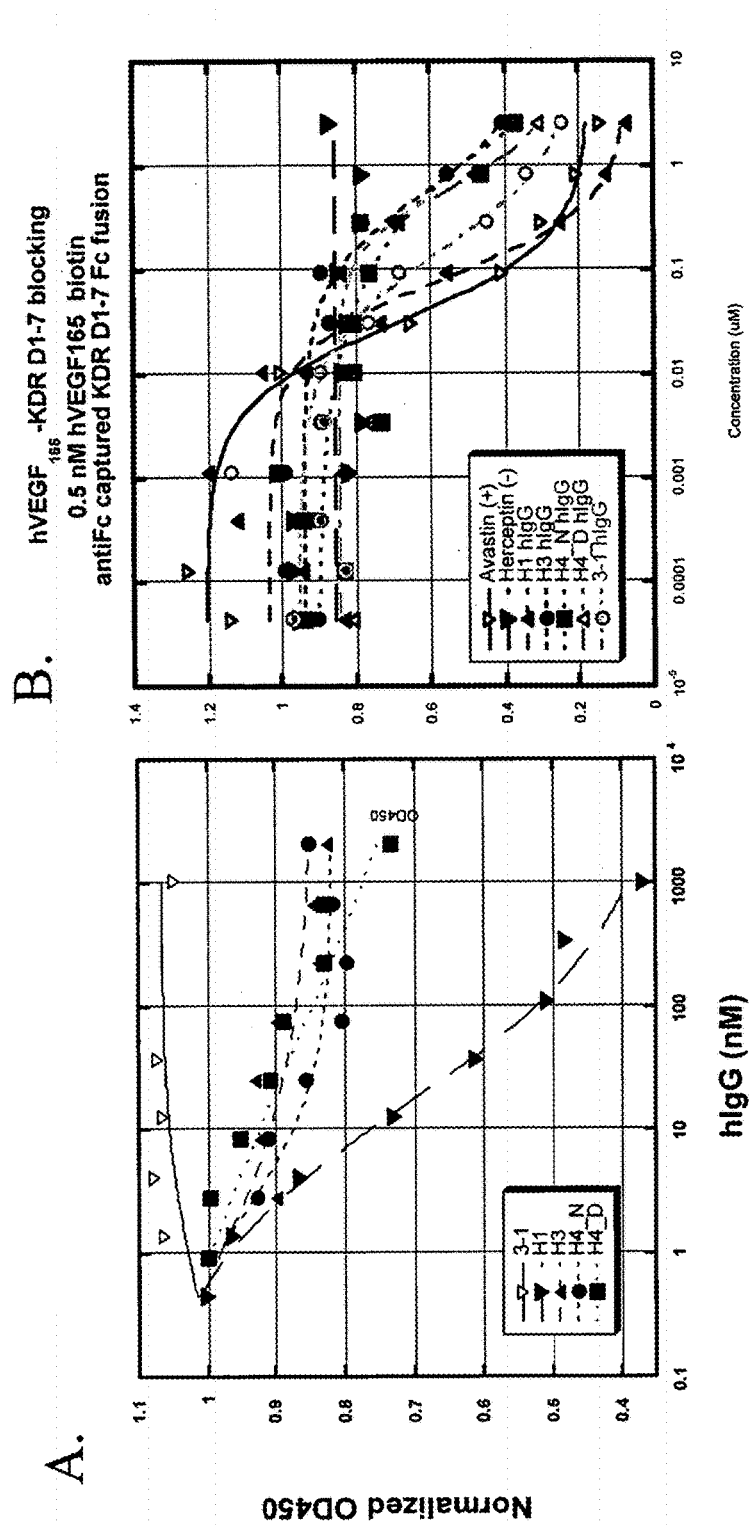
FIGS. 23A and 23B show an anti-VEGF antibody blocking VEGF interaction with VEGFR1 D 1-3 and KDR D1-7.
Figure 24:
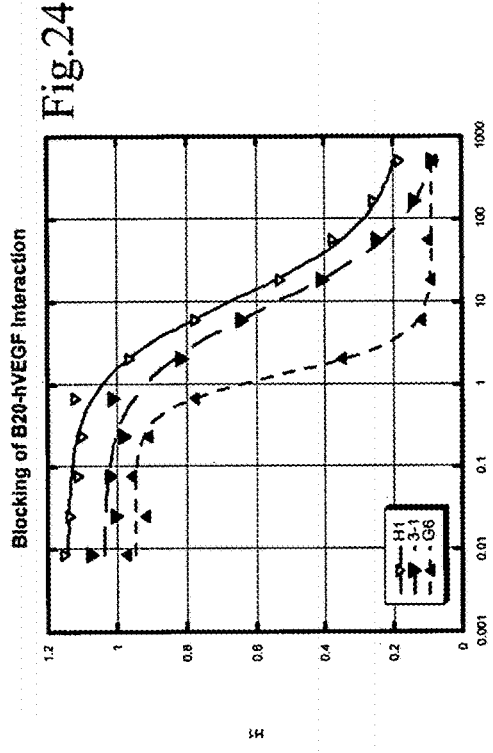
FIG. 24 shows antibodies blocking B20-4.1 and VEGF binding.
Figure 25:
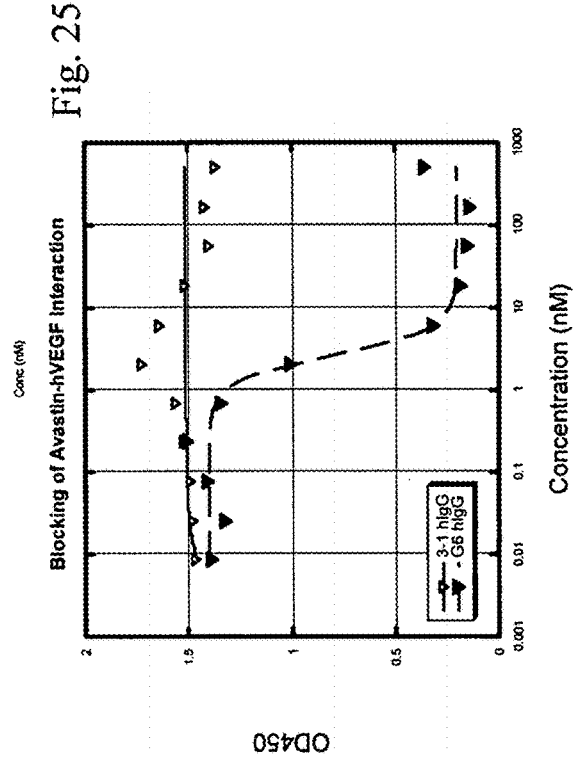
FIG. 25 shows antibodies blocking Avastin® antibody and VEGF binding.

In an attempt to roughly map out the epitopes of the anti-hVEGF antibodies on hVEGF, we studied the ability of these newly isolated anti-VEGF antibody to compete with other hVEGF binding antibodies and VEGF receptors with known binding sites (Fuh et al., 2006; Muller et al., 1998; Wiesmann et al., 1997). The assays were done in a competitive ELISA format where the VEGFR1 (Flt) Domain 1-3 and anti-hVEGF antibodies Avastin® (IgG), B20-4.1 (IgG), G6 (Fab), and KDR Domain 1-7 Fc fusion protein were immobilized on Maxisorp immunoplates at 2 μg/ml. The solution competition binding assay used biotinylated VEGF equilibrated with serial dilutions of purified IgG proteins, and the unbound biotin-VEGF was captured with immobilized Fab or IgG coated on Maxisorb plates and was detected with streptavidin-conjugated HRP (Lee et al., J. Mol. Biol. 340:1073, 2004). Antibodies that block hVEGF from binding other hVEGF-binding antibodies or hVEGF-receptors are likely to share over-lapping epitopes. High concentrations (μM) of the bi-specific hVEGF/Her2-binding antibody, bH1, enabled complete blocking of hVEGF binding to its receptors, VEGFR1 and VEGFR2, suggesting bH1 epitope overlaps sufficiently with VEGFR1 (FIG. 23) and VEGFR2 (FIG. 23). In addition, bH1 blocks hVEGF binding to B20-4.1 (FIG. 24). H3, H4_N, and H4_D also block hVEGF-binding to both receptors, which points to similar epitopes as bH1 (FIG. 23). The incomplete blocking profiles are likely to be a consequence of their relatively low affinity for hVEGF (FIG. 21). 3-1, in contrast, does not block hVEGF from binding VEGFR1, even at the highest concentration (0.5 μM) (FIG. 23). Furthermore, we could not detect 3-1 hIgG blocking of the Avastin® antibody (FIG. 25). However, 3-1 hIgG block hVEGF binding to VEGFR2 (KDR) (FIG. 23) as well as to B20-4.1 (FIG. 24). These results indicate that 3-1 has a unique epitope compared to the other antibodies.

Example 4. Structure-Function Studies of bH1, Anti-hVEGF/Her2 Bi-Specific Antibody To elucidate the nature of the bH1 interaction with its two antigens, VEGF and HER2, structural and functional studies was performed. The Herceptin® antibody and bH1 differ in CDR-L1 ($V^{29}NTA^{32}$ (SEQ ID NO:39) vs. $I^{29}PRSISGY^{32}$ (SEQ ID NO:40)) and CDR-L2 ($S^{50}ASF^{53}$ (SEQ ID NO:5) vs. $W^{50}GSY^{53}$ (SEQ ID NO:25)). The bH1 anti-VEGF/Her2 was chosen as representative for structural characterization based on its dual specific nature and its relatively high affinity for VEGF and Her2. In order to study the functional and structural epitopes on VEGF and Her2, we crystallized the bH1 Fab in complex with $VEGF_{109}$ and the extracellular domain of hHer2 and solved the structures of the two complexes by X-ray crystallography. In addition, we performed alanine and homolog shotgun scanning analysis using combinatorial phage displayed libraries as described (Vajdos et al., 2002).
bH1 Fab Expression, Purification, Crystallization and Data Collection The receptor-binding portion of human VEGF, consisting of residues 8-109, was expressed, refolded and purified as described previously (Christinger et al., 1996). Residue 1-624 of the extra cellular domain of Her2 was expressed and purified as previously described (Franklin et al., 2004; Hudziak and Ullrich, 1991).

For large-scale bH1 Fab preparation, whole cell pellet was obtained from a ten liter *E. coli* fermentation. 220 grams of cell paste was thawed into 1 L PBS, 25 mM EDTA, 1 mM PMSF. The mixture was homogenized and then passed twice through a microfluidizer. The suspension was then centrifuged at 12 k in 250 ml aliquots for 90 minutes. The protein was then loaded onto a Protein G column (25 ml) equilibrated with PBS at 5 ml/minute. The column was washed with equilibration buffer and then eluted with 0.58% acetic acid. The fractions were assayed by SDS PAGE (data not shown). Fractions containing bH1 Fab were pooled and then loaded onto a 50 ml Cation Exchange SP Sepharose column (Pharmacia) equilibrated with 20 mM MES pH 5.5. The Fab was eluted with a sodium chloride gradient in the equilibration buffer. The gradient was linear to 0.5 M NaCl, 20 mM MES pH 5.5. Fractions containing the Fab were identified by SDS-PAGE (data not shown), and pooled. bH1 Fab eluted at a NaCl concentration of approximately 0.5 M. The Fab concentration was determined by measuring the $A_{280}$. The final yield for bH1 Fab was 67 mg/l fermenter growth.

Complexes were obtained by mixing the purified bH1 Fab and VEGF or Her2 ECD in 2:1 molar ratio and purified by size-exclusion chromatography (SP-200, Pharmacia) in 25 mM Tris-HCl, pH 7.5 and 0.3 M sodium chloride for VEGF-Fab complex and with 25 mM Tris-HCl, pH 8 and 0.15 M sodium chloride for the Her2 ECD-Fab complex. The composition of the resulting complexes was verified by SDS PAGE. (Data not shown.) The protein complex was concentrated and used in crystallization trials. Initial hanging-drop experiments using the vapor-diffusion method at 19° C. resulted in small isomorphous crystals from 14 different conditions within 1 week in the case of the bH1-VEGF complex. Crystals of the bH1-Her2 complex appeared in 4 conditions within a week. Crystals from one condition was chosen for further optimization in each case.

For crystallization of bH1 Fab-VEGF (8-109), equal volumes of protein complex solution (10.6 mg/ml protein, 300 mM NaCl, 25 mM Tris-HCl pH 7.5) and crystallization buffer containing 0.15 M D, L Malic Acid pH 7.0, 20% $PEG_{3350}$ was mixed and equilibrated at 19° C. Large crystals appeared after 24 hours which belonged to space group C222, with cell dimensions of a=100.6, b=198.0, c=77.7. The crystal forms contained 1 Fab and 1 VEGF monomer in the asymmetric unit. Prior to data collection the crystals were cryo-protected by transfer between drops containing 5%, 10%, and 15% glycerol in artificial mother liquor, followed by a flash freeze in liquid nitrogen. Data was collected to 2.6 Å at the beam line 5.0.1 of the Advanced Light Source (Berkeley).

Crystals of bH1 Fab-Her2(1-624) was obtained by mixing protein solution (11 mg/ml, 25 mM Tris pH 8 and 150 mM sodium chloride) with crystallization buffer containing 25% w/v $PEG_{2000}$, 0.1M MES pH 6.5. Crystals appeared after 12 hours that belonged to space group $P2_12_12_1$ with cell dimensions of a=62.3, b=115.1, c=208.2. The crystals contained one Her2-Fab complex in the asymmetric unit. Before data collection the crystals were flash frozen in liquid nitrogen with 20% Ethylene Glycol as cryo-protectant. Data was collected to 2.9 Å at the beam line 5.0.1 of the Advanced Light Source (Berkeley).
Data Processing, Structure Determination, and Refinement The data was processed using Denzo and Scalepack (Otwinowski, 1997). The structures of bH1 Fab complexes was solved by Phaser (L. C. Storoni, 2004; Read, 2001). The bH1-Fab-VEGF(8-109) complex was solved using coordinates of VEGF from a previously described VEGF-Fab complex (2FJG) and Fab fragments containing either the variable domains $V_L/V_H$ or the constant domains $C_{H1}/C_L$ of the Herceptin® antibody Fab-Her2 complex (1N8Z). Fragments of Her2 and the variable domain of the Herceptin® antibody Fab from the Her2-Fab complex 1N8Z were used as search models when solving bH1-Her2 structure. The constant domain of the bH1 Fab could not be found using the Herceptin® antibody Fab constant portion as a search model (1N8Z) and had to be docked manually guided by the Herceptin® antibody Fab-Her2 complex structure. Model building and refinement were performed using the programs Refmac (Collaborative Computational Project, 1994) and Coot (Emsley and Cowtan, 2004), respectively. Stereochemical parameters were analyzed using MolProbity (Lovell et al., Proteins 50:437 (2003)). The structures were refined to $R_{value}$=0.22 and $R_{free}$=0.27 for the Fab-VEGF-complex and $R_{value}$=0.25 and $R_{free}$=0.31 for the Fab-Her2-complex. A crystal structure of bH1 Fab in complex with VEGF as well as Her2-ECD was modeled. Some bH1 Fab residues were within 4.5, 4.0, and 3.5 Å of the antigens. The two paratopes (the area on the antibody that makes contact with the antigen) for the two antigens on the same antibody overlap significantly and residues from both light chain and heavy chain are involved with the binding with both antigens. bH1 binds a similar epitope on VEGF as the Avastin® antibody, and bH1 binds Her2 on an essentially identical epitope as the Herceptin® antibody.

The crystal structures of bH1 Fab bound to the extracellular domain (ECD) of HER2 (residue 1-624) and to the VEGF receptor-binding domain (residue 8-109) were determined at 2.9 Å and 2.6 Å resolutions, respectively (FIG. 35A and Table 3). FIG. 35A shows the bH1 Fab/HER2 crystal structure superimposed with the Herceptin® antibody/HER2 complex, and the crystal structure of the bH1 Fab/VEGF complex.

TABLE 3

Crystallographic Studies

|  | bH1 Fab/hVEGF complex | bH1 Fab/HER2-ECD complex |
|---|---|---|
| Data Collection Statistics |  |  |
| Space group | $C222_1$ | $P2_12_12_1$ |
| Unit Cell (Å) | a = 100.6, b = 198.0, c = 77.7 | a = 62.3, b = 115.1, c = 208.2 |
| Beamline, wavelength | ALS 5.0.1 | ALS 5.0.1 |
| Resolution (Å) | 50.0-2.6 | 50.0-2.9 |
| Rsym$^a$ | 0.090 (0.66) | 0.095 (0.66) |
| Number of Observations | 151689 | 192951 |
| Unique Reflections | 24705 | 34149 |
| Completeness (%)* | 99.8 (100) | 100 (100) |
| I/σ (I)* | 16.0 (3.0) | 18.5 (2.6) |
| Refinement Statistics |  |  |
| Content of assymmetric unit | ½ VEGF dimer, 1 Fab | 1 Her2-ECD monomer, 1 Fab |
| Resolution (Å) | 30.0-2.6 | 30.0-2.9 |
| Reflection used | 22977 | 32277 |
| R Factor$^b$, Rfree | 0.19, 0.25 | 0.22, 0.28 |
| RMS Deviation Bonds (Å) | 0.011 | 0.010 |
| RMS Deviation Angles (°) | 1.3 | 1.3 |
| Ramachandran Statistics |  |  |
| Favoured Regions (%) | 96.5% | 89.9% |
| Allowed Regions (%) | 99.4% | 97.9% |
| Outliers (%) | 0.6% | 2.1% |
| Number of Residues | 528 | 1017 |
| Numbers of waters | 49 | 0 |
| Number of Sugars | 0 | 2 |
| Number of Ligands/Ions | 1 (Glycerol) | 1 (MES) |

Rsym$^a$ = Σ|I − <I>|ΣI. <I> is the average intensity of symmetry-related observations of a unique reflection.
R Factor$^b$ = Σ|F0 − Fc|ΣF0. Rfree is calculated as R except for 5% of the reflections excluded from all refinements.
*Values in parenthesis denote values of the highest resolution shell.

Figure 35D:
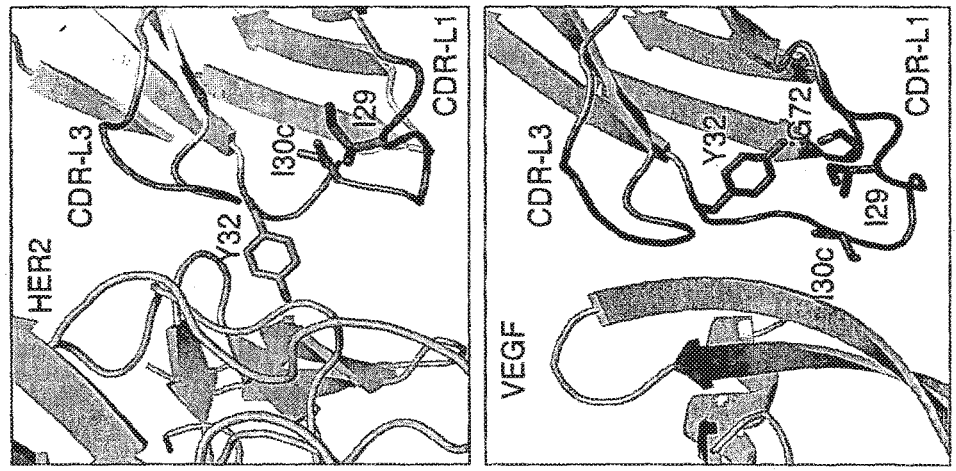
Figure 35C:
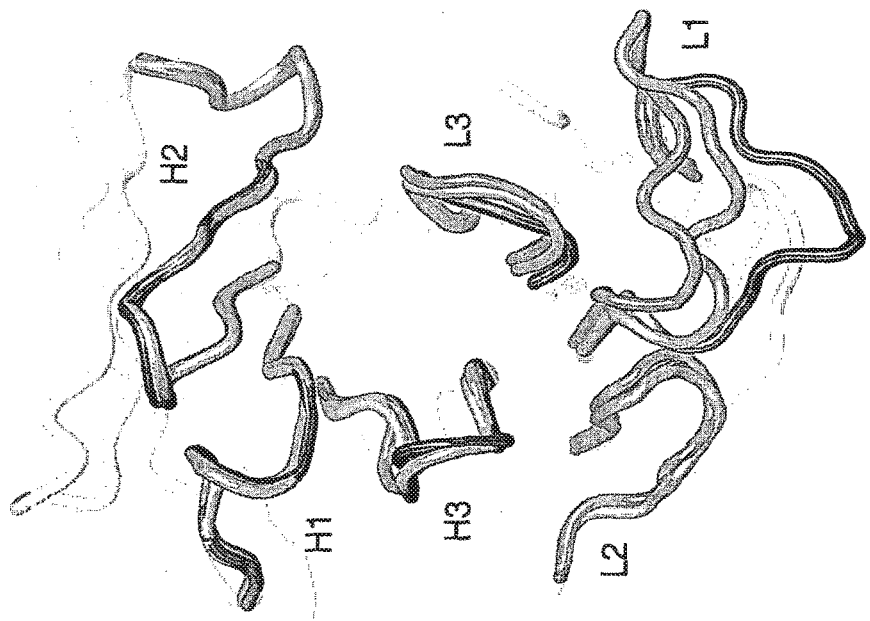
Figure 35E:
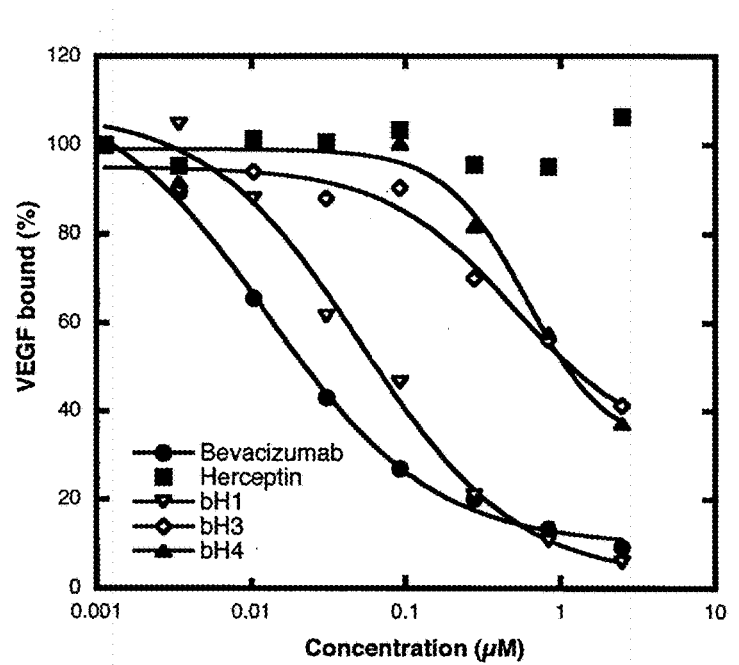
FIG. 35E is a graph showing that anti-VEGF antibodies block hVEGF binding to VEGF receptor 2 (VEGFR2).

In the bH1/HER2 complex, the Fab binds to domain IV of HER2 in a manner similar to the Herceptin® antibody (Cho et al., Nature 421:756, 2003); the two complexes superimpose with a root mean square deviation (r.m.s.d.) of Cα positions of 2.3 Å. In the VEGF complex, bH1 recognizes an epitope that overlaps with the binding sites of the VEGF receptors VEGFR1 and VEGFR2 and of other VEGF antibodies (Wiesmann et al., Cell 91:695, 1997; Muller et al., Proc. Natl. Acad. Sci. USA 94:7192, 1997). Consistently, the bH1 blocking of VEGF binding to its receptors was observed (FIG. 35E). For the data shown in FIG. 35E, biotinylated human $VEGF_{165}$ was equilibrated with increasing concentrations of IgG (x-axis). Unbound $hVEGF_{165}$ was captured on immobilized VEGFR2-ECD Fc fusion and detected spectrophotometrically (optical density at 450 nm, y-axis).

Figure 35F:
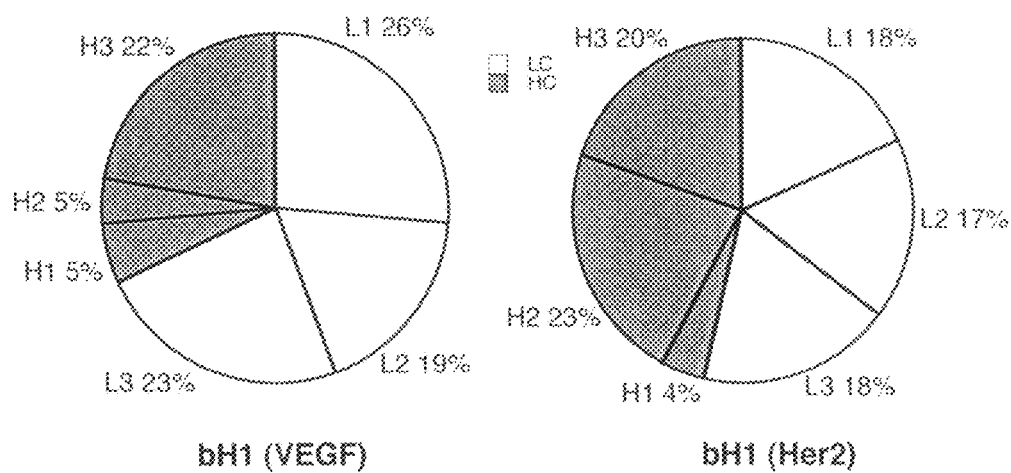
FIG. 35F is a series of pie charts showing the individual CDR contributions to the structural paratope for bH1. The paratope size for VEGF is 730 Å$^2$ and for HER2 is 690 Å$^2$. The heavy chain CDRs are indicated in gray and the light chain CDRs in white.

As shown in FIG. 35B, the binding sites for VEGF and HER2 on bH1 overlap extensively. Twelve out of the fourteen residues that engage HER2 also contact VEGF. Both binding sites include CDR residues from the HC as well as LC. In the HER2 complex, the LC and HC CDRs contribute approximately equal antigen contact area (53% and 47% respectively) while in the VEGF complex, the LC CDRs constitute nearly 70% of the buried surface (FIG. 35F). The HER2 binding site on the Herceptin® antibody and bH1 are similar and differ only in the CDR-L1 and -L2 regions where the Herceptin® antibody sequence is not conserved in bH1 (FIG. 35B). In FIG. 35B, residues on the bH1 or the Herceptin® antibody Fab surface are shaded according to the extent buried by VEGF or HER2 (dark shading and white lettering >75% buried, intermediate shading and white lettering 50-75% buried, light shading and black lettering 25-49% buried). The underlined residues differ between bH1 and the Herceptin® antibody. The white dotted line depicts the divide of light and heavy chain.

The conformation of bH1 Fab in complex with HER2 is markedly similar to that of the VEGF-bound Fab (r.m.s.d.=0.7 Å, Cα). The CDRs of both bH1 Fab structures superimpose well with each other and with the parent Herceptin® antibody Fv and bH1 Fv (HER2) r.m.s.d.=0.6 Å, the Herceptin® antibody Fv and bH1 Fv (VEGF) r.m.s.d.=1.2 Å. The CDR-L1 is an exception and differs significantly in the two complex structures; the deviation is 4.6 Å (Cα of residues 27-32). FIG. 35C shows that the CDR conformations of bH1 Fab bound to VEGF are markedly similar to HER2-bound bH1 and to the Herceptin® antibody, with exception of the CDR-L1. FIG. 35C is a superposition of the CDR loops as tubes of VEGF-bound bH1 (dark shading), HER2-bound bH1 (white) and HER2-bound the Herceptin® antibody (light shading). The CDR-L1 loop exhibits significantly different conformations in the two bH1 structures (r.m.s.d.$_{Cα}$=4.6 for bH1 residues 27-32) (FIG. 35D). In the HER2 complex, the CDR-L1 is minimally involved in antigen interaction and part of the loop (residues 28-30b) appears flexible. For VEGF binding, the entire loop is well structured and contributes 26% of surface area buried by VEGF.

Two residues in CDR-L1, Ile30c and Tyr32, have different conformations and play different roles in bH1 binding to HER2 or VEGF. In the HER2 complex, the side chain of Ile30c is buried in the hydrophobic core formed by CDR-L1 and CDR-L3 residues. In the VEGF complex, this side chain forms hydrophobic contacts with VEGF. The Cα of Tyr32 is in the same position in the two structures, but its side chain is rotated ~130 degrees. In the HER2 complex Tyr32 packs against the receptor, while in the VEGF complex the side chain, together with Ile29, form the hydrophobic core and support the conformation of CDR-L1 and CDR-L3. The CDR-L1 conformation is further stabilized by hydrogen bonds between Tyr32 and the LC framework residue Gly72. The structural analysis confirms that Tyr32 is critical for VEGF binding as mutation to either alanine or phenylalanine is not tolerated. Contrary to VEGF binding, mutation of Tyr32 to alanine (back to the Herceptin® antibody residue) is preferred for HER2 binding. Superposition of the two complexes reveals that VEGF would clash with Tyr32 of CDR-L1 in its HER2 bound state (FIG. 35D). In FIG. 35D the side chains of residues Tyr32, Ile30c, Ile29, and Gly72 are shown as sticks. Residues with temperature factors higher than average are shown in darker shading (residues 28-30b). Hydrogen bonding between Tyr32 and Gly72 is illustrated by a dotted line.

The above results indicate that the capability to rearrange CDR-L1 is necessary for the bi-specificity of bH1. Similar conformational flexibility of CDR-L1 has been shown to play a role in antigen recognition of natural antibodies (Jimenez et al., Proc. Natl. Acad. Sci. USA 100:92, 2003; Mylvaganam et al., J. Mol. Biol. 281:301, 1998). FIGS. 35A-35D and FIG. 36C are generated from the crystal structure coordinates (PDB codes, X, Y, 1N8Z) using PYMOL (DeLano Scientfic, San Carlos, Calif.).

bH1 Shotgun Scanning

To study the antigen-binding sites of bH1 Fab, shotgun scanning combinatorial mutagenesis using phage-displayed Fab libraries was performed (Vajdos et al., J. Mol. Biol. 320:415, 2002; Weiss et al., Proc. Natl. Acad. Sci. USA 97:8950, 2000). Binding selections on the antigens (hVEGF and Her2-ECD) to isolate functional clones followed by DNA sequencing enabled calculations of wild-type/mutant ratios at each varied position (Vajdos et al., 2002). These ratios were then used to determine the contribution of each scanned side-chain to VEGF and Her2 binding. The results enabled mapping of the functional paratope for binding VEGF and Her2.

bH1 Shotgun Library Design

Solvent exposed residues in the CDRs were scanned using phage-displayed libraries in which the wild type residues were allowed to vary as either alanine or wild type (Alanine Scan) or as a homolog residue or wild type (Homolog Scan). The nature of the genetic code required some other substitutions to be included in the library in addition to Wt/Alanine or Wt/Homlog residues (FIG. 28). Separate heavy chain and light chain alanine and homolog scanning libraries were constructed. The libraries are described in FIG. 29. The degeneracy ranged from $1.3 \times 10^5$ to $1.3 \times 10^8$ and the actual library size from $6 \times 10^9$ to $4 \times 10^{10}$.

Construction of Shotgun Scanning Libraries

As noted above, to enable display of bH1 Fab on the surface of M13 bacteriophage, a previously described plasmid AP2009 designed to display hu4D5Fab on phage fused to the C-terminal domain of the M13 gene-3 minor coat protein, was modified to encode bH1Fab using standard molecular biology techniques. The C-terminus of the light chain contained an epitope (gD) tag. "Stop template" versions of the bH1 Fab was used as library template (Sidhu et al., 2004). The light chain alanine and homolog scanning library had stop codons in CDR-L1, CDR-L2 and CDR-L3 and the heavy chain alanine and homolog libraries contained stop codons in each heavy chain CDR. The libraries were constructed by previously described methods (Sidhu et al., 2004) using Kunkel mutagenesis (Kunkel et al., 1987) on the respective stop templates.

Library Selection

NUNC 96-well Maxisorp immunoplates were coated with 5 μg/ml capture target (hVEGF$_{109}$, Her2-ECD or anti-gD mIgG) and blocked with 1% BSA (w/v) in PBS. Phage from the above-described libraries were propagated with KO7 helper phage (NEB) as described (Lee et al., 2004a). The library phage solutions were added to the coated plates at a concentration of $10^{13}$ phage particles/ml and incubated for 1-2 hours at RT. The plates were washed 8 times with PBST and followed by elution of bound phage with 0.1 M HCl for 30 minutes. Enrichment after each round of selection was determined as described previously. After 2 rounds of target selection, 50-1000 fold enrichment was observed for all libraries except LC-Ala and LC-Hom sorted on hVEGF, which showed 5-10-fold enrichment. A number of random clones from each library exhibiting 50-1000-fold enrichment was selected for sequencing as described (Sidhu et al., 2004). Library LC-Ala was screened for hVEGF binding in phage ELISA (Sidhu et al., 2000). Clones that exhibited hVEGF ELISA signals at least two-fold over signals on a control plates coated with BSA were selected for sequencing. The LC-Hom library was subjected to 1 additional round of selection on hVEGF followed by phage ELISA screening and sequencing of VEGF-binding clones.

DNA Sequence Analysis

The high quality sequences from each library from the different target selections were translated and aligned (Data not shown). The number of sequences from each library subject to analysis is summarized in Table 4 below.

TABLE 4

| Number of Sequences Analyzed | |
|---|---|
| Library | Total Sequences |
| LCA-V2b | 51 |
| LCH-V3 | 79 |
| LCA-H2 | 97 |
| LCH-H2 | 50 |
| LCA-gD | 112 |
| LCH-gD | 120 |
| LCA-pL | 60 |
| LCH-pL | 65 |
| HCA-V2 | 100 |
| HCH-V2 | 96 |
| HCA-H2 | 81 |
| HCH-H2 | 96 |
| HCA-gD | 105 |
| HCH-gD | 105 |
| HCA-pl | 102 |
| HCH-pl | 99 |

Figure 33:
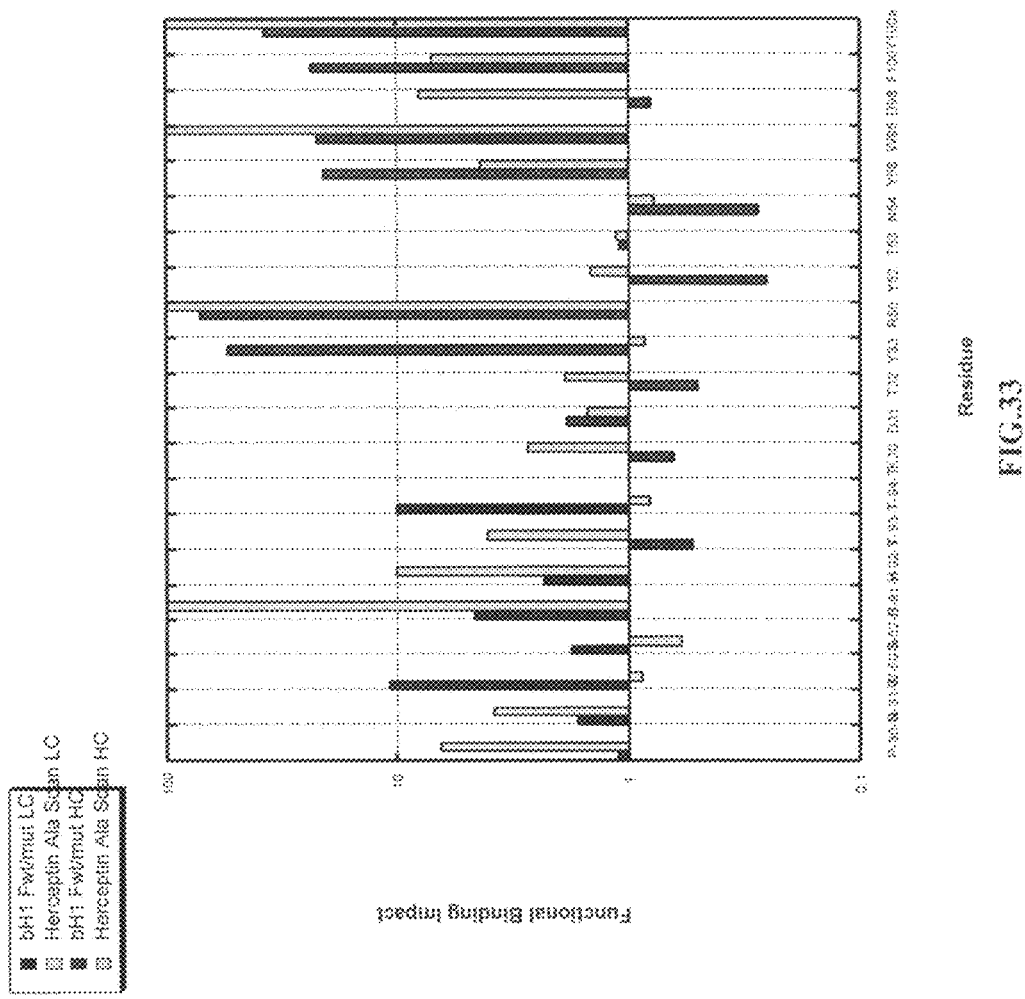
FIG. 33 shows alanine scanning results of bH1 or the Herceptin® antibody mutants.

The Wt/Mut ratios were calculated at each varied position (FIG. 30 and FIG. 31) thus allowing calculation of the $F_{wt/mut}$ values as listed (FIG. 30 and FIG. 31) which are corrected for display by division of the ratios from target selection by those from the display selection as described (Vajdos et al., 2002). A $F_{wt/mut}$ value greater than 1 indicates that Wt is preferred at this position and $F_{wt/mut}$ smaller than 1 indicates the mutation is preferred. $F_{wt/mut} > 5$ indicate its important role in antigen binding. The importance of each scanned CDR residue is illustrated in FIGS. 32A-32D. The result demonstrates that residues from both heavy chain and light chain contribute energetically to the binding of both antigen (Her2 and hVEGF) binding. The impact of bH1 light chain and heavy chain residues on Her2 binding was compared to that of its parent antibody hu4D5 (Kelley and O'Connell, 1993) (FIG. 33).

Figure 37:
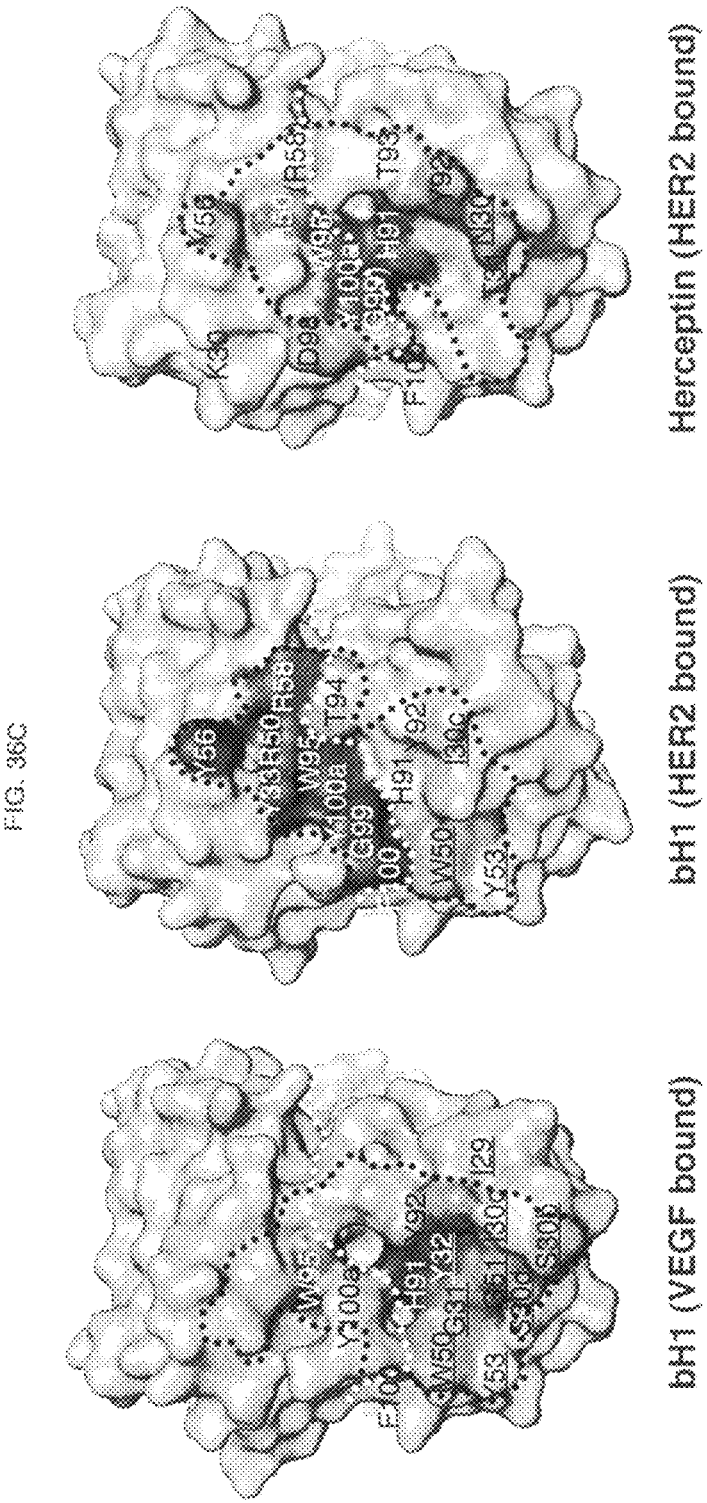

FIGS. 37A-1 through 37A-3 and FIGS. 37B-1 through 37B-3 show shotgun alanine- and homolog scanning of bH1 Fab for binding to VEGF and HER2. The effects of mutation of alanine (m1), or additional mutations (m2, m3; due to limitations of shotgun-alanine codons), or to a homologous amino acid (m4) are calculated as the ratio of occurrence of wild-type and mutants (wt/mut) among the clones binding to human VEGF (FIG. 37A-1 through 37A-3) or HER2 (FIG. 37B-1 through 37B-3). In cases where only the wild-type residue appeared, the ratios are shown as larger than ">" the wild-type count. The identity of the amino acid substitutions (m1-m4) is shown as superscripts on the F values. When the wild-type residue is alanine, it was substituted by glycine (m1). The "*" indicates the extent of the bH1 residues that are buried upon VEGF or HER2 complex formation (*25-49% of accessible area buried, 50-75% of accessible area buried, *greater than or equal to 75% of accessible area buried).

Figure 36:
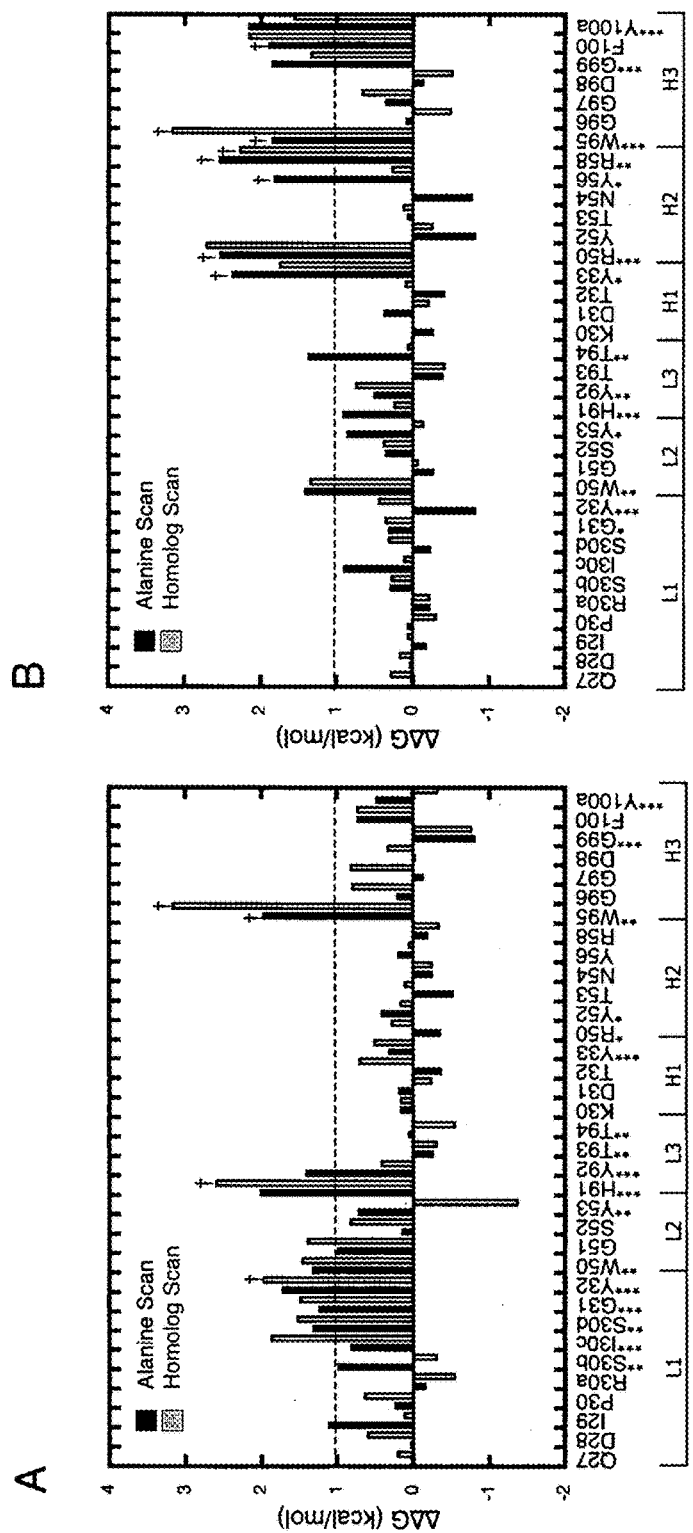
FIGS. 36A through 36C show the energetically important binding sites of bH1 for VEGF and HER2 binding.

The residues that contribute significantly to the energetic interactions make up the functional paratopes, which constitute a subset of the structural binding sites. In contrast to the extensive overlap between the sites of antigen contact the two functional paratopes show limited overlap (FIGS. 36A-36C). In particular, based on shotgun scanning mutagenesis, the ΔΔG values (y-axis, kcal/mol) are plotted for each mutation to alanine (black bar) or a homologous amino acid (white bar) for VEGF (FIG. 36A) or HER2 (FIG. 36B) binding. The "†" represents a lower limit, as mutations were not observed at this position. The "*" indicates the extent of the bH1 residue surface area buried upon VEGF or HER2 complex formation. (*25-49% buried, 50-75%, *>75%). The VEGF binding interaction is mediated primarily by the LC CDRs with Tyr32 of CDR-L1 and His91 of CDR-L3 as the core hot spot ($\Delta\Delta G_{wt/ala}$>1.5 kcal/mol). HER2 binding is mainly contributed by HC CDRs. FIG. 36C shows crystal structures where the bH1 and the Herceptin® antibody residues are shaded on the Fab surface based on their functional importance (dark shading and white lettering, ΔΔG≥1.5 kcal/mol; intermediate shading and black lettering, 1≤ΔΔG<1.5 kcal/mol; light shading and black lettering, 0.5≤ΔΔG<1 kcal/mol of alanine mutation). The black dotted line outlines the contact area as in FIG. 35B. The white dotted line depicts the divide of light and heavy chain.

For VEGF binding and HER2 binding, the functional paratope residues are distributed across HC and LC signifying the synergy of the two chains. Trp95 of CDR-H3 is the only common hot spot residue for the two interactions ($\Delta\Delta G_{wt/ala}$>1.5 kcal/mol). As noted above, the VEGF binding interaction is mediated primarily by the LC CDRs while HER2 binding is dominated by HC CDRs. Compared to the Herceptin® antibody, bH1 with weaker HER2 binding affinity (300 fold) maintains the same core hot spot residues for HER2 binding (Arg50, Trp95, and Tyr100a) while the importance of peripheral residues is redistributed (FIG. 36C). Overall, most of the important side chains in heavy chain contributing hu4D5/Her2 binding are still important for bH1/Her2 binding (ΔΔG>1.5 kcal/mol). There are some changes. Light chain residues have more shuffling in contributions—some residues became less important and some more important. Overall, the functional sites are part of the structural interface from the crystal structure of the bH1-VEGF and bH1-Her2 complexes.

In short, the interaction of bH1 with the two structurally unrelated large proteins is characterized by the engagement of a distinct set of bH1 residues in the energetic interaction with each antigen. While most of the two extensively overlapping binding sites for the two different antigens exhibit a single conformation, the flexibility of one CDR loop (L1) facilitates the accommodation of both HER2 and VEGF. The mechanism is reminiscent of the molecular versatility observed in multi-specific antibodies binding unrelated small haptens or peptides. Previous studies describe multi-specificity mediated either by differential positioning of the small ligands at spatially distinct regions of a single antibody conformation (Sethi et al., Immunity 24:429, 2006) or by multiple pre-existing conformations of the antigen binding site (James et al., Science 299:1362, 2003). The versatility of antibody molecules in antigen recognition is further highlighted by how limited LC mutations can give rise to antibodies that bind two unrelated protein antigens.

bH1 Affinity Maturation

Figure 34:
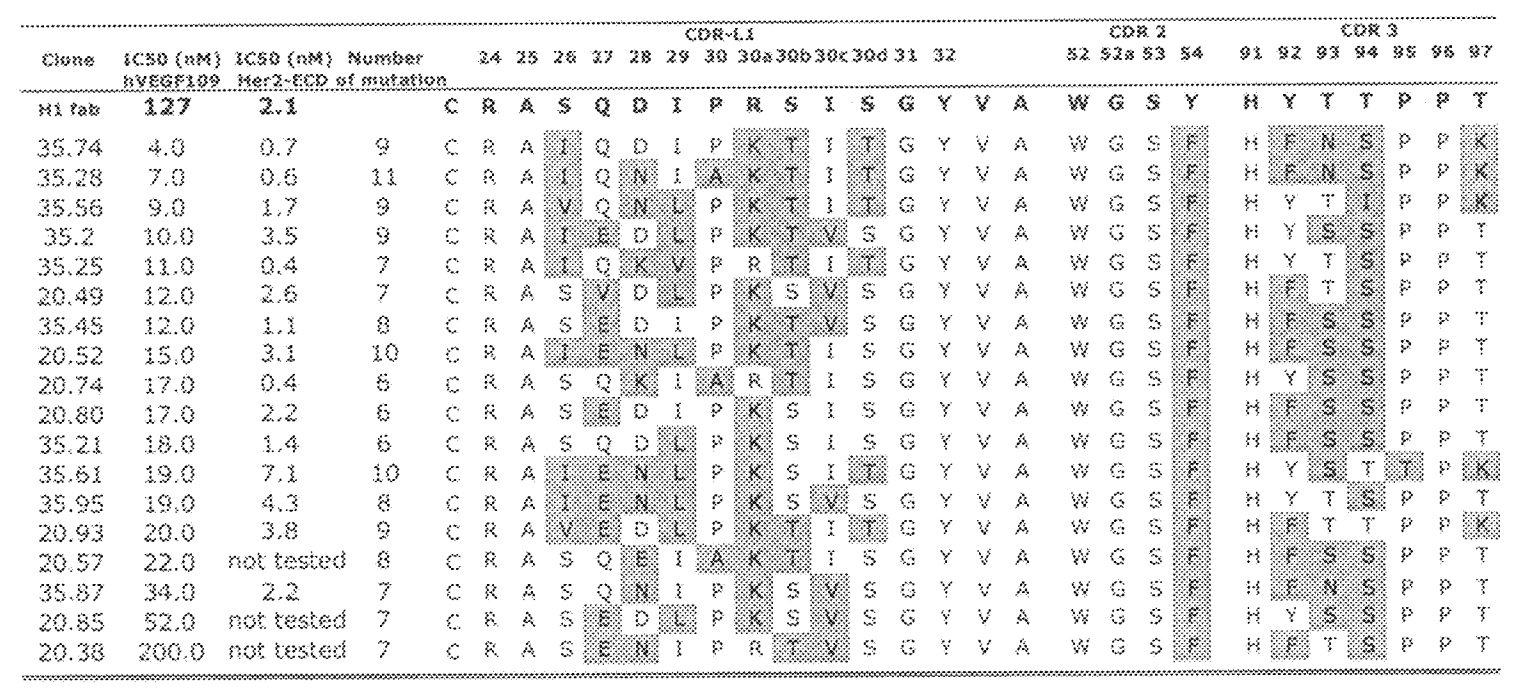

In an attempt to investigate whether the VEGF-binding affinity of bH1 could be increased by optimization of the light chain sequence before the structural and functional results became available, a library was constructed where the CDR residues at highly solvent-accessible positions based on the crystal structure of h4D5[42] Fab (Eigenbrot et al., 2001), which is assumed to closely resemble bH1 Fab, were diversified. Targeted residues were allowed to vary as either wild type or a few homologous residues (FIG. 29). The library was constructed as described in section "Construction of shotgun scanning libraries." A solution-based selection method was used to select for higher affinity VEGF-binders as described. Two rounds of solution-based selection were performed. The stringency was increased in each round of selection by decreasing the concentration of biotinylated VEGF from 50 nM in the first round to 20 nM in the second round. 138 clones were sequenced from the last round of selection. Most clones were found to be unique. A high-throughput ELISA assay with immobilized VEGF (8-109), anti-gD antibody, and Her2-ECD was used to identify clones that bound to VEGF, Her2-ECD, and anti-gD mIgG but not to BSA. The VEGF-ELISA binding signals were normalized by the anti-gD ELISA signals to estimate the relative affinity of the VEGF binding clones. Clones with high VEGF/anti-gD ratios were selected for further characterization. The affinity of the selected clones for VEGF and Her2 was estimated by competition ELISA as phage-displayed Fabs as previously described. The bH1 variants show improved VEGF binding-affinity compared to the parent bH1 clone. Interestingly, some clones have slightly improved $IC_{50}$ values for Her2 binding even though that affinity-based selection for Her2 was not performed. This shows that it is possible to affinity mature the bH1 clone for VEGF binding without affecting Her2 binding ability significantly. There are some VEGF-affinity improved clones that showed reduced Her2 binding affinity compared to the parent bH1 clone. This result indicates that the light chain actively contributes to the binding ability of bH1 to Her2 despite the fact that heavy chain is the main contributor to the binding energy based on the bH1-Her2 complex structure and shotgun alanine scanning analysis. The sequences and $IC_{50}$ values of the characterized clones are summarized in FIG. 34. The finding that most sequences were unique suggests that the light chain sequence of these variants is not yet fully optimized for VEGF binding and that it is possible to further affinity-improve bH1 clone by additional rounds of selection.

As shown in FIG. 41, significant affinity improvement of a single Fab for two antigens is achievable and generally applicable. For instance, the $K_D$ of bH1 for VEGF was increased from 300 to 16 nM and the $K_D$ of bH1 for HER2 was increased from 26 to 1.2 nM.

Example 5. Analysis of IgG Activity in Cell Assays

Figure 26:
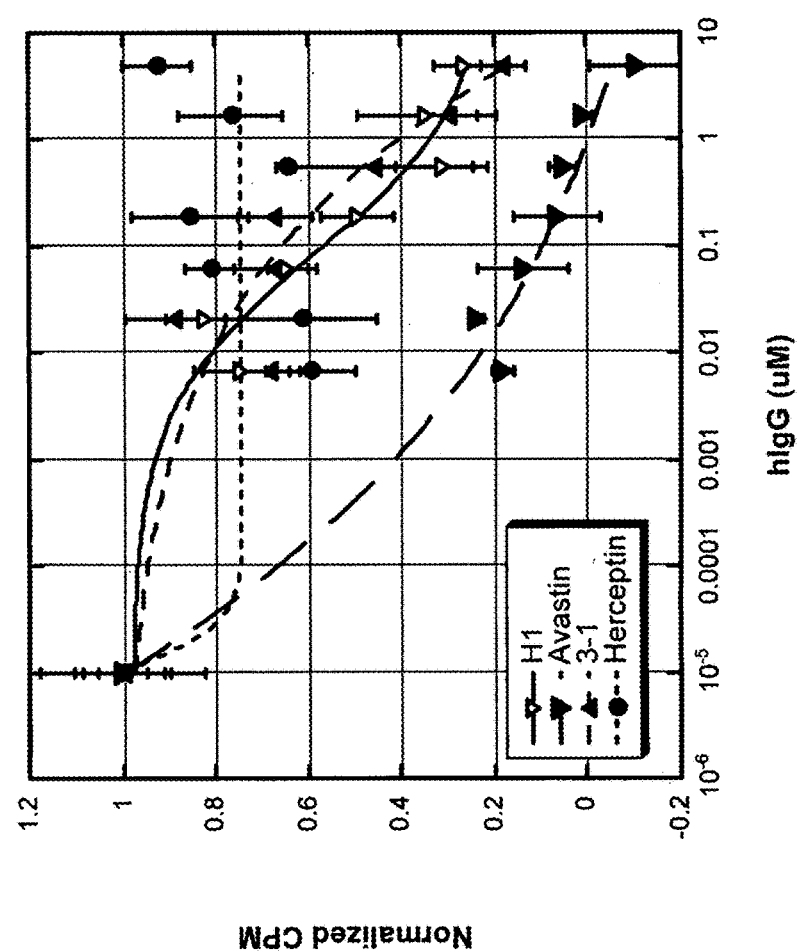
FIG. 26 shows the inhibition of VEGF induced HUVEC cell proliferation with anti-VEGF antibodies.

To check whether the two highest affinity anti-hVEGF antibodies, bH1 and 3-1, could inhibit $hVEGF_{165}$ induced proliferation of human umbilical vein endothelial (HUVEC) cells they were tested in a proliferation assay. Human umbilical vein endothelial cells (HUVEC) (Cambrex, East Rutherford, N.J.) were grown and assayed as described (Fuh et al., J. Biol. Chem. 273:11197, 1998). Approximately 4000 HUVECs were plated in each well of the 96-well cell culture plate and incubated in Dulbecco's modified Eagle's/F-12 medium (1:1) supplemented with 1.0% (v/v) fetal bovine serum (assay medium) for 18 hours. Fresh assay medium with fixed amounts of VEGF (0.2 nM final concentration), which was first titrated as a level of VEGF that can stimulate submaximal DNA synthesis, and increasing concentrations of anti-VEGF antibodies (e.g., bH1) were then added to the cells. After incubation at 37° C. for 18 hours, cells were pulsed with 0.5 µCi/well of [$^3$H]Thymidine for 24 hours and harvested for counting with TopCount Microplate Scintillation counter. The results demonstrate that both 3-1 and bH1 can inhibit VEGF-induced growth of HUVEC cells by preventing hVEGF induced signaling and subsequent proliferation. The Avastin® antibody (anti-VEGF) was used as a positive control and the Herceptin® antibody as a negative control (FIG. 26).

Figure 27:
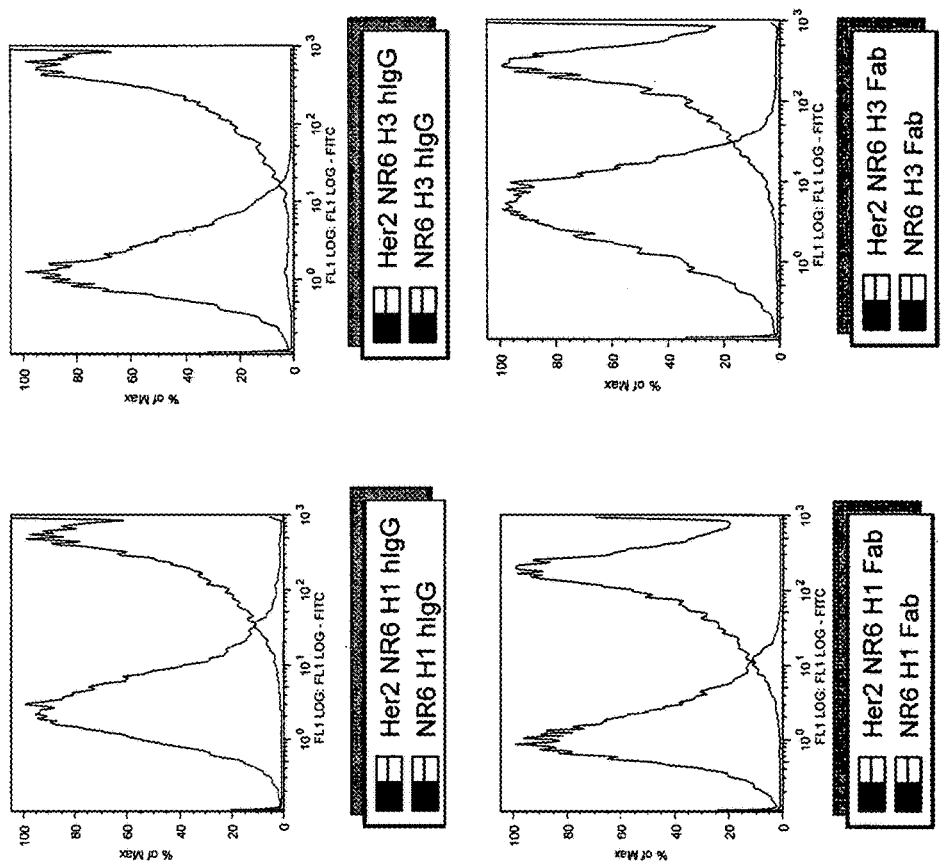
FIG. 27 shows binding of bispecific antibodies to HER2 expressed on NR6 cells.
Figure 32:
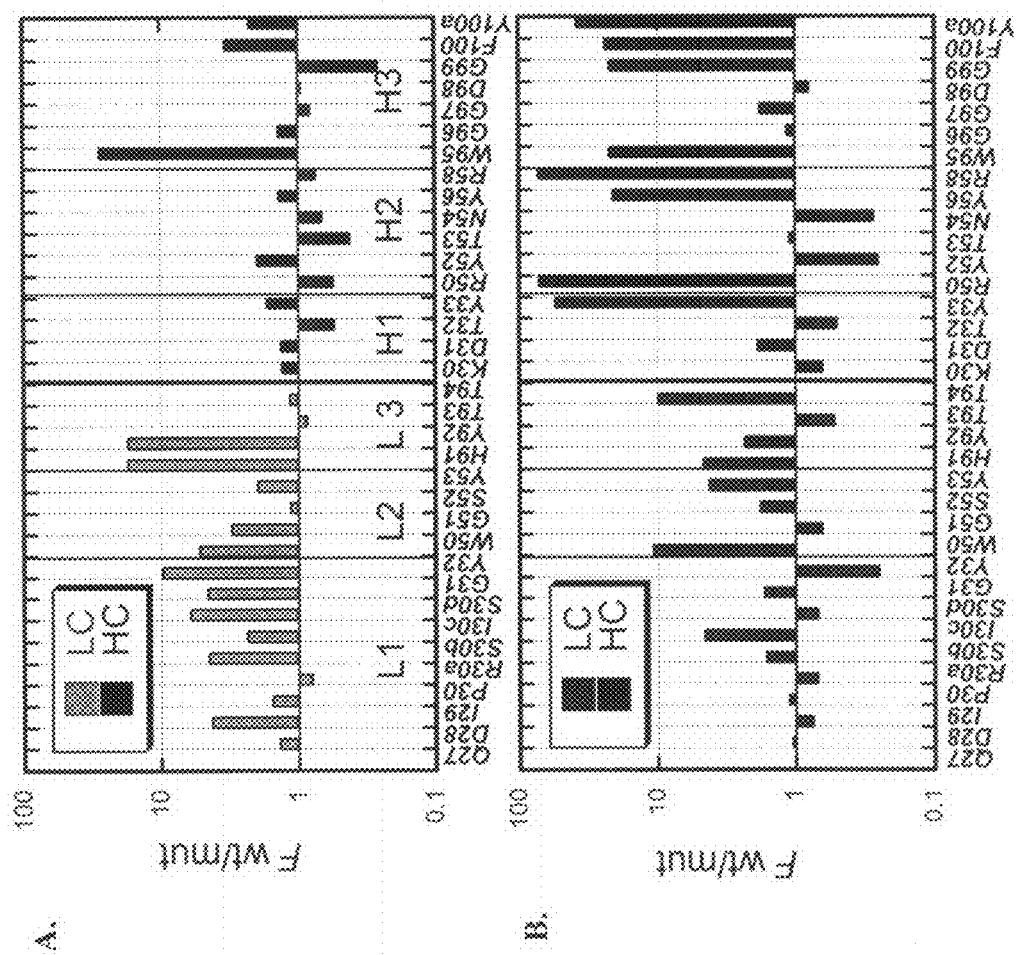
FIG. 32 shows the results of an alanine scan of bH1 for (FIG. 32A) VEGF binding or (FIG. 32B) HER2 binding and the results of a homolog scan of bH1 for (FIG. 32C) VEGF binding or (FIG. 32D) HER2 binding.

To study binding of bi-specific anti-Her2/VEGF antibodies to Her2 expressed on mammalian cells, the binding of bH1 and H3 antibodies to NR6 fibroblast cells over-expressing Her2 (NR6-Her2) was studied by Flow Cytometry. One million NR6-Her2 cells were incubated with 100 µg/ml Fab and IgG for 1 hour, followed by incubation with an Alexa488-conjugated murine anti-human IgG antibody for 1 hour. As negative controls, Fab and IgG binding to non-expressing NR6 cells was studied. As demonstrated in FIG. 27, bH1 and H3 bind specifically to Her2 on NR6 cells as Fab and as IgG.

Figure 42:
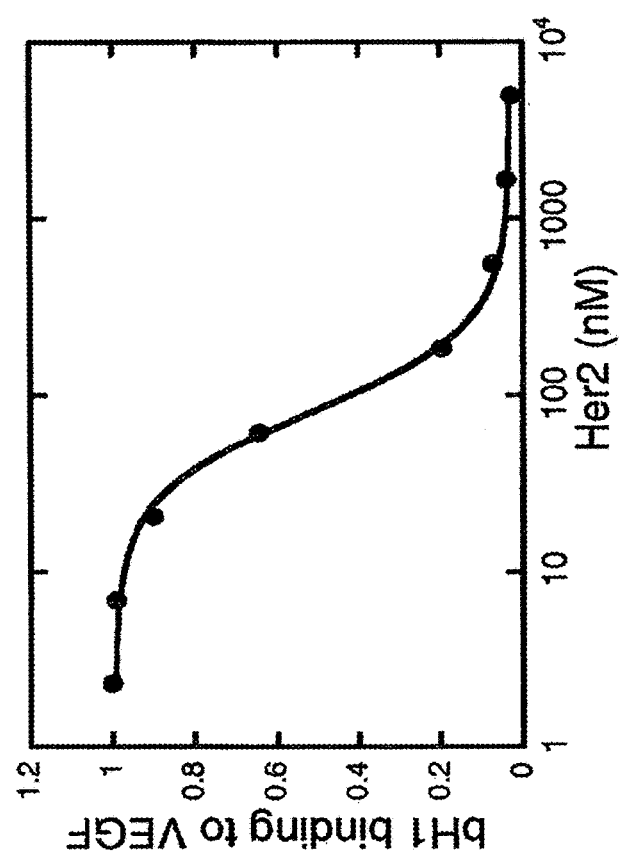
FIG. 42 shows the results of competitive binding experiments for bH1 to VEGF or HER2.
Figure 43:
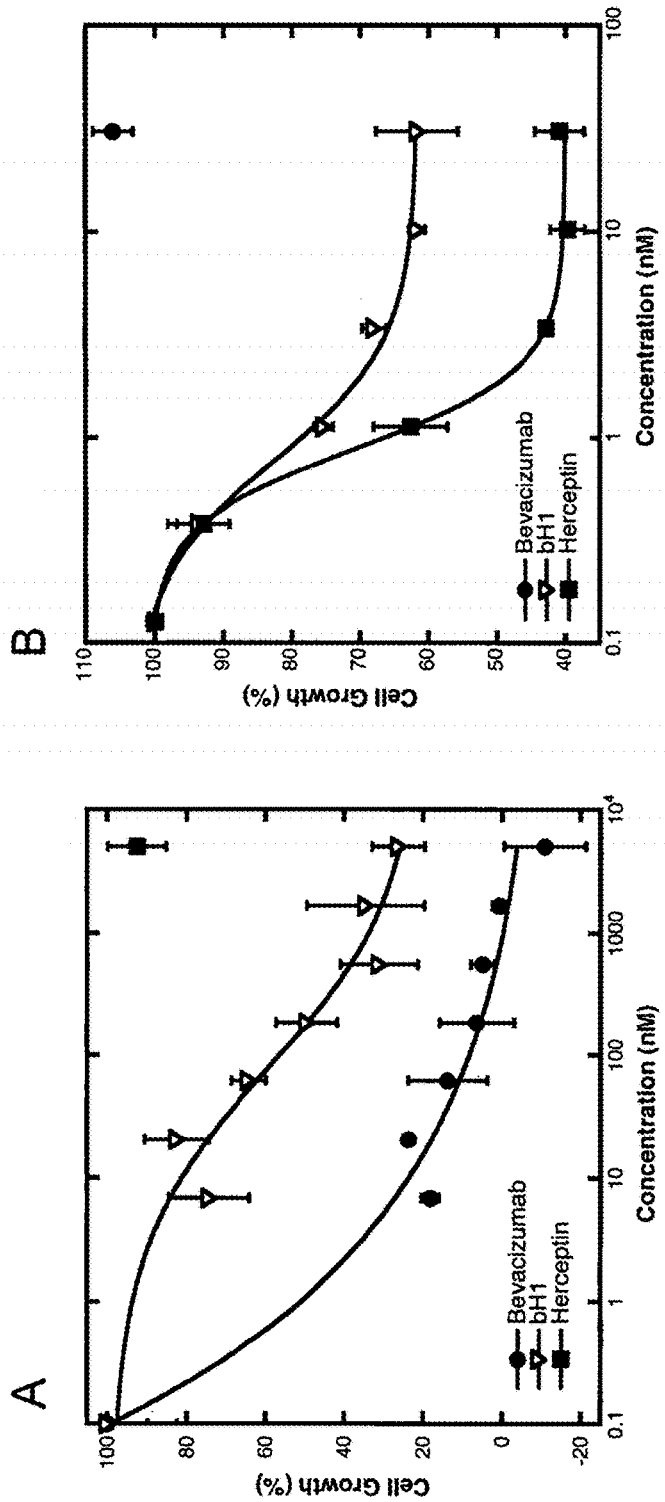
FIGS. 43A and 43B show that bH1 IgG inhibits HER2 and VEGF-mediated cell proliferation.

FIG. 42 shows the results of competitive binding experiments for bH1 to VEGF or HER2. bH1 inhibited VEGF induced proliferation of human umbilical vein endothelial cells (HUVEC) with an $IC_{50}$ of 200 nM, which is consistent with its affinity of 300 nM, and the proliferation of HER2-expressing breast cancer cell line BT474 after 5-day incubation, albeit with lower efficiency than the Herceptin® antibody due to its reduced affinity (FIG. 43A and FIG. 43B). The Herceptin® IgG antibody and bevacizumab (anti-VEGF) served as controls. In particular, breast cancer cells BT474 were cultured in RPMI media supplemented with 10% FBS. For the assays, $10^4$ cells were plated per well in a 96-well plate and incubated overnight (18 hours) at 37° C. Increasing concentrations of antibody were added to the cells. The cells were then incubated at 37° C. for five days, followed by addition of 10% AlamarBlue (Biosource International, Camarillo, Calif.) according to the manufacturer's instructions. The antibody-dependent inhibition of proliferation of the HER2 expressing cells was determined by measuring the fluorescent signal.

The above results indicate the potential of the bi-functional bH1, or its affinity improved variants, to inhibit two mechanisms that are important for tumor growth in vivo.

REFERENCES CITED

Chen, Y., C. Wiesmann, G. Fuh, B. L1, H. W. Christinger, P. McKay, A. M. de Vos, and H. B. Lowman, 1999, Selection and analysis of an optimized anti-VEGF antibody: crystal structure of an affinity-matured Fab in complex with antigen: J Mol Biol, v. 293, p. 865-81.

Cho, H. S., K. Mason, K. X. Ramyar, A. M. Stanley, S. B. Gabelli, D. W. Denney, Jr., and D. J. Leahy, 2003, Structure of the extracellular region of HER2 alone and in complex with the Herceptin Fab: Nature, v. 421, p. 756-60.

Christinger, H. W., Y. A. Muller, L. T. Berleau, B. A. Keyt, B. C. Cunningham, N. Ferrara, and A. M. de Vos, 1996, Crystallization of the receptor binding domain of vascular endothelial growth factor: Proteins, v. 26, p. 353-7.

Collaborative Computational Project, N., 1994: Acta Crystallogr. Section D. Biol. Crystallogr., v. 50, p. 760-763.

Emsley, P., and K. Cowtan, 2004, Coot: model-building tools for molecular graphics: Acta Crystallogr D Biol Crystallogr, v. 60, p. 2126-32.

Fellouse, F. A., B. Li, D. M. Compaan, A. A. Peden, S. G. Hymowitz, and S. S. Sidhu, 2005, Molecular recognition by a binary code: J Mol Biol, v. 348, p. 1153-62.

Franklin, M. C., K. D. Carey, F. F. Vajdos, D. J. Leahy, A. M. de Vos, and M. X. Sliwkowski, 2004, Insights into ErbB signaling from the structure of the ErbB2-pertuzumab complex: Cancer Cell, v. 5, p. 317-28.

Fuh, G., B. L1, C. Crowley, B. Cunningham, and J. A. Wells, 1998, Requirements for binding and signaling of the kinase domain receptor for vascular endothelial growth factor: J Biol Chem, v. 273, p. 11197-204.

Fuh, G., P. Wu, W. C. Liang, M. Ultsch, C. V. Lee, B. Moffat, and C. Wiesmann, 2006, Structure-function studies of two synthetic anti-vascular endothelial growth factor Fabs and comparison with the Avastin Fab: J Biol Chem, v. 281, p. 6625-31.

Hudziak, R. M., and A. Ullrich, 1991, Cell transformation potential of a HER2 transmembrane domain deletion mutant retained in the endoplasmic reticulum: J Biol Chem, v. 266, p. 24109-15.

Kelley, R. F., and M. P. O'Connell, 1993, Thermodynamic analysis of an antibody functional epitope: Biochemistry, v. 32, p. 6828-35.

Kunkel, T. A., J. D. Roberts, and R. A. Zakour, 1987, Rapid and efficient site-specific mutagenesis without phenotypic selection: Methods Enzymol, v. 154, p. 367-82.

L. C. Storoni, A. J. M. a. R. J. R., 2004, Likelihood-enhanced fast rotation functions: Acta Cryst., p. 432-438.

Lasky, L. A., and D. J. Dowbenko, 1984, DNA sequence analysis of the type-common glycoprotein-D genes of herpes simplex virus types 1 and 2: DNA, v. 3, p. 23-9.

Lee, C. V., W. C. Liang, M. S. Dennis, C. Eigenbrot, S. S. Sidhu, and G. Fuh, 2004a, High-affinity human antibodies from phage-displayed synthetic Fab libraries with a single framework scaffold: J Mol Biol, v. 340, p. 1073-93.

Lee, C. V., S. S. Sidhu, and G. Fuh, 2004b, Bivalent antibody phage display mimics natural immunoglobulin: J Immunol Methods, v. 284, p. 119-32.

Liang, W. C., X. Wu, F. V. Peale, C. V. Lee, Y. G. Meng, J. Gutierrez, L. Fu, A. K. Malik, H. P. Gerber, N. Ferrara, and G. Fuh, 2006, Cross-species vascular endothelial growth factor (VEGF)-blocking antibodies completely inhibit the growth of human tumor xenografts and measure the contribution of stromal VEGF: J Biol Chem, v. 281, p. 951-61.

Lowman, H. B., S. H. Bass, N. Simpson, and J. A. Wells, 1991, Selecting high-affinity binding proteins by monovalent phage display: Biochemistry, v. 30, p. 10832-8.

Muller, Y. A., Y. Chen, H. W. Christinger, B. L1, B. C. Cunningham, H. B. Lowman, and A. M. de Vos, 1998, VEGF and the Fab fragment of a humanized neutralizing antibody: crystal structure of the complex at 2.4 Å resolution and mutational analysis of the interface: Structure, v. 6, p. 1153-67.

Otwinowski, Z., and Minor, W., 1997, Processing of X-ray diffraction data collected in oscillation mode: Methods Enzymol., v. 276, p. 307-326.

Presta, L. G., H. Chen, S. J. O'Connor, V. Chisholm, Y. G. Meng, L. Krummen, M. Winkler, and N. Ferrara, 1997, Humanization of an anti-vascular endothelial growth factor monoclonal antibody for the therapy of solid tumors and other disorders: Cancer Res, v. 57, p. 4593-9.

Read, R. J., 2001, Pushing the boundaries of molecular replacement with maximum likelihood: Acta Cryst., v. D57, p. 1373-1382.

Sidhu, S. S., B. Li, Y. Chen, F. A. Fellouse, C. Eigenbrot, and G. Fuh, 2004, Phage-displayed antibody libraries of synthetic heavy chain complementarity determining regions: J Mol Biol, v. 338, p. 299-310.

Sidhu, S. S., H. B. Lowman, B. C. Cunningham, and J. A. Wells, 2000, Phage display for selection of novel binding peptides: Methods Enzymol, v. 328, p. 333-63.

Vajdos, F. F., C. W. Adams, T. N. Breece, L. G. Presta, A. M. de Vos, and S. S. Sidhu, 2002, Comprehensive functional maps of the antigen-binding site of an anti-ErbB2 antibody obtained with shotgun scanning mutagenesis: J Mol Biol, v. 320, p. 415-28.

Wiesmann, C., G. Fuh, H. W. Christinger, C. Eigenbrot, J. A. Wells, and A. M. de Vos, 1997, Crystal structure at 1.7 Å resolution of VEGF in complex with domain 2 of the Flt-1 receptor: Cell, v. 91, p. 695-704.

All patents, patent applications, patent application publications, and other publications cited or referred to in this specification are herein incorporated by reference to the same extent as if each independent patent, patent application, patent application publication or publication was specifically and individually indicated to be incorporated by reference.

The invention claimed is:

1. A method of making a multispecific antibody comprising a variable heavy chain domain ($V_H$) and a variable light chain domain ($V_L$), wherein the $V_H$ and $V_L$ of the multispecific antibody pair together to form an antigen binding site that specifically binds to a first epitope and a second epitope, said method comprising the steps of:
   (1) providing an antibody that comprises a $V_H$ and $V_L$, wherein the $V_H$ and $V_L$ pair together to form an antigen binding site that binds to the first epitope but not the second epitope;
   (2) altering the nucleic acid sequence encoding the $V_L$ of the antibody of step (1), wherein one or more solvent accessible amino acid residues are altered at one or more amino acid residue positions selected from the group consisting of positions 28, 29, 30-32, 50-53, 66-70, and 91-94, according to the Kabat numbering system, and wherein the one or more solvent accessible amino acid residues include an amino acid residue of position 30 or position 93, according to the Kabat numbering system;
   (3) expressing the $V_H$ and the altered nucleic acid sequence of the $V_L$ of step (2); and
   (4) following step (3), selecting for antibody binding to said first epitope and said second epitope, thereby selecting for a multispecific antibody by its ability to bind to both said first epitope and said second epitope, said multispecific antibody comprising the $V_H$ and the altered $V_L$ of step (3), wherein the $V_H$ and $V_L$ of the multispecific antibody pair together to form an antigen binding site that specifically binds to the first epitope and the second epitope.

2. A method of making a multispecific antibody comprising a variable heavy chain domain ($V_H$) and a variable light chain domain ($V_L$), wherein the $V_H$ and $V_L$ of the multispecific antibody pair together to form an antigen binding site that specifically binds to a first epitope and a second epitope, said method comprising the steps of:
   (1) providing an antibody that comprises a $V_H$ and $V_L$, wherein the $V_H$ and $V_L$ pair together to form an antigen binding site that binds to the first epitope but not the second epitope;
   (2) holding the nucleic acid sequence encoding the $V_H$ constant and altering the nucleic acid sequence encoding the $V_L$ of the antibody of step (1), wherein one or more solvent accessible amino acid residues are altered;
   (3) expressing the nucleic acid sequence of the $V_H$ and the altered nucleic acid sequence of the $V_L$ of step (2); and
   (4) following step (3), selecting for antibody binding to said first epitope and said second epitope, thereby selecting for a multispecific antibody by its ability to bind to both said first epitope and said second epitope, said multispecific antibody comprising the $V_H$ and the altered $V_L$ of step (3), wherein the $V_H$ and the $V_L$ of the multispecific antibody pair together to form an antigen binding site that specifically binds to the first epitope and the second epitope.

3. The method according to claim 1 or 2, wherein the nucleic acid sequences targeted for altering in step (2) encode a plurality of predetermined amino acid residues.

4. The method according to claim 3, wherein the nucleic acid sequence is altered based on the diversity of a plurality of naturally occurring light chain amino acid sequences.

5. The method according to claim 3, wherein the plurality of predetermined amino acid residues comprise amino acid residue positions 28-32, 50-53, and 91-94, according to the Kabat numbering system.

6. The method according to claim 1 or 2, wherein the altered $V_L$ are displayed on phage with the $V_H$ during the selection of step (4).

7. The method according to claim 1 or 2, wherein the antibody of step (1) comprises a CDR-H1 comprising IKDTYI (SEQ ID NO:1), a CDR-H2 comprising ARIYPTNGYTRY (SEQ ID NO:2), and a CDR-H3 comprising RWGGDGFY (SEQ ID NO:3).

8. The method according to claim 7, wherein the antibody of step (1) further comprises a CDR-L1 comprising DVSTAV (SEQ ID NO:4), CDR-L2 comprising SASF (SEQ ID NO:5) and a CDR-L3 comprising HYTTPP (SEQ ID NO:6).

9. The method according to claim 1 or 2, wherein the antigen binding site of the multispecific antibody of step (4) binds the first epitope and second epitope mutually exclusively.

10. The method according to claim 1 or 2, wherein the first epitope is from one biological molecule and the second epitope is from a second biological molecule.

11. The method according to claim 10, wherein the first biological molecule and second biological molecule are selected from the group consisting of VEGF/HER2, VEGF-A/HER2, HER2/DR5, VEGF-A/PDGF, HER1/HER2, CD20/BR3, VEGF-A/VEGF-C, VEGF-C/VEGF-D, TNFalpha/TGF-beta, TNFalpha/IL-2, TNF alpha/IL-3, TNFalpha/IL-4, TNFalpha/IL-5, TNFalpha/IL6, TNFalpha/IL8, TNFalpha/IL-9, TNFalpha/IL-10, TNFalpha/IL-11, TNFalpha/IL-12, TNFalpha/IL-13, TNFalpha/IL-14, TNFalpha/IL-15, TNFalpha/IL-16, TNFalpha/IL-17, TNFalpha/IL-18, TNFalpha/IL-19, TNFalpha/IL-20, TNFalpha/IFNalpha, TNFalpha/CD4, VEGF/IL-8, VEGF/MET, VEGFR/MET receptor, HER2/Fc, HER2/HER3; EGFR/HER2, EGFR/HER3, EGFR/HER4, TNFalpha/IL-3, TNFalpha/IL-4, IL-13/CD40L, IL4/CD40L, TNFalpha/ICAM-1, TNFR1/IL-1R, TNFR1/IL-6R, and TNFR1/IL-18R.

12. The method according to claim 11, wherein said first biological molecule and second biological molecule are VEGF/HER2.

13. The method according to claim 1, wherein:
   (a) the one or more solvent accessible amino acid residues include an amino acid residue of position 30, and the method further comprises altering the nucleic acid sequence encoding the $V_L$ of the antibody of step (1) at a solvent accessible amino acid residue at a position selected from the group consisting of position 28, 29, 31, 32, 50, 51, 53, 91, 92, 93, and 94 of the $V_L$; or
   (b) the one or more solvent accessible amino acid residues include an amino acid residue of position 93, and the method further comprises altering the nucleic acid sequence encoding the $V_L$ of the antibody of step (1) at a solvent accessible amino acid residue at a position selected from the group consisting of position 28, 29, 30, 31, 32, 50, 51, 53, 91, 92, and 94 of the $V_L$.

14. The method according to claim 10, wherein the first biological molecule and the second biological molecule are proteins that have less than 60% amino acid identity to each other.

15. The method according to claim 2, wherein the one or more solvent accessible amino acid residues are altered at one or more amino acid residue positions selected from the group consisting of positions 28, 29, 30-32, 50-53, 66-70, and 91-94, according to the Kabat numbering system.

16. The method according to claim 1 or 2, wherein the $V_H$ and $V_L$ of the multispecific antibody pair together to form an antigen binding site that specifically binds to the first epitope and the second epitope with at least $10^4$ M affinity.

17. The method according to claim 16, wherein the $V_H$ and $V_L$ of the multispecific antibody pair together to form an antigen binding site that specifically binds to the first epitope with at least $10^{-6}$ M affinity and the second epitope with at least $10^{-4}$ M affinity.

18. The method according to claim 15, wherein the one or more solvent accessible amino acid residues include an amino acid residue of position 30, according to the Kabat numbering system.

19. The method according to claim 15, wherein the one or more solvent accessible amino acid residues include an amino acid residue of position 93, according to the Kabat numbering system.

20. The method according to claim 17, wherein the $V_H$ and $V_L$ of the multispecific antibody pair together to form an antigen binding site that specifically binds to the first epitope and the second epitope with at least $10^{-6}$ M affinity.

21. The method according to claim 1 or 2, wherein the method further comprises the step of subjecting the multispecific antibody selected in step (4) to affinity maturation.

22. The method according to claim 17, wherein the $V_H$ and $V_L$ of the multispecific antibody pair together to form an antigen binding site that specifically binds to the first epitope with at least $10^{-7}$ M affinity and the second epitope with at least $10^{-5}$ M affinity.

23. The method according to claim 20, wherein the $V_H$ and $V_L$ of the multispecific antibody pair together to form an antigen binding site that specifically binds to the first epitope with at least $10^{-7}$ M affinity and the second epitope with at least $10^{-6}$ M affinity.

24. The method according to claim 17, wherein the $V_H$ and $V_L$ of the multispecific antibody pair together to form an antigen binding site that specifically binds to the first epitope with at least $10^{-8}$ M affinity and the second epitope with at least $10^{-4}$ M affinity.

25. The method according to claim 15, wherein the one or more solvent accessible amino acid residues are altered at one or more amino acid residue positions selected from the group consisting of positions 28, 29, 30, 31, 32, 50, 51, 53, 91, 92, 93, and 94, according to the Kabat numbering system.

26. The method according to claim 1 or 25, wherein the one or more solvent accessible amino acid residues include an amino acid residue of positions 30 and 93, according to the Kabat numbering system.

* * * * *

UNITED STATES PATENT AND TRADEMARK OFFICE
CERTIFICATE OF CORRECTION

PATENT NO. : 10,118,970 B2
APPLICATION NO. : 11/893693
DATED : November 6, 2018
INVENTOR(S) : Germaine Fuh et al.

It is certified that error appears in the above-identified patent and that said Letters Patent is hereby corrected as shown below:

In the Specification

Column 22, Lines 25-26, replace "deaf-fiess" with --deaf-ness--.

Column 31, Line 26, replace "L1/LA" with --L1/L4--.

Column 48, Line 8, replace "L1" with --Li--;
Line 49, replace "L1" with --Li--.

In the Claims

Column 213, Line 4, Claim 16, replace "$10^4$" with --$10^{-4}$--.

Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 631

<210> SEQ ID NO 1
<211> LENGTH: 6
<212> TYPE: PRT
<213> ORGANISM: Artificial Sequence
<220> FEATURE:
<223> OTHER INFORMATION: synthetic

<400> SEQUENCE: 1

Ile Lys Asp Thr Tyr Ile
1               5

<210> SEQ ID NO 2
<211> LENGTH: 12
<212> TYPE: PRT
<213> ORGANISM: Artificial Sequence
<220> FEATURE:
<223> OTHER INFORMATION: synthetic

<400> SEQUENCE: 2

Ala Arg Ile Tyr Pro Thr Asn Gly Tyr Thr Arg Tyr
1               5                   10

<210> SEQ ID NO 3
<211> LENGTH: 8
<212> TYPE: PRT
<213> ORGANISM: Artificial Sequence
<220> FEATURE:
<223> OTHER INFORMATION: synthetic

<400> SEQUENCE: 3

Arg Trp Gly Gly Asp Gly Phe Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: synthetic

<400> SEQUENCE: 4

Asp Val Ser Thr Ala Val
1               5

<210> SEQ ID NO 5
<211> LENGTH: 4
<212> TYPE: PRT
<213> ORGANISM: Artificial Sequence
<220> FEATURE:
<223> OTHER INFORMATION: synthetic

<400> SEQUENCE: 5

Ser Ala Ser Phe
```

```
<210> SEQ ID NO 6
<211> LENGTH: 6
<212> TYPE: PRT
<213> ORGANISM: Artificial Sequence
<220> FEATURE:
<223> OTHER INFORMATION: synthetic

<400> SEQUENCE: 6

His Tyr Thr Thr Pro Pro
1               5

<210> SEQ ID NO 7
<211> LENGTH: 6
<212> TYPE: PRT
<213> ORGANISM: Artificial Sequence
<220> FEATURE:
<223> OTHER INFORMATION: synthetic

<400> SEQUENCE: 7

Phe Thr Asp Tyr Thr Met
1               5

<210> SEQ ID NO 8
<211> LENGTH: 12
<212> TYPE: PRT
<213> ORGANISM: Artificial Sequence
<220> FEATURE:
<223> OTHER INFORMATION: synthetic

<400> SEQUENCE: 8

Ala Asp Val Asn Pro Asn Ser Gly Gly Ser Ile Tyr
1               5                   10

<210> SEQ ID NO 9
<211> LENGTH: 7
<212> TYPE: PRT
<213> ORGANISM: Artificial Sequence
<220> FEATURE:
<223> OTHER INFORMATION: synthetic

<400> SEQUENCE: 9

Arg Asn Leu Gly Pro Ser Phe
1               5

<210> SEQ ID NO 10
<211> LENGTH: 6
<212> TYPE: PRT
<213> ORGANISM: Artificial Sequence
<220> FEATURE:
<223> OTHER INFORMATION: synthetic

<400> SEQUENCE: 10

Asp Val Ser Ile Gly Val
1               5

<210> SEQ ID NO 11
<211> LENGTH: 4
<212> TYPE: PRT
<213> ORGANISM: Artificial Sequence
<220> FEATURE:
<223> OTHER INFORMATION: synthetic

<400> SEQUENCE: 11

Ser Ala Ser Tyr
1
```

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

Tyr Tyr Ile Tyr Pro Tyr
1               5

<210> SEQ ID NO 13
<211> LENGTH: 6
<212> TYPE: PRT
<213> ORGANISM: Artificial Sequence
<220> FEATURE:
<223> OTHER INFORMATION: synthetic

<400> SEQUENCE: 13

Ile Ser Asp Ser Gly Ile
1               5

<210> SEQ ID NO 14
<211> LENGTH: 12
<212> TYPE: PRT
<213> ORGANISM: Artificial Sequence
<220> FEATURE:
<223> OTHER INFORMATION: synthetic

<400> SEQUENCE: 14

Ala Ala Ile Ala Pro Gly Ala Gly Ser Thr Tyr Tyr
1               5                   10

<210> SEQ ID NO 15
<211> LENGTH: 8
<212> TYPE: PRT
<213> ORGANISM: Artificial Sequence
<220> FEATURE:
<223> OTHER INFORMATION: synthetic

<400> SEQUENCE: 15

Arg Phe Val Ser Ala Pro Pro Ser
1               5

<210> SEQ ID NO 16
<211> LENGTH: 5
<212> TYPE: PRT
<213> ORGANISM: Artificial Sequence
<220> FEATURE:
<223> OTHER INFORMATION: synthetic

<400> SEQUENCE: 16

Gly Ser Gly Thr Asp
1               5

<210> SEQ ID NO 17

<400> SEQUENCE: 17

000

<210> SEQ ID NO 18
<211> LENGTH: 6
<212> TYPE: PRT
<213> ORGANISM: Artificial Sequence
<220> FEATURE:

<223> OTHER INFORMATION: synthetic

<400> SEQUENCE: 18

Tyr Ser Thr Val Pro Trp
1               5

<210> SEQ ID NO 19
<211> LENGTH: 214
<212> TYPE: PRT
<213> ORGANISM: ARTIFICIAL SEQUENCE
<220> FEATURE:
<223> OTHER INFORMATION: synthetic

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 227
<212> TYPE: PRT
<213> ORGANISM: ARTIFICIAL SEQUENCE
<220> FEATURE:
<223> OTHER INFORMATION: synthetic

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val

```
            50                  55                  60
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
             100                 105                 110

Gly Thr Leu Val Thr Val Ser Ala Ser Thr Lys Gly Pro Ser Val
         115                 120                 125

Phe Pro Leu Ala Pro Ser Ser Lys Ser Thr Ser Gly Gly Thr Ala Ala
         130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
             195                 200                 205

Pro Ser Asn Thr Lys Val Asp Lys Lys Val Glu Pro Lys Ser Cys Asp
         210                 215                 220

Lys Thr His
225

<210> SEQ ID NO 21
<211> LENGTH: 6
<212> TYPE: PRT
<213> ORGANISM: Artificial Sequence
<220> FEATURE:
<223> OTHER INFORMATION: synthetic

<400> SEQUENCE: 21

Asn Val Trp Asp Trp Val
 1               5

<210> SEQ ID NO 22
<211> LENGTH: 4
<212> TYPE: PRT
<213> ORGANISM: Artificial Sequence
<220> FEATURE:
<223> OTHER INFORMATION: synthetic

<400> SEQUENCE: 22

Pro Ala Ser Ser
 1

<210> SEQ ID NO 23
<211> LENGTH: 5
<212> TYPE: PRT
<213> ORGANISM: Artificial Sequence
<220> FEATURE:
<223> OTHER INFORMATION: synthetic

<400> SEQUENCE: 23

Gly Trp Tyr Ile Ala
 1               5

<210> SEQ ID NO 24
<211> LENGTH: 10
<212> TYPE: PRT
<213> ORGANISM: Artificial Sequence
```

```
<220> FEATURE:
<223> OTHER INFORMATION: synthetic

<400> SEQUENCE: 24

Asp Ile Pro Arg Ser Ile Ser Gly Tyr Val
1               5                   10

<210> SEQ ID NO 25
<211> LENGTH: 4
<212> TYPE: PRT
<213> ORGANISM: Artificial Sequence
<220> FEATURE:
<223> OTHER INFORMATION: synthetic

<400> SEQUENCE: 25

Trp Gly Ser Tyr
1

<210> SEQ ID NO 26
<211> LENGTH: 4
<212> TYPE: PRT
<213> ORGANISM: Artificial Sequence
<220> FEATURE:
<223> OTHER INFORMATION: synthetic

<400> SEQUENCE: 26

His Tyr Thr Thr
1

<210> SEQ ID NO 27
<211> LENGTH: 7
<212> TYPE: PRT
<213> ORGANISM: Artificial Sequence
<220> FEATURE:
<223> OTHER INFORMATION: synthetic

<400> SEQUENCE: 27

Asp Ile Gly Leu Gly Ser Val
1               5

<210> SEQ ID NO 28
<211> LENGTH: 4
<212> TYPE: PRT
<213> ORGANISM: Artificial Sequence
<220> FEATURE:
<223> OTHER INFORMATION: synthetic

<400> SEQUENCE: 28

Trp Ala Ser Tyr
1

<210> SEQ ID NO 29
<211> LENGTH: 7
<212> TYPE: PRT
<213> ORGANISM: Artificial Sequence
<220> FEATURE:
<223> OTHER INFORMATION: synthetic

<400> SEQUENCE: 29

Asp Ile Arg Ser Gly Ser Val
1               5

<210> SEQ ID NO 30
<211> LENGTH: 8
<212> TYPE: PRT
<213> ORGANISM: Artificial Sequence
<220> FEATURE:
```

```
<223> OTHER INFORMATION: synthetic

<400> SEQUENCE: 30

Asp Ile Trp Asn Arg Arg Ala Leu
1               5

<210> SEQ ID NO 31
<211> LENGTH: 4
<212> TYPE: PRT
<213> ORGANISM: Artificial Sequence
<220> FEATURE:
<223> OTHER INFORMATION: synthetic

<400> SEQUENCE: 31

Glu Gly Ser Ser
1

<210> SEQ ID NO 32
<211> LENGTH: 6
<212> TYPE: PRT
<213> ORGANISM: Artificial Sequence
<220> FEATURE:
<223> OTHER INFORMATION: synthetic

<400> SEQUENCE: 32

Gly Gly Ser Tyr Ser Ser
1               5

<210> SEQ ID NO 33
<211> LENGTH: 6
<212> TYPE: PRT
<213> ORGANISM: Artificial Sequence
<220> FEATURE:
<223> OTHER INFORMATION: synthetic

<400> SEQUENCE: 33

Asn Val Gly Arg Pro Val
1               5

<210> SEQ ID NO 34
<211> LENGTH: 4
<212> TYPE: PRT
<213> ORGANISM: Artificial Sequence
<220> FEATURE:
<223> OTHER INFORMATION: synthetic

<400> SEQUENCE: 34

Gly Gly Ser Ser
1

<210> SEQ ID NO 35
<211> LENGTH: 6
<212> TYPE: PRT
<213> ORGANISM: Artificial Sequence
<220> FEATURE:
<223> OTHER INFORMATION: synthetic

<400> SEQUENCE: 35

Tyr Gly Ser Phe Gly Thr
1               5

<210> SEQ ID NO 36
<211> LENGTH: 6
<212> TYPE: PRT
<213> ORGANISM: Artificial Sequence
<220> FEATURE:
<223> OTHER INFORMATION: synthetic
```

```
<400> SEQUENCE: 36

Asn Val Ser Lys His Val
1               5

<210> SEQ ID NO 37
<211> LENGTH: 4
<212> TYPE: PRT
<213> ORGANISM: Artificial Sequence
<220> FEATURE:
<223> OTHER INFORMATION: synthetic

<400> SEQUENCE: 37

Ser Tyr Ser Gly
1

<210> SEQ ID NO 38
<211> LENGTH: 8
<212> TYPE: PRT
<213> ORGANISM: Artificial Sequence
<220> FEATURE:
<223> OTHER INFORMATION: synthetic

<400> SEQUENCE: 38

Asn Ile Arg Asn Gly Gly Gly Leu
1               5

<210> SEQ ID NO 39
<211> LENGTH: 4
<212> TYPE: PRT
<213> ORGANISM: Artificial Sequence
<220> FEATURE:
<223> OTHER INFORMATION: synthetic

<400> SEQUENCE: 39

Val Asn Thr Ala
1

<210> SEQ ID NO 40
<211> LENGTH: 8
<212> TYPE: PRT
<213> ORGANISM: Artificial Sequence
<220> FEATURE:
<223> OTHER INFORMATION: synthetic

<400> SEQUENCE: 40

Ile Pro Arg Ser Ile Ser Gly Tyr
1               5

<210> SEQ ID NO 41

<400> SEQUENCE: 41

000

<210> SEQ ID NO 42

<400> SEQUENCE: 42

000

<210> SEQ ID NO 43
<211> LENGTH: 12
<212> TYPE: DNA
<213> ORGANISM: Artificial Sequence
<220> FEATURE:
<223> OTHER INFORMATION: synthetic
```

```
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t

<400> SEQUENCE: 43
catnnknnkr st                                                            12

<210> SEQ ID NO 44
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(9)
<223> OTHER INFORMATION: n is a, c, g, or t

<400> SEQUENCE: 44
kmtnnnnnnr st                                                            12

<210> SEQ ID NO 45
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(9)
<223> OTHER INFORMATION: n is a, c, g, or t

<400> SEQUENCE: 45
dggnnnnnnr st                                                            12

<210> SEQ ID NO 46
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t

<400> SEQUENCE: 46
nnkgsttccn nk                                                            12

<210> SEQ ID NO 47
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (10)..(11)
<223> OTHER INFORMATION: n is a, c, g, or t

<400> SEQUENCE: 47
```
tgggsttccn nk                                                               12

<210> SEQ ID NO 48
<211> LENGTH: 12
<212> TYPE: DNA
<213> ORGANISM: Artificial Sequence
<220> FEATURE:
<223> OTHER INFORMATION: synthetic

<400> SEQUENCE: 48
kgggsttcct mt                                                               12

<210> SEQ ID NO 49
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: n is a, c, g, or t

<400> SEQUENCE: 49
nnkgsttcct mt                                                               12

<210> SEQ ID NO 50
<211> LENGTH: 18
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: n = 70% G or 10% A or 10% T or 10% C
<220> FEATURE:
<221> NAME/KEY: misc_feature
<222> LOCATION: (2)..(2)
<223> OTHER INFORMATION: n = 70% A or 10% G or 10% T or 10% C
<220> FEATURE:
<221> NAME/KEY: misc_feature
<222> LOCATION: (3)..(3)
<223> OTHER INFORMATION: n = 70% C or 10% A or 10% T or 10% G
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t

<400> SEQUENCE: 50
nnnrttnnkn nktacsta                                                         18

<210> SEQ ID NO 51
<211> LENGTH: 18
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: n = 70% G or 10% A or 10% T or 10% C
<220> FEATURE:
<221> NAME/KEY: misc_feature
<222> LOCATION: (2)..(2)
<223> OTHER INFORMATION: n = 70% A or 10% G or 10% T or 10% C
<220> FEATURE:
<221> NAME/KEY: misc_feature

```
<222> LOCATION: (3)..(3)
<223> OTHER INFORMATION: n = 70% C or 10% G or 10% T or 10% A
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t

<400> SEQUENCE: 51
nnnrttnnkn nkdggsta                                               18

<210> SEQ ID NO 52
<211> LENGTH: 18
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: n = 70% G or 10% A or 10% T or 10% C
<220> FEATURE:
<221> NAME/KEY: misc_feature
<222> LOCATION: (2)..(2)
<223> OTHER INFORMATION: n = 70% A or 10% G or 10% T or 10% C
<220> FEATURE:
<221> NAME/KEY: misc_feature
<222> LOCATION: (3)..(3)
<223> OTHER INFORMATION: n = 70% C or 10% G or 10% T or 10% A
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 52
nnnrttnnkn nknmtsta                                               18

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000
```

```
<210> SEQ ID NO 57
<400> SEQUENCE: 57

000

<210> SEQ ID NO 58
<400> SEQUENCE: 58

000

<210> SEQ ID NO 59
<400> SEQUENCE: 59

000

<210> SEQ ID NO 60
<400> SEQUENCE: 60

000

<210> SEQ ID NO 61
<400> SEQUENCE: 61

000

<210> SEQ ID NO 62
<400> SEQUENCE: 62

000

<210> SEQ ID NO 63
<400> SEQUENCE: 63

000

<210> SEQ ID NO 64
<211> LENGTH: 7
<212> TYPE: PRT
<213> ORGANISM: Artificial Sequence
<220> FEATURE:
<223> OTHER INFORMATION: synthetic

<400> SEQUENCE: 64

Asp Ile Arg Thr Gly Ser Val
1               5

<210> SEQ ID NO 65
<211> LENGTH: 7
<212> TYPE: PRT
<213> ORGANISM: Artificial Sequence
<220> FEATURE:
<223> OTHER INFORMATION: synthetic

<400> SEQUENCE: 65

Asp Ile Arg Val Gly Ser Val
1               5

<210> SEQ ID NO 66
<211> LENGTH: 7
<212> TYPE: PRT
```

```
<213> ORGANISM: Artificial Sequence
<220> FEATURE:
<223> OTHER INFORMATION: synthetic

<400> SEQUENCE: 66

Asp Ile Ala Gly Gly Ser Val
1               5

<210> SEQ ID NO 67
<211> LENGTH: 7
<212> TYPE: PRT
<213> ORGANISM: Artificial Sequence
<220> FEATURE:
<223> OTHER INFORMATION: synthetic

<400> SEQUENCE: 67

Asp Ile Arg Phe Gly Ser Val
1               5

<210> SEQ ID NO 68
<211> LENGTH: 7
<212> TYPE: PRT
<213> ORGANISM: Artificial Sequence
<220> FEATURE:
<223> OTHER INFORMATION: synthetic

<400> SEQUENCE: 68

Asp Ile Lys Ser Gly Ser Val
1               5

<210> SEQ ID NO 69
<211> LENGTH: 7
<212> TYPE: PRT
<213> ORGANISM: Artificial Sequence
<220> FEATURE:
<223> OTHER INFORMATION: synthetic

<400> SEQUENCE: 69

Asp Ile Ala Arg Gly Ser Val
1               5

<210> SEQ ID NO 70
<211> LENGTH: 7
<212> TYPE: PRT
<213> ORGANISM: Artificial Sequence
<220> FEATURE:
<223> OTHER INFORMATION: synthetic

<400> SEQUENCE: 70

Trp Val Pro Ser His Thr Val
1               5

<210> SEQ ID NO 71
<211> LENGTH: 7
<212> TYPE: PRT
<213> ORGANISM: Artificial Sequence
<220> FEATURE:
<223> OTHER INFORMATION: synthetic

<400> SEQUENCE: 71

Asp Ile Asn Gly Gly Ser Val
1               5

<210> SEQ ID NO 72
<211> LENGTH: 7
<212> TYPE: PRT
<213> ORGANISM: Artificial Sequence
```

```
<220> FEATURE:
<223> OTHER INFORMATION: synthetic

<400> SEQUENCE: 72

Asp Ile Leu Gln Gly Ser Val
1               5

<210> SEQ ID NO 73
<211> LENGTH: 7
<212> TYPE: PRT
<213> ORGANISM: Artificial Sequence
<220> FEATURE:
<223> OTHER INFORMATION: synthetic

<400> SEQUENCE: 73

Asp Val Arg Met Gly Ser Val
1               5

<210> SEQ ID NO 74
<211> LENGTH: 7
<212> TYPE: PRT
<213> ORGANISM: Artificial Sequence
<220> FEATURE:
<223> OTHER INFORMATION: synthetic

<400> SEQUENCE: 74

Asp Ile Lys His Gly Ser Val
1               5

<210> SEQ ID NO 75
<211> LENGTH: 7
<212> TYPE: PRT
<213> ORGANISM: Artificial Sequence
<220> FEATURE:
<223> OTHER INFORMATION: synthetic

<400> SEQUENCE: 75

Asp Ile Ala Ser Gly Ser Val
1               5

<210> SEQ ID NO 76
<211> LENGTH: 7
<212> TYPE: PRT
<213> ORGANISM: Artificial Sequence
<220> FEATURE:
<223> OTHER INFORMATION: synthetic

<400> SEQUENCE: 76

Asp Ile Lys Ser Gly Ser Leu
1               5

<210> SEQ ID NO 77
<211> LENGTH: 6
<212> TYPE: PRT
<213> ORGANISM: Artificial Sequence
<220> FEATURE:
<223> OTHER INFORMATION: synthetic

<400> SEQUENCE: 77

Asn Val Trp Asp Trp Val
1               5

<210> SEQ ID NO 78
<211> LENGTH: 7
<212> TYPE: PRT
<213> ORGANISM: Artificial Sequence
<220> FEATURE:
```

<223> OTHER INFORMATION: synthetic

<400> SEQUENCE: 78

Asp Ile Arg Met Gly Ser Val
1               5

<210> SEQ ID NO 79
<211> LENGTH: 6
<212> TYPE: PRT
<213> ORGANISM: Artificial Sequence
<220> FEATURE:
<223> OTHER INFORMATION: synthetic

<400> SEQUENCE: 79

Gln Ile Trp Arg His Leu
1               5

<210> SEQ ID NO 80
<211> LENGTH: 7
<212> TYPE: PRT
<213> ORGANISM: Artificial Sequence
<220> FEATURE:
<223> OTHER INFORMATION: synthetic

<400> SEQUENCE: 80

Asp Ile Ser His Gly Ser Val
1               5

<210> SEQ ID NO 81
<211> LENGTH: 7
<212> TYPE: PRT
<213> ORGANISM: Artificial Sequence
<220> FEATURE:
<223> OTHER INFORMATION: synthetic

<400> SEQUENCE: 81

Asn Ile Ala Met Gly Ser Val
1               5

<210> SEQ ID NO 82
<211> LENGTH: 6
<212> TYPE: PRT
<213> ORGANISM: Artificial Sequence
<220> FEATURE:
<223> OTHER INFORMATION: synthetic

<400> SEQUENCE: 82

Glu Val Tyr Ser Tyr Val
1               5

<210> SEQ ID NO 83
<211> LENGTH: 10
<212> TYPE: PRT
<213> ORGANISM: Artificial Sequence
<220> FEATURE:
<223> OTHER INFORMATION: synthetic

<400> SEQUENCE: 83

Val Ile Arg Lys Ala Phe Gly Gln Pro Leu
1               5                   10

<210> SEQ ID NO 84
<211> LENGTH: 7
<212> TYPE: PRT
<213> ORGANISM: Artificial Sequence
<220> FEATURE:
<223> OTHER INFORMATION: synthetic

```
<400> SEQUENCE: 84

Asp Ile Lys Lys Gly Ser Val
1               5

<210> SEQ ID NO 85
<211> LENGTH: 6
<212> TYPE: PRT
<213> ORGANISM: Artificial Sequence
<220> FEATURE:
<223> OTHER INFORMATION: synthetic

<400> SEQUENCE: 85

Asn Ile Phe Ser His Val
1               5

<210> SEQ ID NO 86
<211> LENGTH: 7
<212> TYPE: PRT
<213> ORGANISM: Artificial Sequence
<220> FEATURE:
<223> OTHER INFORMATION: synthetic

<400> SEQUENCE: 86

Asp Ile Leu Phe Gly Ser Val
1               5

<210> SEQ ID NO 87
<211> LENGTH: 6
<212> TYPE: PRT
<213> ORGANISM: Artificial Sequence
<220> FEATURE:
<223> OTHER INFORMATION: synthetic

<400> SEQUENCE: 87

Asp Ile Trp Arg Trp Leu
1               5

<210> SEQ ID NO 88
<211> LENGTH: 7
<212> TYPE: PRT
<213> ORGANISM: Artificial Sequence
<220> FEATURE:
<223> OTHER INFORMATION: synthetic

<400> SEQUENCE: 88

Asp Ile Tyr Met Gly Ser Val
1               5

<210> SEQ ID NO 89
<211> LENGTH: 7
<212> TYPE: PRT
<213> ORGANISM: Artificial Sequence
<220> FEATURE:
<223> OTHER INFORMATION: synthetic

<400> SEQUENCE: 89

Asp Ile Ser Met Gly Ser Val
1               5

<210> SEQ ID NO 90
<211> LENGTH: 7
<212> TYPE: PRT
<213> ORGANISM: Artificial Sequence
<220> FEATURE:
<223> OTHER INFORMATION: synthetic
```

```
<400> SEQUENCE: 90

Asn Ile Ala Gln Gly Ser Val
1               5

<210> SEQ ID NO 91
<211> LENGTH: 4
<212> TYPE: PRT
<213> ORGANISM: Artificial Sequence
<220> FEATURE:
<223> OTHER INFORMATION: synthetic

<400> SEQUENCE: 91

Trp Gly Ser Phe
1

<210> SEQ ID NO 92
<211> LENGTH: 4
<212> TYPE: PRT
<213> ORGANISM: Artificial Sequence
<220> FEATURE:
<223> OTHER INFORMATION: synthetic

<400> SEQUENCE: 92

Leu Gly Ser Tyr
1

<210> SEQ ID NO 93
<211> LENGTH: 4
<212> TYPE: PRT
<213> ORGANISM: Artificial Sequence
<220> FEATURE:
<223> OTHER INFORMATION: synthetic

<400> SEQUENCE: 93

Trp Ala Ser Phe
1

<210> SEQ ID NO 94
<211> LENGTH: 4
<212> TYPE: PRT
<213> ORGANISM: Artificial Sequence
<220> FEATURE:
<223> OTHER INFORMATION: synthetic

<400> SEQUENCE: 94

Trp Gly Ser Ser
1

<210> SEQ ID NO 95
<211> LENGTH: 4
<212> TYPE: PRT
<213> ORGANISM: Artificial Sequence
<220> FEATURE:
<223> OTHER INFORMATION: synthetic

<400> SEQUENCE: 95

Trp Gly Ser Val
1

<210> SEQ ID NO 96
<211> LENGTH: 4
<212> TYPE: PRT
<213> ORGANISM: Artificial Sequence
<220> FEATURE:
<223> OTHER INFORMATION: synthetic

<400> SEQUENCE: 96
```

Thr Gly Ser Ser
1

<210> SEQ ID NO 97
<211> LENGTH: 4
<212> TYPE: PRT
<213> ORGANISM: Artificial Sequence
<220> FEATURE:
<223> OTHER INFORMATION: synthetic

<400> SEQUENCE: 97

Gly Ala Ser Tyr
1

<210> SEQ ID NO 98
<211> LENGTH: 4
<212> TYPE: PRT
<213> ORGANISM: Artificial Sequence
<220> FEATURE:
<223> OTHER INFORMATION: synthetic

<400> SEQUENCE: 98

Pro Gly Ser Tyr
1

<210> SEQ ID NO 99
<211> LENGTH: 4
<212> TYPE: PRT
<213> ORGANISM: Artificial Sequence
<220> FEATURE:
<223> OTHER INFORMATION: synthetic

<400> SEQUENCE: 99

Ala Gly Ser Ser
1

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106
<211> LENGTH: 7
<212> TYPE: PRT
<213> ORGANISM: Artificial Sequence
<220> FEATURE:
<223> OTHER INFORMATION: synthetic

<400> SEQUENCE: 106

Arg Ile Asn Ser His Thr Val
1               5

<210> SEQ ID NO 107
<211> LENGTH: 6
<212> TYPE: PRT
<213> ORGANISM: Artificial Sequence
<220> FEATURE:
<223> OTHER INFORMATION: synthetic

<400> SEQUENCE: 107

Val Val Ser Met Thr Val
1               5

<210> SEQ ID NO 108
<211> LENGTH: 6
<212> TYPE: PRT
<213> ORGANISM: Artificial Sequence
<220> FEATURE:
<223> OTHER INFORMATION: synthetic

<400> SEQUENCE: 108

Ser Val Ser Ser Ala Val
1               5

<210> SEQ ID NO 109
<211> LENGTH: 6
<212> TYPE: PRT
<213> ORGANISM: Artificial Sequence
<220> FEATURE:
<223> OTHER INFORMATION: synthetic

<400> SEQUENCE: 109

Glu Val Leu Thr Ser Val
1               5

<210> SEQ ID NO 110
<211> LENGTH: 7
<212> TYPE: PRT
<213> ORGANISM: Artificial Sequence
<220> FEATURE:
<223> OTHER INFORMATION: synthetic

<400> SEQUENCE: 110

Asp Val Ser Arg Tyr Asp Leu
1               5

<210> SEQ ID NO 111
<211> LENGTH: 6
<212> TYPE: PRT
<213> ORGANISM: Artificial Sequence
<220> FEATURE:
<223> OTHER INFORMATION: synthetic

```
<400> SEQUENCE: 111

Glu Ile Val Phe Ser Val
1               5

<210> SEQ ID NO 112
<211> LENGTH: 7
<212> TYPE: PRT
<213> ORGANISM: Artificial Sequence
<220> FEATURE:
<223> OTHER INFORMATION: synthetic

<400> SEQUENCE: 112

Ala Val Pro Arg Tyr Gly Val
1               5

<210> SEQ ID NO 113
<211> LENGTH: 8
<212> TYPE: PRT
<213> ORGANISM: Artificial Sequence
<220> FEATURE:
<223> OTHER INFORMATION: synthetic

<400> SEQUENCE: 113

Asp Ile Pro Glu His Phe Arg Leu
1               5

<210> SEQ ID NO 114
<211> LENGTH: 7
<212> TYPE: PRT
<213> ORGANISM: Artificial Sequence
<220> FEATURE:
<223> OTHER INFORMATION: synthetic

<400> SEQUENCE: 114

Tyr Ile Pro Arg Asp Ala Leu
1               5

<210> SEQ ID NO 115
<211> LENGTH: 6
<212> TYPE: PRT
<213> ORGANISM: Artificial Sequence
<220> FEATURE:
<223> OTHER INFORMATION: synthetic

<400> SEQUENCE: 115

Asp Ile Gly Ala Gly Leu
1               5

<210> SEQ ID NO 116
<211> LENGTH: 7
<212> TYPE: PRT
<213> ORGANISM: Artificial Sequence
<220> FEATURE:
<223> OTHER INFORMATION: synthetic

<400> SEQUENCE: 116

Asp Val His Arg Asp Ser Val
1               5

<210> SEQ ID NO 117
<211> LENGTH: 7
<212> TYPE: PRT
<213> ORGANISM: Artificial Sequence
<220> FEATURE:
<223> OTHER INFORMATION: synthetic

<400> SEQUENCE: 117
```

```
Asp Val Gly Gly Leu Gly Leu
1               5

<210> SEQ ID NO 118
<211> LENGTH: 6
<212> TYPE: PRT
<213> ORGANISM: Artificial Sequence
<220> FEATURE:
<223> OTHER INFORMATION: synthetic

<400> SEQUENCE: 118

Asp Ile Phe Pro Arg Val
1               5

<210> SEQ ID NO 119
<211> LENGTH: 7
<212> TYPE: PRT
<213> ORGANISM: Artificial Sequence
<220> FEATURE:
<223> OTHER INFORMATION: synthetic

<400> SEQUENCE: 119

Ala Val Ser Arg His Ala Leu
1               5

<210> SEQ ID NO 120
<211> LENGTH: 7
<212> TYPE: PRT
<213> ORGANISM: Artificial Sequence
<220> FEATURE:
<223> OTHER INFORMATION: synthetic

<400> SEQUENCE: 120

Asn Val Pro Arg Trp Ser Leu
1               5

<210> SEQ ID NO 121
<211> LENGTH: 7
<212> TYPE: PRT
<213> ORGANISM: Artificial Sequence
<220> FEATURE:
<223> OTHER INFORMATION: synthetic

<400> SEQUENCE: 121

Pro Val Phe Arg Arg Gly Leu
1               5

<210> SEQ ID NO 122
<211> LENGTH: 7
<212> TYPE: PRT
<213> ORGANISM: Artificial Sequence
<220> FEATURE:
<223> OTHER INFORMATION: synthetic

<400> SEQUENCE: 122

Gln Val Ser Lys Tyr Asp Val
1               5

<210> SEQ ID NO 123
<211> LENGTH: 7
<212> TYPE: PRT
<213> ORGANISM: Artificial Sequence
<220> FEATURE:
<223> OTHER INFORMATION: synthetic

<400> SEQUENCE: 123
```

Val Ile Ala Arg Tyr Asp Leu
1               5

<210> SEQ ID NO 124
<211> LENGTH: 10
<212> TYPE: PRT
<213> ORGANISM: Artificial Sequence
<220> FEATURE:
<223> OTHER INFORMATION: synthetic

<400> SEQUENCE: 124

Gln Ile Val Thr Pro Thr Ala Val His Val
1               5                   10

<210> SEQ ID NO 125
<211> LENGTH: 8
<212> TYPE: PRT
<213> ORGANISM: Artificial Sequence
<220> FEATURE:
<223> OTHER INFORMATION: synthetic

<400> SEQUENCE: 125

Asp Val Ser Gly Arg Arg Gly Leu
1               5

<210> SEQ ID NO 126
<211> LENGTH: 6
<212> TYPE: PRT
<213> ORGANISM: Artificial Sequence
<220> FEATURE:
<223> OTHER INFORMATION: synthetic

<400> SEQUENCE: 126

Asp Val Asn Arg Tyr Val
1               5

<210> SEQ ID NO 127
<211> LENGTH: 11
<212> TYPE: PRT
<213> ORGANISM: Artificial Sequence
<220> FEATURE:
<223> OTHER INFORMATION: synthetic

<400> SEQUENCE: 127

Asn Val Ser Arg Val Ser Trp Phe Glu Thr Leu
1               5                   10

<210> SEQ ID NO 128
<211> LENGTH: 7
<212> TYPE: PRT
<213> ORGANISM: Artificial Sequence
<220> FEATURE:
<223> OTHER INFORMATION: synthetic

<400> SEQUENCE: 128

Glu Ile Ser Arg Tyr Ala Val
1               5

<210> SEQ ID NO 129
<211> LENGTH: 7
<212> TYPE: PRT
<213> ORGANISM: Artificial Sequence
<220> FEATURE:
<223> OTHER INFORMATION: synthetic

<400> SEQUENCE: 129

Asn Val Pro Leu Asn Asp Val

```
1               5
```

<210> SEQ ID NO 130
<211> LENGTH: 8
<212> TYPE: PRT
<213> ORGANISM: Artificial Sequence
<220> FEATURE:
<223> OTHER INFORMATION: synthetic

<400> SEQUENCE: 130

```
Asp Val Gly Gly Gly Ser Gly Val
1               5
```

<210> SEQ ID NO 131
<211> LENGTH: 10
<212> TYPE: PRT
<213> ORGANISM: Artificial Sequence
<220> FEATURE:
<223> OTHER INFORMATION: synthetic

<400> SEQUENCE: 131

```
Arg Val Ser Asp Ser Leu Gln Asn Ser Val
1               5                   10
```

<210> SEQ ID NO 132
<211> LENGTH: 9
<212> TYPE: PRT
<213> ORGANISM: Artificial Sequence
<220> FEATURE:
<223> OTHER INFORMATION: synthetic

<400> SEQUENCE: 132

```
Ala Val Arg Arg Leu Thr Ala Tyr Val
1               5
```

<210> SEQ ID NO 133
<211> LENGTH: 6
<212> TYPE: PRT
<213> ORGANISM: Artificial Sequence
<220> FEATURE:
<223> OTHER INFORMATION: synthetic

<400> SEQUENCE: 133

```
Asp Ile Ser Arg Tyr Leu
1               5
```

<210> SEQ ID NO 134
<211> LENGTH: 6
<212> TYPE: PRT
<213> ORGANISM: Artificial Sequence
<220> FEATURE:
<223> OTHER INFORMATION: synthetic

<400> SEQUENCE: 134

```
Lys Ile Gln Ala Tyr Val
1               5
```

<210> SEQ ID NO 135
<211> LENGTH: 8
<212> TYPE: PRT
<213> ORGANISM: Artificial Sequence
<220> FEATURE:
<223> OTHER INFORMATION: synthetic

<400> SEQUENCE: 135

```
Asp Val His Pro Ser Pro Arg Val
1               5
```

<210> SEQ ID NO 136
<211> LENGTH: 8
<212> TYPE: PRT
<213> ORGANISM: Artificial Sequence
<220> FEATURE:
<223> OTHER INFORMATION: synthetic

<400> SEQUENCE: 136

Asn Ile Val Val Arg Pro Tyr Val
1               5

<210> SEQ ID NO 137
<211> LENGTH: 8
<212> TYPE: PRT
<213> ORGANISM: Artificial Sequence
<220> FEATURE:
<223> OTHER INFORMATION: synthetic

<400> SEQUENCE: 137

Asp Ile Arg Gly Gln Arg Gly Val
1               5

<210> SEQ ID NO 138
<211> LENGTH: 6
<212> TYPE: PRT
<213> ORGANISM: Artificial Sequence
<220> FEATURE:
<223> OTHER INFORMATION: synthetic

<400> SEQUENCE: 138

Val Val Arg Gln His Val
1               5

<210> SEQ ID NO 139
<211> LENGTH: 7
<212> TYPE: PRT
<213> ORGANISM: Artificial Sequence
<220> FEATURE:
<223> OTHER INFORMATION: synthetic

<400> SEQUENCE: 139

Asp Ile Gly Leu Leu Asn Leu
1               5

<210> SEQ ID NO 140
<211> LENGTH: 4
<212> TYPE: PRT
<213> ORGANISM: Artificial Sequence
<220> FEATURE:
<223> OTHER INFORMATION: synthetic

<400> SEQUENCE: 140

Trp Gly Ser His
1

<210> SEQ ID NO 141
<211> LENGTH: 4
<212> TYPE: PRT
<213> ORGANISM: Artificial Sequence
<220> FEATURE:
<223> OTHER INFORMATION: synthetic

<400> SEQUENCE: 141

Lys Gly Ser Ser
1

```
<210> SEQ ID NO 142
<211> LENGTH: 4
<212> TYPE: PRT
<213> ORGANISM: Artificial Sequence
<220> FEATURE:
<223> OTHER INFORMATION: synthetic

<400> SEQUENCE: 142

Gly Ala Ser Ser
1

<210> SEQ ID NO 143
<211> LENGTH: 4
<212> TYPE: PRT
<213> ORGANISM: Artificial Sequence
<220> FEATURE:
<223> OTHER INFORMATION: synthetic

<400> SEQUENCE: 143

Ser Ala Ser Ser
1

<210> SEQ ID NO 144
<211> LENGTH: 4
<212> TYPE: PRT
<213> ORGANISM: Artificial Sequence
<220> FEATURE:
<223> OTHER INFORMATION: synthetic

<400> SEQUENCE: 144

Phe Ala Ser Ser
1

<210> SEQ ID NO 145
<211> LENGTH: 4
<212> TYPE: PRT
<213> ORGANISM: Artificial Sequence
<220> FEATURE:
<223> OTHER INFORMATION: synthetic

<400> SEQUENCE: 145

Trp Gly Ser Asp
1

<210> SEQ ID NO 146
<211> LENGTH: 4
<212> TYPE: PRT
<213> ORGANISM: Artificial Sequence
<220> FEATURE:
<223> OTHER INFORMATION: synthetic

<400> SEQUENCE: 146

Trp Gly Ser Gln
1

<210> SEQ ID NO 147
<211> LENGTH: 4
<212> TYPE: PRT
<213> ORGANISM: Artificial Sequence
<220> FEATURE:
<223> OTHER INFORMATION: synthetic

<400> SEQUENCE: 147

Ala Gly Ser Tyr
1
```

```
<210> SEQ ID NO 148
<211> LENGTH: 4
<212> TYPE: PRT
<213> ORGANISM: Artificial Sequence
<220> FEATURE:
<223> OTHER INFORMATION: synthetic

<400> SEQUENCE: 148

Trp Ala Ser Ser
1

<210> SEQ ID NO 149
<211> LENGTH: 4
<212> TYPE: PRT
<213> ORGANISM: Artificial Sequence
<220> FEATURE:
<223> OTHER INFORMATION: synthetic

<400> SEQUENCE: 149

Asp Ala Ser Ser
1

<210> SEQ ID NO 150
<211> LENGTH: 4
<212> TYPE: PRT
<213> ORGANISM: Artificial Sequence
<220> FEATURE:
<223> OTHER INFORMATION: synthetic

<400> SEQUENCE: 150

Gly Gly Ser Tyr
1

<210> SEQ ID NO 151
<211> LENGTH: 4
<212> TYPE: PRT
<213> ORGANISM: Artificial Sequence
<220> FEATURE:
<223> OTHER INFORMATION: synthetic

<400> SEQUENCE: 151

His Gly Ser Ser
1

<210> SEQ ID NO 152
<211> LENGTH: 4
<212> TYPE: PRT
<213> ORGANISM: Artificial Sequence
<220> FEATURE:
<223> OTHER INFORMATION: synthetic

<400> SEQUENCE: 152

Leu Gly Ser Ser
1

<210> SEQ ID NO 153
<211> LENGTH: 4
<212> TYPE: PRT
<213> ORGANISM: Artificial Sequence
<220> FEATURE:
<223> OTHER INFORMATION: synthetic

<400> SEQUENCE: 153

Ser Gly Ser Ser
1

<210> SEQ ID NO 154
```

```
<211> LENGTH: 4
<212> TYPE: PRT
<213> ORGANISM: Artificial Sequence
<220> FEATURE:
<223> OTHER INFORMATION: synthetic

<400> SEQUENCE: 154

Arg Ala Ser Ser
1

<210> SEQ ID NO 155
<211> LENGTH: 5
<212> TYPE: PRT
<213> ORGANISM: Artificial Sequence
<220> FEATURE:
<223> OTHER INFORMATION: synthetic

<400> SEQUENCE: 155

Gly Gly Ser Tyr Ser
1               5

<210> SEQ ID NO 156
<211> LENGTH: 5
<212> TYPE: PRT
<213> ORGANISM: Artificial Sequence
<220> FEATURE:
<223> OTHER INFORMATION: synthetic

<400> SEQUENCE: 156

Tyr Ser Asn Arg Thr
1               5

<210> SEQ ID NO 157
<211> LENGTH: 5
<212> TYPE: PRT
<213> ORGANISM: Artificial Sequence
<220> FEATURE:
<223> OTHER INFORMATION: synthetic

<400> SEQUENCE: 157

Tyr Gly Ser Tyr Ser
1               5

<210> SEQ ID NO 158
<211> LENGTH: 5
<212> TYPE: PRT
<213> ORGANISM: Artificial Sequence
<220> FEATURE:
<223> OTHER INFORMATION: synthetic

<400> SEQUENCE: 158

Tyr Gly Ser Phe Gly
1               5

<210> SEQ ID NO 159
<211> LENGTH: 4
<212> TYPE: PRT
<213> ORGANISM: Artificial Sequence
<220> FEATURE:
<223> OTHER INFORMATION: synthetic

<400> SEQUENCE: 159

Tyr Ser Ser Ser
1

<210> SEQ ID NO 160
<211> LENGTH: 5
```

```
<212> TYPE: PRT
<213> ORGANISM: Artificial Sequence
<220> FEATURE:
<223> OTHER INFORMATION: synthetic

<400> SEQUENCE: 160

Ser Gly Tyr His Thr
1               5

<210> SEQ ID NO 161
<211> LENGTH: 5
<212> TYPE: PRT
<213> ORGANISM: Artificial Sequence
<220> FEATURE:
<223> OTHER INFORMATION: synthetic

<400> SEQUENCE: 161

Gly Asp Ser Lys Ser
1               5

<210> SEQ ID NO 162
<211> LENGTH: 5
<212> TYPE: PRT
<213> ORGANISM: Artificial Sequence
<220> FEATURE:
<223> OTHER INFORMATION: synthetic

<400> SEQUENCE: 162

Ser Gly Trp Ser Ala
1               5

<210> SEQ ID NO 163
<211> LENGTH: 6
<212> TYPE: PRT
<213> ORGANISM: Artificial Sequence
<220> FEATURE:
<223> OTHER INFORMATION: synthetic

<400> SEQUENCE: 163

Gly Gly Trp Ser Glu Thr
1               5

<210> SEQ ID NO 164
<211> LENGTH: 6
<212> TYPE: PRT
<213> ORGANISM: Artificial Sequence
<220> FEATURE:
<223> OTHER INFORMATION: synthetic

<400> SEQUENCE: 164

Trp Ala Ser Trp Asp Ala
1               5

<210> SEQ ID NO 165
<211> LENGTH: 5
<212> TYPE: PRT
<213> ORGANISM: Artificial Sequence
<220> FEATURE:
<223> OTHER INFORMATION: synthetic

<400> SEQUENCE: 165

Ser Glu Ser Arg Ser
1               5

<210> SEQ ID NO 166
<211> LENGTH: 6
<212> TYPE: PRT
```

```
<213> ORGANISM: Artificial Sequence
<220> FEATURE:
<223> OTHER INFORMATION: synthetic

<400> SEQUENCE: 166

Trp Thr Trp Ala Asp Thr
1               5

<210> SEQ ID NO 167
<211> LENGTH: 5
<212> TYPE: PRT
<213> ORGANISM: Artificial Sequence
<220> FEATURE:
<223> OTHER INFORMATION: synthetic

<400> SEQUENCE: 167

Gly Gly Ala Asp Thr
1               5

<210> SEQ ID NO 168
<211> LENGTH: 4
<212> TYPE: PRT
<213> ORGANISM: Artificial Sequence
<220> FEATURE:
<223> OTHER INFORMATION: synthetic

<400> SEQUENCE: 168

Gly His Ser Gly
1

<210> SEQ ID NO 169
<211> LENGTH: 5
<212> TYPE: PRT
<213> ORGANISM: Artificial Sequence
<220> FEATURE:
<223> OTHER INFORMATION: synthetic

<400> SEQUENCE: 169

Trp Asp Gly Lys Ala
1               5

<210> SEQ ID NO 170
<211> LENGTH: 6
<212> TYPE: PRT
<213> ORGANISM: Artificial Sequence
<220> FEATURE:
<223> OTHER INFORMATION: synthetic

<400> SEQUENCE: 170

Trp Val Thr His Glu Thr
1               5

<210> SEQ ID NO 171
<211> LENGTH: 5
<212> TYPE: PRT
<213> ORGANISM: Artificial Sequence
<220> FEATURE:
<223> OTHER INFORMATION: synthetic

<400> SEQUENCE: 171

Gly Leu Arg His Gly
1               5

<210> SEQ ID NO 172
<211> LENGTH: 5
<212> TYPE: PRT
<213> ORGANISM: Artificial Sequence
```

```
<220> FEATURE:
<223> OTHER INFORMATION: synthetic

<400> SEQUENCE: 172

Ser Gly Phe Arg Ser
1               5

<210> SEQ ID NO 173
<211> LENGTH: 5
<212> TYPE: PRT
<213> ORGANISM: Artificial Sequence
<220> FEATURE:
<223> OTHER INFORMATION: synthetic

<400> SEQUENCE: 173

Ala Gly Ala Arg Ala
1               5

<210> SEQ ID NO 174
<211> LENGTH: 4
<212> TYPE: PRT
<213> ORGANISM: Artificial Sequence
<220> FEATURE:
<223> OTHER INFORMATION: synthetic

<400> SEQUENCE: 174

Gly Thr Thr Thr
1

<210> SEQ ID NO 175
<211> LENGTH: 5
<212> TYPE: PRT
<213> ORGANISM: Artificial Sequence
<220> FEATURE:
<223> OTHER INFORMATION: synthetic

<400> SEQUENCE: 175

Gly Ala Ala Tyr Ala
1               5

<210> SEQ ID NO 176
<211> LENGTH: 5
<212> TYPE: PRT
<213> ORGANISM: Artificial Sequence
<220> FEATURE:
<223> OTHER INFORMATION: synthetic

<400> SEQUENCE: 176

Gly Ile Asp Leu Ala
1               5

<210> SEQ ID NO 177
<211> LENGTH: 5
<212> TYPE: PRT
<213> ORGANISM: Artificial Sequence
<220> FEATURE:
<223> OTHER INFORMATION: synthetic

<400> SEQUENCE: 177

Trp Phe Thr Trp Gly
1               5

<210> SEQ ID NO 178
<211> LENGTH: 5
<212> TYPE: PRT
<213> ORGANISM: Artificial Sequence
<220> FEATURE:
```

```
<223> OTHER INFORMATION: synthetic

<400> SEQUENCE: 178

Gly Val Tyr Asn Ala
1               5

<210> SEQ ID NO 179
<211> LENGTH: 5
<212> TYPE: PRT
<213> ORGANISM: Artificial Sequence
<220> FEATURE:
<223> OTHER INFORMATION: synthetic

<400> SEQUENCE: 179

Trp Ala His Tyr Gly
1               5

<210> SEQ ID NO 180
<211> LENGTH: 5
<212> TYPE: PRT
<213> ORGANISM: Artificial Sequence
<220> FEATURE:
<223> OTHER INFORMATION: synthetic

<400> SEQUENCE: 180

Gly Leu Asp Leu Ala
1               5

<210> SEQ ID NO 181
<211> LENGTH: 6
<212> TYPE: PRT
<213> ORGANISM: Artificial Sequence
<220> FEATURE:
<223> OTHER INFORMATION: synthetic

<400> SEQUENCE: 181

Tyr Gly Trp Arg Arg Thr
1               5

<210> SEQ ID NO 182
<211> LENGTH: 5
<212> TYPE: PRT
<213> ORGANISM: Artificial Sequence
<220> FEATURE:
<223> OTHER INFORMATION: synthetic

<400> SEQUENCE: 182

Ala Asn Val Asp Thr
1               5

<210> SEQ ID NO 183
<211> LENGTH: 6
<212> TYPE: PRT
<213> ORGANISM: Artificial Sequence
<220> FEATURE:
<223> OTHER INFORMATION: synthetic

<400> SEQUENCE: 183

Gly Ser Gly Ser Ser Thr
1               5

<210> SEQ ID NO 184
<211> LENGTH: 5
<212> TYPE: PRT
<213> ORGANISM: Artificial Sequence
<220> FEATURE:
<223> OTHER INFORMATION: synthetic
```

```
<400> SEQUENCE: 184

Ser Asp Ala Ser Ala
1               5

<210> SEQ ID NO 185
<211> LENGTH: 6
<212> TYPE: PRT
<213> ORGANISM: Artificial Sequence
<220> FEATURE:
<223> OTHER INFORMATION: synthetic

<400> SEQUENCE: 185

Trp Ala Asp Ile Ser Thr
1               5

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194
```

000

<210> SEQ ID NO 195
<400> SEQUENCE: 195
000

<210> SEQ ID NO 196
<400> SEQUENCE: 196
000

<210> SEQ ID NO 197
<400> SEQUENCE: 197
000

<210> SEQ ID NO 198
<400> SEQUENCE: 198
000

<210> SEQ ID NO 199
<400> SEQUENCE: 199
000

<210> SEQ ID NO 200
<400> SEQUENCE: 200
000

<210> SEQ ID NO 201
<400> SEQUENCE: 201
000

<210> SEQ ID NO 202
<400> SEQUENCE: 202
000

<210> SEQ ID NO 203
<400> SEQUENCE: 203
000

<210> SEQ ID NO 204
<400> SEQUENCE: 204
000

<210> SEQ ID NO 205
<400> SEQUENCE: 205
000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

```
<210> SEQ ID NO 217
<211> LENGTH: 6
<212> TYPE: PRT
<213> ORGANISM: Artificial Sequence
<220> FEATURE:
<223> OTHER INFORMATION: synthetic

<400> SEQUENCE: 217

Tyr Ile Trp Asn Tyr Val
1               5

<210> SEQ ID NO 218
<211> LENGTH: 5
<212> TYPE: PRT
<213> ORGANISM: Artificial Sequence
<220> FEATURE:
<223> OTHER INFORMATION: synthetic

<400> SEQUENCE: 218

Ser Trp Trp Ala Gly
1               5

<210> SEQ ID NO 219

<400> SEQUENCE: 219

000

<210> SEQ ID NO 220
<211> LENGTH: 7
<212> TYPE: PRT
<213> ORGANISM: Artificial Sequence
<220> FEATURE:
<223> OTHER INFORMATION: synthetic

<400> SEQUENCE: 220

Glu Ile Phe Pro Tyr Tyr Val
1               5

<210> SEQ ID NO 221
<211> LENGTH: 4
<212> TYPE: PRT
<213> ORGANISM: Artificial Sequence
<220> FEATURE:
<223> OTHER INFORMATION: synthetic

<400> SEQUENCE: 221

Gly Trp Asp Gly
1

<210> SEQ ID NO 222
<211> LENGTH: 6
<212> TYPE: PRT
<213> ORGANISM: Artificial Sequence
<220> FEATURE:
<223> OTHER INFORMATION: synthetic

<400> SEQUENCE: 222

Tyr Val Trp Gln Tyr Val
1               5

<210> SEQ ID NO 223
<211> LENGTH: 4
<212> TYPE: PRT
<213> ORGANISM: Artificial Sequence
<220> FEATURE:
<223> OTHER INFORMATION: synthetic
```

```
<400> SEQUENCE: 223

His Ala Ser Ser
1

<210> SEQ ID NO 224
<211> LENGTH: 5
<212> TYPE: PRT
<213> ORGANISM: Artificial Sequence
<220> FEATURE:
<223> OTHER INFORMATION: synthetic

<400> SEQUENCE: 224

Gly Tyr Trp Val Ala
1               5

<210> SEQ ID NO 225
<211> LENGTH: 6
<212> TYPE: PRT
<213> ORGANISM: Artificial Sequence
<220> FEATURE:
<223> OTHER INFORMATION: synthetic

<400> SEQUENCE: 225

Asp Val Phe Thr Ser Val
1               5

<210> SEQ ID NO 226
<211> LENGTH: 4
<212> TYPE: PRT
<213> ORGANISM: Artificial Sequence
<220> FEATURE:
<223> OTHER INFORMATION: synthetic

<400> SEQUENCE: 226

Asp Ala Ser Tyr
1

<210> SEQ ID NO 227
<211> LENGTH: 5
<212> TYPE: PRT
<213> ORGANISM: Artificial Sequence
<220> FEATURE:
<223> OTHER INFORMATION: synthetic

<400> SEQUENCE: 227

Arg Tyr Ile Trp Ala
1               5

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000
```

<210> SEQ ID NO 231

<400> SEQUENCE: 231

000

<210> SEQ ID NO 232
<211> LENGTH: 7
<212> TYPE: PRT
<213> ORGANISM: Artificial Sequence
<220> FEATURE:
<223> OTHER INFORMATION: synthetic

<400> SEQUENCE: 232

Asp Ile Met Leu Gly Ser Val
1               5

<210> SEQ ID NO 233
<211> LENGTH: 7
<212> TYPE: PRT
<213> ORGANISM: Artificial Sequence
<220> FEATURE:
<223> OTHER INFORMATION: synthetic

<400> SEQUENCE: 233

Asp Ile Gly Leu Gly Ser Val
1               5

<210> SEQ ID NO 234
<211> LENGTH: 7
<212> TYPE: PRT
<213> ORGANISM: Artificial Sequence
<220> FEATURE:
<223> OTHER INFORMATION: synthetic

<400> SEQUENCE: 234

Asp Ile Arg Gly Gly Ser Val
1               5

<210> SEQ ID NO 235
<211> LENGTH: 7
<212> TYPE: PRT
<213> ORGANISM: Artificial Sequence
<220> FEATURE:
<223> OTHER INFORMATION: synthetic

<400> SEQUENCE: 235

Asp Ile Ala Lys Gly Ser Val
1               5

<210> SEQ ID NO 236
<211> LENGTH: 7
<212> TYPE: PRT
<213> ORGANISM: Artificial Sequence
<220> FEATURE:
<223> OTHER INFORMATION: synthetic

<400> SEQUENCE: 236

Asp Ile Leu Ala Gly Ser Val
1               5

<210> SEQ ID NO 237
<211> LENGTH: 7
<212> TYPE: PRT
<213> ORGANISM: Artificial Sequence
<220> FEATURE:
<223> OTHER INFORMATION: synthetic

```
<400> SEQUENCE: 237

Asp Ile Ser Arg Gly Ser Val
1               5

<210> SEQ ID NO 238
<211> LENGTH: 7
<212> TYPE: PRT
<213> ORGANISM: Artificial Sequence
<220> FEATURE:
<223> OTHER INFORMATION: synthetic

<400> SEQUENCE: 238

Asn Ile Tyr Ala Gly Ser Leu
1               5

<210> SEQ ID NO 239
<211> LENGTH: 7
<212> TYPE: PRT
<213> ORGANISM: Artificial Sequence
<220> FEATURE:
<223> OTHER INFORMATION: synthetic

<400> SEQUENCE: 239

Asp Ile Ala Phe Gly Ser Leu
1               5

<210> SEQ ID NO 240
<211> LENGTH: 7
<212> TYPE: PRT
<213> ORGANISM: Artificial Sequence
<220> FEATURE:
<223> OTHER INFORMATION: synthetic

<400> SEQUENCE: 240

Asp Ile Lys Ala Gly Ser Val
1               5

<210> SEQ ID NO 241
<211> LENGTH: 7
<212> TYPE: PRT
<213> ORGANISM: Artificial Sequence
<220> FEATURE:
<223> OTHER INFORMATION: synthetic

<400> SEQUENCE: 241

Asp Ile Leu Lys Gly Ser Val
1               5

<210> SEQ ID NO 242
<211> LENGTH: 7
<212> TYPE: PRT
<213> ORGANISM: Artificial Sequence
<220> FEATURE:
<223> OTHER INFORMATION: synthetic

<400> SEQUENCE: 242

Asp Ile Leu Ile Gly Ser Val
1               5

<210> SEQ ID NO 243
<211> LENGTH: 7
<212> TYPE: PRT
<213> ORGANISM: Artificial Sequence
<220> FEATURE:
<223> OTHER INFORMATION: synthetic

<400> SEQUENCE: 243
```

```
Asp Ile Val Ser Gly Ser Val
1               5

<210> SEQ ID NO 244

<400> SEQUENCE: 244

000

<210> SEQ ID NO 245
<211> LENGTH: 7
<212> TYPE: PRT
<213> ORGANISM: Artificial Sequence
<220> FEATURE:
<223> OTHER INFORMATION: synthetic

<400> SEQUENCE: 245

Asp Ile Arg Gln Gly Ser Val
1               5

<210> SEQ ID NO 246
<211> LENGTH: 7
<212> TYPE: PRT
<213> ORGANISM: Artificial Sequence
<220> FEATURE:
<223> OTHER INFORMATION: synthetic

<400> SEQUENCE: 246

Asp Ile Lys Val Gly Ser Val
1               5

<210> SEQ ID NO 247
<211> LENGTH: 7
<212> TYPE: PRT
<213> ORGANISM: Artificial Sequence
<220> FEATURE:
<223> OTHER INFORMATION: synthetic

<400> SEQUENCE: 247

Asp Ile Arg Glu Gly Ser Val
1               5

<210> SEQ ID NO 248
<211> LENGTH: 7
<212> TYPE: PRT
<213> ORGANISM: Artificial Sequence
<220> FEATURE:
<223> OTHER INFORMATION: synthetic

<400> SEQUENCE: 248

Asp Ile Gly Ser Gly Ser Val
1               5

<210> SEQ ID NO 249
<211> LENGTH: 7
<212> TYPE: PRT
<213> ORGANISM: Artificial Sequence
<220> FEATURE:
<223> OTHER INFORMATION: synthetic

<400> SEQUENCE: 249

Asp Ile Leu Thr Gly Ser Val
1               5

<210> SEQ ID NO 250
<211> LENGTH: 7
```

<212> TYPE: PRT
<213> ORGANISM: Artificial Sequence
<220> FEATURE:
<223> OTHER INFORMATION: synthetic

<400> SEQUENCE: 250

Asn Ile Arg Thr Gly Ser Val
1               5

<210> SEQ ID NO 251
<211> LENGTH: 7
<212> TYPE: PRT
<213> ORGANISM: Artificial Sequence
<220> FEATURE:
<223> OTHER INFORMATION: synthetic

<400> SEQUENCE: 251

Asp Ile Ser Ser Gly Ser Val
1               5

<210> SEQ ID NO 252
<211> LENGTH: 7
<212> TYPE: PRT
<213> ORGANISM: Artificial Sequence
<220> FEATURE:
<223> OTHER INFORMATION: synthetic

<400> SEQUENCE: 252

Asp Ile Ser Val Gly Ser Val
1               5

<210> SEQ ID NO 253
<211> LENGTH: 7
<212> TYPE: PRT
<213> ORGANISM: Artificial Sequence
<220> FEATURE:
<223> OTHER INFORMATION: synthetic

<400> SEQUENCE: 253

Asp Val Arg Gln Gly Ser Val
1               5

<210> SEQ ID NO 254
<211> LENGTH: 7
<212> TYPE: PRT
<213> ORGANISM: Artificial Sequence
<220> FEATURE:
<223> OTHER INFORMATION: synthetic

<400> SEQUENCE: 254

Asp Ile Gln Ser Gly Ser Val
1               5

<210> SEQ ID NO 255
<211> LENGTH: 7
<212> TYPE: PRT
<213> ORGANISM: Artificial Sequence
<220> FEATURE:
<223> OTHER INFORMATION: synthetic

<400> SEQUENCE: 255

Asp Ile Met Ser Gly Ser Val
1               5

<210> SEQ ID NO 256
<211> LENGTH: 7
<212> TYPE: PRT

```
<213> ORGANISM: Artificial Sequence
<220> FEATURE:
<223> OTHER INFORMATION: synthetic

<400> SEQUENCE: 256

Asp Ile Ile Gly Gly Ser Val
1               5

<210> SEQ ID NO 257
<211> LENGTH: 7
<212> TYPE: PRT
<213> ORGANISM: Artificial Sequence
<220> FEATURE:
<223> OTHER INFORMATION: synthetic

<400> SEQUENCE: 257

Asp Ile Leu Gly Gly Ser Val
1               5

<210> SEQ ID NO 258
<211> LENGTH: 7
<212> TYPE: PRT
<213> ORGANISM: Artificial Sequence
<220> FEATURE:
<223> OTHER INFORMATION: synthetic

<400> SEQUENCE: 258

Asp Ile Arg Leu Gly Ser Val
1               5

<210> SEQ ID NO 259
<211> LENGTH: 7
<212> TYPE: PRT
<213> ORGANISM: Artificial Sequence
<220> FEATURE:
<223> OTHER INFORMATION: synthetic

<400> SEQUENCE: 259

Asp Ile Gly Ala Gly Ser Val
1               5

<210> SEQ ID NO 260
<211> LENGTH: 7
<212> TYPE: PRT
<213> ORGANISM: Artificial Sequence
<220> FEATURE:
<223> OTHER INFORMATION: synthetic

<400> SEQUENCE: 260

Asp Ile Ala Thr Gly Ser Leu
1               5

<210> SEQ ID NO 261
<211> LENGTH: 7
<212> TYPE: PRT
<213> ORGANISM: Artificial Sequence
<220> FEATURE:
<223> OTHER INFORMATION: synthetic

<400> SEQUENCE: 261

Asp Ile Leu Ser Gly Ser Val
1               5

<210> SEQ ID NO 262
<211> LENGTH: 7
<212> TYPE: PRT
<213> ORGANISM: Artificial Sequence
```

```
<220> FEATURE:
<223> OTHER INFORMATION: synthetic

<400> SEQUENCE: 262

Gly Ile Arg Thr Gly Ser Val
1               5

<210> SEQ ID NO 263
<211> LENGTH: 7
<212> TYPE: PRT
<213> ORGANISM: Artificial Sequence
<220> FEATURE:
<223> OTHER INFORMATION: synthetic

<400> SEQUENCE: 263

Asp Ile Ala Met Gly Ser Val
1               5

<210> SEQ ID NO 264
<211> LENGTH: 7
<212> TYPE: PRT
<213> ORGANISM: Artificial Sequence
<220> FEATURE:
<223> OTHER INFORMATION: synthetic

<400> SEQUENCE: 264

Asp Ile Lys Leu Gly Ser Val
1               5

<210> SEQ ID NO 265
<211> LENGTH: 7
<212> TYPE: PRT
<213> ORGANISM: Artificial Sequence
<220> FEATURE:
<223> OTHER INFORMATION: synthetic

<400> SEQUENCE: 265

Asn Ile Tyr Ser Gly Ser Leu
1               5

<210> SEQ ID NO 266
<211> LENGTH: 7
<212> TYPE: PRT
<213> ORGANISM: Artificial Sequence
<220> FEATURE:
<223> OTHER INFORMATION: synthetic

<400> SEQUENCE: 266

Asp Ile Arg Ala Gly Ser Val
1               5

<210> SEQ ID NO 267
<211> LENGTH: 7
<212> TYPE: PRT
<213> ORGANISM: Artificial Sequence
<220> FEATURE:
<223> OTHER INFORMATION: synthetic

<400> SEQUENCE: 267

Asp Ile Ala Ala Gly Ser Val
1               5

<210> SEQ ID NO 268
<211> LENGTH: 7
<212> TYPE: PRT
<213> ORGANISM: Artificial Sequence
<220> FEATURE:
```

```
<223> OTHER INFORMATION: synthetic

<400> SEQUENCE: 268

Asp Ile Gln Thr Gly Ser Val
1               5

<210> SEQ ID NO 269
<211> LENGTH: 7
<212> TYPE: PRT
<213> ORGANISM: Artificial Sequence
<220> FEATURE:
<223> OTHER INFORMATION: synthetic

<400> SEQUENCE: 269

Asp Ile Thr Met Gly Ser Val
1               5

<210> SEQ ID NO 270
<211> LENGTH: 7
<212> TYPE: PRT
<213> ORGANISM: Artificial Sequence
<220> FEATURE:
<223> OTHER INFORMATION: synthetic

<400> SEQUENCE: 270

Asp Ile Gly Met Gly Ser Val
1               5

<210> SEQ ID NO 271
<211> LENGTH: 7
<212> TYPE: PRT
<213> ORGANISM: Artificial Sequence
<220> FEATURE:
<223> OTHER INFORMATION: synthetic

<400> SEQUENCE: 271

Asp Ile Gln Arg Gly Ser Val
1               5

<210> SEQ ID NO 272
<211> LENGTH: 7
<212> TYPE: PRT
<213> ORGANISM: Artificial Sequence
<220> FEATURE:
<223> OTHER INFORMATION: synthetic

<400> SEQUENCE: 272

Asp Ile Gly Gly Gly Ser Val
1               5

<210> SEQ ID NO 273
<211> LENGTH: 7
<212> TYPE: PRT
<213> ORGANISM: Artificial Sequence
<220> FEATURE:
<223> OTHER INFORMATION: synthetic

<400> SEQUENCE: 273

Asp Ile Lys Phe Gly Ser Val
1               5

<210> SEQ ID NO 274
<211> LENGTH: 7
<212> TYPE: PRT
<213> ORGANISM: Artificial Sequence
<220> FEATURE:
<223> OTHER INFORMATION: synthetic
```

<400> SEQUENCE: 274

Asp Ile Arg Arg Gly Ser Val
1               5

<210> SEQ ID NO 275
<211> LENGTH: 7
<212> TYPE: PRT
<213> ORGANISM: Artificial Sequence
<220> FEATURE:
<223> OTHER INFORMATION: synthetic

<400> SEQUENCE: 275

Asp Ile Arg Ile Gly Ser Val
1               5

<210> SEQ ID NO 276
<211> LENGTH: 7
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: Xaa can be any naturally occurring amino acid

<400> SEQUENCE: 276

Asp Ile Val Xaa Gly Ser Val
1               5

<210> SEQ ID NO 277
<211> LENGTH: 7
<212> TYPE: PRT
<213> ORGANISM: Artificial Sequence
<220> FEATURE:
<223> OTHER INFORMATION: synthetic

<400> SEQUENCE: 277

Asp Ile Ala His Gly Ser Val
1               5

<210> SEQ ID NO 278
<211> LENGTH: 7
<212> TYPE: PRT
<213> ORGANISM: Artificial Sequence
<220> FEATURE:
<223> OTHER INFORMATION: synthetic

<400> SEQUENCE: 278

Asp Ile Lys Asn Gly Ser Val
1               5

<210> SEQ ID NO 279
<211> LENGTH: 7
<212> TYPE: PRT
<213> ORGANISM: Artificial Sequence
<220> FEATURE:
<223> OTHER INFORMATION: synthetic

<400> SEQUENCE: 279

Asp Ile Lys Trp Gly Ser Val
1               5

<210> SEQ ID NO 280
<211> LENGTH: 7
<212> TYPE: PRT

```
<213> ORGANISM: Artificial Sequence
<220> FEATURE:
<223> OTHER INFORMATION: synthetic

<400> SEQUENCE: 280

Asn Ile Arg Ser Gly Ser Val
1               5

<210> SEQ ID NO 281
<211> LENGTH: 6
<212> TYPE: PRT
<213> ORGANISM: Artificial Sequence
<220> FEATURE:
<223> OTHER INFORMATION: synthetic

<400> SEQUENCE: 281

Asp Val Trp Lys Trp Val
1               5

<210> SEQ ID NO 282
<211> LENGTH: 6
<212> TYPE: PRT
<213> ORGANISM: Artificial Sequence
<220> FEATURE:
<223> OTHER INFORMATION: synthetic

<400> SEQUENCE: 282

Asp Ile Trp His Trp Val
1               5

<210> SEQ ID NO 283
<211> LENGTH: 4
<212> TYPE: PRT
<213> ORGANISM: Artificial Sequence
<220> FEATURE:
<223> OTHER INFORMATION: synthetic

<400> SEQUENCE: 283

Trp Gly Ser Trp
1

<210> SEQ ID NO 284
<211> LENGTH: 4
<212> TYPE: PRT
<213> ORGANISM: Artificial Sequence
<220> FEATURE:
<223> OTHER INFORMATION: synthetic

<400> SEQUENCE: 284

Trp Gly Ser Leu
1

<210> SEQ ID NO 285
<211> LENGTH: 4
<212> TYPE: PRT
<213> ORGANISM: Artificial Sequence
<220> FEATURE:
<223> OTHER INFORMATION: synthetic

<400> SEQUENCE: 285

Trp Gly Ser Met
1

<210> SEQ ID NO 286
<211> LENGTH: 4
<212> TYPE: PRT
<213> ORGANISM: Artificial Sequence
```

```
<220> FEATURE:
<223> OTHER INFORMATION: synthetic

<400> SEQUENCE: 286

Trp Gly Ser Thr
1

<210> SEQ ID NO 287
<211> LENGTH: 4
<212> TYPE: PRT
<213> ORGANISM: Artificial Sequence
<220> FEATURE:
<223> OTHER INFORMATION: synthetic

<400> SEQUENCE: 287

Trp Gly Ser Cys
1

<210> SEQ ID NO 288
<211> LENGTH: 4
<212> TYPE: PRT
<213> ORGANISM: Artificial Sequence
<220> FEATURE:
<223> OTHER INFORMATION: synthetic

<400> SEQUENCE: 288

Trp Gly Ser Asn
1

<210> SEQ ID NO 289
<211> LENGTH: 4
<212> TYPE: PRT
<213> ORGANISM: Artificial Sequence
<220> FEATURE:
<223> OTHER INFORMATION: synthetic

<400> SEQUENCE: 289

Trp Gly Ser Glu
1

<210> SEQ ID NO 290
<211> LENGTH: 4
<212> TYPE: PRT
<213> ORGANISM: Artificial Sequence
<220> FEATURE:
<223> OTHER INFORMATION: synthetic

<400> SEQUENCE: 290

Ala Ala Ser Ser
1

<210> SEQ ID NO 291
<211> LENGTH: 4
<212> TYPE: PRT
<213> ORGANISM: Artificial Sequence
<220> FEATURE:
<223> OTHER INFORMATION: synthetic

<400> SEQUENCE: 291

Trp Gly Ser Ala
1

<210> SEQ ID NO 292
<211> LENGTH: 4
<212> TYPE: PRT
<213> ORGANISM: Artificial Sequence
<220> FEATURE:
```

<223> OTHER INFORMATION: synthetic

<400> SEQUENCE: 292

His Phe Asn Ala
1

<210> SEQ ID NO 293
<400> SEQUENCE: 293
000

<210> SEQ ID NO 294
<400> SEQUENCE: 294
000

<210> SEQ ID NO 295
<400> SEQUENCE: 295
000

<210> SEQ ID NO 296
<400> SEQUENCE: 296
000

<210> SEQ ID NO 297
<400> SEQUENCE: 297
000

<210> SEQ ID NO 298
<400> SEQUENCE: 298
000

<210> SEQ ID NO 299
<400> SEQUENCE: 299
000

<210> SEQ ID NO 300
<400> SEQUENCE: 300
000

<210> SEQ ID NO 301
<400> SEQUENCE: 301
000

<210> SEQ ID NO 302
<400> SEQUENCE: 302
000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

<210> SEQ ID NO 310

<400> SEQUENCE: 310

000

<210> SEQ ID NO 311

<400> SEQUENCE: 311

000

<210> SEQ ID NO 312

<400> SEQUENCE: 312

000

<210> SEQ ID NO 313

<400> SEQUENCE: 313

000

<210> SEQ ID NO 314

<400> SEQUENCE: 314

000

<210> SEQ ID NO 315
<400> SEQUENCE: 315
000

<210> SEQ ID NO 316
<400> SEQUENCE: 316
000

<210> SEQ ID NO 317
<400> SEQUENCE: 317
000

<210> SEQ ID NO 318
<400> SEQUENCE: 318
000

<210> SEQ ID NO 319
<400> SEQUENCE: 319
000

<210> SEQ ID NO 320
<400> SEQUENCE: 320
000

<210> SEQ ID NO 321
<400> SEQUENCE: 321
000

<210> SEQ ID NO 322
<400> SEQUENCE: 322
000

<210> SEQ ID NO 323
<400> SEQUENCE: 323
000

<210> SEQ ID NO 324
<400> SEQUENCE: 324
000

<210> SEQ ID NO 325
<400> SEQUENCE: 325
000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

-continued

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

```
<400> SEQUENCE: 348
000

<210> SEQ ID NO 349
<400> SEQUENCE: 349
000

<210> SEQ ID NO 350
<400> SEQUENCE: 350
000

<210> SEQ ID NO 351
<400> SEQUENCE: 351
000

<210> SEQ ID NO 352
<400> SEQUENCE: 352
000

<210> SEQ ID NO 353
<400> SEQUENCE: 353
000

<210> SEQ ID NO 354
<400> SEQUENCE: 354
000

<210> SEQ ID NO 355
<400> SEQUENCE: 355
000

<210> SEQ ID NO 356
<400> SEQUENCE: 356
000

<210> SEQ ID NO 357
<400> SEQUENCE: 357
000

<210> SEQ ID NO 358
<400> SEQUENCE: 358
000

<210> SEQ ID NO 359
<400> SEQUENCE: 359
```

000

<210> SEQ ID NO 360
<400> SEQUENCE: 360
000

<210> SEQ ID NO 361
<400> SEQUENCE: 361
000

<210> SEQ ID NO 362
<400> SEQUENCE: 362
000

<210> SEQ ID NO 363
<400> SEQUENCE: 363
000

<210> SEQ ID NO 364
<400> SEQUENCE: 364
000

<210> SEQ ID NO 365
<400> SEQUENCE: 365
000

<210> SEQ ID NO 366
<400> SEQUENCE: 366
000

<210> SEQ ID NO 367
<400> SEQUENCE: 367
000

<210> SEQ ID NO 368
<400> SEQUENCE: 368
000

<210> SEQ ID NO 369
<400> SEQUENCE: 369
000

<210> SEQ ID NO 370
<400> SEQUENCE: 370
000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

```
<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393
```

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400

<400> SEQUENCE: 400

000

<210> SEQ ID NO 401

<400> SEQUENCE: 401

000

<210> SEQ ID NO 402

<400> SEQUENCE: 402

000

<210> SEQ ID NO 403

<400> SEQUENCE: 403

000

<210> SEQ ID NO 404

<400> SEQUENCE: 404

000

<210> SEQ ID NO 405

<400> SEQUENCE: 405

000

<210> SEQ ID NO 406

<400> SEQUENCE: 406

000

<210> SEQ ID NO 407

<400> SEQUENCE: 407

000

<210> SEQ ID NO 408

<400> SEQUENCE: 408

000

<210> SEQ ID NO 409

<400> SEQUENCE: 409

000

<210> SEQ ID NO 410

<400> SEQUENCE: 410

000

<210> SEQ ID NO 411

<400> SEQUENCE: 411

000

<210> SEQ ID NO 412

<400> SEQUENCE: 412

000

<210> SEQ ID NO 413

<400> SEQUENCE: 413

000

<210> SEQ ID NO 414

<400> SEQUENCE: 414

000

<210> SEQ ID NO 415

<400> SEQUENCE: 415

000

<210> SEQ ID NO 416

<400> SEQUENCE: 416

000

<210> SEQ ID NO 417

<400> SEQUENCE: 417

000

<210> SEQ ID NO 418

<400> SEQUENCE: 418

000

<210> SEQ ID NO 419

<400> SEQUENCE: 419

000

<210> SEQ ID NO 420

<400> SEQUENCE: 420

000

<210> SEQ ID NO 421
<211> LENGTH: 6
<212> TYPE: PRT
<213> ORGANISM: Artificial Sequence
<220> FEATURE:
<223> OTHER INFORMATION: synthetic

<400> SEQUENCE: 421

Asp Ile Trp Arg Ala Val
1               5

<210> SEQ ID NO 422
<211> LENGTH: 6
<212> TYPE: PRT
<213> ORGANISM: Artificial Sequence
<220> FEATURE:
<223> OTHER INFORMATION: synthetic

<400> SEQUENCE: 422

Asp Ile Trp Arg Trp Val
1               5

<210> SEQ ID NO 423
<211> LENGTH: 7
<212> TYPE: PRT
<213> ORGANISM: Artificial Sequence
<220> FEATURE:
<223> OTHER INFORMATION: synthetic

<400> SEQUENCE: 423

Tyr Val Tyr Ser Thr Thr Val
1               5

<210> SEQ ID NO 424
<211> LENGTH: 7
<212> TYPE: PRT
<213> ORGANISM: Artificial Sequence
<220> FEATURE:

```
<223> OTHER INFORMATION: synthetic

<400> SEQUENCE: 424

Asp Ile His Ser Gly Ser Val
1               5

<210> SEQ ID NO 425
<211> LENGTH: 7
<212> TYPE: PRT
<213> ORGANISM: Artificial Sequence
<220> FEATURE:
<223> OTHER INFORMATION: synthetic

<400> SEQUENCE: 425

Asp Ile Pro Ser Ile Tyr Val
1               5

<210> SEQ ID NO 426
<211> LENGTH: 6
<212> TYPE: PRT
<213> ORGANISM: Artificial Sequence
<220> FEATURE:
<223> OTHER INFORMATION: synthetic

<400> SEQUENCE: 426

Asn Val Trp Ser His Val
1               5

<210> SEQ ID NO 427
<211> LENGTH: 5
<212> TYPE: PRT
<213> ORGANISM: Artificial Sequence
<220> FEATURE:
<223> OTHER INFORMATION: synthetic

<400> SEQUENCE: 427

Ile Trp Arg Tyr Val
1               5

<210> SEQ ID NO 428
<211> LENGTH: 4
<212> TYPE: PRT
<213> ORGANISM: Artificial Sequence
<220> FEATURE:
<223> OTHER INFORMATION: synthetic

<400> SEQUENCE: 428

Pro Ala Ser Asn
1

<210> SEQ ID NO 429
<211> LENGTH: 4
<212> TYPE: PRT
<213> ORGANISM: Artificial Sequence
<220> FEATURE:
<223> OTHER INFORMATION: synthetic

<400> SEQUENCE: 429

Asn Gly Ser Ser
1

<210> SEQ ID NO 430
<211> LENGTH: 5
<212> TYPE: PRT
<213> ORGANISM: Artificial Sequence
<220> FEATURE:
<223> OTHER INFORMATION: synthetic
```

<400> SEQUENCE: 430

Gly Tyr Tyr Ile Ala
1               5

<210> SEQ ID NO 431
<211> LENGTH: 4
<212> TYPE: PRT
<213> ORGANISM: Artificial Sequence
<220> FEATURE:
<223> OTHER INFORMATION: synthetic

<400> SEQUENCE: 431

Ser Asp Tyr Thr
1

<210> SEQ ID NO 432
<211> LENGTH: 5
<212> TYPE: PRT
<213> ORGANISM: Artificial Sequence
<220> FEATURE:
<223> OTHER INFORMATION: synthetic

<400> SEQUENCE: 432

Ser Tyr Trp Val Ala
1               5

<210> SEQ ID NO 433
<211> LENGTH: 4
<212> TYPE: PRT
<213> ORGANISM: Artificial Sequence
<220> FEATURE:
<223> OTHER INFORMATION: synthetic

<400> SEQUENCE: 433

His Ala Gly Ala
1

<210> SEQ ID NO 434
<211> LENGTH: 5
<212> TYPE: PRT
<213> ORGANISM: Artificial Sequence
<220> FEATURE:
<223> OTHER INFORMATION: synthetic

<400> SEQUENCE: 434

Ala Phe Trp Val Ser
1               5

<210> SEQ ID NO 435
<211> LENGTH: 4
<212> TYPE: PRT
<213> ORGANISM: Artificial Sequence
<220> FEATURE:
<223> OTHER INFORMATION: synthetic

<400> SEQUENCE: 435

Ala Ser Ser Ala
1

<210> SEQ ID NO 436
<211> LENGTH: 5
<212> TYPE: PRT
<213> ORGANISM: Artificial Sequence
<220> FEATURE:
<223> OTHER INFORMATION: synthetic

```
<400> SEQUENCE: 436

Arg Tyr Trp Val Ala
1               5

<210> SEQ ID NO 437
<211> LENGTH: 5
<212> TYPE: PRT
<213> ORGANISM: Artificial Sequence
<220> FEATURE:
<223> OTHER INFORMATION: synthetic

<400> SEQUENCE: 437

Arg Leu Trp Phe Thr
1               5

<210> SEQ ID NO 438
<211> LENGTH: 5
<212> TYPE: PRT
<213> ORGANISM: Artificial Sequence
<220> FEATURE:
<223> OTHER INFORMATION: synthetic

<400> SEQUENCE: 438

Gly Phe Trp Ile Gly
1               5

<210> SEQ ID NO 439
<211> LENGTH: 4
<212> TYPE: PRT
<213> ORGANISM: Artificial Sequence
<220> FEATURE:
<223> OTHER INFORMATION: synthetic

<400> SEQUENCE: 439

His Asp Gln Ala
1

<210> SEQ ID NO 440
<211> LENGTH: 5
<212> TYPE: PRT
<213> ORGANISM: Artificial Sequence
<220> FEATURE:
<223> OTHER INFORMATION: synthetic

<400> SEQUENCE: 440

Gly Leu Trp Tyr Ser
1               5

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000
```

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471

<400> SEQUENCE: 471

000

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

<210> SEQ ID NO 488

<400> SEQUENCE: 488

000

<210> SEQ ID NO 489

```
<400> SEQUENCE: 489
000

<210> SEQ ID NO 490
<400> SEQUENCE: 490
000

<210> SEQ ID NO 491
<400> SEQUENCE: 491
000

<210> SEQ ID NO 492
<400> SEQUENCE: 492
000

<210> SEQ ID NO 493
<400> SEQUENCE: 493
000

<210> SEQ ID NO 494
<400> SEQUENCE: 494
000

<210> SEQ ID NO 495
<400> SEQUENCE: 495
000

<210> SEQ ID NO 496
<400> SEQUENCE: 496
000

<210> SEQ ID NO 497
<400> SEQUENCE: 497
000

<210> SEQ ID NO 498
<400> SEQUENCE: 498
000

<210> SEQ ID NO 499
<400> SEQUENCE: 499
000

<210> SEQ ID NO 500
<211> LENGTH: 7
<212> TYPE: PRT
```

```
<213> ORGANISM: Artificial Sequence
<220> FEATURE:
<223> OTHER INFORMATION: synthetic

<400> SEQUENCE: 500

Ala Ile Ser His Leu Gly Leu
1               5

<210> SEQ ID NO 501
<211> LENGTH: 7
<212> TYPE: PRT
<213> ORGANISM: Artificial Sequence
<220> FEATURE:
<223> OTHER INFORMATION: synthetic

<400> SEQUENCE: 501

Asp Ile His Ala Asn Thr Val
1               5

<210> SEQ ID NO 502
<211> LENGTH: 6
<212> TYPE: PRT
<213> ORGANISM: Artificial Sequence
<220> FEATURE:
<223> OTHER INFORMATION: synthetic

<400> SEQUENCE: 502

Asp Ile Gly Ala Ser Val
1               5

<210> SEQ ID NO 503
<211> LENGTH: 7
<212> TYPE: PRT
<213> ORGANISM: Artificial Sequence
<220> FEATURE:
<223> OTHER INFORMATION: synthetic

<400> SEQUENCE: 503

Asp Val Pro Ala Gly Ala Val
1               5

<210> SEQ ID NO 504
<211> LENGTH: 7
<212> TYPE: PRT
<213> ORGANISM: Artificial Sequence
<220> FEATURE:
<223> OTHER INFORMATION: synthetic

<400> SEQUENCE: 504

Glu Val Ala Ser Val Ser Val
1               5

<210> SEQ ID NO 505

<400> SEQUENCE: 505

000

<210> SEQ ID NO 506

<400> SEQUENCE: 506

000

<210> SEQ ID NO 507

<400> SEQUENCE: 507
```

```
000

<210> SEQ ID NO 508

<400> SEQUENCE: 508

000

<210> SEQ ID NO 509
<211> LENGTH: 6
<212> TYPE: PRT
<213> ORGANISM: Artificial Sequence
<220> FEATURE:
<223> OTHER INFORMATION: synthetic

<400> SEQUENCE: 509

Tyr Ile Trp Arg Tyr Val
1               5

<210> SEQ ID NO 510

<400> SEQUENCE: 510

000

<210> SEQ ID NO 511

<400> SEQUENCE: 511

000

<210> SEQ ID NO 512

<400> SEQUENCE: 512

000

<210> SEQ ID NO 513

<400> SEQUENCE: 513

000

<210> SEQ ID NO 514

<400> SEQUENCE: 514

000

<210> SEQ ID NO 515

<400> SEQUENCE: 515

000

<210> SEQ ID NO 516

<400> SEQUENCE: 516

000

<210> SEQ ID NO 517

<400> SEQUENCE: 517

000
```

<210> SEQ ID NO 518
<400> SEQUENCE: 518
000

<210> SEQ ID NO 519
<400> SEQUENCE: 519
000

<210> SEQ ID NO 520
<400> SEQUENCE: 520
000

<210> SEQ ID NO 521
<400> SEQUENCE: 521
000

<210> SEQ ID NO 522
<400> SEQUENCE: 522
000

<210> SEQ ID NO 523
<400> SEQUENCE: 523
000

<210> SEQ ID NO 524
<400> SEQUENCE: 524
000

<210> SEQ ID NO 525
<400> SEQUENCE: 525
000

<210> SEQ ID NO 526
<400> SEQUENCE: 526
000

<210> SEQ ID NO 527
<400> SEQUENCE: 527
000

<210> SEQ ID NO 528
<400> SEQUENCE: 528
000

<210> SEQ ID NO 529

```
<400> SEQUENCE: 529

000

<210> SEQ ID NO 530

<400> SEQUENCE: 530

000

<210> SEQ ID NO 531

<400> SEQUENCE: 531

000

<210> SEQ ID NO 532

<400> SEQUENCE: 532

000

<210> SEQ ID NO 533
<211> LENGTH: 6
<212> TYPE: PRT
<213> ORGANISM: Artificial Sequence
<220> FEATURE:
<223> OTHER INFORMATION: synthetic

<400> SEQUENCE: 533

Gly Gly Ser Tyr Ser Ser
1               5

<210> SEQ ID NO 534
<211> LENGTH: 6
<212> TYPE: PRT
<213> ORGANISM: Artificial Sequence
<220> FEATURE:
<223> OTHER INFORMATION: synthetic

<400> SEQUENCE: 534

Tyr Gly Ser Tyr Ser Ala
1               5

<210> SEQ ID NO 535
<211> LENGTH: 6
<212> TYPE: PRT
<213> ORGANISM: Artificial Sequence
<220> FEATURE:
<223> OTHER INFORMATION: synthetic

<400> SEQUENCE: 535

Tyr Gly Ser Phe Gly Thr
1               5

<210> SEQ ID NO 536

<400> SEQUENCE: 536

000

<210> SEQ ID NO 537

<400> SEQUENCE: 537

000
```

<210> SEQ ID NO 538

<400> SEQUENCE: 538

000

<210> SEQ ID NO 539

<400> SEQUENCE: 539

000

<210> SEQ ID NO 540

<400> SEQUENCE: 540

000

<210> SEQ ID NO 541

<400> SEQUENCE: 541

000

<210> SEQ ID NO 542

<400> SEQUENCE: 542

000

<210> SEQ ID NO 543

<400> SEQUENCE: 543

000

<210> SEQ ID NO 544

<400> SEQUENCE: 544

000

<210> SEQ ID NO 545

<400> SEQUENCE: 545

000

<210> SEQ ID NO 546

<400> SEQUENCE: 546

000

<210> SEQ ID NO 547

<400> SEQUENCE: 547

000

<210> SEQ ID NO 548

<400> SEQUENCE: 548

000

<210> SEQ ID NO 549

-continued

<400> SEQUENCE: 549

000

<210> SEQ ID NO 550

<400> SEQUENCE: 550

000

<210> SEQ ID NO 551

<400> SEQUENCE: 551

000

<210> SEQ ID NO 552

<400> SEQUENCE: 552

000

<210> SEQ ID NO 553

<400> SEQUENCE: 553

000

<210> SEQ ID NO 554

<400> SEQUENCE: 554

000

<210> SEQ ID NO 555

<400> SEQUENCE: 555

000

<210> SEQ ID NO 556

<400> SEQUENCE: 556

000

<210> SEQ ID NO 557

<400> SEQUENCE: 557

000

<210> SEQ ID NO 558

<400> SEQUENCE: 558

000

<210> SEQ ID NO 559

<400> SEQUENCE: 559

000

<210> SEQ ID NO 560

<400> SEQUENCE: 560

000

<210> SEQ ID NO 561
<400> SEQUENCE: 561
000

<210> SEQ ID NO 562
<400> SEQUENCE: 562
000

<210> SEQ ID NO 563
<400> SEQUENCE: 563
000

<210> SEQ ID NO 564
<400> SEQUENCE: 564
000

<210> SEQ ID NO 565
<400> SEQUENCE: 565
000

<210> SEQ ID NO 566
<400> SEQUENCE: 566
000

<210> SEQ ID NO 567
<400> SEQUENCE: 567
000

<210> SEQ ID NO 568
<400> SEQUENCE: 568
000

<210> SEQ ID NO 569
<400> SEQUENCE: 569
000

<210> SEQ ID NO 570
<400> SEQUENCE: 570
000

<210> SEQ ID NO 571
<400> SEQUENCE: 571
000

<210> SEQ ID NO 572

<400> SEQUENCE: 572

000

<210> SEQ ID NO 573

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591
<211> LENGTH: 9
<212> TYPE: PRT
<213> ORGANISM: Artificial Sequence
<220> FEATURE:
<223> OTHER INFORMATION: synthetic

<400> SEQUENCE: 591

Asp Ile Pro Arg Ser Ile Ser Gly Tyr
1               5

<210> SEQ ID NO 592
<211> LENGTH: 10
<212> TYPE: PRT
<213> ORGANISM: Artificial Sequence
<220> FEATURE:
<223> OTHER INFORMATION: synthetic

<400> SEQUENCE: 592

Gln Asp Ile Pro Arg Ser Ile Ser Gly Tyr

```
                1               5                    10
```

<210> SEQ ID NO 593
<211> LENGTH: 4
<212> TYPE: PRT
<213> ORGANISM: Artificial Sequence
<220> FEATURE:
<223> OTHER INFORMATION: synthetic

<400> SEQUENCE: 593

Lys Asp Thr Tyr
1

<210> SEQ ID NO 594
<211> LENGTH: 6
<212> TYPE: PRT
<213> ORGANISM: Artificial Sequence
<220> FEATURE:
<223> OTHER INFORMATION: synthetic

<400> SEQUENCE: 594

Arg Tyr Thr Asn Tyr Arg
1               5

<210> SEQ ID NO 595
<211> LENGTH: 7
<212> TYPE: PRT
<213> ORGANISM: Artificial Sequence
<220> FEATURE:
<223> OTHER INFORMATION: synthetic

<400> SEQUENCE: 595

Trp Gly Gly Asp Gly Phe Tyr
1               5

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600

<400> SEQUENCE: 600

000

<210> SEQ ID NO 601

```
<400> SEQUENCE: 601

000

<210> SEQ ID NO 602

<400> SEQUENCE: 602

000

<210> SEQ ID NO 603
<211> LENGTH: 16
<212> TYPE: PRT
<213> ORGANISM: Artificial Sequence
<220> FEATURE:
<223> OTHER INFORMATION: synthetic

<400> SEQUENCE: 603

Cys Arg Ala Ile Gln Asp Ile Pro Lys Thr Ile Thr Gly Tyr Val Ala
1               5                   10                  15

<210> SEQ ID NO 604
<211> LENGTH: 16
<212> TYPE: PRT
<213> ORGANISM: Artificial Sequence
<220> FEATURE:
<223> OTHER INFORMATION: synthetic

<400> SEQUENCE: 604

Cys Arg Ala Ile Gln Asn Ile Ala Lys Thr Ile Thr Gly Tyr Val Ala
1               5                   10                  15

<210> SEQ ID NO 605
<211> LENGTH: 16
<212> TYPE: PRT
<213> ORGANISM: Artificial Sequence
<220> FEATURE:
<223> OTHER INFORMATION: synthetic

<400> SEQUENCE: 605

Cys Arg Ala Val Gln Asn Leu Pro Lys Thr Ile Thr Gly Tyr Val Ala
1               5                   10                  15

<210> SEQ ID NO 606
<211> LENGTH: 16
<212> TYPE: PRT
<213> ORGANISM: Artificial Sequence
<220> FEATURE:
<223> OTHER INFORMATION: synthetic

<400> SEQUENCE: 606

Cys Arg Ala Ile Glu Asp Leu Pro Lys Thr Val Ser Gly Tyr Val Ala
1               5                   10                  15

<210> SEQ ID NO 607
<211> LENGTH: 16
<212> TYPE: PRT
<213> ORGANISM: Artificial Sequence
<220> FEATURE:
<223> OTHER INFORMATION: synthetic

<400> SEQUENCE: 607

Cys Arg Ala Ile Gln Lys Val Pro Arg Thr Ile Thr Gly Tyr Val Ala
1               5                   10                  15

<210> SEQ ID NO 608
<211> LENGTH: 16
```

<212> TYPE: PRT
<213> ORGANISM: Artificial Sequence
<220> FEATURE:
<223> OTHER INFORMATION: synthetic

<400> SEQUENCE: 608

Cys Arg Ala Ser Val Asp Leu Pro Lys Ser Val Ser Gly Tyr Val Ala
1               5                   10                  15

<210> SEQ ID NO 609
<211> LENGTH: 16
<212> TYPE: PRT
<213> ORGANISM: Artificial Sequence
<220> FEATURE:
<223> OTHER INFORMATION: synthetic

<400> SEQUENCE: 609

Cys Arg Ala Ser Glu Asp Ile Pro Lys Thr Val Ser Gly Tyr Val Ala
1               5                   10                  15

<210> SEQ ID NO 610
<211> LENGTH: 16
<212> TYPE: PRT
<213> ORGANISM: Artificial Sequence
<220> FEATURE:
<223> OTHER INFORMATION: synthetic

<400> SEQUENCE: 610

Cys Arg Ala Ile Glu Asn Leu Pro Lys Thr Ile Ser Gly Tyr Val Ala
1               5                   10                  15

<210> SEQ ID NO 611
<211> LENGTH: 16
<212> TYPE: PRT
<213> ORGANISM: Artificial Sequence
<220> FEATURE:
<223> OTHER INFORMATION: synthetic

<400> SEQUENCE: 611

Cys Arg Ala Ser Gln Lys Ile Ala Arg Thr Ile Ser Gly Tyr Val Ala
1               5                   10                  15

<210> SEQ ID NO 612
<211> LENGTH: 16
<212> TYPE: PRT
<213> ORGANISM: Artificial Sequence
<220> FEATURE:
<223> OTHER INFORMATION: synthetic

<400> SEQUENCE: 612

Cys Arg Ala Ser Glu Asp Ile Pro Lys Ser Ile Ser Gly Tyr Val Ala
1               5                   10                  15

<210> SEQ ID NO 613
<211> LENGTH: 16
<212> TYPE: PRT
<213> ORGANISM: Artificial Sequence
<220> FEATURE:
<223> OTHER INFORMATION: synthetic

<400> SEQUENCE: 613

Cys Arg Ala Ser Gln Asp Leu Pro Lys Ser Ile Ser Gly Tyr Val Ala
1               5                   10                  15

<210> SEQ ID NO 614
<211> LENGTH: 16
<212> TYPE: PRT

```
<213> ORGANISM: Artificial Sequence
<220> FEATURE:
<223> OTHER INFORMATION: synthetic

<400> SEQUENCE: 614

Cys Arg Ala Ile Glu Asn Leu Pro Lys Ser Ile Thr Gly Tyr Val Ala
1               5                   10                  15

<210> SEQ ID NO 615
<211> LENGTH: 16
<212> TYPE: PRT
<213> ORGANISM: Artificial Sequence
<220> FEATURE:
<223> OTHER INFORMATION: synthetic

<400> SEQUENCE: 615

Cys Arg Ala Ile Glu Asn Leu Pro Lys Ser Val Ser Gly Tyr Val Ala
1               5                   10                  15

<210> SEQ ID NO 616
<211> LENGTH: 16
<212> TYPE: PRT
<213> ORGANISM: Artificial Sequence
<220> FEATURE:
<223> OTHER INFORMATION: synthetic

<400> SEQUENCE: 616

Cys Arg Ala Val Glu Asp Leu Pro Lys Thr Ile Thr Gly Tyr Val Ala
1               5                   10                  15

<210> SEQ ID NO 617
<211> LENGTH: 16
<212> TYPE: PRT
<213> ORGANISM: Artificial Sequence
<220> FEATURE:
<223> OTHER INFORMATION: synthetic

<400> SEQUENCE: 617

Cys Arg Ala Ser Gln Glu Ile Ala Lys Thr Ile Ser Gly Tyr Val Ala
1               5                   10                  15

<210> SEQ ID NO 618
<211> LENGTH: 16
<212> TYPE: PRT
<213> ORGANISM: Artificial Sequence
<220> FEATURE:
<223> OTHER INFORMATION: synthetic

<400> SEQUENCE: 618

Cys Arg Ala Ser Gln Asn Ile Pro Lys Ser Val Ser Gly Tyr Val Ala
1               5                   10                  15

<210> SEQ ID NO 619
<211> LENGTH: 16
<212> TYPE: PRT
<213> ORGANISM: Artificial Sequence
<220> FEATURE:
<223> OTHER INFORMATION: synthetic

<400> SEQUENCE: 619

Cys Arg Ala Ser Glu Asp Leu Pro Lys Ser Val Ser Gly Tyr Val Ala
1               5                   10                  15

<210> SEQ ID NO 620
<211> LENGTH: 16
<212> TYPE: PRT
<213> ORGANISM: Artificial Sequence
```

```
<220> FEATURE:
<223> OTHER INFORMATION: synthetic

<400> SEQUENCE: 620

Cys Arg Ala Ser Glu Asn Ile Pro Arg Thr Val Ser Gly Tyr Val Ala
1               5                   10                  15

<210> SEQ ID NO 621
<211> LENGTH: 16
<212> TYPE: PRT
<213> ORGANISM: Artificial Sequence
<220> FEATURE:
<223> OTHER INFORMATION: synthetic

<400> SEQUENCE: 621

Cys Arg Ala Ser Gln Asp Ile Pro Arg Ser Ile Ser Gly Tyr Val Ala
1               5                   10                  15

<210> SEQ ID NO 622
<211> LENGTH: 7
<212> TYPE: PRT
<213> ORGANISM: Artificial Sequence
<220> FEATURE:
<223> OTHER INFORMATION: synthetic

<400> SEQUENCE: 622

His Tyr Thr Thr Pro Pro Thr
1               5

<210> SEQ ID NO 623
<211> LENGTH: 7
<212> TYPE: PRT
<213> ORGANISM: Artificial Sequence
<220> FEATURE:
<223> OTHER INFORMATION: synthetic

<400> SEQUENCE: 623

His Phe Asn Ser Pro Pro Lys
1               5

<210> SEQ ID NO 624
<211> LENGTH: 7
<212> TYPE: PRT
<213> ORGANISM: Artificial Sequence
<220> FEATURE:
<223> OTHER INFORMATION: synthetic

<400> SEQUENCE: 624

His Tyr Thr Ile Pro Pro Lys
1               5

<210> SEQ ID NO 625
<211> LENGTH: 7
<212> TYPE: PRT
<213> ORGANISM: Artificial Sequence
<220> FEATURE:
<223> OTHER INFORMATION: synthetic

<400> SEQUENCE: 625

His Tyr Ser Ser Pro Pro Thr
1               5

<210> SEQ ID NO 626
<211> LENGTH: 7
<212> TYPE: PRT
<213> ORGANISM: Artificial Sequence
<220> FEATURE:
```

<223> OTHER INFORMATION: synthetic

<400> SEQUENCE: 626

His Tyr Thr Ser Pro Pro Thr
1               5

<210> SEQ ID NO 627
<211> LENGTH: 7
<212> TYPE: PRT
<213> ORGANISM: Artificial Sequence
<220> FEATURE:
<223> OTHER INFORMATION: synthetic

<400> SEQUENCE: 627

His Phe Thr Ser Pro Pro Thr
1               5

<210> SEQ ID NO 628
<211> LENGTH: 7
<212> TYPE: PRT
<213> ORGANISM: Artificial Sequence
<220> FEATURE:
<223> OTHER INFORMATION: synthetic

<400> SEQUENCE: 628

His Phe Ser Ser Pro Pro Thr
1               5

<210> SEQ ID NO 629
<211> LENGTH: 7
<212> TYPE: PRT
<213> ORGANISM: Artificial Sequence
<220> FEATURE:
<223> OTHER INFORMATION: synthetic

<400> SEQUENCE: 629

His Tyr Ser Thr Thr Pro Lys
1               5

<210> SEQ ID NO 630
<211> LENGTH: 7
<212> TYPE: PRT
<213> ORGANISM: Artificial Sequence
<220> FEATURE:
<223> OTHER INFORMATION: synthetic

<400> SEQUENCE: 630

His Phe Thr Thr Pro Pro Lys
1               5

<210> SEQ ID NO 631
<211> LENGTH: 7
<212> TYPE: PRT
<213> ORGANISM: Artificial Sequence
<220> FEATURE:
<223> OTHER INFORMATION: synthetic

<400> SEQUENCE: 631

His Phe Asn Ser Pro Pro Thr
1               5